(12) United States Patent
Dietrich et al.

(10) Patent No.: US 12,116,586 B2
(45) Date of Patent: Oct. 15, 2024

(54) COMPOSITIONS AND METHODS FOR IMPROVING CROP YIELDS THROUGH TRAIT STACKING

(71) Applicant: Monsanto Technology LLC, St. Louis, MO (US)

(72) Inventors: Charles R. Dietrich, Chesterfield, MO (US); Natalia Ivleva, Webster Groves, MO (US); Thomas L. Slewinski, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 17/820,205

(22) Filed: Aug. 16, 2022

(65) Prior Publication Data

US 2023/0242931 A1    Aug. 3, 2023

Related U.S. Application Data

(62) Division of application No. 16/276,620, filed on Feb. 15, 2019, now Pat. No. 11,441,153.

(60) Provisional application No. 62/631,221, filed on Feb. 15, 2018.

(51) Int. Cl.
C12N 15/82    (2006.01)

(52) U.S. Cl.
CPC ..... *C12N 15/8261* (2013.01); *C12N 15/8218* (2013.01); *C12N 15/8297* (2013.01)

(58) Field of Classification Search
None
See application file for complete search history.

(56) References Cited

U.S. PATENT DOCUMENTS

| | | |
|---|---|---|
| 5,188,958 A | 2/1993 | Moloney et al. |
| 5,322,938 A | 6/1994 | Mcpherson et al. |
| 5,352,605 A | 10/1994 | Fraley et al. |
| 5,463,174 A | 10/1995 | Moloney et al. |
| 5,510,474 A | 4/1996 | Quail et al. |
| 5,538,880 A | 7/1996 | Lundquist et al. |
| 5,550,318 A | 8/1996 | Adams et al. |
| 5,591,616 A | 1/1997 | Hiei et al. |
| 5,641,876 A | 6/1997 | Mcelroy et al. |
| 5,750,871 A | 5/1998 | Moloney et al. |
| 5,824,877 A | 10/1998 | Hinchee et al. |
| 5,850,019 A | 12/1998 | Maiti et al. |
| 5,159,135 B1 | 10/2000 | Umbeck et al. |
| 6,153,812 A | 11/2000 | Fry et al. |
| 6,160,208 A | 12/2000 | Lundquist et al. |
| 6,194,636 B1 | 2/2001 | Mcelroy et al. |
| 6,225,529 B1 | 5/2001 | Lappegard et al. |
| 6,232,526 B1 | 5/2001 | Mcelroy et al. |
| 6,372,211 B1 | 4/2002 | Isaac et al. |
| 6,376,750 B1 | 4/2002 | Yu et al. |
| 6,384,301 B1 | 5/2002 | Martinell et al. |
| 6,399,861 B1 | 6/2002 | Anderson et al. |
| 6,420,547 B1 | 7/2002 | Maiti et al. |
| 6,429,357 B1 | 8/2002 | Mcelroy et al. |
| 6,723,897 B2 | 4/2004 | Brown et al. |
| 7,049,490 B2 | 5/2006 | Tanaka et al. |
| 7,057,088 B2 | 6/2006 | Tanaka et al. |
| 7,154,028 B2 | 12/2006 | Tanaka et al. |
| 7,491,813 B2 | 2/2009 | Wu et al. |
| 7,518,035 B2 | 4/2009 | Cheikh et al. |
| 7,547,774 B2 | 6/2009 | Flasinski et al. |
| 8,835,353 B2 | 9/2014 | Fugiel et al. |
| 9,309,512 B2 | 4/2016 | Allen et al. |
| 11,441,153 B2 | 9/2022 | Dietrich |
| 2002/0053095 A1 | 5/2002 | Brown et al. |
| 2003/0233679 A1 | 12/2003 | Brown et al. |
| 2004/0053411 A1 | 3/2004 | Cullen et al. |
| 2004/0121321 A1 | 6/2004 | Brown et al. |
| 2004/0216189 A1 | 10/2004 | Houmard et al. |
| 2004/0268441 A1 | 12/2004 | Vance et al. |
| 2005/0037988 A1 | 2/2005 | Zamore et al. |
| 2005/0064474 A1 | 3/2005 | Urnov |
| 2005/0144669 A1 | 6/2005 | Reinhart et al. |
| 2005/0197253 A1 | 9/2005 | Stoller et al. |
| 2005/0251883 A1 | 11/2005 | Amasino et al. |
| 2006/0200878 A1 | 9/2006 | Lutfiyya et al. |

(Continued)

FOREIGN PATENT DOCUMENTS

| | | |
|---|---|---|
| CN | 102174519 A | 9/2011 |
| CN | 102757486 A | 10/2012 |

(Continued)

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Doerks et al., (TIG, 14:248-250, 1998).*
Smith et al. (Nature Biotechnology, 15:1222-1223, 1997).*
Bork et al. (TIG, 12:425-427, 1996).*
Heuer et al. (Plant physiology, 127:33-45; 2001).*
Rounsley et al. (Plant Cell, 7:1259-1269, 1995).*

(Continued)

*Primary Examiner* — Vinod Kumar
(74) *Attorney, Agent, or Firm* — MORRISON & FOERSTER LLP

(57) ABSTRACT

The present disclosure provides modified, transgenic, or genome edited/mutated corn plants that are semi-dwarf and have one or more improved ear traits relative to a control plant, such as increase in ear diameter, single kernel weight, ear fresh weight, ear area, ear volume, ear length, number of kernels per ear, and yield. The modified, transgenic, or genome edited/mutated corn plants comprise a transgene encoding one or more MADS-box polypeptides and have a reduced expression of one or more GA20 or GA3 oxidase genes. Also provided are methods for producing the modified, transgenic, or genome edited/mutated corn plants.

11 Claims, 14 Drawing Sheets

Specification includes a Sequence Listing.

(56) References Cited

U.S. PATENT DOCUMENTS

| | | |
|---|---|---|
| 2006/0253933 A1 | 11/2006 | Brown et al. |
| 2007/0174931 A1 | 7/2007 | Brown et al. |
| 2007/0174938 A1 | 7/2007 | Vanderkimpen et al. |
| 2007/0294789 A1 | 12/2007 | Ghiglione et al. |
| 2008/0034453 A1 | 2/2008 | Cheikh et al. |
| 2008/0131581 A1 | 6/2008 | Schneeberger et al. |
| 2009/0031441 A1 | 1/2009 | Matsuoka et al. |
| 2009/0070898 A1 | 3/2009 | Allen et al. |
| 2009/0117617 A1 | 5/2009 | Holmes et al. |
| 2009/0313725 A1 | 12/2009 | Yu et al. |
| 2010/0095406 A1 | 4/2010 | Yu et al. |
| 2011/0004958 A1 | 1/2011 | Aloni et al. |
| 2011/0035839 A1 | 2/2011 | Lutfiyya et al. |
| 2011/0145940 A1 | 6/2011 | Voytas et al. |
| 2011/0167517 A1 | 7/2011 | Danilevskaya et al. |
| 2011/0185456 A1 | 7/2011 | Cheikh et al. |
| 2011/0296555 A1 | 12/2011 | Ivashuta et al. |
| 2011/0301073 A1 | 12/2011 | Gregory |
| 2012/0142062 A1 | 6/2012 | Doyon et al. |
| 2012/0216318 A1 | 8/2012 | La Rosa et al. |
| 2013/0117869 A1 | 5/2013 | Duchateau et al. |
| 2013/0283461 A1 | 10/2013 | Abad et al. |
| 2014/0165228 A1 | 6/2014 | Danilevskaya et al. |
| 2014/0344996 A1 | 11/2014 | Inze et al. |
| 2015/0052634 A1 | 2/2015 | Park et al. |
| 2015/0247154 A1 | 9/2015 | Ivashuta et al. |
| 2015/0307889 A1 | 10/2015 | Petolino et al. |
| 2015/0376641 A1 | 12/2015 | Etzioni et al. |
| 2016/0010109 A1 | 1/2016 | Albertsen et al. |
| 2016/0017349 A1 | 1/2016 | Ayele et al. |
| 2016/0046956 A1 | 2/2016 | Yu et al. |
| 2016/0050920 A1 | 2/2016 | Ott et al. |
| 2016/0076046 A1 | 3/2016 | Alexandrov et al. |
| 2017/0114356 A1 | 4/2017 | Li et al. |

FOREIGN PATENT DOCUMENTS

| | | |
|---|---|---|
| CN | 103451200 A | 12/2013 |
| EP | 1398382 B1 | 11/2005 |
| KR | 20150045611 A | 4/2015 |
| WO | 1994028141 A1 | 12/1994 |
| WO | 1995015389 A1 | 6/1995 |
| WO | 1995023230 A1 | 8/1995 |
| WO | 199909174 A1 | 2/1999 |
| WO | 1999016890 A2 | 4/1999 |
| WO | 199966029 A2 | 12/1999 |
| WO | 2000009722 A2 | 2/2000 |
| WO | 2000012733 A1 | 3/2000 |
| WO | 2002055725 A2 | 7/2002 |
| WO | 2003008540 A2 | 1/2003 |
| WO | 2004070039 A2 | 8/2004 |
| WO | 2006032916 A2 | 3/2006 |
| WO | 2009126470 A2 | 10/2009 |
| WO | 2010002984 A1 | 1/2010 |
| WO | 2013037959 A1 | 3/2013 |
| WO | 2013086499 A2 | 6/2013 |
| WO | 2014055477 A2 | 4/2014 |
| WO | 2015168124 A1 | 11/2015 |

OTHER PUBLICATIONS

Alvarez-Buylla et al. (PNAS., 97:5328-5333, Published May 2000).*
Yang et al. (Molecular Genetics and Genomics; 289:873-883; 2014).*
Kaufmann et al. (Gene, 347:183-198, 2005).*
Petti et al. (Plant Physiol., 169:705-716; Sep. 2015).*
Gutterson (HortScience 30:964-966, 1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Nunes et al. (Planta 224:125-132; 2006).*
Arziman et al. (Nucleic Acids Research, 33:582-588, 2005).*
Bonawitz et al., (Annu. Rev. Genet. 44: 337-363, 2010).*
Paul et al., Plant Cell Reports; 35:1417-1427; 2016.*
Nishimura et al. (Plant Cell Physiol., 41(5):583-590, 2000).*
Yang et al. (PNAS, 98:11438-11443, 2001).*
McConnell et al. (Nature, 411:709-713, 2001).*
Qiao et al. (Plant Mol Biol Reporter, 29:952-960, 2011).*
Wills et al. (Journal of Heredity, 109(3): pp. 333-338; published Sep. 5, 2017).*
Yang et al. (GenBank Sequence Accession No. EU179378.1; pp. 1-2, Published 2009).*
Wingen et al. (NCBI, GenBank Sequence Accession No. AJ850299.1; pp. 1-2, Published May 10, 2012).*
Ware (NCBI, GenBank Sequence Accession No. ONM35853.1, Published Feb. 6, 2017).*
Ware (NCBI, GenBank Sequence Accession No. AQK99102.1, Published Feb. 7, 2017).*
Albani, D. et al (1997). "The Wheat Transcriptional Activator SPA: A Seed-Specific bZIP Protein That Recognizes the GCN4-like Motif in the Bifactorial Endosperm Box of Prolamin Genes," The Plant Cell 9:171-184.
Allen, E. et al. (Apr. 22, 2005). "MicroRNA-directed Phasing During Trans-Acting SiRNA Biogenesis in Plants," Cell 121(2):207-221.
Allen, E. et al. (Dec. 2004). "Evolution of MicroRNA Genes by Inverted Duplication of Target Gene Sequences in *Arabidopsis thaliana*," Nat. Genet. 36(12):1282-1290.
Altschul, S. F. et al. (Oct. 1990). "Basic Local Alignment Search Tool," J. Mol. Biol. 215(3):403-410.
Altschul, S. F. et al. (Sep. 1, 1997). "Gapped BLAST and PSI-BLAST: A New Generation of Protein Database Search Programs," Nucleic Acids Res. 25(17):3389-3402.
Alvarez-Buylla, E. R. et al. (May 9, 2000). "An Ancestral MADS-box Gene Duplication Occurred before the Divergence of Plants and Animals," PNAS 97(10):5328-5333.
Aryan, A. P. et al. (Jan. 1991). "Structural and Functional Analysis of Promoter from Gliadin, an Endosperm- Specific Storage Protein Gene of *Triticum aestivum* L," Mol and Gen Genet 225(1):65-71.
Arziman, Z. et al. (Jul. 1, 2005). "E-RNAi: A Web Application to Design Optimized RNAi Constructs," Nucleic Acids Research 33:582-588.
Ashikari, M. et al. (2002). "Loss-of-function of a Rice Gibberellin Biosynthetic Gene, GA20 oxidase (GA20ox-2), Led to the Rice 'Green Revolution'," Breeding Science 52(2):143-150.
Atanassova, R. et al. (May 1998). "Functional Analysis of the Promoter Region of a Maize (*Zea mays* L.) H3 Histone Gene in Transgenic *Arabidopsis thaliana*," Plant Mol Biol 37:275-285.
Axtell, M. J. et al. (Nov. 3, 2006). "A Two-Hit Trigger for SiRNA Biogenesis in Plants," Cell 127(3):565-577.
Beurdeley, M. et al. (Apr. 23, 2013). "Compact Designer TALENs for Efficient Genome Engineering," Nature Communications 4:1762, 8 pages.
Bonawitz, N. D. et al. (2010). "The Genetics of Lignin Biosynthesis: Connecting Genotype to Phenotype," Annu. Rev. Genet. 44: 337-363.
Bork, P. et al. (Oct. 1996). "Go Hunting in Sequence Databases but Watch Out for the Traps," Trends Genet. 12(10):425-427.
Bruening, G. (Nov. 10, 1998). "Plant Gene Silencing Regularized," Proc. Natl. Acad. Sci. 95(23):13349-13351.
Cai, P. et al. (Mar. 6, 2012). "Molecular Cloning, Characterization, and Expression Analysis of Genes Encoding Gibberellin 20-Oxidase in Dasypyrum Villosum Dwarf Mutant," Plant Mol Biol Reporter 30:1110-1116.
Carrera, E. et al. (May 2000). "Changes in GA 20-oxidase Gene Expression Strongly Affect Stem Length, Tuber Induction and Tuber Yield of Potato Plants," Plant J. 22(3):247-256.
Cejudo, F. J. et al. (Dec. 1992). "Analysis of the Gibberellin-Responsive Promoter of a Cathepsin B-like Gene from Wheat," Plant Mol Biol 20(5):849-856.
Cermak, T. et al. (Jul. 2011). "Efficient Design and Assembly of Custom TALEN and Other TAL Effector-Based Constructs for DNA Targeting," Nucleic Acids Research 39(12):e82, 11 pages.

(56) References Cited

OTHER PUBLICATIONS

Chen, Y. et al. (Dec. 2014). "The Maize DWARF1 Encodes a Gibberellin 3-Oxidase and Is Dual Localized to the Nucleus and Cytosol," Plant Physiology 166(4):2028-2039.
Chen, Y. et al. (May 2015). "New Insight in the Gibberellin Biosynthesis and Signal Transduction," Plant Signaling & Behavior 10(5):e1000140, 3 pages.
Chen, Z. et al. (Dec. 30, 2013). "Identification and Functional Analysis of Flowering Related microRNAs in Common Wild Rice (*Oryza rufipogon* Griff.)," PLoS ONE, 8:e82844, 13 pages.
Chenna, R. et al. (Jul. 1, 2003). "Multiple Sequence Alignment with the Clustal Series of Programs," Nucleic Acids Research 31(13):3497-3500.
Cho, M. J. et al. (Jun. 1999). "Inheritance of Tissue-Specific Expression of Barley Hordein Promoter-UidA Fusions in Transgenic Barley Plants," Theor Appl Gen 98:1253-1262.
Ciampitti, I. A. et al. (Feb. 28, 2011). "A Comprehensive Study of Plant Density Consequences on Nitrogen Uptake Dynamics of Maize Plants from Vegetative to Reproductive Stages," Field Crops Research 121(1):2-18.
Colbert, T. et al. (Jun. 2001). "High-throughput Screening for Induced Point Mutations," Plant Physiol 126(2):480-484.
Coles, J. P. et al. (Mar. 1999). "Modification of Gibberellin Production and Plant Development in *Arabidopsis* by Sense and Antisense Expression of Gibberellin 20-oxidase Genes," Plant J. 17(5):547-556.
Colliver, S. P. et al. (Nov. 1997). "Differential Modification of Flavonoid and Isoflavonoid Biosynthesis with an Antisense Chalcone Synthase Construct in Transgenic Lotus Corniculatus," Plant Molecular Biology 35:509-522.
Colot, V. et al. (Mar. 1989). "Molecular Characterization of an Active Wheat LMW Glutenin Gene and its Relation to Other Wheat and Barley Prolamin Genes," Mol Gen Genet 216:81-90.
Conkling, M. A. et al. (Jul. 1990). "Isolation of Transcriptionally Regulated Root-Specific Genes from Tobacco," Plant Physiol. 93(3):1203-1211.
Davis, G. et al. (Nov. 1999). "Gibberellin Biosynthesis in Maize. Metabolic Studies with GA1s, GA24, GA2s, GA1, and 2,3-Dehydro-GA91," Plant Physiology 121(3):1037-1045.
Derose, R. T. et al. (Dec. 1996). "Analysis of Kafirin Promoter Activity in Transgenic Tobacco Seeds," Plant Mol Biol 32(6):1029-1035.
Diaz, I. et al. (Sep. 20, 1995). "The Promoter of the Gene Itr1 from Barley Confers a Different Tissue Specificity in Transgenic Tobacco," Mol Gen Genet 248(5):592-598.
Doerks, T. et al. (Jun. 1998). "Protein Annotation: Detective Work for Function Prediction," Trends Genet. 14(6):248-250.
Doyle, E. L. et al. (Jul. 2012). "Nucleic Acids TAL Effector-Nucleotide Targeter (TALE-NT) 2.0: Tools for TAL Effector Design and Target Prediction," Research 40:W117-122.
Du, J. et al. (Feb. 10, 2009). "Cloning and Characterization of an Up-regulated GA 20-oxidase Gene in Hybrid Maize," Natural Science 19(2):161-166.
Elomaa, P. et al. (1996). "Transformation of Antisense Constructs of the Chalcone Synthase Gene Superfamily into Gerbera Hybrida: Differential Effect on the Expression of Family Members," Molecular Breeding 2(1):41-50.
Emery, J. F. et al. (Oct. 14, 2003). "Radial Patterning of *Arabidopsis* Shoots by Class III HD-ZIP and KANADI Genes," Current Biology 13(20):1768-1774.
Eriksson, S. et al. (Sep. 2006). "GA4 Is the Active Gibberellin in the Regulation of LEAFY Transcription and *Arabidopsis* Floral Initiation," The Plant Cell 18(9):2172-2181.
European Extended Search Report mailed on Oct. 5, 2021, for European Patent Application No. 19753661.8, filed Feb. 15, 2018, 9 pages.
Fagoaga, C. et al. (2007). "Engineering of Gibberellin Levels in Citrus by Sense and Antisense Overexpression of a GA 20-Oxidase Gene Modifies Plant Architecture," Journal of Experimental Botany 58(6):1407-1420.

Fambrini, M. et al. (Mar. 2011). "The Extreme Dwarf Phenotype of the GA-Sensitive Mutant of Sunflower, Dwarf2, is Generated by a Deletion in the Ent-Kaurenoic Acid Oxidase1 (HaKAO1) Gene Sequence," Plant Mal Biol 75(4-5):431-450.
Franco-Zorrilla, J. M. et al. (Aug. 2007). "Target Mimicry Provides a New Mechanism for Regulation of MicroRNA Activity," Nature Genetics 39(8):1033-1037.
Furtado, A. et al. (Apr. 2009). "Analysis of Promoters in Transgenic Barley and Wheat," Plant Biotechnol J. 7(3):240-253.
Furtado, A. et al. (Sep. 2008). "Comparison of Promoters in Transgenic Rice," Plant Biotechnol J. 6(7):679-693.
Gabsalilow, L. et al. (Apr. 2013). "Site- and Strand-Specific Nicking of DNA by Fusion Proteins Derived from MutH and I-Scel or TALE Repeats," Nucleic Acids Research 41(7):e83, 11 pages.
Gaj, T. et al. (Jul. 2013). "ZFN, TALEN and CRISPR/Cas-based Methods for Genome Engineering," Trends Biotechnol. 31(7):397-405.
GenBank Accession No. AJ850299.1, last updated May 10, 2012, located at a href="https://www.ncbi.nlm.nih.gov/nuccore/AJ850299.1" target="_blank"https://www.ncbi.nlm.nih.gov/nuccore/AJ850299.1/a last visited on Nov. 11, 2022, 5 pages.
GenBank Accession No. AY105651.1, last updated May 28, 2008, located at a href="https://www.ncbi.nlm.nih.gov/nuccore/AY105651.1/" target="_blank"https://www.ncbi.nlm.nih.gov/nuccore/AY105651.1//a last visited on Nov. 11, 2022, 2 pages.
GenBank Accession No. EU179378.1, last updated 2009, located at a href="https://www.ncbi.nlm.nih.gov/nuccore/EU179378.1/" target="_blank"https://www.ncbi.nlm.nih.gov/nuccore/EU179378.1//a last visited on Nov. 11, 2022, two pages.
Gramzow, L. et al. (Jun. 28, 2010). "A Hitchhiker's Guide to the MADS World of Plants," Genome Biol. 11: 214, 11 pages.
Griffiths-Jones, S. et al. (Jan. 1, 2003). "Rfam: an RNA Family Database," Nucleic Acids Res. 31(1):439-441.
Guo, H. H. et al. (Jun. 14, 2004). "Protein Tolerance to Random Amino Acid Change," PNAS 101(25):9205-9210.
Gupta, R. et al. (Jun. 28, 2013). "Gibberellic Acid in Plant: Still a Mystery Unresolved," Plant Signaling & Behavior 8(9):e25504, 5 pages.
Gutterson, N (Aug. 1995). "Anthocyanin Biosynthetic Genes and Their Application to Flower Color Modification through Sense Suppression," HortScience 30(5):964-966.
Hedden, P. (Jan. 2003). "The Genes of the Green Revolution," TRENDS in Genetics 19(1):5-9.
Hedden, P. et al. (Jun. 1997). "Gibberellin Biosynthesis: Enzymes, Genes and Their Regulation," Annu. Rev. Plant Physiol. Plant Mal. Biol. 48:431-460.
Hedden, P. et al. (May 15, 2012). "Gibberellin Biosynthesis and its Regulation," Biochem. J. 444(1):11-25.
Heuer, S. et al. (Sep. 2001). "The Maize MADS Box Gene ZmMADS3 Affects Node Number and Spikelet Development and is Co-expressed with ZmMADS1 During Flower Development, in Egg Cells, and Early Embryogenesis," Plant Physiology 127(1):33-45.
Horvath, H. et al. (Feb. 15, 2000). "The Production of Recombinant Proteins in Transgenic Barley Grains," PNAS 97(4):1914-1919.
Huang, D. et al. (Jun. 2015). "A Gibberellin-Mediated DELLA-NAC Signaling Cascade Regulates Cellulose Synthesis in Rice," The Plant Cell 27(6):1681-1696.
International Search Report and Written Opinion mailed on Dec. 28, 2017, for PCT Application No. PCT/US2017/047405, filed on Aug. 17, 2017, 20 pages.
International Search Report and Written Opinion mailed on Jul. 9, 2019, for PCT Application No. PCT/US2019/018136, filed on Feb. 15, 2019, 17 pages.
J. Craig Venter Institute, Maize Cell Genomics Database, located at a href="http://maize.jcvi.org/cellgenomics/index.php" target="_blank"http://maize.jcvi.org/cellgenomics/index.php/a, last accessed Mar. 21, 2001.
Jia, Q. et al. (May 2009). "GA-20 Oxidase as a Candidate for the Semidwarf Gene sdw 1/denso in Barley," Funct Integr Genomics 9(2):255-262.
Jia, Q. et al. (Nov. 14, 2015). "Molecular Characterization and Functional Analysis of Barley Semi-Dwarf Mutant Riso No. 9265," BMC Genomics 16(927), 11 pages.

(56) References Cited

OTHER PUBLICATIONS

Jones-Rhoades, M. W. et al. (Jun. 18, 2004). "Computational Identification of Plant MicroRNAs and Their Targets, Including a Stress-Induced miRNA," Mal. Cell 14(6):787-799.

Joshi, J. B. et al. (Jan. 2015). "A Maize Alpha-Zein Promoter Drives an Endosperm-Specific Expression of Transgene in Rice," Physiol Mol Biol Plants 21(1):35-42.

Kalla, R. et al. (1994). "The Promoter of the Barley Aleurone-specific Gene Encoding a Putative 7 kDa Lipid Transfer Protein Confers Aleurone Cell-specific Expression in Transgenic Rice," The Plant J. 6(6):849-860.

Katoh, T. et al. (2007). "Specific Residues at Every Third Position of siRNA Shape its Efficient RNAi Activity," Nucleic Acids Res. 35(4):e27, 14 pages.

Kaufmann, K. et al. (Mar. 14, 2005). "MIKC-type MADS-domain Proteins: Structural Modularity, Protein Interactions and Network Evolution in Land Plants," Gene 347(2):183-198.

Keskin, O. et al. (Jan. 1, 2009). "A New, Structurally Nonredundant, Diverse Data Set of Protein-Protein Interfaces and its Implications," Protein Science 13(4):1043-1055.

Kim, V. N. (May 1, 2005). "MicroRNA Biogenesis: Coordinated Cropping and Dicing," Nature Rev. Mal. Cell. Biol. 6:376-385.

King, R. W. et al. (Mar. 2008). "Selective Deactivation of Gibberellins Below the Shoot Apex is Critical to Flowering but Not to Stem Elongation of Lolium," Molecular Plant 1(2):295-307.

Kobayashi, M. et al. (Feb. 1996). "Gibberellin Metabolism in Maize (The Stepwise Conversion of Gibberellin A12-Aldehyde to Gibberellin A20)," Plant Physiol. 110(2):413-418.

Kosugi, S. et al. (Apr. 11, 1991). "Upstream Sequences of Rice Proliferating Cell Nuclear Antigen (PCNA) Gene Mediate Expression of PCNA-GUS Chimeric Gene in Meristems of Transgenic Tobacco Plants," Nucl. Acids Res. 19(7):1571-1576.

Kusaba, S. et al. (Feb. 2001). "Isolation and Expression Analysis of Gibberellin 20-Oxidase Homologous Gene in Apple," Journal of Experimental Botany 52(335):375-376.

Lam, E. et al. (Oct. 1, 1989). "Site-specific Mutations Alter in Vitro Factor Binding and Change Promoter Expression Pattern in Transgenic Plants," PNAS USA 86(20):7890-7894.

Lamacchia, C. et al. (Feb. 2001). "Endosperm-specific Activity of a Storage Protein Gene Promoter in Transgenic Wheat Seed," J Exp Bot 52(355):243-250.

Lanahan, M. B. et al. (Feb. 1992). "A Gibberellin Response Complex in Cereal Alpha-Amylase Gene Promoters," The Plant Cell 4(2):203-211.

Larkin, M. A. et al. (Nov. 1, 2001). "Clustal Wand Clustal Version 2.0," Bioinformatics 23(21):2947-2948.

Last, D. I. et al. (May 1991). "PEmu: An Improved Promoter for Gene Expression in Cereal Cells," Theor. Appl. Genet. 81:581-588.

Leah, R. et al. (Oct. 1994). "Identification of an Enhancer/Silencer Sequence Directing the Aleurone-Specific Expression of a Barley Chitinase Gene," Plant J. 6(4):579-589.

Matzke, A. J. et al. (Mar. 1990). "Deletion Analysis of a Zein Gene Promoter in Transgenic Tobacco Plants," Plant Mol Biol. 14(3):323-332.

Mccallum, C. M. et al. (Apr. 2000). "Targeted Screening for Induced Mutations," Nat. Biotechnol. 18(4):455-457.

Mcconnell, J. R. et al. (Jun. 7, 2001). "Role of PHABULOSA and PHAVOLUTA in Determining Radial Patterning in Shoots," Nature 411(6838):709-713.

Mccormick, S. et al. (Apr. 1986). "Leaf Disc Transformation of Cultivated Tomato (L. *Esculentum*) Using Agrobacterium Tumefaciens," Plant Cell Reports 5:81-84.

Mcelroy, D. et al. (Dec. 1991). "Construction of Expression Vectors Based on the Rice Actin 1 (Act1) 5' Region for Use in Monocot Transformation," Mal. Gen. Genet. 231(1):150-160.

Mena, M. et al. (Oct. 1998). "An Endosperm-Specific DOF Protein from Barley, Highly Conserved in Wheat, Binds to and Activates Transcription from the Prolamin-Box of a Native B-hordein Promoter in Barley Endosperm," The Plant Journal 16(1):53-62.

Merida, A. et al. (Jun. 1999). "Expression of the Granule-Bound Starch Synthase I (Waxy) Gene from Snapdragon Is Developmentally and Circadian Clock Regulated," Plant Physiol. 120(2):401-410.

Mitchum, M. G. et al. (Mar. 2006). "Distinct and Overlapping Roles of Two Gibberellin 3-Oxidases in *Arabidopsis* Development, " The Plant Journal 45(5):804-818.

Molina, I. et al. (May 2009). "Transformation of a Dwarf *Arabidopsis* Mutant Illustrates Gibberellin Hormone Physiology and the Function of a Green Revolution Gene," Biochemistry and Molecular Biology Education 37(3):170-177.

Muller, M. et al. (1993). "The Nitrogen Response of a Barley C-hordein Promoter is Controlled by Positive and Negative Regulation of the GCN4 and Endosperm Box," The Plant Journal 4(2):343-355.

Mutasa-Gottgens, E. et al. (Mar. 5, 2009). "Gibberellin as a Factor in Floral Regulatory Networks, Journal of Experimental Botany," 60(7):1979-1989.

Nakase, M. et al. (Feb. 1997). "Characterization of a Novel Rice bZIP Protein which Binds to the Alpha-Globulin Promoter," Plant Mol. Biol. 33(3):513-522.

Ngo, J. T. et al. (1994). "Computational Complexity, Protein Structure Prediction, and the Levinthal Paradox" Chapter 14 in The Protein Folding Problem and Tertiary Structure Prediction, Merz, K. et al eds., Springer Science & Business Media pp. 492-495.

Nishimura, A. et al. (May 2000). "Over-expression of Tobacco Knotted1-Type Class1 Homeobox Genes Alters Various Leaf Morphology," Plant Cell Physiol. 41(5):583-590.

Nuccio, M. L. (2018). "A Brief History of Promoter Development for Use in Transgenic Maize Applications," Methods Mol Biol. 1676:61-93.

Nunes, A. C. S. et al. (Jun. 2006). "RNAi-mediated Silencing of the Myo-Inositol-1-Phosphate Synthase Gene (GmMIPS1) in Transgenic Soybean Inhibited Seed Development and Reduced Phytate Content," Planta 224:125-132.

Ohtsubo, N. et al. (Nov. 1993). "Proximal Promoter Region of the Wheat Histone H3 Gene Confers S Phase-Specific Gene Expression in Transformed Rice Cells," Pant Mol Biol 23(3):553-565.

Oikawa, T. et al. (Jul. 2004). "A Role of OsGA20oxl, Encoding an Isoform of Gibberellin 20-oxidase, for Regulation of Plant Stature in Rice," Plant Molecular Biology 55(5):687-700.

Onate, L. et al. (Apr. 2, 1999). "Barley BLZ2, a Seed-specific bZIP Protein that Interacts with BLZ1 in Vivo and Activates Transcription from the GCN4-like Motif of B-hordein Promoters in Barley Endosperm," J Biol Chem 274(14):9175-9182.

Opsahl-Ferstad, H. G. et al. (Jul. 1997). "ZmEsr, a Novel Endosperm-Specific Gene Expressed in a Restricted Region Around the Maize Embryo," Plant J. 12(1): 235-246.

Osvald, M. et al. (Oct. 5, 2007). "Development and Characterization of a Chimaeric Tissue-Specific Promoter in Wheat and Rice Endosperm," In Vitro Cellular & Dev Biol. Plant 44(1):1-7.

Parizotto, E. A. et al. (Sep. 15, 2004). "In Vivo Investigation of the Transcription, Processing, Endonucleolytic Activity, and Functional Relevance of the Spatial Distribution of a Plant MiRNA," Genes Dev. 18(18):2237-2242.

Pater, B. S. D. et al. (Nov. 1992). "The Promoter of the Rice Gene GOS2 is Active in Various Different Monocol Tissues and Binds Rice Nuclear Factor ASF-1," The Plant Journal 2(6):837-844.

Paul, J. W. et al. (Jul. 2016). "CRISPR/Cas9 for Plant Genome Editing: Accomplishments, Problems and Prospects," Plant Cell Reports 35(7):1417-1427.

Peiffer, J. A. et al. (Apr. 2014). "The Genetic Architecture of Maize Height," Genetics 196(4):1337-1356.

Peng, J. et al. (Jul. 15, 1999). "Green Revolution' Genes Encode Mutant Gibberellin Response Modulators," Nature 400:256-261.

Petti, C. et al. (Sep. 2015). "Mapping of a Cellulose-Deficient Mutant Named dwarfl-1 in Sorghum Bicolor to the Green Revolution Gene Gibberellin20-oxidase Reveals a Positive Regulatory Association between Gibberellin and Cellulose Biosynthesis," Plant Physiology 169(1):705-716.

(56) References Cited

OTHER PUBLICATIONS

Piston, F. et al. (May 2009). "Analysis of the Activity of a γ-gliadin Promoter in Transgenic Wheat and Characterization of Gliadin Synthesis in Wheat by MALDI-TOF During Grain Development," Mol Breed 23(4):655-667.

Plackett, A. R. G. et al. (Mar. 2012). "Analysis of the Developmental Roles of the *Arabidopsis* Gibberellin 20-Oxidases Demonstrates that GA20ox1,—2 and—3 are the Dominant Paralogs," The Plant Cell 24(3):941-960.

Postma-Haarsma, A. D. et al. (Jan. 1999). "Characterization of the KNOX Class Homeobox Genes Oskn2 and Oskn3 Identified in a Collection of cDNA Libraries Covering the Early Stages of Rice Embryogenesis," Plant Mol. Biol. 39(2):257-271.

Qiao, F. et al. (2007). "Modification of Plant Height Via RNAi Suppression of OsGA20ox2 Gene in Rice," Euphytica 158(1-2):35-45.

Qiao, F. et al. (2011). "The Influence of RNAi Targeting of OsGA20ox2 Gene on Plant Height in Rice," Plant Molecular Biology Reporter 29(4):952-960.

Qiao, F. et al. (2013). "Alteration of Rice Growth and Development Via Antisense Expression of OsGA20ox2 Gene," African Journal of Biotechnology 12(5):3898-3904.

Qin, X. et al. (Feb. 2013). "Gibberellin 20-Oxidase Gene OsGA20ox3 Regulates Plant Stature and Disease Development in Rice," Mol Plant Microbe Interact. 26(2):227-239.

Qu, L. Q. et al. (Mar. 2004). "Evaluation of Tissue Specificity and Expression Strength of Rice Seed Component Gene Promoters in Transgenic Rice," Plant Biotechnol. J. 2(2):113-125.

Qu, L. Q. et al. (May 7, 2008). "Expression Pattern and Activity of Six Glutelin Gene Promoters in Transgenic Rice," J Exp Bot 59(9):2417-2424.

Rafalski, J. A. et al. (1984). "Developmentally Regulated Plant Genes: The Nucleotide Sequence of a Wheat Gliadin Genomic Clone," EMBO J. 3(6):1409-1415.

Reynolds, A. et al. (Feb. 1, 2004). "Rational SiRNA Design for RNA Interference," Nature Biotechnol. 22:326-330.

Rhoades, M. W. et al. (Aug. 23, 2002). "Prediction of Plant MicroRNA Targets," Cell 110(4):513-520.

Rieu, I. et al. (Feb. 2008). "The Gibberellin Biosynthetic Genes AtGA20ox1 and AtGA20ox2 Act, Partially Redundantly, to Promote Growth and Development throughout the *Arabidopsis* Life Cycle," The Plant Journal 53(3):488-504.

Ross, J. J. et al. (Jul. 1997). "Gibberellin Mutants," Physiologia Plantarum 100(3):550-560.

Rounsley, S. D. et al. (Aug. 1995). "Diverse Roles for MADS Box Genes in *Arabidopsis* Development," Plant Cell 7(8):1259-1269.

Russnogle, J. (Feb. 1, 1998). "Dwarf Corn Earns Tall Praise," located at a href="https://www.farmprogress.com/dwarf-corn-earns-tall-praise" target="_blank"https://www.farmprogress.com/dwarf-corn-earns-tall praise/a last visited on Sep. 21, 2021, 4 pages.

Sarkar, S. et al. (Feb. 2004). "Relationship Between Gibberellins, Height, and Stress Tolerance in Barely (*Hordeum vulgare* L.) Seedlings," Plant Growth Regulation 42:125-135.

Sasaki, A. et al. (Apr. 18, 2002). "A Mutant Gibberellin-Synthesis Gene in Rice," Nature 416:701-702.

Sato, Y. et al. (Jul. 1996). "A Rice Homeobox Gene, OSHJ, is Expressed Before Organ Differentiation in a Specific Region During Early Embryogenesis," PNAS USA 93(15):8117-8122.

Selinger, D. A. et al. (Jun. 1998). "The Maize Regulatory Gene B-Peru Contains a DNA Rearrangement that Specifies Tissue-Specific Expression through Both Positive and Negative Promoter Elements," Genetics 149(2):1125-1138.

Singh, D. et al. (Aug. 1999). "The Green Revolution and the Evolution of Agricultural Education and Research in India," Genome 42(4):557-561.

Skriver, K. et al. (Aug. 1991). "Cis-acting DNA Elements Responsive to Gibberellin and its Antagonist Abscisic Acid," PNAS USA 88(16):7266-7270.

Smith, T. F. et al. (Nov. 1, 1997). "The Challenges of Genome Sequence Annotation or 'The Devil is in the Details'," Nature Biotechnology 15:1222-1223.

Song, Y. H. et al. (Oct. 2013). "Flowering Time Regulation: Photoperiod- and Temperature-Sensing in Leaves," Trends in Plant Science 18(10):575-583.

Sorensen, M. B. et al. (Apr. 10, 1996). "Hordein Promoter Methylation and Transcriptional Activity in Wild-Type and Mutant Barley Endosperm," Mol and Gen Genet 250(6):750-760.

Sun, T. et al. (Sep. 24, 2008). "Gibberellin Metabolism, Perception and Signaling Pathways in *Arabidopsis*," The *Arabidopsis* Book 6:e0103, 28 pages.

Sunkar, R. et al. (Aug. 2004). "Novel and Stress-Regulated MicroRNAs and Other Small RNAs from *Arabidopsis*," Plant Cell 16(8):2001-2019.

Thilmony, R. et al. (2014, e-pub Dec. 9, 2013). "The Wheat HMW-glutenin 1Dy10 Gene Promoter Controls Endosperm Expression in Brachypodium Distachyon," GM Crops Food 5(1):36-43.

Thompson, J. D. et al. (Nov. 11, 1994). "CLUSTAL W: Improving the Sensitivity of Progressive Multiple Sequence Alignment through Sequence Weighting, Position-Specific Gap Penalties and Weight Matrix Choice," Nucleic Acids Research 22(22):4673-4680.

Thornton, J. M. et al. (Nov. 2000). "From Structure to Function: Approaches and Limitations," Nature structural Biology 7:991-994.

Tollenaar, M. et al. (Jan. 1978). "Effect of Defoliation on Kernel Development in Maize," Can. J Plant Sci. 58(1):207-221.

Tong, H. et al. (Apr. 2016). "REPLY: Brassinosteroid Promotes Cells Elongation by Regulating Both Synthesis and Signaling of Gibberellin: Critical Comments on Ross and Quittenden's Letter," Plant Cell Advance Publication 28(4):833-835.

Traore, S. B. et al. (Sep. 1, 2000). "Corn: BT and Non-Bt Maize Growth and Development as Affected by Temperature and Drought Stress," Agron. J 92(5):1027-1035.

UniProtKB Accession No. Q84V78, last updated Nov. 14, 2006, located at a href="https://www.ncbi.nlm.nih.gov/protein/Q84V78" target="_blank"https://www.ncbi.nlm.nih.gov/protein/Q84V78/a last visited on Nov. 11, 2022, 1 page.

Unterholzner, S. J. et al. (Apr. 2016). "REPLY: Interaction Between Brassinosteroids and Gibberellins: Synthesis or Signaling? In *Arabidopsis*, Both!" Plant Cell Advance Publication 28(4):836-839.

Urakami, E. et al. (Oct. 2008) "Immunomodulation of Gibberellin Biosynthesis Using an Anti-Precursor Gibberellin Antibody Confers Gibberellin-Deficient Phenotypes," Planta 228(5):863-873.

Van Herpen, T. W. J. M. et al. (Sep. 2008). "Detailed Analysis of the Expression of an Alpha-gliadin Promoter and the Deposition of Alpha-gliadin Protein During Wheat Grain Development," Ann Bot 102(3):331-342.

Vaucheret, H. (Sep. 6, 2005). "MicroRNA-Dependent Trans-Acting siRNA Production," Science STKE 2005 (300):pe43.

Wagner, T. A. et al. (Feb. 2001). "Wall-Associated Kinases Are Expressed throughout Plant Development and Are Required for Cell Expansion," The Plant Cell 13(2):303-318.

Wang, Y. et al. (Jun. 12, 2013). "Gibberellin Biosynthetic Deficiency Is Responsible for Maize Dominant Dwarf11 (D 11) Mutant Phenotype: Physiological and Transcriptomic Evidence," PLoS One 8(6): e66466, 8 pages.

Wells, J. A. (Sep. 18, 1990). "Additivity of Mutational Effects in Proteins," Biochemistry 29(37):8509-8517.

Weng, J. et al. (2011). "Genome-Wide Association Study Identifies Candidate Genes That Affect Plant Height in Chinese Elite Maize (*Zea mays* L.) Inbred Lines," PLoS One 6(12): e29229, 8 pages.

Wills, D. M. et al. (May 2018). "Defining the Role of the MADS-Box Gene, Zea Agamous-like1, a Target of Selection During Maize Domestication," Journal of Heredity 109(3):333-338.

Woo, Y. M. et al. (Oct. 2001). "Genomics Analysis of Genes Expressed in Maize endosperm Identifies Novel Seed Proteins and Clarifies Patterns of Zein Gene Expression," The Plant Cell 13(10):2297-2318.

Wu, C. Y. et al. (1998). "Promoters of Rice Seed Storage Protein Genes Direct Endosperm-Specific Gene Expression In Transgenic Rice," Plant Cell Physiology 39(8):885-889.

(56) References Cited

OTHER PUBLICATIONS

Wu, L. S. H. et al. (1998). "Genomic Cloning of the 18kDa Oleosin and Detection of Triacylglycerols and Oleosin Isoforms in Maturing Rice and Postgerminative Seedlings," J. Biochem 123: 386-391.

Wu, Q. et al. (2013). "Fluorescent Protein Marker Lines in Maize: Generation and Applications," Int. J. Dev. Biol. 57(6-8):535-543.

Wu, X. et al. (Jun. 2014). "Target Specificity of the CRISPR-Cas9 System," Quant Biol. 2(2):59-70.

Xiao, J. et al. (Nov. 2006). "Dissection of GA 20-oxidase Members Affecting Tomato Morphology by RNA Mediated Silencing," Plant Growth Regulation 50:179-189.

Xu, Y. et al. (Jan. 1995). "Characterization of a Rice Gene Family Encoding Root-Specific Proteins," Plant Mal Biol. 27(2):237-248.

Yamaguchi, N. et al. (May 9, 2014). "Gibberellin Acts Positively Then Negatively to Control Onset of Flower Formation in *Arabidopsis*," Science 344(6184):638-641.

Yamaguchi, S. (2008). "Gibberellin Metabolism and its Regulation," Annu. Rev. Plant Biol. 59:225-251.

Yang, D. et al. (Sep. 25, 2001). "Expression of the REB Transcriptional Activator in Rice Grains Improves the Yield of Recombinant Proteins Whose Genes are Controlled by a Reb-Responsive Promoter," PNAS 98(20):11438-11443.

Yang, Z. et al. (May 16, 2014). "GhAGL 15s, Preferentially Expressed During Somatic Embryogenesis, Promote Embryogenic Callus Formation in Cotton (*Gossypium hirsutum* L.)," Molecular Genetics and Genomics 289:873-883.

Yanik, M. et al. (Dec. 5, 2013). "TALE-PvuII Fusion Proteins—Novel Tools for Gene Targeting," PLoS One 8(12):e82539:13 pages.

Yin, X. et al. (May 1, 2011). "In-Season Prediction of Corn Yield Using Plant Height under Major Production Systems," Agronomy Journal 103(3):923-929.

Yoshikawa, M. et al. (Sep. 15, 2005). "A Pathway for the Biogenesis of Trans-Acting siRNAs in *Arabidopsis*," Genes Dev. 19(18):2164-2175.

Yu, S. M. et al. (Dec. 15, 1992). "Regulation of Alpha-amylase-encoding Gene Expression in Germinating Seeds and Cultured Cells of Rice," Gene 122(2):247-253.

Zeng, Y. et al. (Jun. 2002). "Both Natural and Designed Micro RNAs Can Inhibit the Expression of Cognate mRNAs When Expressed in Human Cells," Mal. Cell 9(6):1327-1333.

Khvorova, A. et al. (Oct. 17, 2003). "Functional siRNAs and miRNAs Exhibit Strand Bias," Cell 115(2):209-216.

\* cited by examiner

COMPOSITIONS AND METHODS FOR IMPROVING CROP YIELDS THROUGH TRAIT STACKING

CROSS-REFERENCE TO RELATED APPLICATION

This application is a Divisional of U.S. application Ser. No. 16/276,620, filed Feb. 15, 2019, which claims benefit under 35 U.S.C. § 119(e) of U.S. Provisional Appln. No. 62/631,221, filed Feb. 15, 2018, the contents of each of which are incorporated by reference herein in their entirety.

REFERENCE TO AN ELECTRONIC SEQUENCE LISTING

The contents of the electronic sequence listing (777052058210SUBSEQLIST.xml; Size: 402,048 bytes; and Date of Creation: Apr. 19, 2023) is herein incorporated by reference in its entirety.

FIELD

The present disclosure relates to modified, transgenic, and/or genome edited or mutated corn plants that are semi-dwarf and have one or more improved ear traits relative to a control plant, as well as methods for producing transgenic and/or genome edited or mutated corn plants through stacking.

BACKGROUND

Cereal crop yields have been steadily increasing over the past decades due to improved agronomic practices and traits. However, there continues to be a need in the art for improved corn yield through intrinsic yield gains and/or reduced yield losses from improved lodging resistance, stress tolerances and other traits.

SUMMARY

Figure 1:
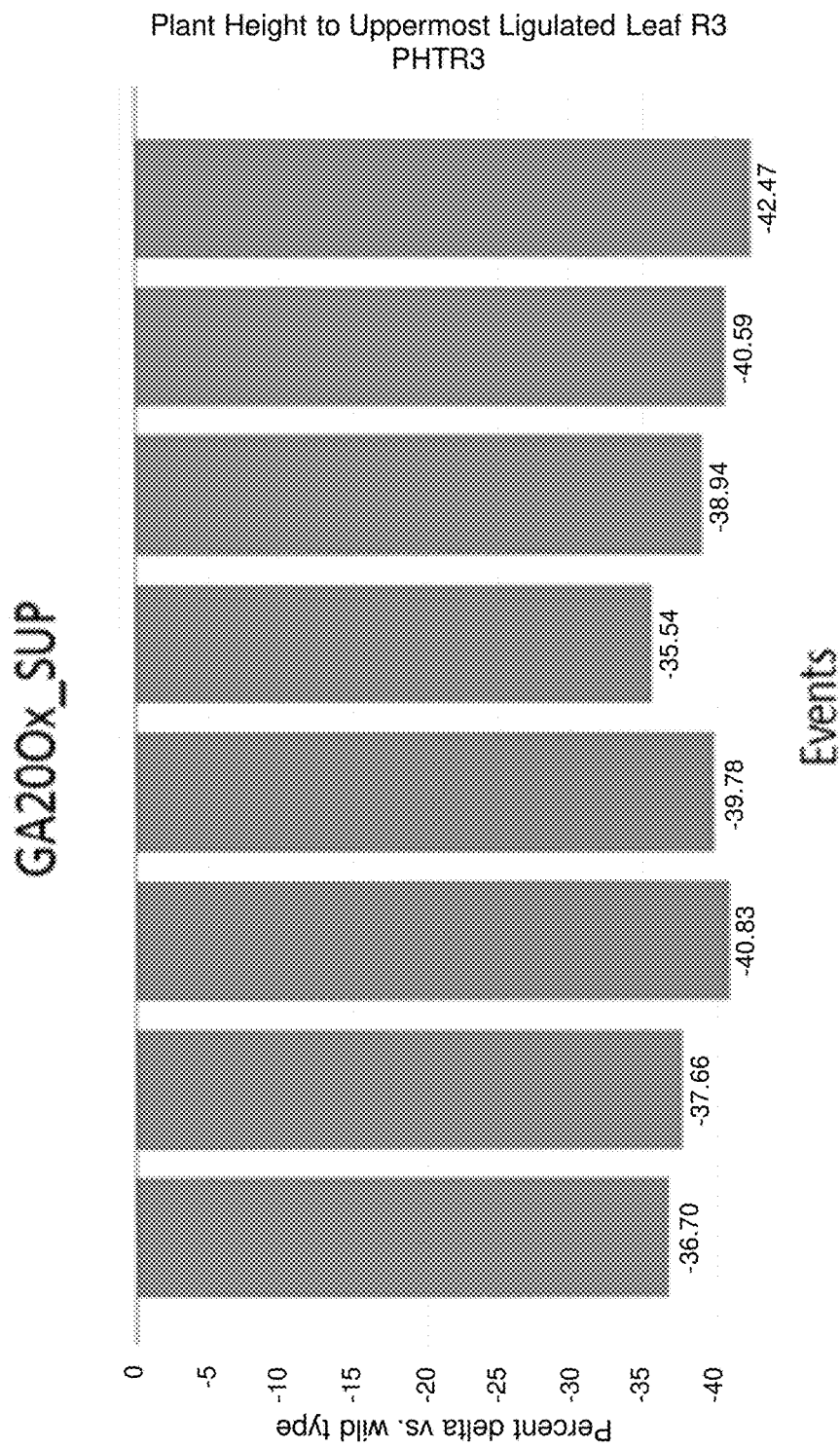
FIG. 1 shows plant heights of corn plants comprising a DNA sequence encoding an miRNA for the suppression of GA20 oxidase ("GA20Ox_SUP single") across eight transformation events, relative to control corn plants.

The present specification provides a modified corn plant or a plant part thereof comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a MADS-box polypeptide.

The present specification also provides a plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a MADS-box polypeptide.

Also provided by the present specification is a method for producing a modified corn plant, the method comprising: a) introducing into a corn cell a first recombinant expression cassette comprising a DNA sequence encoding a MADS-box polypeptide, wherein the corn cell comprises a second recombinant expression cassette comprising a transcribable DNA sequence encoding a non-coding RNA for suppression of one or more GA3 oxidase genes and/or one or more GA20 oxidase genes; and b) regenerating or developing a modified corn plant from the corn cell, wherein the modified corn plant comprises the first and second recombinant expression cassettes.

Further provided by the present specification is a method for producing a modified corn plant, the method comprising a) introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a MADS-box polypeptide; and b) regenerating or developing a modified corn plant from the corn cell, wherein the modified corn plant comprises the first and second recombinant expression cassettes.

In an aspect, the present specification provides a method for producing a modified corn plant, the method comprising a) introducing into a corn cell a first recombinant expression cassette comprising a transcribable DNA sequence encoding a non-coding RNA for suppression of one or more GA3 oxidase genes and/or GA20 oxidase genes; b) introducing into the corn cell of step (a) a second recombinant expression cassette comprising a DNA sequence encoding a MADS-box polypeptide to create a modified corn cell; and c) regenerating or developing a modified corn plant from the modified corn cell of step (b), wherein the modified corn plant comprises the first and second recombinant expression cassettes In another aspect, the present specification provides a method for producing a modified corn plant, the method comprising a) introducing into a corn cell a first recombinant expression cassette comprising a DNA sequence encoding a MADS-box polypeptide; b) introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and c) regenerating or developing a modified corn plant from the modified corn cell of step (b), wherein the modified corn plant comprises the first and second recombinant expression cassettes.

In yet another aspect, the present specification provides a method for producing a modified corn plant, the method comprising: a) crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a MADS-box polypeptide; and b) producing a progeny corn plant comprising the recombinant expression cassette and has the reduced expression of the one or more endogenous GA3 oxidase genes and/or GA20 oxidase genes.

The present specification provides a method for producing a modified corn plant, the method comprising: a) introducing into a corn cell a recombinant expression cassette comprising a DNA sequence encoding a MADS-box polypeptide, wherein the DNA sequence is operably linked to a plant-expressible promoter, and wherein the corn cell comprises one or more mutations and/or edits in one or more endogenous GA3 oxidase and/or GA20 oxidase genes; and b) regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

The present specification also provides a method for producing a modified corn plant, the method comprising: a) mutating or editing one or more endogenous GA3 oxidase genes and/or one or more GA20 oxidase genes in a corn cell, wherein the corn cell comprises a recombinant expression cassette encoding a MADS-box polypeptide, wherein the DNA sequence is operably linked to a plant-expressible promoter; and b) regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

Also provided by the present specification is a modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a MADS-box polypeptide, wherein the DNA sequence is operably linked to a plant-expressible promoter.

Further provided by the present specification is a plurality of modified corn plants in a field, each modified corn plant comprising 1) one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and 2) a recombinant expression cassette comprising a DNA sequence encoding a MADS-box polypeptide, wherein the DNA sequence is operably linked to a plant-expressible promoter.

In an aspect, the present specification provides a recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a MADS-box polypeptide, wherein the DNA sequence is operably linked to a plant-expressible promoter.

In an aspect, the present specification provides a recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a MADS-box polypeptide, wherein the DNA sequence is operably linked to a plant-expressible promoter.

DESCRIPTION

Definitions

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007.

Any references cited herein, including, e.g., all patents, published patent applications, and non-patent publications, are incorporated by reference in their entirety. To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, a "plant" includes an explant, plant part, seedling, plantlet or whole plant at any stage of regeneration or development. The term "cereal plant" as used herein refers to a monocotyledonous (monocot) crop plant that is in the Poaceae or Gramineae family of grasses and is typically harvested for its seed, including, for example, wheat, corn, rice, millet, barley, sorghum, oat and rye. As commonly understood, a "corn plant" or "maize plant" refers to any plant of species Zea mays and includes all plant varieties that can be bred with corn, including wild maize species.

As used herein, a "plant part" can refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure can be viable, nonviable, regenerable, and/or non-regenerable. A "propagule" can include any plant part that can grow into an entire plant.

As used herein, a "transgenic plant" refers to a plant whose genome has been altered by the integration or insertion of a recombinant DNA molecule, construct, cassette or sequence for expression of a non-coding RNA molecule, mRNA and/or protein in the plant. A transgenic plant includes an $R_0$ plant developed or regenerated from an originally transformed plant cell(s) as well as progeny transgenic plants in later generations or crosses from the $R_0$ transgenic plant that comprise the recombinant DNA molecule, construct, cassette or sequence. A plant having an integrated or inserted recombinant DNA molecule, construct, cassette or sequence is considered a transgenic plant even if the plant also has other mutation(s) or edit(s) that would not themselves be considered transgenic.

A plant cell is a biological cell of a plant, taken from a plant or derived through culture from a cell taken from a plant. As used herein, a "transgenic plant cell" refers to any plant cell that is transformed with a stably-integrated recombinant DNA molecule, construct, cassette, or sequence. A transgenic plant cell can include an originally-transformed plant cell, a transgenic plant cell of a regenerated or developed $R_0$ plant, a transgenic plant cell cultured from another transgenic plant cell, or a transgenic plant cell from any progeny plant or offspring of the transformed $R_0$ plant, including cell(s) of a plant seed or embryo, or a cultured plant cell, callus cell, etc.

As used herein, the term "transcribable DNA sequence" refers to a DNA sequence that can be transcribed into an RNA molecule. The RNA molecule can be coding or non-coding and may or may not be operably linked to a promoter and/or other regulatory sequences.

For purposes of the present disclosure, a "non-coding RNA molecule" is a RNA molecule that does not encode a protein. Non-limiting examples of a non-coding RNA molecule include a microRNA (miRNA), a miRNA precursor, a small interfering RNA (siRNA), a siRNA precursor, a small RNA (18-26 nt in length) and precursors encoding the same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA).

The terms "suppressing"/"suppression" or "reduced"/"reduction" when used in reference to a gene(s), refers to a lowering, reduction, or elimination of the expression level of a mRNA and/or protein encoded by the gene(s), and/or a lowering, reduction, or elimination of the activity of a protein encoded by the gene(s) in a plant, plant cell or plant tissue at one or more stage(s) of plant development, as compared to the expression level of such target mRNA and/or protein, and/or the activity of such encoded protein in a wild-type or control plant, cell or tissue at the same stage(s) of plant development.

As used herein, the term "consecutive" in reference to a polynucleotide or protein sequence means without deletions or gaps in the sequence.

As commonly understood in the art, a "mutation" refers to any alteration of the nucleotide sequence of the genome, extrachromosomal DNA, or other genetic element of an organism (e.g., a gene or regulatory element operably linked to a gene in a plant), such as a nucleotide insertion, deletion, inversion, substitution, duplication, etc.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" can also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

It is recognized that residue positions of proteins that are not identical often differ by conservative amino acid substitutions, where amino acid residues are substituted for other amino acid residues with similar size and chemical properties (e.g., charge, hydrophobicity, polarity, etc.), and therefore may not change the functional properties of the molecule. When sequences differ in conservative substitutions, the percent sequence similarity can be adjusted upwards to correct for the conservative nature of the non-identical substitution(s). Sequences that differ by such conservative substitutions are said to have "sequence similarity" or "similarity." Thus, "percent similarity" or "percent similar" as used herein in reference to two or more protein sequences is calculated by (i) comparing two optimally aligned protein sequences over a window of comparison, (ii) determining the number of positions at which the same or similar amino acid residue occurs in both sequences to yield the number of matched positions, (iii) dividing the number of matched positions by the total number of positions in the window of comparison (or the total length of the reference or query protein if a window of comparison is not specified), and then (iv) multiplying this quotient by 100% to yield the percent similarity. Conservative amino acid substitutions for proteins are known in the art.

For optimal alignment of sequences to calculate their percent identity or similarity, various pair-wise or multiple sequence alignment algorithms and programs are known in the art, such as ClustalW, or Basic Local Alignment Search Tool® (BLAST®), etc., that can be used to compare the sequence identity or similarity between two or more nucleotide or protein sequences. Although other alignment and comparison methods are known in the art, the alignment between two sequences (including the percent identity ranges described above) can be as determined by the ClustalW or BLAST® algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s).

As commonly understood in the art, the term "promoter" can generally refer to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present disclosure can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or most tissues of the plant are referred to as "constitutive" promoters. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. An "inducible" promoter is a promoter that initiates transcription in response to an environmental stimulus such as cold, drought or light, or other stimuli, such as wounding or chemical application. A promoter can also be classified in terms of its origin, such as being heterologous, homologous, chimeric, synthetic, etc.

As used herein, a "plant-expressible promoter" or a "heterologous plant-expressible promoter" refers to a promoter that can initiate, assist, affect, cause, and/or promote the transcription and expression of its associated transcribable DNA sequence, coding sequence or gene in a corn plant cell or tissue.

As used herein, a "heterologous plant-expressible promoter" refers to a plant-expressible promoter which does not naturally occur adjacent to or associated with the referenced gene or nucleic acid sequence in its natural environment, but which is positioned by laboratory manipulation.

As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue(s) can comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters.

As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature—e.g., the promoter or regulatory sequence has a different origin relative to the associated polynucleotide sequence and/or the promoter or regulatory sequence is not naturally occurring in a plant species to be transformed with the promoter or regulatory sequence.

As used herein, a "functional portion" of a promoter sequence refers to a part of the promoter sequence that provides essentially the same or similar expression pattern of an operably linked coding sequence or gene as the full promoter sequence. For this definition, "essentially the same or similar" means that the pattern and level of expression of a coding sequence operably linked to the functional portion of the promoter sequence closely resembles the pattern and level of expression of the same coding sequence operably linked to the full promoter sequence.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, the term "isolated" refers to at least partially separating a molecule from other molecules typically associated with it in its natural state. In an aspect, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

As used herein, an "encoding region" or "coding region" refers to a portion of a polynucleotide that encodes a functional unit or molecule (e.g., without being limiting, a mRNA, protein, or non-coding RNA sequence or molecule).

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more gene(s) relative to a wild-type or control plant, plant seed, plant part, plant cell, and/or plant genome, such as via a transgenic event or a genome editing event or mutation affecting the expression level or activity of one or more genes. Modified plants, plant parts, seeds, etc., can be subjected to or created by mutagenesis, genome editing or site-directed integration (e.g., without being limiting, via methods using site-specific nucleases), genetic transformation (e.g., without being limiting, via methods of *Agrobacterium* transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more genes. A modified seed provided herein can give rise to a modified plant provided herein. A modified plant, plant seed, plant part, plant cell, or plant genome provided herein can comprise a recombinant DNA construct or vector or genome edit as provided herein. A "modified plant product" can be any product made from a modified plant, plant part, plant cell, or plant chromosome provided herein, or any portion or component thereof.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a transgene, expression cassette, mutation, and/or genome edit affecting one or more genes. For purposes of comparison to a modified plant, plant seed, plant part, plant cell and/or plant genome, a "wild-type plant" (or likewise a "wild-type" plant seed, plant part, plant cell and/or plant genome) refers to a non-transgenic, non-mutated, and non-genome edited control plant, plant seed, plant part, plant cell and/or plant genome. Alternatively as can be specified herein, such a "control plant" (or likewise a "control" plant seed, plant part, plant cell and/or plant genome) can refer to a plant (or plant seed, plant part, plant cell and/or plant genome) that (i) is used for comparison to a modified plant (or modified plant seed, plant part, plant cell and/or plant genome) having a stack of two or more transgene(s), expression cassette(s), mutation(s) and/or genome edit(s), (ii) has the same or similar genetic background (e.g., same parental lines, hybrid cross, inbred line, testers, etc.) as the modified plant (or plant seed, plant part, plant cell and/or plant genome), but (iii) lacks at least one of the two or more transgene(s), expression cassette(s), mutation(s) and/or genome edit(s) of the modified plant (e.g., a stack in comparison to a single of one of the members of the stack). As used herein, such a "control" plant, plant seed, plant part, plant cell and/or plant genome can also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, "crossed" or "cross" means to produce progeny via fertilization (e.g., cells, seeds or plants) and includes crosses between plants (sexual) and self-fertilization (selfing).

As used herein, "ear trait" of a corn plant refers to a characteristic of an ear of a corn plant. In an aspect, an ear trait can include, but is not limited to, ear diameter, single kernel weight, ear fresh weight, ear area, ear volume, ear length, number of kernels per ear, and/or yield. In another aspect, an ear trait can include, but is not limited to, ear tip void, ear void, kernel number, kernel number per row, kernels per field area, kernel rank, kernel row number, kernel weight, number of florets, and/or grain yield estimate. In yet another aspect, an ear trait can include, but is not limited to, ear attitude, ear cob color, ear cob diameter, ear cob strength, ear dry husk color, ear fresh husk color, ear husk bract, ear husk cover, ear husk opening, ear number per stalk, ear shank length, ear shelling percent, ear silk color, ear taper, ear weight, ear rot rating, kernel aleurone color, kernel cap color, kernel endosperm color, kernel endosperm type, kernel grade, kernel length, kernel pericarp color, kernel row direction, kernel side color, kernel thickness, kernel type, kernel width, cob weight, and/or prolificacy. A modified or genome edited/mutated corn plant of the present disclosure exhibits one or more improved ear trait compared to a control corn plant. In an aspect, a modified or genome edited/mutated corn plant exhibits an increased ear diameter relative to a control corn plant. In an aspect, a modified or genome edited/mutated corn plant exhibits increased single kernel weight relative to a control corn plant. In an aspect, a modified or genome edited/mutated corn plant exhibits an increased ear fresh weight relative to a control corn plant. In an aspect, a modified or genome edited/mutated corn plant exhibits an increased ear area relative to a control corn plant. In an aspect, a modified or genome edited/mutated corn plant exhibits an increased ear volume relative to a control corn plant. In an aspect, a modified or genome edited/mutated corn plant exhibits an increased ear length relative to a control corn plant. In an aspect, a modified or genome edited/mutated corn plant exhibits an increased number of kernels per ear relative to a control corn plant. In an aspect, a modified or genome edited/mutated corn plant exhibits an increased yield relative to a control corn plant.

As used herein, "yield" refers to the total amount of an agricultural product (e.g., seeds, fruit, etc.) produced or harvested from a plurality of crop plants per unit area of land cultivation (e.g., a field of crop plants) as understood in the art. Yield can be measured or estimated in a greenhouse, in a field, or under specific environment, treatment and/or stress conditions. For example, as known and understood in the art, yield can be measured in units of kilograms per hectare, bushels per acre, or the like. Indeed, yield can be measured in terms of "broad acreage yield" or "BAY" as known and understood in the art.

As used herein, "root trait" of a corn plant refers to characteristics of the root of a corn plant, including, but is not limited to, root growth rate, root length, root thickness, root branching, root anchorage, crown root lateral root density rating, and/or root dry weight. A transgenic or genome edited/mutated corn plant of the present disclosure exhibits one or more improved root traits compared to a control corn plant.

As used herein, "comparable conditions" for plants refers to the same or similar environmental conditions and agronomic practices for growing and making meaningful comparisons between two or more plant genotypes so that neither environmental conditions nor agronomic practices would significantly contribute to, or explain, any differences observed between the two or more plant genotypes. Environmental conditions include, for example, light, temperature, water, humidity, soil, and nutrition (e.g., nitrogen and phosphorus).

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase.

As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence using a targeted genome editing technique. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant using a targeted genome editing technique.

As used herein, a "target site" for genome editing refers to the location of a polynucleotide sequence within a plant genome that is targeted and cleaved by a site-specific nuclease introducing a double stranded break (or single-stranded nick) into the nucleic acid backbone of the polynucleotide sequence and/or its complementary DNA strand. A site-specific nuclease can bind to a target site, such as via a non-coding guide RNA (e.g., without being limiting, a CRISPR RNA (crRNA) or a single-guide RNA (sgRNA) as described further below). A non-coding guide RNA provided herein can be complementary to a target site (e.g., complementary to either strand of a double-stranded nucleic acid molecule or chromosome at the target site). A "target site" also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some aspects a target region can be subjected to a mutation, deletion, insertion or inversion. As used herein, "flanked" when used to describe a target region of a polynucleotide sequence or molecule, refers to two or more target sites of the polynucleotide sequence or molecule surrounding the target region, with one target site on each side of the target region.

Apart from genome editing, the term "target site" can also be used in the context of gene suppression to refer to a portion of a mRNA molecule (e.g., a "recognition site") that is complementary to at least a portion of a non-coding RNA molecule (e.g., a miRNA, siRNA, etc.) encoded by a suppression construct. As used herein, a "target site" for a RNA-guided nuclease can comprise the sequence of either complementary strand of a double-stranded nucleic acid (DNA) molecule or chromosome at the target site. It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA can be tolerated.

As used herein, a "donor molecule", "donor template", or "donor template molecule" (collectively a "donor template"), which can be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" can be used for site-directed integration of a transgene or suppression construct, or as a template to introduce a mutation, such as an insertion, deletion, etc., into a target site within the genome of a plant. A targeted genome editing technique provided herein can comprise the use of one or more, two or more, three or more, four or more, or five or more donor molecules or templates. A donor template can be a single-stranded or double-stranded DNA or RNA molecule or plasmid. A donor template can also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template. Further, the donor template can be linear or circular, and can be single-stranded or double-stranded. A donor template can be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively.

An insertion sequence of a donor template can comprise one or more genes or sequences that each encode a transcribed non-coding RNA or mRNA sequence and/or a translated protein sequence. A transcribed sequence or gene of a donor template can encode a protein or a non-coding RNA molecule. An insertion sequence of a donor template can comprise a polynucleotide sequence that does not comprise a functional gene or an entire gene sequence (e.g., the donor template can simply comprise regulatory sequences, such as a promoter sequence, or only a portion of a gene or coding sequence), or may not contain any identifiable gene expression elements or any actively transcribed gene sequence. An insertion sequence of a donor template provided herein can comprise a transcribable DNA sequence that can be transcribed into an RNA molecule, which can be non-coding and may or may not be operably linked to a promoter and/or other regulatory sequence.

As used herein, the term "guide RNA" or "gRNA" is a short RNA sequence comprising (1) a structural or scaffold RNA sequence necessary for binding or interacting with an RNA-guided nuclease and/or with other RNA molecules (e.g., tracrRNA), and (2) an RNA sequence (referred to herein as a "guide sequence") that is identical or complementary to a target sequence or a target site. A "single-chain guide RNA" (or "sgRNA") is a RNA molecule comprising a crRNA covalently linked a tracrRNA by a linker sequence, which can be expressed as a single RNA transcript or molecule. The guide RNA comprises a guide or targeting sequence (a "guide sequence") that is identical or complementary to a target site within the plant genome, such as at or near a GA oxidase gene. A protospacer-adjacent motif (PAM) can be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. The genomic PAM sequence on the sense (+) strand adjacent to the target site (relative to the targeting sequence of the guide RNA) can comprise 5'-NGG-3'. However, the corresponding sequence of the guide RNA (i.e., immediately downstream (3') to the targeting sequence of the guide RNA) can generally not be complementary to the genomic PAM sequence. The guide RNA can typically be a non-coding RNA molecule that does not encode a protein.

As used herein, an "RNA-guided nuclease" refers to an RNA-guided DNA endonuclease associated with the CRISPR system. Non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In an aspect, the RNA-guided nuclease is Cas9. In an aspect, the RNA-guided nuclease comprises the N and C terminal nuclear localization sequences (NLS).

DESCRIPTION

The present disclosure provides certain stacked combinations of transgenes and/or mutations or edits in corn plants, plant parts, etc., comprising a transgene that encodes one or more MADS-box polypeptides, such as maize ZMM19, in addition to a reduction in the expression level of one or more GA20 and/or GA3 oxidase genes through suppression, mutation and/or editing of the GA oxidase genes, wherein the corn plants have a semi-dwarf phenotype and one or more improved traits related to yield, lodging resistance, and/or stress tolerance. As described in co-pending PCT Application No. PCT/US2017/047405, the entire contents and disclosure of which are incorporated herein by reference, reducing the level of active GAs in corn or other cereal plants, such as through suppression, mutation or editing of one or more GA20 and/or GA3 oxidase genes, can result in a semi-dwarf phenotype with improved agronomic traits, such as lodging resistance and/or increased yield. However, it is proposed herein that lower active GA levels can be combined with an expression cassette or transgene encoding a MADS-box protein, such as ZMM19, to produce a semi-dwarf corn plant having positive ear traits leading to further increased yield, thus providing greater agronomic benefits than either MADS-box gene expression or lower active GA levels alone.

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20$^{th}$ century, which was largely responsible for the Green Revolution. However, successful yield gains in other cereal crops, such as corn, have not been realized through manipulation of the GA pathway. Corn or maize is unique among the grain-producing grasses in that it forms separate male (tassel) and female (ear) inflorescences, and mutations in the GA pathway in corn have been shown to negatively impact reproductive development. Indeed, some mutations in the GA pathway genes in corn have been associated with various off-types that are incompatible with yield, which has led researchers away from finding semi-dwarf, high-yielding corn varieties via manipulation of the GA pathway.

Despite these prior difficulties in achieving higher grain yields in corn through manipulation of the GA pathway, co-pending PCT Application No. PCT/US2017/047405 describes a way to manipulate active GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants with reduced GA levels can also have one or more additional yield and/or stress tolerance traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Active or bioactive gibberellic acids (i.e., "active gibberellins" or "active GAs") are known in the art for a given plant species, as distinguished from inactive GAs. For example, active GAs in corn and higher plants include the following: GA1, GA3, GA4, and GA7. Thus, an "active GA-producing tissue" is a plant tissue that produces one or more active GAs.

Certain biosynthetic enzymes (e.g., GA20 oxidase and GA3 oxidase) and catabolic enzymes (e.g., GA2 oxidase) in the GA pathway participate in GA synthesis and degradation, respectively, to affect active GA levels in plant tissues. Thus, in addition to suppression of certain GA20 oxidase genes, it is further proposed that suppression of a GA3 oxidase gene in a constitutive or tissue-specific or tissue-preferred manner can also produce corn plants having a short stature phenotype and increased lodging resistance, with possible increased yield, but without off-types in the ear.

Without being bound by theory, it is proposed that incomplete suppression of GA20 or GA3 oxidase gene(s) and/or targeting of a subset of one or more GA oxidase gene(s) can be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, can be sufficient to produce a short-stature plant with increased lodging resistance, but without significant off-types in reproductive tissues. Expression of a GA20 or GA3 oxidase suppression element in a tissue-specific or tissue-preferred manner can be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) can be targeted for suppression using a vascular promoter, such as a rice tungro baciliform virus (RTBV) promoter, that drives expression in vascular tissues of plants. The expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn plant that produce active GAs can reduce plant height and increase lodging resistance, and off-types can be avoided in those plants if active GA levels are not also significantly impacted or lowered in reproductive tissues, such as the developing female organ or ear of the plant. If active GA levels could be reduced in the stalk, stem, or internode(s) of corn or cereal plants without significantly affecting GA levels in reproductive tissues (e.g., the female or male reproductive organs or inflorescences), then corn or cereal plants having reduced plant height and increased lodging resistance could be created without off-types in the reproductive tissues of the plant.

Without being limited by theory, it is further proposed that short stature, semi-dwarf phenotypes in corn plants can result from a sufficient level of expression of a suppression construct targeting certain GA oxidase gene(s) in active GA-producing tissue(s) of the plant. For targeted suppression of certain GA20 oxidase genes in corn, restricting the pattern of expression to avoid reproductive ear tissues may not be necessary to avoid reproductive off-types in the developing ear. However, expression of a GA20 oxidase suppression construct at low levels, and/or in a limited number of plant tissues, can be insufficient to cause a significant short stature, semi-dwarf phenotype. Given that the observed semi-dwarf phenotype with targeted GA20 oxidase suppression is the result of shortening the stem internodes of the plant, it was surprisingly found that suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), can be sufficient to produce semi-dwarf plants, even though the short stature trait is due to shortening of the stem internodes. Given that GAs can migrate through the vasculature of the plant, manipulating GA oxidase genes in plant tissue(s) where active GAs are produced can result in a short stature, semi-dwarf plant, even though this can be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues causes a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. A semi-dwarf phenotype was also observed with expression of the same GA20 oxidase suppression construct using other vascular promoters and with various constitutive promoters without any observable off-types.

By targeting a subset of one or more endogenous GA3 or GA20 oxidase genes for suppression within a plant, a more pervasive pattern of expression (e.g., with a constitutive promoter) can be used to produce semi-dwarf plants without significant reproductive off-types and/or other undesirable traits in the plant, even with expression of the suppression construct in reproductive tissue(s). Indeed, suppression elements and constructs are provided herein that selectively target the GA20 oxidase_3 and/or GA20 oxidase_5 genes for suppression, which can be operably linked to a vascular, leaf and/or constitutive promoter.

Thus, recombinant DNA constructs and modified corn plants are provided herein comprising a GA20 or GA3 oxidase suppression element or sequence operably linked to a plant expressible promoter, which can be a constitutive or tissue-specific or tissue-preferred promoter. Such a tissue-specific or tissue-preferred promoter can drive expression of its associated GA oxidase suppression element or sequence in one or more active GA-producing tissue(s) of the plant to suppress or reduce the level of active GAs produced in those tissue(s). Such a tissue-specific or tissue-preferred promoter can drive expression of its associated GA oxidase suppression construct or transgene during one or more vegetative stage(s) of development. Such a tissue-specific or tissue-preferred promoter can also have little or no expression in one or more cell(s) or tissue(s) of the developing female organ or ear of the plant to avoid the possibility of off-types in those reproductive tissues. According to an aspect, the tissue-specific or tissue-preferred promoter is a vascular promoter, such as the RTBV promoter. The sequence of the RTBV promoter is provided herein as SEQ ID NO: 65, and a truncated version of the RTBV promoter is further provided herein as SEQ ID NO: 66. However, other types of tissue-specific or tissue preferred promoters can potentially be used for GA3 oxidase suppression in active GA-producing tissues of a corn or cereal plant to produce a semi-dwarf phenotype without significant off-types. As introduced above, instead of suppressing one or more GA oxidase gene(s), active GA levels can also be reduced in a corn plant by mutation or editing of one or more GA20 and/or GA3 oxidase gene(s).

Corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1, and the DNA and protein sequences by SEQ ID NOs for each of these GA3 oxidase genes are provided in Table 2.

TABLE 1

DNA and protein sequences by sequence identifier for GA20 oxidase genes in corn.

| GA20 oxidase Gene | cDNA | Coding Sequence (CDS) | Protein |
| --- | --- | --- | --- |
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
| --- | --- | --- | --- |
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |

In addition to lowering active GA levels in corn plants through suppression, mutation or editing of GA oxidase gene(s), such corn plants as provided herein may further comprise an ectopically expressed transgene expressing one or more MADS-box polypeptides.

MADS-box polypeptides typically have transcription factor activity and are involved in controlling all major aspects of the life of land plants. The MADS-box polypeptides, encoded by the MADS box gene, are characterized by the highly conserved DNA-binding MADS domain (about 58 amino acids), and is named after MCM1, AGAMOUS, DEFICIENS and SRF (serum response factor) proteins.

Without being bound by any theory, MADS-box polypeptides can be classified into type I and type II subfamilies. Type I polypeptides do not have distinct conserved domains other than the SRF-like MADS domain. Type II polypeptides are commonly referred to as MIKC-type polypeptides after their domain structure: MADS domain, intervening (I) domain, keratin-like (K) domain, and carboxyl-terminal (C) domains. Type I polypeptides do not have K domain. See Gramzow and Theissen, *Genome Biol.*, 11: 214 (2010), the content and disclosure of which are incorporated by reference.

Without being bound by any theory, MADS-box polypeptides can bind to DNA as dimers and/or multimeric complexes and can thus regulate target gene by direct transcriptional activation or repression. Dimers of MADS-box polypeptides can bind to CArG-boxes, i.e., stretches of DNA with a consensus sequence of 5'-CC[A/T]$_6$GG-3', or very similar sequences thereof. The number of CArG-boxes in genomes is enormous, and different MADS-box polypeptides can recognize different sets of target genes, and thus play a universal role in plant development and/or growth.

Without being bound by any theory, in plants, type II MADS-box polypeptides are suggested to be able to 1) control various aspects of sporophyte development, 2) determine flowering time, 3) specify floral meristem identify, floral organ identity, fruit formation, and seed pigmentation, and/or 4) play generally critical roles in gametophyte development.

As used herein, a MADS-box polynucleotide refers to a polynucleotide, gene or coding sequence encoding a polypeptide containing at least one SRF-TF MADS-box Pfam domain and a K-box Pfam domain, and encompasses any variants (e.g., polymorphisms), isoforms, homologs, orthologs, and/or paralogs thereof. On the sequence level, the SRF-TF MADS-box domain is located on the N-terminal side of the K-box domain, or stated differently, the K-box domain is located on the C-terminal side of the SRF-TF MADS-box domain.

In an aspect, a MADS-box polypeptide of the present disclosure is a maize ZMM19 polypeptide or homologs, orthologs, and/or paralogs thereof. In an aspect, a MADS-box polypeptide of the present disclosure comprises an amino acid sequence comprising SEQ ID NO: 168, or a functional fragment thereof. In another aspect, a MADS-box polynucleotide provided herein comprises an amino acid sequence selected from the group consisting of SEQ ID NOs: 175-199, and any homologs, orthologs, and paralogs thereof.

According to another aspect, a modified corn plant or a plant part thereof is provided comprising 1) a first recombinant expression cassette (or a construct) comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette (or a construct) comprising a DNA sequence encoding an MADS-box polypeptide.

According to another aspect, a plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding an MADS-box polypeptide. In an aspect, the modified corn plants have increased yield relative to control corn plants. In another aspect, the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

Such modified corn plants can have semi-dwarf plant height in addition to one or more improved yield-related traits as described further herein, relative to control corn plant(s) that do not have the first and second expression cassettes or the combination of MADS-box transgene and edited/mutated GA oxidase gene(s). Modified corn plants comprising a combination of the first and second expression cassettes, or a combination of an expression cassette comprising a MADS-box transgene and one or more mutated or edited GA oxidase genes, can each be referred to as a "stack" or "stacked" combination. Such stacked combinations for the reduction of active GA levels and expression of a MADS-box transgene can be brought together in the same corn plant, or population of corn plants, by (1) crossing a first plant comprising a GA oxidase suppression element(s), edit(s) and/or mutation(s) to a second plant comprising a MADS-box transgene, (2) co-transformation of a plant or plant part with a GA oxidase suppression element(s) and a MADS-box transgene, (3) transformation of a plant or plant part already having a GA oxidase suppression element(s), edit(s) and/or mutation(s) with a MADS-box transgene, (4) transformation of a plant or plant part already having a MADS-box transgene with a GA oxidase suppression element(s), or (5) editing or mutating a GA oxidase gene(s) in a plant or plant part already having a MADS-box transgene, each of which can be followed by further crosses to obtain a desired genotype, plant parts can be regenerated, grown or developed into plants, and plant parts can be taken from any of the foregoing plants.

As provided above, a corn plant or plant part can comprise a first expression cassette comprising a first sequence encoding a non-coding RNA molecule that targets one or more GA20 or GA3 oxidase gene(s) for suppression. In an aspect, the non-coding RNA molecule can target one or more GA20 oxidase gene(s) for suppression, such as a GA20 oxidase_3 gene, a GA20 oxidase_4 gene, a GA20 oxidase_5 gene, or any combination thereof. According to an aspect, the first expression cassette comprises a first transcribable DNA sequence encoding a non-coding RNA targeting a GA20 oxidase_3 gene for suppression. According to another aspect, the first expression cassette comprises a first transcribable DNA sequence encoding a non-coding RNA targeting a GA20 oxidase_5 gene for suppression. According to another aspect, the first expression cassette comprises a first transcribable DNA sequence encoding a non-coding RNA that targets both the GA20 oxidase_3 gene and the GA20 oxidase_5 gene for suppression. In addition to targeting a mature mRNA sequence (including either or both of the untranslated or exonic sequences), a non-coding RNA molecule can also target the intronic sequences of a GA20 oxidase gene or transcript.

A genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

A genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

For suppression of a GA20 oxidase_3 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 7 and 8.

For suppression of a GA20 oxidase_4 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 10 and 11.

For suppression of a GA20 oxidase_5 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 13 and 14.

For suppression of a GA20 oxidase_3 gene and a GA20 oxidase_5 gene, a transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 7 and 8; and the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 13 and 14.

In an aspect, a non-coding RNA molecule encoded by a transcribable DNA sequence comprises (i) a sequence that is at least 95%, at least 96%, at least 97%, at least 98%, at least 99%, at least 99.5%, or 100% complementary to SEQ ID NO: 39, 41, 43 or 45, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 40, 42, 44 or 46. According to an aspect, the non-coding RNA molecule encoded by a transcribable DNA sequence can comprise a sequence with one or more mismatches, such as 1, 2, 3, 4, 5 or more complementary mismatches, relative to the sequence of a target or recognition site of a targeted GA20 oxidase gene mRNA, such as a sequence that is nearly complementary to SEQ ID NO: 40 but with one or more complementary mismatches relative to SEQ ID NO: 40. According to a particular aspect, the non-coding RNA molecule encoded by the transcribable DNA sequence comprises a sequence that is 100% identical to SEQ ID NO: 40, which is 100% complementary to a target sequence within the cDNA and coding sequences of the GA20 oxidase_3 (i.e., SEQ ID NOs: 7 and 8, respectively), and/or to a corresponding sequence of a mRNA encoded by an endogenous GA20 oxidase_3 gene. However, the sequence of a non-coding RNA molecule encoded by a transcribable DNA sequence that is 100% identical to SEQ ID NO: 40, 42, 44 or 46 may not be perfectly complementary to a target sequence within the cDNA and coding sequences of the GA20 oxidase_5 gene (i.e., SEQ ID NOs: 13 and 14, respectively), and/or to a corresponding sequence of a mRNA encoded by an endogenous GA20 oxidase_5 gene. For example, the closest complementary match between the non-coding RNA molecule or miRNA sequence in SEQ ID NO: 40 and the cDNA and coding sequences of the GA20 oxidase_5 gene can include one mismatch at the first position of SEQ ID NO: 39 (i.e., the "C" at the first position of SEQ ID NO: 39 is replaced with a "G"; i.e., GTCCATCATGCGGTGCAACTA). However, the non-coding RNA molecule or miRNA sequence in SEQ ID NO: 40 can still bind and hybridize to the mRNA encoded by the endogenous GA20 oxidase_5 gene despite this slight mismatch.

For suppression of a GA20 oxidase_1 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 1 and 2.

For suppression of a GA20 oxidase_2 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 4 and 5.

For suppression of a GA2 oxidase 6, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 16 and 17.

For suppression of a GA20 oxidase_7 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 19 and 20.

For suppression of a GA20 oxidase_8 gene, a first transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 22 and 23.

For suppression of a GA20 oxidase_9 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 25 and 26.

A non-coding RNA can target an intron sequence of a GA20 oxidase gene instead of, or in addition to, an exonic, 5' UTR or 3' UTR of the GA20 oxidase gene. Thus, a non-coding RNA targeting the GA20 oxidase_3 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 34, and/or of nucleotides 3666-3775 or 4098-5314 of SEQ ID NO: 34.

In another aspect, a non-coding RNA molecule targeting the GA20 oxidase_5 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 35, and/or of nucleotides 3792-3906 or 4476-5197 of SEQ ID NO: 35.

In another aspect, a non-coding RNA molecule targeting the GA20 oxidase_4 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 38, and/or of nucleotides 1996-2083 or 2412-2516 of SEQ ID NO: 38.

In another aspect, a first expression cassette comprises a first transcribable DNA sequence encoding a non-coding RNA targeting a GA3 oxidase gene(s) for suppression in corn, such as a GA3 oxidase_1 gene or a GA3 oxidase_2 gene. In another aspect, a first transcribable DNA sequence encoding a non-coding RNA targets both the GA3 oxidase_1 gene and the GA3 oxidase_2 gene for suppression. In addition to targeting a mature mRNA sequence (including either or both of the untranslated or exonic sequences), a non-coding RNA molecule can also target the intronic sequences of a GA3 oxidase gene or transcript.

The genomic DNA sequence of GA3 oxidase_1 is provided in SEQ ID NO: 36, and the genomic DNA sequence of GA3 oxidase_2 is provided in SEQ ID NO: 37. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon; nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. For the GA3 oxidase_2 gene, nucleotides 1-38 of SEQ ID NO: 37 correspond to the 5-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR.

For suppression of a GA3 oxidase_1 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 28 and 29.

As mentioned above, a non-coding RNA molecule can target an intron sequence of a GA3 oxidase gene instead of, or in addition to, an exonic, 5' UTR or 3' UTR of the GA oxidase gene. Thus, a non-coding RNA molecule targeting the GA3 oxidase_1 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 36, and/or of nucleotides 515-879 or 1039-1158 of SEQ ID NO: 36.

For suppression of a GA3 oxidase_2 gene, a first transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 31 and 32.

As mentioned above, a non-coding RNA molecule can target an intron sequence of a GA3 oxidase gene instead of, or in addition to, an exonic, 5' UTR or 3' UTR of the GA3 oxidase gene. Thus, a non-coding RNA molecule targeting the GA3 oxidase_2 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 37, and/or of nucleotides 533-692 or 852-982 of SEQ ID NO: 37.

For suppression of a GA3 oxidase_1 gene and a GA3 oxidase_2 gene, a transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 28 and 29; and the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 31 and 32.

In an aspect, a transcribable DNA sequence for the suppression of a GA20 oxidase gene and/or a GA3 oxidase comprises a sequence selected from the group consisting of SEQ ID NOs: 47, 49, 51, 53, 55, 57, 59, 61, and 63. In another aspect, a transcribable DNA sequence for the suppression of a GA20 oxidase gene and/or a GA3 oxidase encodes a non-coding RNA sequence, wherein the non-coding RNA sequence comprises a sequence selected from the group consisting of SEQ ID NOs: 48, 50, 52, 54, 56, 58, 60, 62, and 64.

In an aspect, an expression cassette is provided comprising a second DNA sequence encoding a MADS-box polypeptide. In an aspect, an expression cassette is provided comprising a second DNA sequence encoding ZMM19. In another aspect, the second DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NO: 169. In another aspect, the second DNA sequence comprises a sequence encoding a polypeptide that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof. The second DNA sequence encoding a MADS-box polypeptide is operatively linked to a plant-expressible promoter. In an aspect, such a plant-expressible promoter operably linked to a DNA sequence encoding a MADS-box polypeptide is a root promoter, such as a root-specific or root-preferred promoter. In another aspect, such a plant-expressible promoter operably linked to a DNA sequence encoding a MADS-box polypeptide is a meristem promoter, such as a meristem-specific promoter or a meristem-preferred promoter. In another aspect, such a plant-expressible promoter operably linked to a DNA sequence encoding a MADS-box polypeptide is a seed or kernel promoter, such as a seed-preferred promoter, a seed-specific promoter, or a seed-germinating promoter.

In an aspect, such a root promoter is an *Oryza sativa* Rcc3 gene promoter. In an aspect, such a root promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 170, or a functional portion thereof. In an aspect, such a seed or kernel promoter is from a maize putative embryo-specific (Esp) gene promoter. In an aspect, such a seed or kernel promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 174, or a functional portion thereof.

In an aspect, an expression cassette is provided comprising a second DNA sequence encoding a MADS-box polypeptide. In another aspect, the second DNA sequence encodes a protein that comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to an amino acid sequence selected from the group consisting of SEQ ID NOs: 175-199, or a functional fragment thereof. The second DNA sequence encoding a MADS-box polypeptide is operatively linked to a plant-expressible promoter. In an aspect, such a plant-expressible promoter operably linked to a DNA sequence encoding a MADS-box polypeptide is a root promoter, such as a root-specific or root-preferred promoter. In another aspect, such a plant-expressible promoter operably linked to a DNA sequence encoding a MADS-box polypeptide is a meristem promoter, such as a meristem-specific promoter or a meristem-preferred promoter. In another aspect, such a plant-expressible promoter operably linked to a DNA sequence encoding a MADS-box polypeptide is a kernel or seed promoter, such as a seed-preferred or seed-specific promoter. Examples of a root promoter, a meristem promoter, and a seed or kernel promoter are provided herein.

In addition to targeting a mature mRNA sequence, a non-coding RNA molecule can instead target an intronic sequence of a GA oxidase gene or mRNA transcript, or a GA oxidase mRNA sequence overlapping coding and non-coding sequences. According to other aspects, a recombinant DNA molecule, vector or construct is provided comprising a transcribable DNA sequence encoding a non-coding RNA (precursor) molecule that is cleaved or processed into a mature non-coding RNA molecule that binds or hybridizes to a target mRNA in a plant cell, wherein the target mRNA molecule encodes a GA20 or GA3 oxidase protein, and wherein the transcribable DNA sequence is operably linked to a constitutive or tissue-specific or tissue-preferred promoter.

Any method known in the art for suppression of a target gene can be used to suppress GA oxidase gene(s) according to aspects of the present disclosure including expression of antisense RNAs, double stranded RNAs (dsRNAs) or inverted repeat RNA sequences, or via co-suppression or RNA intereference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules can be used that target the non-coding genomic sequences or regions within or near a gene to cause silencing of the gene. Accordingly, any of these methods can be used for the targeted suppression of an endogenous GA oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

In an aspect, an expression level(s) of one or more endogenous GA20 oxidase and/or GA3 oxidase gene(s) is/are reduced or eliminated in the modified corn plant, thereby suppressing the endogenous GA20 oxidase and/or GA3 oxidase gene(s).

According to an aspect, a modified or transgenic plant is provided having the expression level(s) of one or more GA20 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant.

According to an aspect, a modified or transgenic plant is provided having the expression level(s) of one or more GA3 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant.

According to an aspect, a modified or transgenic plant is provided having the expression level(s) of one or more GA20 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

According to an aspect, a modified or transgenic plant is provided having the expression level(s) of one or more GA3 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

According to an aspect, the at least one tissue of a modified or transgenic plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In an aspect, the non-coding RNA is a precursor miRNA or siRNA capable of being processed or cleaved to form a mature miRNA or siRNA.

In an aspect, suppression of an endogenous GA20 oxidase gene or a GA3 oxidase gene is tissue-specific (e.g., only in leaf and/or vascular tissue). Suppression of a GA20 oxidase gene can be constitutive and/or vascular or leaf tissue specific or preferred. In other aspects, suppression of a GA20 oxidase gene or a GA3 oxidase gene is constitutive and not tissue-specific. According to an aspect, expression of an endogenous GA20 oxidase gene and/or a GA3 oxidase gene is reduced in one or more tissue types (e.g., in leaf and/or vascular tissue(s)) of a modified or transgenic plant as compared to the same tissue(s) of a control plant.

Engineered miRNAs can be useful for targeted gene suppression with increased specificity. See, e.g., Parizotto et al., *Genes Dev.* 18:2237-2242 (2004), and U.S. Patent Application Publication Nos. 2004/0053411, 2004/0268441, 2005/0144669, and 2005/0037988, the contents and disclosures of which are incorporated herein by reference. miRNAs are non-protein coding RNAs. When a miRNA precursor molecule is cleaved, a mature miRNA is formed that is typically from about 19 to about 25 nucleotides in length (commonly from about 20 to about 24 nucleotides in length in plants), such as 19, 20, 21, 22, 23, 24, or 25 nucleotides in length, and has a sequence corresponding to the gene targeted for suppression and/or its complement. Mature miRNA hybridizes to target mRNA transcripts and guides the binding of a complex of proteins to the target transcripts, which can function to inhibit translation and/or result in degradation of the transcript, thus negatively regulating or suppressing expression of the targeted gene. miRNA precursors are also useful in plants for directing in-phase production of siRNAs, trans-acting siRNAs (ta-siRNAs), in a process that requires a RNA-dependent RNA polymerase to cause suppression of a target gene. See, e.g., Allen et al., *Cell*, 121:207-221 (2005), Vaucheret, *Science STKE*, 2005: pe43 (2005), and Yoshikawa et al. *Genes Dev.*, 19:2164-2175 (2005), the contents and disclosures of which are incorporated herein by reference.

Without being limited by any scientific theory, plant miRNAs regulate their target genes by recognizing and binding to a complementary or near-perfectly complementary sequence (miRNA recognition site) in the target mRNA transcript, followed by cleavage of the transcript by RNase III enzymes, such as ARGONAUTE 1. In plants, certain mismatches between a given miRNA recognition site and the corresponding mature miRNA are typically not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) *Nature Genetics*, 39:1033-1037; and Axtell et al. (2006) *Cell*, 127:565-577.

Many microRNA genes (MIR genes) have been identified and made publicly available in a database ("miRBase", available on line at microrna.sanger.ac.uk/sequences; also see Griffiths-Jones et al. (2003) *Nucleic Acids Res.*, 31:439-441). MIR genes have been reported to occur in intergenic regions, both isolated and in clusters in the genome, but can also be located entirely or partially within introns of other genes (both protein-coding and non-protein-coding). For a review of miRNA biogenesis, see Kim (2005) *Nature Rev. Mol. Cell. Biol.*, 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (foldback structures containing a stem-loop arrangement that is processed to the mature miRNA) as well as the usual 5' "cap" and polyadenylated tail of an mRNA. See, for example, FIG. 1 in Kim (2005) *Nature Rev. Mol. Cell. Biol.*, 6:376-385.

Transgenic expression of miRNAs (whether a naturally occurring sequence or an artificial sequence) can be employed to regulate expression of the miRNA's target gene or genes. Recognition sites of miRNAs have been validated in all regions of a mRNA, including the 5' untranslated region, coding region, intron region, and 3' untranslated region, indicating that the position of the miRNA target or recognition site relative to the coding sequence may not necessarily affect suppression (see, e.g., Jones-Rhoades and Bartel (2004). *Mol. Cell,* 14:787-799, Rhoades et al. (2002) *Cell,* 110:513-520, Allen et al. (2004) *Nat. Genet.,* 36:1282-1290, Sunkar and Zhu (2004) Plant Cell, 16:2001-2019). miRNAs are important regulatory elements in eukaryotes, and transgenic suppression with miRNAs is a useful tool for manipulating biological pathways and responses. A description of native miRNAs, their precursors, recognition sites, and promoters is provided in U.S. Patent Application Publication No. 2006/0200878, the contents and disclosures of which are incorporated herein by reference.

Designing an artificial miRNA sequence can be achieved by substituting nucleotides in the stem region of a miRNA precursor with a sequence that is complementary to the intended target, as demonstrated, for example, by Zeng et al. (2002) *Mol. Cell,* 9:1327-1333. According to many aspects, the target can be a sequence of a GA20 oxidase gene or a GA3 oxidase gene. One non-limiting example of a general method for determining nucleotide changes in a native miRNA sequence to produce an engineered miRNA precursor for a target of interest includes the following steps: (a) selecting a unique target sequence of at least 18 nucleotides specific to the target gene, e.g., by using sequence alignment tools such as BLAST (see, for example, Altschul et al. (1990) *J. Mol. Biol.,* 215:403-410; Altschul et al. (1997) *Nucleic Acids Res.,* 25:3389-3402); cDNA and/or genomic DNA sequences can be used to identify target transcript orthologues and any potential matches to unrelated genes, thereby avoiding unintentional silencing or suppression of non-target sequences; (b) analyzing the target gene for undesirable sequences (e.g., matches to sequences from non-target species), and score each potential target sequence for GC content, Reynolds score (see Reynolds et al. (2004) *Nature* Biotechnol., 22:326-330), and functional asymmetry characterized by a negative difference in free energy ("ΔΔG") (see Khvorova et al. (2003) *Cell,* 115:209-216). Preferably, target sequences (e.g., 19-mers) can be selected that have all or most of the following characteristics: (1) a Reynolds score >4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. In an aspect, a non-coding RNA molecule used here to suppress a target gene (e.g., a GA20 or GA3 oxidase gene) is designed to have a target sequence exhibiting one or more, two or more, three or more, four or more, or five or more of the foregoing characteristics. Positions at every third nucleotide of a suppression element can be important in influencing RNAi efficacy; for example, an algorithm, "siExplorer" is publicly available at rna.chem.t.u-tokyo.ac.jp/siexplorer.htm (see Katoh and Suzuki (2007) *Nucleic Acids Res.,* 10.1093/nar/gkl1120); (c) determining a reverse complement of the selected target sequence (e.g., 19-mer) to use in making a modified mature miRNA. Relative to a 19-mer sequence, an additional nucleotide at position 20 can be matched to the selected target or recognition sequence, and the nucleotide at position 21 can be chosen to either be unpaired to prevent spreading of silencing on the target transcript or paired to the target sequence to promote spreading of silencing on the target transcript; and (d) transforming the artificial miRNA into a plant.

Multiple sense and/or anti-sense suppression elements for more than one GA oxidase target can be arranged serially in tandem or arranged in tandem segments or repeats, such as tandem inverted repeats, which can also be interrupted by one or more spacer sequence(s), and the sequence of each suppression element can target one or more GA oxidase gene(s). Furthermore, a sense or anti-sense sequence of the suppression element may not be perfectly matched or complementary to the targeted GA oxidase gene sequence, depending on the sequence and length of the suppression element. Even shorter RNAi suppression elements from about 19 nucleotides to about 27 nucleotides in length can have one or more mismatches or non-complementary bases, yet still be effective at suppressing the target GA oxidase gene. Accordingly, a sense or anti-sense suppression element sequence can be at least 80%, at least 85%, at least 90%, at least 95%, at least 96%, at least 97%, at least 98%, at least 99%, at least 99.5% or 100% identical to a corresponding sequence of at least a segment or portion of the targeted GA oxidase gene, or its complementary sequence, respectively.

For suppression of GA oxidase gene(s) using an inverted repeat or a transcribed dsRNA, a transcribable DNA sequence or suppression element can comprise a sense sequence that comprises a segment or portion of a targeted GA oxidase gene and an anti-sense sequence that is complementary to a segment or portion of the targeted GA oxidase gene, where the sense and anti-sense DNA sequences are arranged in tandem. The sense and/or anti-sense sequences, respectively, can each be less than 100% identical or complementary to a segment or portion of the targeted GA oxidase gene as described above. A sense and anti-sense sequences can be separated by a spacer sequence, such that the RNA molecule transcribed from the suppression element forms a stem, loop or stem-loop structure between the sense and anti-sense sequences. A suppression element can instead comprise multiple sense and anti-sense sequences that are arranged in tandem, which can also be separated by one or more spacer sequences. Suppression elements comprising multiple sense and anti-sense sequences can be arranged as a series of sense sequences followed by a series of anti-sense sequences, or as a series of tandemly arranged sense and anti-sense sequences. Alternatively, one or more sense DNA sequences can be expressed separately from the one or more anti-sense sequences (i.e., one or more sense DNA sequences can be expressed from a first transcribable DNA sequence, and one or more anti-sense DNA sequences can be expressed from a second transcribable DNA sequence, wherein the first and second transcribable DNA sequences are expressed as separate transcripts).

For suppression of GA oxidase gene(s) using a microRNA (miRNA), the transcribable DNA sequence or suppression element can comprise a DNA sequence derived from a miRNA sequence native to a virus or eukaryote, such as an animal or plant, or modified or derived from such a native miRNA sequence. Such native or native-derived miRNA sequences can form a fold back structure and serve as a scaffold for the precursor miRNA (pre-miRNA), and can correspond to the stem region of a native miRNA precursor sequence, such as from a native (or native-derived) primary-miRNA (pri-miRNA) or pre-miRNA sequence. However, in addition to these native or native-derived miRNA scaffold or preprocessed sequences, engineered or synthetic miRNAs of the present aspects further comprise a sequence corresponding to a segment or portion of the targeted GA oxidase gene(s). Thus, in addition to the pre-processed or scaffold miRNA sequences, the suppression element can further comprise a sense and/or anti-sense sequence that corresponds to a segment or portion of a targeted GA oxidase gene, and/or a sequence that is complementary thereto, although one or more sequence mismatches can be tolerated.

GA oxidase gene(s) can also be suppressed using one or more small interfering RNAs (siRNAs). The siRNA pathway involves the non-phased cleavage of a longer double-stranded RNA intermediate ("RNA duplex") into small interfering RNAs (siRNAs). The size or length of siRNAs ranges from about 19 to about 25 nucleotides or base pairs, but common classes of siRNAs include those containing 21 or 24 base pairs. Thus, a transcribable DNA sequence or suppression element can encode a RNA molecule that is at least about 19 to about 25 nucleotides (or more) in length, such as at least 19, 20, 21, 22, 23, 24, or 25 nucleotides in length. For siRNA suppression, a recombinant DNA molecule, construct or vector can be provided comprising a transcribable DNA sequence and suppression element encoding a siRNA molecule for targeted suppression of a GA oxidase gene(s). A transcribable DNA sequence and suppression element can be at least 19 nucleotides in length and have a sequence corresponding to one or more GA oxidase gene(s), and/or a sequence complementary to one or more GA oxidase gene(s).

GA oxidase gene(s) can also be suppressed using one or more trans-acting small interfering RNAs (ta-siRNAs). In the ta-siRNA pathway, miRNAs serve to guide in-phase processing of siRNA primary transcripts in a process that requires an RNA-dependent RNA polymerase for production of a double-stranded RNA precursor. ta-siRNAs are defined by lack of secondary structure, a miRNA target site that initiates production of double-stranded RNA, requirements of DCL4 and an RNA-dependent RNA polymerase (RDR6), and production of multiple perfectly phased ~21-nt small RNAs with perfectly matched duplexes with 2-nucleotide 3' overhangs (see Allen et al. (2005) *Cell*, 121:207-221). The size or length of ta-siRNAs ranges from about 20 to about 22 nucleotides or base pairs, but are mostly commonly 21 base pairs. A transcribable DNA sequence or suppression element of the present invention can encode a RNA molecule that is at least about 20 to about 22 nucleotides in length, such as 20, 21, or 22 nucleotides in length. For ta-siRNA suppression, a recombinant DNA molecule, construct or vector is thus provided comprising a transcribable DNA sequence or suppression element encoding a ta-siRNA molecule for targeted suppression of a GA oxidase gene(s). Such a transcribable DNA sequence and suppression element can be at least 20 nucleotides in length and have a sequence corresponding to one or more GA oxidase gene(s) and/or a sequence complementary to one or more GA oxidase gene(s). For methods of constructing suitable ta-siRNA scaffolds, see, e.g., U.S. Pat. No. 9,309,512, which is incorporated herein by reference in its entirety.

According to an aspect of the present disclosure, a seed of the modified corn plant is produced, in which the seed comprises a first expression cassette and DNA sequence encoding a non-coding RNA for suppression of one more GA20 oxidase genes and/or one or more GA3 oxidase genes, or one or more mutated or edited GA20 and/or GA3 oxidase genes, and a second expression cassette and DNA sequence encoding one or more MADS-box polypeptides. In an aspect, a progeny plant grown from the seed is semi-dwarf and has one or more improved ear traits, relative to a control corn plant that does not have the suppression element, mutation or edit and the MADS-box transgene. In another aspect, a commodity or commodity product is produced from the seed of the modified corn plant comprising the first transcribable DNA sequence encoding a non-coding RNA for suppression of one more GA20 oxidase genes and/or one or more GA3 oxidase genes, or one or more mutated or edited GA20 and/or GA3 oxidase genes, and the second DNA sequence encoding one or more MADS-box polypeptides.

A transgenic plant can be produced by any suitable transformation method as provided herein to produce a transgenic $R_0$ plant, which can then be selfed or crossed to other plants to generate $R_1$ seed and subsequent progeny generations and seed through additional crosses, etc. Aspects of the present disclosure further include a plant cell, tissue, explant, plant part, etc., comprising one or more transgenic cells having a transformation event or genomic insertion of a recombinant DNA or polynucleotide sequence comprising a transcribable DNA sequence encoding a non-coding RNA molecule that targets an endogenous GA3 or GA20 oxidase gene for suppression and a transgene encoding a MADS-box polypeptide Transgenic plants, plant cells, seeds, and plant parts of the present disclosure can be homozygous or hemizygous for a transgenic event or insertion in at least one plant cell thereof, or a targeted genome editing event or mutation, and plants, plant cells, seeds, and plant parts of the present disclosure can contain any number of copies of such transgenic event(s), insertion(s) mutation(s), and/or edit(s). The dosage or amount of expression of a transgene or transcribable DNA sequence can be altered by its zygosity and/or number of copies, which can affect the degree or extent of phenotypic changes in the transgenic plant, etc.

Transgenic plants provided herein can include a variety of monocot cereal plants, including crop plants, such as corn, wheat, rice and sorghum. Indeed, recombinant DNA molecules or constructs of the present disclosure can be used to create beneficial traits in cereal plants such as corn without off-types using only a single copy of the transgenic event, insertion or construct.

Aspects of the present disclosure further include methods for making or producing transgenic plants, such as by transformation, crossing, etc., wherein the method comprises introducing a recombinant DNA molecule, construct or sequence into a plant cell, and then regenerating or developing the transgenic plant from the transformed or edited plant cell, which can be performed under selection pressure favoring a transgenic event.

Provided in the present disclosure is a method for producing a modified corn plant, the method comprising: introducing into a corn cell a first recombinant expression cassette comprising a DNA sequence encoding a MADS-box polypeptide, wherein the corn cell comprises a second recombinant expression cassette comprising a transcribable DNA sequence encoding a non-coding RNA for suppression of one or more GA3 oxidase genes and/or one or more GA20 oxidase genes; and regenerating or developing a modified corn plant from the corn cell, wherein the modified corn plant comprises the first and second recombinant expression cassettes.

Also provided in the present disclosure is a method for producing a transgenic corn plant, the method comprising: (a) introducing into a first corn cell a transgene that encodes one or more MADS-box polypeptides to create a transgenic corn cell, wherein the first corn cell comprises a transcribable DNA sequence encoding a non-coding RNA for suppression of one or more GA3 oxidase genes or GA20 oxidase genes; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising:

introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a MADS-box polypeptide; and regenerating or developing a modified corn plant from the corn cell, wherein the modified corn plant comprises the first and second recombinant expression cassettes.

Also provided in the present disclosure is a method for producing a transgenic corn plant, the method comprising: (a) introducing into a first corn cell a transcribable DNA sequence encoding a non-coding RNA for suppression of one or more GA3 oxidase genes or GA20 oxidase genes to create a transgenic corn cell, wherein the first corn cell comprises a transgene that encodes one or more MADS-box polypeptides; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a MADS-box polypeptide; and regenerating or developing a modified corn plant from the corn cell, wherein the modified corn plant comprises the first and second recombinant expression cassettes.

Also provided in the present disclosure is a method for producing a transgenic corn plant, the method comprising (a) introducing into a first corn cell 1) a transcribable DNA sequence encoding a non-coding RNA for suppression of one or more GA3 oxidase genes or GA20 oxidase genes and 2) a transgene that encodes one or more MADS-box polypeptides, to create a transgenic corn cell; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising introducing into a corn cell a first recombinant expression cassette comprising a transcribable DNA sequence encoding a non-coding RNA for suppression of one or more GA3 oxidase genes and/or GA20 oxidase genes; introducing into the corn cell of step (a) a second recombinant expression cassette comprising a DNA sequence encoding a MADS-box polypeptide to create a modified corn cell; and regenerating or developing a modified corn plant from the modified corn cell of step (b), wherein the modified corn plant comprises the first and second recombinant expression cassettes.

Also provided in the present disclosure is a method for producing a modified corn plant, the method comprising introducing into a corn cell a first recombinant expression cassette comprising a DNA sequence encoding a MADS-box polypeptide; introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and regenerating or developing a modified corn plant from the modified corn cell of step (b), wherein the modified corn plant comprises the first and second recombinant expression cassettes.

Also provided in the present disclosure is a method for producing a transgenic corn plant, the method comprising (a) introducing into a first corn cell a transcribable DNA sequence encoding a non-coding RNA for suppression of one or more GA3 oxidase genes and/or one or more GA20 oxidase genes to create a transgenic corn cell, wherein the first corn cell is genome edited or mutated and comprises a transgene that encodes one or more MADS-box polypeptides; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the DNA sequence and the transgene.

Also provided in the present disclosure is a method for producing a transgenic corn plant, the method comprising (a) introducing into a first corn cell a DNA sequence that encodes one or more MADS-box polypeptides to create a transgenic corn cell, wherein the first corn cell is genome edited or mutated and has a reduced expression of one or more endogenous GA3 oxidase genes and/or one or more GA20 oxidase genes; and (b) generating a transgenic corn plant from the transgenic corn cell. In an aspect, the first corn cell comprises one or more mutation(s) or edit(s) at or near one or more endogenous GA20 oxidase and/or GA3 oxidase gene(s) (e.g., a mutation or edit in two or more endogenous GA20 oxidase and/or GA3 oxidase gene(s), wherein the expression of the endogenous GA20 oxidase and/or GA3 oxidase gene(s) is reduced relative to a wildtype control. In an aspect, the method further comprises identifying a transgenic corn plant with a desired trait. In another aspect, the identified transgenic corn plant is semi-dwarf and has one or more improved ear traits, relative to a control corn plant not having both the DNA sequence and the reduced expression of the one or more endogenous GA3 oxidase and/or GA20 oxidase genes.

Also provided in the present disclosure is a method for producing a modified corn plant, the method comprising: crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a MADS-box polypeptide; and producing a progeny corn plant comprising the recombinant expression cassette and has the reduced expression of the one or more endogenous GA3 oxidase genes and/or GA20 oxidase genes.

Also provided in the present disclosure is a method for producing a transgenic corn plant, the method comprising (a) crossing a first corn plant with a second corn plant to create a modified corn plant, wherein the expression of one or more endogenous GA3 oxidase gene(s) and/or one or more GA20 oxidase gene(s) is reduced in the first corn plant relative to a wildtype control, and wherein the second corn plant comprises a transgene encoding one or more MADS-box polypeptides; and (b) producing an offspring of the transgenic corn plant of step (a). In an aspect, the method further comprises identifying a modified corn plant with a desired trait. In another aspect, the identified modified corn plant is semi-dwarf and has one or more improved ear traits, relative to a control corn plant not having both the transgene and a reduced expression of the one or more endogenous GA3 oxidase and/or GA20 oxidase gene(s).

According to an aspect of the present disclosure, methods are provided for transforming a cell, tissue or explant with a recombinant DNA molecule or construct comprising DNA sequences or transgenes operably linked to one or more promoters to produce a transgenic or genome edited cell. According to other aspects of the present disclosure, methods are provided for transforming a plant cell, tissue or explant with a recombinant DNA molecule or construct comprising transcribable DNA sequences or transgenes operably linked to one or more plant-expressible promoters to produce a transgenic or genome edited plant or plant cell.

Numerous methods for transforming chromosomes or plastids in a plant cell with a recombinant DNA molecule or construct are known in the art, which can be used according to methods of the present disclosure to produce a transgenic plant cell and plant. Any suitable method or technique for transformation of a plant cell known in the art can be used according to present methods.

Effective methods for transformation of plants include bacterially mediated transformation, such as *Agrobacterium*-mediated or *Rhizobium*-mediated transformation and microprojectile particle bombardment-mediated transformation. A variety of methods are known in the art for transforming explants with a transformation vector via bacterially mediated transformation or microprojectile particle bombardment and then subsequently culturing, etc., those explants to regenerate or develop transgenic plants.

In an aspect, the methods for producing a transgenic or modified corn plant disclosed in the present disclosure comprise obtaining the first corn cell and the transgenic corn cell via *Agrobacterium*-mediated transformation.

In another aspect, the methods for producing a transgenic or modified corn plant disclosed in the present disclosure comprise obtaining the first corn cell and the transgenic corn cell via microprojectile particle bombardment-mediated transformation.

In yet another aspect, the methods for producing a transgenic corn plant disclosed in the present disclosure comprises (1) introducing into a first corn cell a transgene via site-directed integration to create a modified or mutated corn cell, wherein the transgene encodes one or more MADS-box polypeptides, and (2) introducing into the modified or mutated corn cell a transcribable DNA sequence via transformation to create a transgenic corn cell, wherein the transcribable DNA sequence encodes a non-coding RNA for suppression of one or more GA3 oxidase genes and/or one or more GA20 oxidase genes. In an aspect, the transformation can be *Agrobacterium*-mediated transformation or microprojectile particle bombardment-mediated transformation.

In still another aspect, the methods for producing a transgenic corn plant disclosed in the present disclosure comprise (1) obtaining a modified corn cell via genome editing, wherein the modified corn cell has a reduced expression of one or more GA3 oxidase genes and/or one or more GA20 oxidase genes; and (2) introducing into the modified corn cell a transgene via transformation to create a transgenic corn cell, wherein the transgene encodes one or more MADS-box polypeptides. In an aspect, the transformation can be *Agrobacterium*-mediated transformation or microprojectile particle bombardment-mediated transformation.

Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile particle bombardment with particles coated with recombinant DNA are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

In an aspect, described herein are methods of integrating an insertion sequence encoding one or more MADS-box polypeptides into the genome of a plant cell via site-directed integration. Such methods comprise creating a double-stranded break (DSB) in the genome of the plant cell such that the insertion sequence is integrated at the site of the DSB. In an aspect, the insertion/donor sequence encoding one or more MADS-box polypeptides can be integrated in a targeted manner into the genome of a cell at the location of a DSB. DSB s can be created by any mechanism, including but are not limited to, zinc finger nucleases (ZFN), transcription activator-like effector nuclease (TALEN), meganucleases, recombinases, transposases, and RNA-guided nucleases (e.g., Cas9 and Cpf1) in a CRISPR based genome editing system.

When Cas9 cleaves targeted DNA, endogenous double stranded break (DSB) repair mechanisms are activated. DSBs can be repaired via non-homologous end joining (NHEJ), which can incorporate insertions or deletions (indels) into the targeted locus. If two DSBs flanking one target region are created, the breaks can be repaired by reversing the orientation of the targeted DNA. Alternatively, if an insertion sequence of a donor template with homology to the target DNA sequence is provided, the DSB can be repaired via homology-directed repair or homologous recombination (HR). This repair mechanism allows for the precise integration of an insertion sequence into the targeted DNA sequence.

As used herein, an "insertion sequence" of a donor template is a sequence designed for targeted insertion into the genome of a plant cell, which can be of any suitable length. For example, an insertion sequence can be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length.

According to some aspects, a donor template may not comprise a sequence for insertion into a genome, and instead comprise one or more homology sequences that include(s) one or more mutations, such as an insertion, deletion, substitution, etc., relative to the genomic sequence at a target site within the genome of a plant. Alternatively, a donor template can comprise a sequence that does not comprise a coding or transcribable DNA sequence, wherein the insertion sequence is used to introduce one or more mutations into a target site within the genome of a plant.

A donor template provided herein can comprise at least one, at least two, at least three, at least four, at least five, at least six, at least seven, at least eight, at least nine, or at least ten genes or transcribable DNA sequences. Alternatively, a donor template can comprise no genes. Without being limiting, a gene or transcribable DNA sequence of a donor template can include, for example, an insecticidal resistance gene, an herbicide tolerance gene, a nitrogen use efficiency gene, a water use efficiency gene, a nutritional quality gene, a DNA binding gene, a selectable marker gene, an RNAi or suppression construct, a site-specific genome modification enzyme gene, a single guide RNA of a CRISPR/Cas9 system, a geminivirus-based expression cassette, or a plant viral expression vector system. A donor template can comprise a promoter, such as a tissue-specific or tissue-preferred promoter, a constitutive promoter, or an inducible promoter. A donor template can comprise a leader, enhancer, promoter, transcriptional start site, 5'-UTR, one or more exon(s), one or more intron(s), transcriptional termination site, region or sequence, 3'-UTR, and/or polyadenylation signal. The leader, enhancer, and/or promoter can be operably linked to a gene or transcribable DNA sequence encoding a non-coding RNA, a guide RNA, an mRNA and/or protein.

In an aspect, an insertion sequence of a donor template of the present disclosure comprises a DNA sequence encoding a MADS-box polypeptide, wherein the MADS-box polypeptide is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 175-199.

In an aspect, an insertion sequence of a donor template of the present disclosure comprises a DNA sequence encoding a maize ZMM19 polypeptide, wherein the DNA sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

In an aspect, a "modified plant(s)," "modified corn plant(s)," "transgenic plant(s)," or "transgenic corn plant(s)" produced according to a method disclosed in the present disclosure comprises (1) a first transcribable DNA sequence encoding a non-coding RNA for suppression of one or more GA20 oxidase genes and/or one or more GA3 oxidase genes, and (2) a second DNA sequence encoding one or more MADS-box polypeptides.

In another aspect, a "modified plant(s)," "modified corn plant(s)," "transgenic plant(s)," or "transgenic corn plant(s)" produced according to a method disclosed in the present disclosure comprises (1) a DNA sequence encoding one or more MADS-box polypeptides, and (2) a reduced expression of one or more endogenous GA3 oxidase genes or GA20 oxidase genes relative to a wildtype control. In an aspect, the reduced expression of the one or more endogenous GA20 oxidase genes or GA3 oxidase genes is caused by a mutation or edit at or near the one or more endogenous GA20 oxidase genes or GA3 oxidase genes.

Transgenic or modified plants produced by transformation methods can be chimeric or non-chimeric for the transformation event depending on the methods and explants used. Methods are further provided for expressing a non-coding RNA molecule that targets an endogenous GA oxidase gene for suppression in one or more plant cells or tissues under the control of a plant-expressible promoter, such as a constitutive, tissue-specific, tissue-preferred, vascular and/or leaf promoter as provided herein. Such methods can be used to create transgenic cereal or corn plants having a shorter, semi-dwarf stature, reduced internode length, increased stalk/stem diameter, and/or improved lodging resistance. Such transgenic cereal or corn plants can further have other traits that can be beneficial for yield, such as reduced green snap, deeper roots, increased leaf area, earlier canopy closure, improved drought tolerance, increased nitrogen use efficiency, increased water use efficiency, higher stomatal conductance, lower ear height, increased foliar water content, reduced anthocyanin content and/or area in leaves under normal or nitrogen or water limiting stress conditions, increased ear weight, increased seed or kernel number, increased seed or kernel weight, increased yield, and/or increased harvest index, relative to a wild type or control plant. As used herein, "harvest index" refers to the mass of the harvested grain divided by the total mass of the above-ground biomass of the plant over a harvested area.

Alternatively, nucleotide sequences of the disclosure can be introduced into an organism and allowed to undergo recombination with homologous regions of the organism's genome. Such homologous recombination approaches are well known to those of ordinary skill in the art and can be used to stably incorporate sequences of the disclosure into an organism. In an aspect, nucleotide sequences of the disclosure can be used to introduce "knockout mutations" into a specific gene of an organism that shares substantial homology to the sequences of the disclosure. A knockout mutation is any mutation in the sequence of a gene that eliminates or substantially reduces the function or the level of the product encoded by the gene. Methods involving transformation of an organism followed by homologous recombination to stably integrate the sequences of the disclosure into the genome organism are encompassed by the disclosure. The disclosure is particularly directed to methods where sequences of the disclosure are utilized to alter the growth of an organism. Such methods encompass use of the sequences of the disclosure to interfere with the function of one or more GA20 oxidase genes or GA3 oxidase genes. In an aspect, a knockout mutation of one or more GA20 oxidase or GA3 oxidase genes can be introduced into a corn cell via recombination to reduce the expression of the one or more of GA20 oxidase or GA3 oxidase genes in the corn cell.

Cells that have been transformed can be grown into plants in accordance with conventional ways. See, for example, McCormick et al. (1986) *Plant Cell Reports* 5:81-84. These plants can then be grown, and either pollinated with the same transformed strain or different strains, and the resulting hybrid having constitutive expression of the desired phenotypic characteristic identified. Two or more generations can be grown to ensure that constitutive expression of the desired phenotypic characteristic is stably maintained and inherited and then seeds harvested to ensure constitutive expression of the desired phenotypic characteristic has been achieved.

In an aspect, the methods for producing a transgenic or modified corn plant further comprises culturing the transgenic corn plant of step (b) or a plant part thereof in the presence of a selection agent. In another aspect, the selection agent is kanamycin.

Recipient cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell.

Transformation of a target plant material or explant can be practiced in tissue culture on nutrient media, for example a mixture of nutrients that allow cells to grow in vitro or cell culture. Transformed explants, cells or tissues can be subjected to additional culturing steps, such as callus induction, selection, regeneration, etc., as known in the art. Transformation can also be carried out without creation or use of a callus tissue. Transformed cells, tissues or explants containing a recombinant DNA sequence insertion or event can be grown, developed or regenerated into transgenic plants in culture, plugs, or soil according to methods known in the art. Transgenic plants can be further crossed to themselves or other plants to produce transgenic seeds and progeny. A transgenic plant can also be prepared by crossing a first plant comprising the recombinant DNA sequence or transformation event with a second plant lacking the insertion. For example, a recombinant DNA construct or sequence can be introduced into a first plant line that is amenable to transformation, which can then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line, but for the introduction of the recombinant DNA construct or sequence.

Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference.

Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In an aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction.

Transgenic plants can be further crossed to themselves or other plants to produce transgenic seeds and progeny. A transgenic plant can also be prepared by crossing a first plant comprising the recombinant DNA sequence or transformation event with a second plant lacking the insertion. For example, a recombinant DNA construct or sequence can be introduced into a first plant line that is amenable to transformation, which can then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line but for the introduction of the recombinant DNA construct or sequence.

A plant, cell, or explant provided herein can be of an elite variety or an elite line. An elite variety or an elite line refers to any variety that has resulted from breeding and selection for superior agronomic performance. A plant, cell, or explant provided herein can be a hybrid plant, cell, or explant. As used herein, a "hybrid" is created by crossing two plants from different varieties, lines, or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

For *Agrobacterium*-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. In other words, the transgene, a transcribable DNA sequence, transgene or expression cassette encoding the site-specific nuclease(s), and/or sgRNA(s) or crRNA(s) would be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant.

A plant selectable marker transgene in a transformation vector or construct of the present disclosure can be used to assist in the selection of transformed cells or tissue due to the presence of a selection agent, such as an antibiotic or herbicide, wherein the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_0$ plant.

A plant selectable marker transgene in a transformation vector or construct of the present disclosure can be used to assist in the selection of transformed cells or tissue due to the presence of a selection agent, such as an antibiotic or herbicide, wherein the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes can also be used, which provide an ability to visually screen for transformants, such as luciferase or green fluorescent protein (GFP), or a gene expressing a beta glucuronidase or uidA gene (GUS) for which various chromogenic substrates are known. In some aspects, a vector or polynucleotide provided herein comprises at least one selectable marker gene selected from the group consisting of nptII, aph IV, aadA, aac3, aacC4, bar, pat, DMO, EPSPS, aroA, GFP, and GUS. Plant transformation can also be carried out in the absence of selection during one or more steps or stages of culturing, developing or regenerating transformed explants, tissues, plants and/or plant parts.

An aspect of the present disclosure relate to screening cells, tissues or plants for mutations, targeted edits or transgenes and selecting cells or plants comprising targeted edits or transgenes. Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In an aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified or transgenic plants or plant cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, marker genotyping, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

Modified corn plants of the present disclosure having a reduced plant height and improved ear traits relative to a wild-type or control plant can comprise a mutation (e.g., an insertion, deletion, substitution, etc.) introduced through other plant mutagenesis technique or genome editing, wherein expression of one or more GA20 or GA3 oxidase gene is reduced or eliminated in one or more tissues of the modified plant. Modified corn plants of the present disclosure having a reduced plant height and improved ear traits relative to a wild-type or control plant can comprise a transgene encoding one or more MADS-box polypeptides. The transgene can be introduced through other plant mutagenesis technique or genome editing.

Plant mutagenesis techniques (excluding genome editing) can include chemical mutagenesis (i.e., treatment with a chemical mutagen, such as an azide, hydroxylamine, nitrous acid, acridine, nucleotide base analog, or alkylating agent— e.g., EMS (ethylmethane sulfonate), MNU (N-methyl-N-nitrosourea), etc.), physical mutagenesis (e.g., gamma rays, X-rays, UV, ion beam, other forms of radiation, etc.), and insertional mutagenesis (e.g., transposon or T-DNA insertion). Plants or various plant parts, plant tissues or plant cells can be subjected to mutagenesis. Treated plants can be reproduced to collect seeds or produce a progeny plant, and treated plant parts, plant tissues or plant cells can be developed or regenerated into plants or other plant tissues. Mutations generated with chemical or physical mutagenesis techniques can include a frameshift, missense or nonsense mutation leading to loss of function or expression of a targeted gene, such as a GA3 or GA20 oxidase gene.

One method for mutagenesis of a gene is called "TILLING" (for targeting induced local lesions in genomes), in which mutations are created in a plant cell or tissue, preferably in the seed, reproductive tissue or germline of a plant, for example, using a mutagen, such as an EMS treatment. The resulting plants are grown and self-fertilized, and the progeny are used to prepare DNA samples. PCR amplification and sequencing of a nucleic acid sequence of a GA20 or GA3 oxidase gene can be used to identify whether a mutated plant has a mutation in the GA oxidase gene. Plants having mutations in the GA20 or GA3 oxidase gene can then be tested for an altered trait, such as reduced plant height. Alternatively, mutagenized plants can be tested for an altered trait, such as reduced plant height, and then PCR amplification and sequencing of a nucleic acid sequence of a GA20 or GA3 oxidase gene can be used to determine whether a plant having the altered trait also has a mutation in the GA oxidase gene. See, e.g., Colbert et al., 2001, Plant Physiol 126:480-484; and McCallum et al., 2000, Nat. Biotechnol., 18:455-457. TILLING can be used to identify mutations that alter the expression a gene or the activity of proteins encoded by a gene, which can be used to introduce and select for a targeted mutation in a GA20 or GA3 oxidase gene of a corn or cereal plant.

Provided in the present disclosure is a recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a MADS-box polypeptide, wherein the DNA sequence is operably linked to a plant-expressible promoter. In an aspect, the first and second expression cassettes are in a single T-DNA segment of a transformation vector. In another aspect, the first and second expression cassettes are in two different T-DNA segments of a transformation vector.

In an aspect, the transcribable DNA sequence encodes a non-coding RNA for suppression of a GA3 oxidase_1 gene, a GA3 oxidase_2 gene, or both. In another aspect, the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37. In another aspect, the transcribable DNA sequence encodes a non-coding RNA comprising a sequence that is 80% complementary to at least 15 consecutive nucleotides of one or more of SEQ ID NOs: 28, 29, 31, 32, 36, and 37.

In another aspect, the transcribable DNA sequence encodes a non-coding RNA for suppression of a GA20 oxidase_3 gene, a GA20 oxidase_4 gene, a GA20 oxidase_5 gene, or a combination thereof. In another aspect, the transcribable DNA sequence comprises a sequence that is at least 80% complementary to at least 15 consecutive nucleotides of SEQ ID NO: 39, 53, or 55. In another aspect, the transcribable DNA sequence encodes a sequence that is at least 80% complementary to at least 15 consecutive nucleotides of SEQ ID NO: 40, 54, or 56.

In an aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9, 12, 15, 30, or 33.

In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

In an aspect, the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199, or a functional fragment thereof.

In an aspect, the DNA sequence comprised in the second expression cassette encodes a maize ZMM19 polypeptide. In another aspect, the MADS-box polypeptide comprises an amino acid sequence that is at least 60% identical to SEQ ID NO: 168, or a functional fragment thereof. In another aspect, the DNA sequence comprises a sequence that is at least 60% identical to SEQ ID NO: 169.

Also provided herein is a recombinant DNA construct comprising 1) a first transcribable DNA sequence encoding a non-coding RNA for suppression of one or more GA20 oxidase or one or more GA3 oxidase genes, and 2) a second DNA sequence encoding one or more MADS-box polypeptides.

In an aspect, a recombinant DNA construct of the present disclosure comprises a transcribable DNA sequence encoding a non-coding RNA for suppression of one or more GA20 oxidase or one or more GA3 oxidase genes, wherein the DNA sequence is operably linked to a plant-expressible promoter. Such a recombinant DNA construct can be used to transform a corn plant cell expressing a transgene encoding one or more MADS-box polypeptides to create a transgenic corn plant with desired traits. In another aspect, desired traits comprise semi-dwarf and improved ear traits as compared to a control corn plant not having the transgene and the DNA sequence.

In an aspect, a recombinant DNA construct of the present disclosure comprises a DNA sequence encoding one or more MADS-box polypeptides, wherein the DNA sequence is operably linked to a plant-expressible promoter. Such a recombinant DNA construct can be used to transform a corn plant cell having a reduced expression of one or more GA20 oxidase genes and/or one or more GA3 oxidase genes to create a transgenic corn plant with desired traits. In another aspect, desired traits comprise semi-dwarf and improved ear traits as compared to a control corn plant not having the DNA sequence and the reduced expression of the one or more GA20 oxidase genes and/or GA3 oxidase genes.

Also provided in the present disclosure is a transgenic corn plants comprising the recombinant DNA construct. In an aspect, the first and second DNA sequences are in a single T-DNA molecule. In another aspect, the first and second DNA sequences are in two different T-DNA molecules. In an aspect, the first transcribable DNA sequence is operably linked to a plant-expressible promoter.

In an aspect, a recombinant DNA construct of the present disclosure comprises a transcribable DNA sequence encoding a non-coding RNA molecule, wherein the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9, 12, 15, 30 or 33, and wherein the transcribable DNA sequence is operably linked to a plant-expressible promoter. In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31 or 32.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 15. In yet another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or SEQ ID NO: 14.

In another aspect, the non-coding RNA molecule comprises a sequence that is (i) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9; and/or (ii) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 15.

In another aspect, the non-coding RNA molecule comprises a sequence that is (i) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 or 8; and/or (ii) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or 14.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 12.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 10 or 11.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein, the endogenous GA3 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 30 or 33.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 28, 29, 31 or 32.

In an aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 3, 6, 9, 12, 15, 18, 21, 24, 27, 30 and 33.

In another aspect, the non-coding RNA molecule comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 1, 2, 4, 5, 7, 8, 10, 11, 13, 14, 16, 17, 19, 20, 22, 23, 25, 26, 28, 29, 31, and 32.

In an aspect, a recombinant DNA molecule, vector or construct is provided for suppression of an endogenous GA oxidase (or GA oxidase-like) gene in a corn or cereal plant, the recombinant DNA molecule, vector or construct comprising a transcribable DNA sequence encoding a non-coding RNA molecule, wherein the non-coding RNA molecule comprises a sequence that is (i) at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of any one or more of SEQ ID NO: 84, 85, 87, 88, 89, 91, 92, 93, 95, 96, 98, 99, 100, 102, 103, 105, 106, 107, 109, 110, 111, 113, 114, 115, 117, 119, 120, 122, 123, 124, 126, 127, 128, 130, 131, 132, 134, 135, and/or 137, and/or (ii) at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding a protein in the cereal plant that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to any one or more of SEQ ID NO: 86, 90, 94, 97, 101, 104, 108, 112, 116, 118, 121, 125, 129, 133, and/or 136. Likewise, a non-coding RNA molecule can target an endogenous GA oxidase (or GA oxidase-like) gene in a cereal plant having a percent identity to the GA oxidase gene(s) shown to affect plant height in corn. Thus, a non-coding RNA molecule is further provided comprising a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous protein in a cereal plant that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to any one or more of SEQ ID NO: 9, 12, 15, 30, and/or 33. As mentioned above, the non-coding RNA molecule can target an exon, intron and/or UTR sequence of a GA oxidase (or GA oxidase-like) gene.

A recombinant DNA construct of the present disclosure can comprise or be included within a DNA transformation vector for use in transformation of a target plant cell, tissue or explant. Such a transformation vector of the present disclosure can generally comprise sequences or elements necessary or beneficial for effective transformation in addition to at least one selectable marker gene, at least one expression cassette and/or transcribable DNA sequence encoding one or more site-specific nucleases, and, optionally, one or more sgRNAs or crRNAs.

According to an aspect of the present disclosure, suitable tissue-specific or tissue preferred promoters can include those promoters that drive or cause expression of its associated suppression element or sequence at least in the vascular and/or leaf tissue(s) of a corn or cereal plant, or possibly other tissues.

Expression of the GA oxidase suppression element or construct with a tissue-specific or tissue-preferred promoter can also occur in other tissues of the cereal or corn plant outside of the vascular and leaf tissues, but active GA levels in the developing reproductive tissues of the plant (particularly in the female reproductive organ or ear) are preferably not significantly reduced or impacted (relative to wild type or control plants), such that development of the female organ or ear can proceed normally in the transgenic plant without off-types in the ear and a loss in yield potential.

According to some aspects, constructs and transgenes are provided comprising the first transcribable DNA sequence and the second DNA sequence that are operably linked to a constitutive or tissue-specific or tissue-preferred promoter, such as a vascular or leaf promoter.

In an aspect, the plant-expressible promoter is a vascular promoter. Any vascular promoters known in the art can potentially be used as the tissue-specific or tissue-preferred promoter. Examples of vascular promoters include the RTBV promoter, a known sucrose synthase gene promoter, such as a corn sucrose synthase-1 (Sus1 or Sh1) promoter, a corn Sh1 gene paralog promoter, a barley sucrose synthase promoter (Ss1) promoter, a rice sucrose synthase-1 (RSs1) promoter, or a rice sucrose synthase-2 (RSs2) promoter, a known sucrose transporter gene promoter, such as a rice sucrose transporter promoter (SUT1), or various known viral promoters, such as a Commelina yellow mottle virus (CoYMV) promoter, a wheat dwarf geminivirus (WDV) large intergenic region (LIR) promoter, a maize streak geminivirus (MSV) coat protein (CP) promoter, or a rice yellow stripe 1 (YS1)-like or OsYSL2 promoter, and any functional sequence portion or truncation of any of the foregoing promoters with a similar pattern of expression, such as a truncated RTBV promoter.

In another aspect, the vascular promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 67, SEQ ID NO: 68, SEQ ID NO: 69, SEQ ID NO: 70, or SEQ ID NO: 71, or a functional portion thereof.

In another aspect, the plant-expressible promoter is a rice tungro bacilliform virus (RTBV) promoter. In an aspect, the RTBV promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 65 or SEQ ID NO: 66, or a functional portion thereof.

In another aspect, the plant-expressible promoter is a leaf promoter. Any leaf promoters known in the art can potentially be used as the tissue-specific or tissue-preferred promoter. Examples of leaf promoters include a corn pyruvate phosphate dikinase or PPDK promoter, a corn fructose 1,6 bisphosphate aldolase or FDA promoter, and a rice Nadh-Gogat promoter, and any functional sequence portion or truncation of any of the foregoing promoters with a similar pattern of expression. Other examples of leaf promoters from monocot plant genes include a ribulose biphosphate carboxylase (RuBisCO) or RuBisCO small subunit (RBCS) promoter, a chlorophyll a/b binding protein gene promoter, a phosphoenolpyruvate carboxylase (PEPC) promoter, and a Myb gene promoter, and any functional sequence portion or truncation of any of these promoters with a similar pattern of expression.

In another aspect, the leaf promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 72, SEQ ID NO: 73 or SEQ ID NO: 74, or a functional portion thereof.

In another aspect, the plant-expressible promoter is a constitutive promoter. Examples of constitutive promoters that can be used in monocot plants, such as cereal or corn plants, include, for example, various actin gene promoters, such as a rice Actin 1 promoter (see, e.g., U.S. Pat. No. 5,641,876) and a rice Actin 2 promoter (see, e.g., U.S. Pat. No. 6,429,357), a CaMV 35S or 19S promoter (see, e.g., U.S. Pat. No. 5,352,605), a maize ubiquitin promoter (see, e.g., U.S. Pat. No. 5,510,474), a *Coix lacryma-jobi* polyubiquitin promoter, a rice or maize Gos2 promoter (see, e.g., Pater et al., *Plant J.*, 2(6): 837-44 1992), a FMV 35S promoter (see, e.g., U.S. Pat. No. 6,372,211), a dual enhanced CMV promoter (see, e.g., U.S. Pat. No. 5,322,938), a MMV promoter (see, e.g., U.S. Pat. No. 6,420,547), a PCLSV promoter (see, e.g., U.S. Pat. No. 5,850,019), an Emu promoter (see, e.g., Last et al., *Theor. Appl. Genet.*, 81:581 (1991); and Mcelroy et al., *Mol. Gen. Genet.*, 231: 150 (1991)), a tubulin promoter from maize, rice or other species, a nopaline synthase (nos) promoter, an octopine synthase (ocs) promoter, a mannopine synthase (mas) promoter, or a plant alcohol dehydrogenase (e.g., maize Adhl) promoter, any other promoters including viral promoters known or later-identified in the art to provide constitutive expression in a cereal or corn plant, any other constitutive promoters known in the art that can be used in monocot or cereal plants, and any functional sequence portion or truncation of any of the foregoing promoters.

In another aspect, the constitutive promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

Tissue-specific and tissue-preferred promoters that drive, etc., a moderate or strong level of expression of their associated transcribable DNA sequence in active GA-producing tissue(s) of a plant can be preferred. Furthermore, such tissue-specific and tissue-preferred should drive, etc., expression of their associated transcribable DNA sequence during one or more vegetative stage(s) of plant development when the plant is growing and/or elongating including one or more of the following vegetative stage(s): $V_E$, V1, V2, V3, V4, V5, V6, V7, V8, V9, V10, V11, V12, V13, V14, Vn, $V_T$, such as expression at least during V3-V12, V4-V12, V5-V12, V6-V12, V7-V12, V8-V12, V3-V14, V5-V14, V6-V14, V7-V14, V8-V14, V9-V14, V10-V14, etc., or during any other range of vegetative stages when growth and/or elongation of the plant is occurring.

According to an aspect, the plant-expressible promoter can preferably drive expression constitutively or in at least a portion of the vascular and/or leaf tissues of the plant. Different promoters driving expression of a suppression element targeting the endogenous GA20 oxidase_3 and/or GA20 oxidase_5 gene(s), the GA20 oxidase_4 gene, the GA3 oxidase_1 and/or GA3 oxidase_2 gene(s) in corn, or similar genes and homologs in other cereal plants, can be effective at reducing plant height and increasing lodging resistance to varying degrees depending on their particular pattern and strength of expression in the plant. However, some tissue-specific and tissue-preferred promoters driving expression of a GA20 or GA3 oxidase suppression element in a plant may not produce a short stature or anti-lodging phenotypes due to the spatial-temporal pattern of expression of the promoter during plant development, and/or the amount or strength of expression of the promoter being too low or weak. Furthermore, some suppression constructs can only reduce and not eliminate expression of the targeted GA20 or GA3 oxidase gene(s) when expressed in a plant, and thus depending on the pattern and strength of expression with a given promoter, the pattern and level of expression of the GA20 or GA3 oxidase suppression construct with such a promoter may not be sufficient to produce an observable plant height and lodging resistance phenotype in plants.

Any other vascular and/or leaf promoters known in the art can also be used, including promoter sequences from related genes (e.g., sucrose synthase, sucrose transporter, and viral gene promoter sequences) from the same or different plant species or virus that have a similar pattern of expression. Further provided are promoter sequences with a high degree of homology to any of the foregoing. Examples of vascular and/or leaf promoters can further include other known, engineered and/or later-identified promoter sequences shown to have a pattern of expression in vascular and/or leaf tissue(s) of a cereal or corn plant. Furthermore, any known or later-identified constitutive promoter can also be used for expression of a GA20 oxidase or GA3 oxidase suppression element.

According to some aspects, recombinant expression cassettes, constructs, transgenes, and recombinant DNA donor template molecules are provided comprising a DNA sequence encoding a MADS-box polypeptide operably linked to a meristem promoter, a root promoter, or a seed or kernel promoter. For a review or resource of some promoter types and examples available in the art, see, e.g., Lagrimini, L.M. (editor), Maize: Methods and Protocols (Humana Press), Chapter 4: A Brief History of Promoter Development for Use in Transgenic Maize Applications, Vol. 1676, and the Maize Cell Genomics Database pp. 61-93 (2017); (maize [dot]jcvi[dot]org/cellgenomics/index[dot]php), the entire contents and disclosures of which are incorporated herein by reference.

In an aspect, a DNA sequence encoding a MADS-box polypeptide is operably linked to a meristem promoter, such as a meristem-specific promoter or a meristem-preferred promoter. A meristem-preferred promoter refers to a promoter that preferentially or predominantly causes or drives expression of a gene (or transgene) operably linked to the promoter in one or more meristem tissues of a corn or maize plant although the meristem-preferred promoter may also cause or drive expression of the gene (or transgene) operably linked to the promoter in other tissues. A meristem-specific promoter refers to a promoter that causes or drives expression of a gene (or transgene) operably linked to the promoter specifically in one or more meristem tissues of a corn plant. As used herein, a "meristem promoter" refers to any meristem-preferred promoter or meristem-specific promoter. A meristem promoter includes any promoter which causes or drives, or can cause or drive, meristem-specific or meristem-preferred expression of a gene or transgene operably linked to the promoter in a corn or maize seed, including any such promoter from a monocot or Poaceae plant, such as maize, barley, wheat, oat, millet, sorghum, rice, etc.

According to present embodiments, a meristem promoter can include any meristem promoter known in the art to cause or drive expression of a gene (or transgene) in one or more meristem tissues of a corn or maize plant, such as for example, a promoter from a WAK1 or WAK2 gene (see, e.g., Wagner et al., The Plant Cell 13(2): 303-318 (2001)), a metallothionein gene, a rice OSH1 gene (see, e.g., Sato et al, PNAS USA 93(15): 8117-8122 (1996)), a PCNA gene (see, e.g., Kosugi et al., Nucl. Acids Res. 19: 1571-1576 (1991)), a histone gene, such as a maize histone H3C4 gene (see, e.g., Ohtsubo et al., Pant Mol Biol 23(3):553-565 (1993); and Atanassova et al., Plant Mol Biol, 37: 275-285 (1998)), a maize WUSCHEL gene or a maize RAMOSA3 gene (see, e.g., Wu et al Int. J. Dev. Biol. 57: 535-543 (2013)), or a functional portion of any of the foregoing known meristem promoters, or a promoter sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to any of the foregoing known seed promoters, or any functional portion thereof. All of the above-cited references are incorporated herein by reference in their entirety. In another aspect, a meristem promoter comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 200-205, or a functional portion thereof.

In an aspect, a DNA sequence encoding a MADS-box polypeptide is operably linked to a root promoter, such as a root-specific promoter or a root-preferred promoter. Such a root promoter can confer transcription in root tissue, e.g., root endodermis, root epidermis, and/or root vascular tissues. A root-preferred promoter refers to a promoter that preferentially or predominantly causes or drives expression of a gene (or transgene) operably linked to the promoter in one or more root tissues of a corn or maize plant, such as the root endodermis, root epidermis, root vascular tissue, etc., although the root-preferred promoter may also cause or drive expression of the gene (or transgene) operably linked to the promoter in other tissues. A root-specific promoter refers to a promoter that causes or drives expression of a gene (or transgene) operably linked to the promoter specifically in one or more root tissues of a corn plant, such as the root endodermis, root epidermis, root vascular tissue, etc. As used herein, a "root promoter" refers to any root-preferred promoter or root-specific promoter. A root promoter includes any promoter which causes or drives, or can cause or drive, root-specific or root-preferred expression of a gene or transgene operably linked to the promoter in a corn or maize seed, including any such promoter from a monocot or Poaceae plant, such as maize, barley, wheat, oat, millet, sorghum, rice, etc.

According to present embodiments, a root promoter can include any root promoter known in the art to cause or drive expression of a gene (or transgene) in one or more root tissues of a corn or maize plant, such as for example, a root-specific subdomain of the CaMV 35S promoter (see, e.g., Lam et al., PNAS USA, 86:7890-7894 (1989)) or other root cell specific promoters (see, e.g., Plant Physiol., 93:1203-1211 (1990)), one of the YP0128, YP0275, PT0625, PT0660, PT0683, PT0758, PT0613, PT0672, PT0678, PT0688, and PT0837 promoters (see, e.g., US Patent Pub. No. 2008/0131581), a GL5 promoter (see, e.g., US Patent Pub. No. 2007/174938), or a promoter from an acid chitanse gene, a RCc2 or RCc3 gene (see, e.g., U.S. Pat. No. 7,547,774 (rice); PCT Pub. No. WO 2009/126470 (millet); and Plant Mol Biol. 27(2): 237-48 (1995)), or a Zm.PIIG gene (see, e.g., U.S. Pat. No. 7,491,813), or a functional portion of any of the foregoing known root promoters, or a promoter sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to any of the foregoing known root promoters, or any functional portion thereof. In another aspect, a root promoter comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 206-209, or a functional portion thereof.

In an aspect, a DNA sequence encoding a MADS-box polypeptide is operably linked to a seed or kernel promoter, such as a seed- or kernel-specific promoter or a seed- or kernel-preferred promoter. A seed-preferred or kernel-preferred promoter refers to a promoter that preferentially or predominantly causes or drives expression of a gene (or transgene) operably linked to the promoter in one or more tissues of a seed or kernel of a corn or maize plant, such as in one or more of a seed endosperm, embryo, scutellum, etc., although the seed-preferred or kernel-preferred promoter may also cause or drive expression of the gene (or transgene) operably linked to the promoter in other tissues. A seed-specific or kernel-specific promoter refers to a promoter that causes or drives expression of a gene (or transgene) operably linked to the promoter specifically in one or more tissues of a seed or kernel of a corn or maize plant, such as in one or more of a seed endosperm, embryo, scutellum, etc. As used herein, a "seed promoter" or a "kernel promoter" refers to any seed-preferred (or kernel-preferred) promoter or any seed-specific (or kernel-specific) promoter. A seed or kernel promoter includes any promoter which causes or drives, or can cause or drive, seed-specific or seed-preferred expression of a gene or transgene operably linked to the promoter in a corn or maize seed, including any such promoter from a monocot or Poaceae plant, such as maize, barley, wheat, oat, millet, sorghum, rice, etc.

According to present embodiments, a seed or kernel promoter can include any seed or kernel promoter known in the art to cause or drive expression of a gene (or transgene) in one or more tissues of a corn or maize seed, such as for example, a promoter from a zein gene (see, e.g., Matzke et al., Plant Mol Biol, 14(3): 323-32 (1990); The Plant Cell, 13(10): 2297-2318 (2001); and Joshi et al., Physiol Mol Biol Plants, 21(1): 35-42 (2015)), such as alpha-zeins, gamma-zeins, and delta-zeins, including maize 15 kDa zein, 19 kDa zein, 22 kDa zein, or 27 kDa zein, or other prolamin gene, such as a B1-, C- or D-hordein gene, an alpha-, beta- or gamma-gliadin gene, a secalin gene, a kafirin gene, an avenin gene, etc. (see, e.g., Horvath et al., PNAS 97(4): 1914-19 (2000); Cho et al., Theor Appl Gen 98:1253-62 (1999); Muller et al., The Plant Journal 4(2):343-355 (1993); Sorensen et al., Mol and Gen Genet 250(6):750-60 (1996); Van Herpen et al., Ann Bot 102(3) 331-342 (2008); Aryan et al., Mol and Gen Genet 225(1):65-71 (1991); Rafalski et al., EMBO J 3(6):1409-15 (1984); Piston et al., Mol Breed 23(4):655-667 (2009); Derose et al., Plant Mol Biol 32(6): 1029-35 (1997); and PCT Application Pub. No. WO 1999/016890); a granule bound starch synthase (waxy) gene (see, e.g., Merida et al., Plant Physiol. 120(2):401-410 (1999)), a LMW or HMW glutenin or glutelin gene (see, e.g., Thilmony et al., GM Crops Food, 5(1): 36-43 (2014); Furtado et al., Plant Biotechnol J 7(3):240-53 (2009); Furtado et al., Plant Biotechnol J 6(7):679-93 (2008); Lamacchia et al., J Exp Bot 52(355):243-50 (2001); Osvald et al., In Vitro Cellular & Dev Biol. Plant 44(1): 1-7 (2008); Qu et al., J Exp Bot 59(9):2417-2424 (2008); and Colot et al., Mol Gen Genet 216:81-90 (1989)), a Ciml (cytokinin-induced message) gene, a seed-preferred ADP-glucose pyrophosphorylase gene, such as a maize shrunken gene, a globulin-1 (Glb-1) or alpha-globulin gene (see, e.g., Wu et al., Plant Cell Physiology 39(8) 885-889 (1998); and Nakase et al. Plant Mol. Biol. 33(3):513-522 (1997)), a REB1/0HP-1 gene, a DOF gene (see, e.g., Mena et al, The Plant Journal, 116(1): 53-62 (1998), a lipid transfer protein (ltp) gene, such as a Ltp1 or Ltp2 gene (see, e.g., PCT Application Pub Nos. WO 1995/15389 and WO 1995/23230; and Kalla et al., The Plant J. 6(6): 849-60 (1994)), a SPA gene (see, e.g., Albani et al, The Plant Cell 9:171-184 (1997), a rice OSH1 gene (see, e.g., Sato et al, PNAS USA 93(15): 8117-8122 (1996)), an oleosin gene (see, e.g., Wu et al, J. Biochem 123: 386-391 (1998)), an ESR gene (see, e.g., Opsahl-Ferstad et al., Plant J. 12(1): 235-46 (1997), a KNOX gene (see, e.g., Postma-Haarsma et al, Plant Mol. Biol. 39(2): 257-71 (1999)), an amylase gene (see, e.g., Lanahan et al, The Plant Cell 4: 203-211 (1992); Yu et al., Gene 122(2): 247-253 (1992); and Shiver et al, PNAS USA 88(16): 7266-7270 (1991)), cathepsin Beta-like gene (see, e.g., Cejudo et al., Plant Mol Biol 20(5): 849-856 (1992)), chitinase or Chi26 gene (see, e.g., Leah et al., Plant J. 6(4): 579-89, 1994), B-Peru gene allele (see, e.g., Selinger et al., Genetics 149(2); 1125-38 (1998)), blz2 gene (see, e.g., Onate et al., J Biol Chem 274(14): 9175-82 (1999)), a trypsin inhibitor gene, such as Itr1 (see, e.g., Diaz et al., Mol Gen Genet 248(5): 592-8 (1995)), an end1 or end2 gene (see, e.g., PCT Application Pub No. WO 2000/12733), an alanine aminotransferase gene (see, e.g., Qu et al., Plant Biotechnol. J. 2: 113-125 (2004)), a glycine rich RNA binding (GRP) protein (see, e.g., U.S. Pat. No. 6,376,750), a ZM.39486 gene (see, e.g., U.S. Pat. No. 7,518,035), or a milps (myo-inositol-1-phosphate synthase) gene (see, e.g., U.S. Pat. No. 6,225,529), or a PRO0005, PRO0058, PRO0095, PRO0117, PRO0151, PRO0173, or PRO0175 promoter (see, e.g., WO 2004/070039), or a functional portion of any of the foregoing known seed promoters, or a promoter sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to any of the foregoing known seed promoters, or any functional portion thereof. All of the above-cited references are incorporated herein by reference in their entirety. In another aspect, a seed or kernel promoter comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 210-217, or a functional portion thereof. In another aspect, a seed or kernel promoter is from a maize putative embryo-specific (Esp) gene promoter and/or comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 174, or a functional portion thereof.

The following are exemplary promoters of the present specification.

TABLE 3

Exemplary promoters

| SEQ ID NO. | Expression Pattern | Sequence Name | Source organism |
| --- | --- | --- | --- |
| 200 | Meristem Preferred | P-Zm.H2a-1-1:1:1 | Zea mays |
| 201 | Meristem Preferred | P-At.Erl1:3 | Arabidopsis thaliana |
| 202 | Meristem Preferred | P-Zm.Wus1 | Zea mays |
| 203 | Meristem Preferred | P-Zm.RAMOSA3 | Zea mays |
| 204 | Meristem Preferred | P-Zm.PCNA2 | Zea mays |
| 205 | Meristem Preferred | P-Zm.WAK | Zea mays |
| 206 | Root Preferred | P-Os.Rcc3-1:1:24 | Oryza sativa |
| 207 | Root Preferred | P-SETit.Ifr-1:1:2 | Setaria italica |
| 208 | Root Preferred | P-At.Mt-1a-1:1:1 | Arabidopsis thaliana |

TABLE 3-continued

Exemplary promoters

| SEQ ID NO. | Expression Pattern | Sequence Name | Source organism |
|---|---|---|---|
| 209 | Root Preferred | P-Zm.RCC3 | Zea mays |
| 210 | Seed Preferred | P-At.rd29b-1:1:8 | Arabidopsis thaliana |
| 211 | Seed Preferred | P-Zm.Nac-1:1:2 | Zea mays |
| 212 | Seed Preferred | P-Zm.Esp-1:1:1 | Zea mays |
| 213 | Seed Preferred | P-At.Cab1-1:1:1 | Arabidopsis thaliana |
| 214 | Seed Preferred | P-Zm.Bt1-1:1:1 | Zea mays |
| 215 | Seed Preferred | P-Zm.Zein | Zea mays |
| 216 | Seed endosperm Preferred | P-Zm.39486-1:1:1 | Zea mays |
| 217 | Seed endosperm Preferred | P-Zm.miR167g-1:1:8 | Zea mays |

In addition to its associated promoter, a transcribable DNA sequence or a transgene can also be operatively linked to one or more additional regulatory element(s), such as an enhancer(s), leader, transcription start site (TSS), linker, 5' and 3' untranslated region(s) (UTRs), intron(s), polyadenylation signal, termination region or sequence, etc., that are suitable, necessary or preferred for strengthening, regulating or allowing expression of the transcribable DNA sequence in a plant cell. Such additional regulatory element(s) can be optional and/or used to enhance or optimize expression of the transgene or transcribable DNA sequence. As provided herein, an "enhancer" can be distinguished from a "promoter" in that an enhancer typically lacks a transcription start site, TATA box, or equivalent sequence and is thus insufficient alone to drive transcription. As used herein, a "leader" can be defined generally as the DNA sequence of the 5'-UTR of a gene (or transgene) between the transcription start site (TSS) and 5' end of the transcribable DNA sequence or protein coding sequence start site of the transgene.

In an aspect, the second DNA sequence encoding one or more MADS-box polypeptides comprised in a recombinant DNA construct of the present application is operably linked to a plant-expressible promoter, such as a constitutive or tissue-specific promoter. According to an aspect, the plant-expressible promoter is a medium or high-constitutive promoter with a high-constitutive promoter having a relatively more robust or strong constitutive expression. In an aspect, the plant-expressible promoter is a constitutive promoter, which can be selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

In an aspect, a transformation vector comprising the recombinant DNA construct is produced. In another aspect, a transgenic corn plant or a plant part thereof comprising the recombinant DNA construct is produced. In still another aspect, the transgenic corn plant is semi-dwarf and has one or more improved ear traits, relative to a control corn plant not having both the first transcribable DNA sequence and the second DNA sequence.

A recombinant DNA molecule or construct of the present disclosure can comprise or be included within a DNA transformation vector for use in transformation of a target plant cell, tissue or explant. Such a transformation vector can generally comprise sequences or elements necessary or beneficial for effective transformation in addition to at least one transgene, expression cassette and/or transcribable DNA sequence.

For Agrobacterium-mediated, Rhizobia-mediated or other bacteria-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. Thus, a transcribable DNA sequence, transgene or expression cassette can be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant. According to alternative aspects, the transcribable DNA sequence, transgene or expression cassette encoding a non-coding RNA molecule targeting an endogenous GA oxidase gene for suppression and the plant selectable marker transgene (or other gene of agronomic interest) can be present in separate T-DNA segments on the same or different recombinant DNA molecule(s), such as for co-transformation. A transformation vector or construct can further comprise prokaryotic maintenance elements, which can be located in the vector outside of the T-DNA region(s).

The present disclosure provides a modified corn plant with a semi-dwarf phenotype and one or more improved ear traits relative to a control plant. The modified corn plant has its expression of one or more GA20 oxidase genes and/or one or more GA3 oxidase genes reduced and comprises a transgene expressing one or more MADS-box polypeptides. In an aspect, the reduced expression of the one or more GA20 oxidase genes and/or one or more GA3 oxidase genes is caused by a mutation or edit at or near the one or more GA20 oxidase genes and/or GA3 oxidase genes introduced via genome editing. In another aspect, the reduced expression of one or more GA20 oxidase genes and/or one or more GA3 oxidase genes is caused by a site-directed integration of a transcribable DNA sequence encoding a non-coding RNA for suppression of the one or more GA20 oxidase genes and/or one or more GA3 oxidase genes. In an aspect, the site-directed integration is mediated by genome editing. In an aspect, the introduction of the transgene expressing one or more MADS-box polypeptides is caused by a site-directed integration of a sequence comprising the transgene. In another aspect, the site-directed integration is mediated by genome editing.

In an aspect, a genome editing system provided herein comprises a CRISPR system. The CRISPR systems are based on RNA-guided engineered nucleases that use complementary base pairing to recognize DNA sequences at target sites. In an aspect, a vector provided herein can comprise any combination of a nucleic acid sequence encoding a RNA-guided nuclease.

In an aspect, a method and/or composition provided herein comprises one or more, two or more, three or more, four or more, or five or more Cas9 nucleases. In an aspect, a method and/or composition provided herein comprises one or more polynucleotides encoding one or more, two or more, three or more, four or more, or five or more Cas9 nucleases. In another aspect, a Cas9 nuclease provided herein is capable of generating a targeted DSB. In an aspect, a method and/or composition provided herein comprises one or more, two or more, three or more, four or more, or five or more Cpf1 nucleases. In an aspect, a method and/or composition provided herein comprises one or more polynucleotides encoding one or more, two or more, three or more, four or more, or five or more Cpf1 nucleases. In another aspect, a Cpf1 nuclease provided herein is capable of generating a targeted DSB.

In an aspect, a vector or construct provided herein comprises polynucleotides encoding at least 1, at least 2, at least 3, at least 4, at least 5, at least 6, at least 7, at least 8, at least 9, or at least 10 site-specific nuclease. In another aspect, a cell provided herein already comprises a site-specific nuclease. In an aspect, a polynucleotide encoding a site-specific nuclease provided herein is stably transformed into a cell. In another aspect, a polynucleotide encoding a site-specific nuclease provided herein is transiently transformed into a cell. In another aspect, a polynucleotide encoding a site-specific nuclease is under the control of a regulatable promoter, a constitutive promoter, a tissue specific promoter, or any promoter useful for expression of the site-specific nuclease.

In an aspect, vectors comprising polynucleotides encoding a site-specific nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

In an aspect, a vector comprises in cis a cassette encoding a site-specific nuclease and an insertion sequence such that when contacted with the genome of a cell, the site-specific nuclease enables site-specific integration of the insertion sequence. In an aspect, a first vector comprises a cassette encoding a site-specific nuclease and a second vector comprises an insertion sequence such that when contacted with the genome of a cell, the site-specific nuclease provided in trans enables site-specific integration of the insertion sequence.

Site-specific nucleases provided herein can be used as part of a targeted editing technique. Non-limiting examples of site-specific nucleases used in methods and/or compositions provided herein include meganucleases, zinc finger nucleases (ZFNs), transcription activator-like effector nucleases (TALENs), RNA-guided nucleases (e.g., Cas9 and Cpf1), a recombinase (without being limiting, for example, a serine recombinase attached to a DNA recognition motif, a tyrosine recombinase attached to a DNA recognition motif), a transposase (without being limiting, for example, a DNA transposase attached to a DNA binding domain), or any combination thereof. In an aspect, a method provided herein comprises the use of one or more, two or more, three or more, four or more, or five or more site-specific nucleases to induce one, two, three, four, five, or more than five DSBs at one, two, three, four, five, or more than five target sites.

In an aspect, a genome editing system provided herein (e.g., a meganuclease, a ZFN, a TALEN, a CRISPR/Cas9 system, a CRISPR/Cpf1 system, a recombinase, a transposase), or a combination of genome editing systems provided herein, is used in a method to introduce one or more insertions, deletions, substitutions, or inversions to a locus in a cell to introduce a mutation, or generate a dominant negative allele or a dominant positive allele.

Site-specific nucleases, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), Natronobacterium gregoryi Argonaute (NgAgo), homologs thereof, or modified versions thereof), Cas9 nucleases (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof), induce a double-strand DNA break at the target site of a genomic sequence that is then repaired by the natural processes of HR or NHEJ. Sequence modifications then occur at the cleaved sites, which can include inversions, deletions, or insertions that result in gene disruption in the case of NHEJ, or integration of nucleic acid sequences by HR.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1.

In another aspect a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof. In another aspect, an RNA-guided nuclease provided herein is selected from the group consisting of a Cas9 or a Cpf1.

In another aspect an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof.

In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof, an Argonaute (non-limiting examples of Argonaute proteins include *Thermus thermophilus* Argonaute (TtAgo), *Pyrococcus furiosus* Argonaute (PfAgo), Natronobacterium gregoryi Argonaute (NgAgo), homologs thereof, modified versions thereof), a DNA guide for an Argonaute protein, and any combination thereof. In another aspect, an RNA-guided nuclease provided herein is selected from the group consisting of Cas9 and Cpf1.

In another aspect, an RNA-guided nuclease provided herein comprises Cas9. In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In an aspect a site-specific nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo. In another aspect, an RNA-guided nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can also be positioned upstream or downstream of a sequence encoding a leader, an enhancer, a transcriptional start site, a promoter, a 5'-UTR, an exon, an intron, a 3'-UTR, a polyadenylation site, or a termination sequence. In an aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

In an aspect, a target site bound by an RNA-guided nuclease is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In an aspect, a targeted genome editing technique described herein can comprise the use of a recombinase. In an aspect, a tyrosine recombinase attached to a DNA recognition motif is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA binding domain. The Flp-FRT site-directed recombination system comes from the 2μ plasmid from the baker's yeast *Saccharomyces cerevisiae*. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif.

ZFNs are synthetic proteins consisting of an engineered zinc finger DNA-binding domain fused to the cleavage domain of the FokI restriction nuclease. ZFNs can be designed to cleave almost any long stretch of double-stranded DNA for modification of the zinc finger DNA-binding domain. ZFNs form dimers from monomers composed of a non-specific DNA cleavage domain of FokI nuclease fused to a zinc finger array engineered to bind a target DNA sequence.

DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

FokI nuclease domain requires dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs can be introduced as ZFN proteins, as polynucleotides encoding ZFN proteins, and/or as combinations of proteins and protein-encoding polynucleotides.

In an aspect, a method and/or composition provided herein comprises one or more, two or more, three or more, four or more, or five or more ZFNs. In another aspect, a ZFN provided herein is capable of generating a targeted DSB. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or *Agrobacterium*-mediated transformation).

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some aspects, a meganuclease can comprise a scaffold or base enzyme selected from the group consisting of I-CreI, I-CeuI, I-MsoI, I-SceI, I-AniI, and I-DrnoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease can be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI and FokI, AlwI, MlyI, SbfI, SdaI, StsI, CleDORF, Clo051, Pept071. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research*. 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNAWorks can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation).

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase.

Provided in the present disclosure is a modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a MADS-box polypeptide, wherein the DNA sequence is operably linked to a plant-expressible promoter. In an aspect, the modified corn plant is semi-dwarf and has one or more improved ear traits, relative to a control corn plant that does not comprise both the one or more mutations or edits and the recombinant expression cassette. In another aspect, the one or more mutations or edits are selected from the group consisting of an insertion, a substitution, an inversion, a deletion, a duplication, and a combination thereof. In yet another aspect, the one or more mutations or edits are introduced using a meganuclease, a zinc-finger nuclease (ZFN), a RNA-guided endonuclease, a TALE-endonuclease (TALEN), a recombinase, or a transposase.

Also provided is a plurality of modified corn plants in a field, each modified corn plant comprising one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and a recombinant expression cassette comprising a DNA sequence encoding a MADS-box polypeptide, wherein the DNA sequence is operably linked to a plant-expressible promoter. In an aspect, the modified corn plants have increased yield relative to control corn plants. In another aspect, the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants. In an aspect, such a plant-expressible promoter is a root promoter, such as a root-specific or root-preferred promoter. In another aspect, such a plant-expressible promoter is a meristem promoter, such as a meristem-specific promoter or a meristem-preferred promoter. In another aspect, such a plant-expressible promoter is a kernel or seed promoter, such as a seed-preferred or seed-specific promoter. In an aspect, a root promoter is an *Oryza sativa* Rcc3 gene promoter. In an aspect, a plant-expressible or root promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 170, or a functional portion thereof. In an aspect, a seed or kernel promoter is a maize putative embryo-specific (Esp) gene promoter. In an aspect, a plant-expressible or seed or kernel promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 174, or a functional portion thereof.

Also provided is a genome edited or mutated corn plant comprising (1) a mutation or edit at or near an endogenous GA20 oxidase or GA3 oxidase gene, wherein the expression of the endogenous GA20 oxidase or GA3 oxidase gene is reduced relative to a wildtype control, and (2) a heterologous DNA sequence encoding a MADS-box polypeptide. In an aspect, the genome edited or mutated corn plant is semi-dwarf and has one or more improved ear traits, relative to a control corn plant that does not comprise both the mutation and the heterologous DNA sequence. In an aspect, a genome edited or mutated corn cell is obtained via a CRISPR based genome editing system.

Aspects of the present disclosure further include methods for making or producing modified plants, such as by genome editing, crossing, etc., wherein the method comprises editing the genomic locus of an endogenous GA3 or GA20 oxidase gene and introducing a transgene encoding one or more MADS-box polypeptide, and then regenerating or developing the modified plant from the edited plant cell.

In an aspect, a method comprises introducing a mutation or edit via CRISPR based genome editing at or near one or more endogenous GA3 or GA20 oxidase genes to reduce the expression of the one or more endogenous GA3 or GA20 oxidase genes. The method comprises creating a double-stranded break (DSB) in the genome of the plant cell, wherein a mutation or edit is introduced therein, thereby reducing the expression of the one or more endogenous GA3 or GA20 oxidase genes. In an aspect, the mutation or edit can be created (or integrated with a donor template) in a targeted manner into the genome of a cell at the location of a DSB via RNA-guided nucleases (e.g., Cas9 and Cpf1). In another aspect, a guide RNA recognizes a target site and acts in association with an RNA-guided nuclease that creates a DSB at the target site, wherein a mutation or edit is created (or integrated with a donor template) into the target site. In another aspect, the target site is near or at one or more endogenous GA3 or GA20 oxidase genes.

In an aspect, a method comprises introducing an insertion sequence encoding one or more MADS-box polypeptides into the genome of a plant cell via site-directed integration. Such a method comprises creating a DSB in the genome of the plant cell such that the insertion sequence is integrated at the site of the DSB. In an aspect, the insertion sequence encoding one or more MADS-box polypeptides can be inserted or integrated in a targeted manner into the genome of a cell at the location of a DSB via RNA-guided nucleases (e.g., Cas9 and Cpf1) in a CRISPR based genome editing system. In another aspect, a guide RNA recognizes a target site and acts in association with an RNA-guided nuclease that creates a double-stranded break at the target site, wherein the insertion sequence encoding one or more MADS-box polypeptides inserts or integrates into the target site.

In an aspect, an insertion sequence of a donor template of the present disclosure comprises a DNA sequence encoding a MADS-box polypeptide, wherein the MADS-box polypeptide sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 175-199 and a functional fragment thereof.

In an aspect, an insertion sequence of a donor template of the present disclosure comprises a DNA sequence encoding a ZMM19 polypeptide, wherein the DNA sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169. In another aspect, an insertion sequence of the present disclosure comprises a DNA sequence encoding a polypeptide comprising an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof.

Provided in the present disclosure is a method for producing a modified corn plant, the method comprising: introducing into a corn cell a recombinant expression cassette comprising a DNA sequence encoding a MADS-box polypeptide, wherein the DNA sequence is operably linked to a plant-expressible promoter, and wherein the corn cell comprises one or more mutations and/or edits in one or more endogenous GA3 oxidase and/or GA20 oxidase genes; and regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits. In an aspect, the method further comprises introducing a recombinant DNA construct encoding a guide RNA that targets the one or more endogenous GA3 oxidase and/or GA20 oxidase genes. In an aspect, such a plant-expressible promoter is a root promoter, such as a root-specific or root-preferred promoter. In another aspect, such a plant-expressible promoter is a meristem promoter, such as a meristem-specific promoter or a meristem-preferred promoter. In another aspect, such a plant-expressible promoter is a kernel or seed promoter, such as a seed-preferred or seed-specific promoter. In an aspect, a root promoter is an *Oryza sativa* Rcc3 gene promoter. In an aspect, a plant-expressible or root promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 170, or a functional portion thereof. In an aspect, a seed or kernel promoter is from a maize putative embryo-specific (Esp) gene promoter. In an aspect, a plant-expressible or seed or kernel promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 174, or a functional portion thereof.

In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes. In another aspect, In yet another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto. In an aspect, the guide RNA is a CRISPR RNA (crRNA) or a single-chain guide RNA (sgRNA), or the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

Also provided is a method for producing a genome edited or mutated corn plant, the method comprising: (a) introducing into a first corn cell a transgene that encodes one or more MADS-box polypeptides to create a genome edited or mutated corn cell, wherein the first corn cell has its expression of one or more endogenous GA3 oxidase genes or GA20 oxidase genes reduced relative to a wildtype control; and (b) generating a genome edited or mutated corn plant from the genome edited or mutated corn cell. In an aspect, the method further comprises identifying a genome edited or mutated corn plant with a desired trait. In another aspect, the identified genome edited or mutated corn plant is semi-dwarf and has one or more improved ear traits, relative to a control corn plant not having both the transgene and a reduced expression of one or more endogenous GA3 oxidase genes or GA20 oxidase genes.

In another aspect, the first corn cell of step (a) is obtained by being provided with a first guide RNA and a first RNA-guided nuclease, and wherein the genome edited or mutated corn cell of step (b) is obtained by being provided with a second guide RNA, an insertion sequence, and a second RNA-guided nuclease.

In another aspect, the first guide RNA recognizes a target site in a GA20 oxidase, wherein the first guide RNA acts in association with the first RNA-guided nuclease that creates a double-stranded break at the target site, and whereby the expression of the endogenous GA20 oxidase is reduced.

In another aspect, the method further comprises integrating into the double-stranded break at least one insertion, at least one substitution, at least one inversion, at least one deletion, at least one duplication, or a combination thereof.

In yet another aspect, the second guide RNA recognizes a target site and acts in association with the second RNA-guided nuclease that creates a double-stranded break at the target site, wherein the insertion sequence integrates into the target site, and wherein the donor/insertion sequence encodes a MADS-box polypeptide, such as ZMM19 polypeptide.

Provided in the present disclosure is A method for producing a modified corn plant, the method comprising: mutating or editing one or more endogenous GA3 oxidase genes and/or one or more GA20 oxidase genes in a corn cell, wherein the corn cell comprises a recombinant expression cassette encoding a MADS-box polypeptide, wherein the DNA sequence is operably linked to a plant-expressible promoter; and regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

In an aspect, the mutating or editing is obtained by using a site-specific nuclease selected from the group consisting of a RNA-guided endonuclease, a meganuclease, a zinc-finger nuclease (ZFN), a TALE-endonuclease (TALEN), a recombinase, and a transposase. In another aspect, a method further comprises introducing a recombinant DNA construct encoding a guide RNA that targets the one or more endogenous GA3 oxidase and/or GA20 oxidase genes. In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto. In another aspect, the guide RNA is a CRISPR RNA (crRNA) or a single-chain guide RNA (sgRNA). In yet another aspect, the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

Also provided is a method for producing a genome edited or mutated corn plant, the method comprising: (a) reducing the expression of one or more endogenous GA3 oxidase genes or GA20 oxidase genes in a first corn cell to create a genome edited or mutated corn cell, wherein the first corn cell comprises a transgene that encodes one or more MADS-box polypeptides; and (b) generating a genome edited or mutated corn plant from the genome edited or mutated corn cell. In an aspect, the method further comprises identifying a genome edited or mutated corn plant with a desired trait. In another aspect, the identified genome edited or mutated corn plant is semi-dwarf and has one or more improved ear traits, relative to a control corn plant not having both the transgene and a reduced expression of one or more endogenous GA3 oxidase genes or GA20 oxidase genes.

In an aspect, the first corn cell of step (a) is obtained by being provided with a first guide RNA, an insertion sequence, and a first RNA-guided nuclease, and wherein the genome edited or mutated corn cell of step (b) is obtained by being provided with a second guide RNA and a second RNA-guided nuclease.

In another aspect, the first guide RNA recognizes a target site and acts in association with the first RNA-guided nuclease that creates a double-stranded break at the target site, wherein the insertion sequence integrates into the target site, and wherein the insertion sequence encodes a ZMM19 polypeptide.

In another aspect, the second guide RNA recognizes a target site in a GA20 oxidase, wherein the second guide RNA acts in association with the second RNA-guided nuclease that creates a double-stranded break at the target site, and whereby the expression level of the endogenous GA20 oxidase is reduced.

The gRNA can be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. The guide sequence of the guide RNA can be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence can be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

For genome editing at or near the GA20 oxidase_3 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 34 or a sequence complementary thereto (e.g., 12, 13, 14, 15, 16, 17, 18, 19, 20, 21, 22, 23, 24, 25 or more consecutive nucleotides of SEQ ID NO: 34 or a sequence complementary thereto).

For genome editing at or near the GA20 oxidase_4 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 38 or a sequence complementary thereto (e.g., 12, 13, 14, 15, 16, 17, 18, 19, 20, 21, 22, 23, 24, 25 or more consecutive nucleotides of SEQ ID NO: 38 or a sequence complementary thereto).

For genome editing at or near the GA20 oxidase_5 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 35 or a sequence complementary thereto (e.g., 10, 11, 12, 13, 14, 15, 16, 17, 18, 19, 20, 21, 22, 23, 24, 25 or more consecutive nucleotides of SEQ ID NO: 35 or a sequence complementary thereto).

In an aspect, a guide RNA for targeting an endogenous GA20 oxidase_3 and/or GA20 oxidase_5 gene is provided comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 138-167.

For genome editing at or near the GA3 oxidase_1 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 36 or a sequence complementary thereto (e.g., 10, 11, 12, 13, 14, 15, 16, 17, 18, 19, 20, 21, 22, 23, 24, 25 or more consecutive nucleotides of SEQ ID NO: 36 or a sequence complementary thereto).

For genome editing at or near the GA3 oxidase_2 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 37 or a sequence complementary thereto (e.g., 10, 11, 12, 13, 14, 15, 16, 17, 18, 19, 20, 21, 22, 23, 24, 25 or more consecutive nucleotides of SEQ ID NO: 37 or a sequence complementary thereto).

In an aspect, a guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 87, 91, 95, 98, 105, 109, 113, 117, 122, 126, 130 or 137, or a sequence complementary thereto.

In an aspect, a guide RNA comprises a sequence complementary to a protospacer adjacent motif (PAM) sequence present in the genome of a corn plant immediately adjacent to a target DNA sequence at or near the genomic locus of one or more endogenous GA20 or GA3 oxidase gene.

In addition to the guide sequence, a guide RNA can further comprise one or more other structural or scaffold sequence(s), which can bind or interact with an RNA-guided endonuclease. Such scaffold or structural sequences can further interact with other RNA molecules (e.g., tracrRNA). Methods and techniques for designing targeting constructs and guide RNAs for genome editing and site-directed integration at a target site within the genome of a plant using an RNA-guided endonuclease are known in the art.

Mutations such as deletions, insertions, inversions and/or substitutions can be introduced at a target site via imperfect repair of the DSB or nick to produce a knock-out or knock-down of a GA oxidase gene. Such mutations can be generated by imperfect repair of the targeted locus even without the use of a donor template molecule. A "knock-out" of a GA oxidase gene can be achieved by inducing a DSB or nick at or near the endogenous locus of the GA oxidase gene that results in non-expression of the GA oxidase protein or expression of a non-functional protein, whereas a "knock-down" of a GA oxidase gene can be achieved in a similar manner by inducing a DSB or nick at or near the endogenous locus of the GA oxidase gene that is repaired imperfectly at a site that does not affect the coding sequence of the GA oxidase gene in a manner that would eliminate the function of the encoded GA oxidase protein.

For example, the site of the DSB or nick within the endogenous locus can be in the upstream or 5' region of the GA oxidase gene (e.g., a promoter and/or enhancer sequence) to affect or reduce its level of expression. Similarly, such targeted knock-out or knock-down mutations of a GA oxidase gene can be generated with a donor template molecule to direct a particular or desired mutation at or near the target site via repair of the DSB or nick.

The donor template molecule can comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a GA oxidase gene can be achieved by deleting or inverting at least a portion of the gene or by introducing a frame shift or premature stop codon into the coding sequence of the gene. A deletion of a portion of a GA oxidase gene can also be introduced by generating DSBs or nicks at two target sites and causing a deletion of the intervening target region flanked by the target sites.

Provided herein is a recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a MADS-box polypeptide, wherein the DNA sequence is operably linked to a plant-expressible promoter.

In an aspect, the DNA donor template molecule comprises two of the homology sequences, wherein the two homology sequences flank the insertion sequence. In another aspect, the insertion sequence comprises a recombinant DNA construct or expression cassette comprising a DNA sequence encoding a MADS-box polypeptide, wherein the MADS-box polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199, or a functional fragment thereof.

In another aspect, the MADS-box polypeptide comprises a maize ZMM19 polypeptide. In another aspect, the DNA sequence comprised in the expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169. In another aspect, the MADS-box polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof. In another aspect, a recombinant DNA construct or expression cassette comprising a DNA sequence encoding a MADS-box polypeptide operably linked to a plant-expressible promoter. The plant-expressible promoter can comprise a DNA sequence that is at least 80%, at least 85%, at least 90%, at least 95%, at least 96%, at least 97%, at least 98%, at least 99%, at least 99.5% or 100% identical to SEQ ID NO: 170, 174, or a functional portion thereof. In another aspect, the plant-expressible promoter is selected from the group consisting of a meristem promoter, a root promoter, a seed or kernel promoter, and a combination thereof.

In another aspect, a DNA donor template molecule further comprises a transcribable DNA sequence encoding a non-coding RNA for suppression of one or more GA20 oxidase genes and/or one or more GA3 oxidase genes, wherein the transcribable DNA sequence is operably linked to a promoter.

In an aspect, a donor template comprising at least one homology sequence or homology arm, wherein the at least one homology sequence or homology arm is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of an endogenous GA oxidase gene of a corn or cereal plant.

In another aspect, the at least one homology sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In an aspect, a donor template comprising two homology arms including a first homology arm and a second homology arm, wherein the first homology arm comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a first flanking DNA sequence, wherein the second homology arm comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a second flanking DNA sequence, and wherein the first flanking DNA sequence and the second flanking DNA sequence are genomic sequences at or near the genomic locus of an endogenous GA oxidase gene of a corn or cereal plant.

In another aspect, each of the two homology arms is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In another aspect, the method further comprises integrating into the double-stranded break at least one insertion, at least one substitution, at least one inversion, at least one deletion, at least one duplication, or a combination thereof.

In yet another aspect, an insertion sequence of a donor template comprises a sequence encoding a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NOs: 168, or a functional fragment thereof. In still another aspect, an insertion sequence of a donor template comprises a sequence encoding a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 175-199 and a functional fragment thereof.

Further provided is a method for producing a modified corn plant, the method comprising: (a) crossing a first corn plant with a second corn plant to create a modified corn plant, wherein the expression of one or more endogenous GA3 oxidase genes or GA20 oxidase genes is reduced in the first corn plant relative to a wildtype control, and wherein the second corn plant comprising a transgene encoding one or more MADS-box polypeptides; and (b) producing an offspring of the modified corn plant of step (a). In an aspect, the method further comprises identifying a modified corn plant with a desired trait. In another aspect, the identified modified corn plant is semi-dwarf and has one or more improved ear traits, relative to a control corn plant not having both the transgene and a reduced expression of one or more endogenous GA3 oxidase genes or GA20 oxidase genes.

In an aspect, a target site can comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides.

In an aspect, the target site is a GA3 oxidase_1 gene. In another aspect, the target site is a GA3 oxidase_2 gene. In yet another aspect, the target site is a combination of the GA3 oxidase_1 and GA3 oxidase_2 genes. In still another aspect, the target site is within the open reading frame of the GA3 oxidase_1 or GA3 oxidase_2 gene. In still another aspect, the target site is within the promoter/enhancer of the GA3 oxidase_1 or GA3 oxidase_2 gene. In still another aspect, the target site is within the intron of the GA3 oxidase_1 or GA3 oxidase_2 gene. In still another aspect, the target site is within the 5'UTR of the GA3 oxidase_1 or GA3 oxidase_2 gene. In still another aspect, the target site is within the 3'UTR of the GA3 oxidase_1 or GA3 oxidase_2 gene.

In an aspect, the target site is a GA20 oxidase_3 gene. In another aspect, the target site is a GA20 oxidase_4 gene. In another aspect, the target site is a GA20 oxidase_5 gene. In yet another aspect, the target site is a combination of the GA20 oxidase_3 gene, GA20 oxidase_4 gene, and GA20 oxidase_5 gene. In still another aspect, the target site is within the open reading frame of the GA20 oxidase_3, GA20 oxidase_4, or GA20 oxidase_5 gene. In still another aspect, the target site is within the promoter/enhancer of the GA20 oxidase_3, GA20 oxidase_4, or GA20 oxidase_5 gene. In still another aspect, the target site is within the intron of the GA20 oxidase_3, GA20 oxidase_4, or GA20 oxidase_5 gene. In still another aspect, the target site is within the 5'UTR of the GA20 oxidase_3, GA20 oxidase_4, or GA20 oxidase_5 gene. In still another aspect, the target site is within the 3'UTR of the GA20 oxidase_3, GA20 oxidase_4, or GA20 oxidase_5 gene.

In an aspect, the target site comprises a nucleotide sequence selected from the group consisting of SEQ ID NOs: 34, 35, and 38.

A targeted genome editing technique provided herein can comprise the use of one or more, two or more, three or more, four or more, or five or more donor molecules or templates. A "donor template" can be a single-stranded or double-stranded DNA or RNA molecule or plasmid.

According to other aspects, an insertion sequence of a donor template can comprise a transcribable DNA sequence that encodes a non-coding RNA molecule, which targets one or more GA oxidase gene(s), such as a GA3 oxidase or GA20 oxidase gene(s), for suppression. In an aspect, the transcribable DNA sequence that encodes a non-coding RNA for the suppression of the GA3 oxidase and/or GA20 oxidase gene(s) is selected from the group consisting of SEQ ID NOs: 35-38. In another aspect, an insertion sequence of a donor template can comprise a DNA sequence encoding one or more MADS-box polypeptides, wherein the DNA sequence encodes protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and 175-199. In yet another aspect, an insertion sequence of a donor template can comprise a first transcribable DNA sequence encoding a non-coding RNA molecule for the suppression of the one or more GA3 oxidase or GA20 oxidase gene(s), wherein the first transcribable DNA sequence is selected from the group consisting of SEQ ID NOs: 35-38; and an insertion sequence of a donor template can comprise a second DNA sequence encoding one or more MADS-box polypeptides, wherein the second DNA sequence encodes a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and 175-199, or a functional fragment thereof.

An insertion sequence provided herein can be of any length. For example, a donor or insertion sequence provided herein is between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000 or between 20 and 10,000 nucleotides in length.

In an aspect, a sequence can be inserted into a double-stranded break created by a CRISPR based genome editing system without the presence of a donor template. In an aspect, at least one insertion, at least one substitution, at least one deletion, at least one duplication, and/or at least one inversion can be inserted/introduced into a double-stranded break created by a CRISPR based genome editing system via non-homologous end joining (NHEJ) without a donor template. In an aspect, at least one insertion, at least one substitution, at least one deletion, at least one duplication, and/or at least one inversion can be inserted/introduced into a double-stranded break created by a CRISPR based genome editing system via homologous recombination (HR) with a donor template.

According to other aspects, at least one insertion is integrated into the double-stranded break at the GA3 oxidase or GA20 oxidase locus and introduces a premature stop codon therein which leads to truncation of the GA3 oxidase or GA20 oxidase proteins and subsequent suppression of the GA3 oxidase or GA20 oxidase genes. In an aspect, the at least one insertion is a single nucleobase insertion. In another aspect, the single nucleobase insertion is selected from the group consisting of guanine, cytosine, adenine, thymine, and uracil. In an aspect, the at least one insertion is inserted within the open reading frame of the GA3 oxidase or GA20 oxidase gene. In another aspect, the at least one insertion is inserted within the promoter/enhancer, intron, 5'UTR, 3'UTR, or a combination thereof.

In another aspect, the at least one insertion at the GA3 oxidase or GA20 oxidase locus comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

According to an aspect, at least one substitution is integrated into the double-stranded break at the GA3 oxidase or GA20 oxidase locus that leads to the suppression of the GA3 oxidase or GA20 oxidase gene. In an aspect, the at least one substitution is integrated within the open reading frame of the GA3 oxidase or GA20 oxidase gene. In another aspect, the at least one substitution is integrated within the promoter/enhancer, intron, 5' UTR, 3' UTR, or a combination thereof.

According to an aspect, at least one deletion is introduced into the double-stranded break at the GA3 oxidase or GA20 oxidase locus that leads to the suppression of the GA3 oxidase or GA20 oxidase gene. In an aspect, the at least one deletion is introduced within the open reading frame of the GA3 oxidase or GA20 oxidase gene. In another aspect, the at least one deletion is introduced within the promoter/enhancer, intron, 5'UTR, 3'UTR, or a combination thereof.

According to an aspect, at least one duplication is introduced into the double-stranded break at the GA3 oxidase or GA20 oxidase locus that leads to the suppression of the GA3 oxidase or GA20 oxidase gene. In an aspect, the at least one duplication is introduced within the open reading frame of the GA3 oxidase or GA20 oxidase gene. In another aspect, the at least one duplication is introduced within the promoter/enhancer, intron, 5'UTR, 3'UTR, or a combination thereof.

According to an aspect, at least one inversion is integrated into the double-stranded break at the GA3 oxidase or GA20 oxidase locus that leads to the suppression of the GA3 oxidase or GA20 oxidase gene. In an aspect, the at least one inversion is integrated within the open reading frame of the GA3 oxidase or GA20 oxidase gene. In another aspect, the at least one inversion is integrated within the promoter/enhancer, intron, 5'UTR, 3'UTR, or a combination thereof.

According to an aspect, a recombinant DNA construct or vector can comprise a first polynucleotide sequence encoding a site-specific nuclease and a second polynucleotide sequence encoding a guide RNA that can be introduced into a plant cell together via plant transformation techniques. Alternatively, two recombinant DNA constructs or vectors can be provided including a first recombinant DNA construct or vector and a second DNA construct or vector that can be introduced into a plant cell together or sequentially via plant transformation techniques, where the first recombinant DNA construct or vector comprises a polynucleotide sequence encoding a site-specific nuclease and the second recombinant DNA construct or vector comprises a polynucleotide sequence encoding a guide RNA.

According to an aspect, a recombinant DNA construct or vector comprising a polynucleotide sequence encoding a site-specific nuclease can be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA can be introduced via plant transformation techniques into a plant cell that already comprises (or is transformed with) a recombinant DNA construct or vector comprising a polynucleotide sequence encoding a site-specific nuclease. According to yet further aspects, a first plant comprising (or transformed with) a recombinant DNA construct or vector comprising a polynucleotide sequence encoding a site-specific nuclease can be crossed with a second plant comprising (or transformed with) a recombinant DNA construct or vector comprising a polynucleotide sequence encoding a guide RNA. Such recombinant DNA constructs or vectors can be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Dwarf or semi-dwarf corn disclosed herein can have characteristics that make it suitable for grain and forage production, especially, production in short-season environments. In particular, limited heat units in short-season environments reduce grain yield and lessen the probability of the crop reaching physiological maturity in a given year. The disclosed dwarf or semi-dwarf corn plants require fewer heat units (e.g., required 10%) than conventional hybrids to reach anthesis and generally reach physiological maturity earlier than conventional cultivars. Semi-dwarf corn plants disclosed herein are less prone to stalk and root lodging due to the shorter stalks and lower ear placement. Corn plants disclosed herein also have the potential to produce high-quality forage due to its high ear-to-stover ratio.

Short stature or semi-dwarf corn plants can also have one or more additional traits, including, but not limited to, increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, increased seed number, increased seed weight, and increased prolificacy, and/or increased harvest index.

According to aspects of the present disclosure, modified, transgenic, or genome edited/mutated cereal or corn plants are provided that have at least one beneficial agronomic trait and at least one female reproductive organ or ear that is substantially or completely free of off-types. The beneficial agronomic trait can include, but is not limited to, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. As used herein, "harvest index" refers to the mass of the harvested grain divided by the total mass of the above-ground biomass of the plant over a harvested area.

In an aspect, a modified, transgenic, or genome edited/mutated corn plant exhibits improved lodging resistance, reduced green snap, or both, relative to a control corn plant.

In an aspect, the height at maturity of a modified, transgenic, or genome edited/mutated corn plant exhibiting semi-dwarf phenotype is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, relative to a control corn plant grown under comparable conditions.

According to another aspect of the present disclosure, a modified, transgenic, or genome edited/mutated corn plant provided herein comprises a height that is between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 15%, between 1% and 10%, between 1% and 5%, or between 1% and 2%, of that of a control plant grown under comparable conditions.

According to another aspect of the present disclosure, a modified, transgenic, or genome edited/mutated corn plant provided herein comprises a height that is between 2% and 75%, between 5% and 75%, between 10% and 75%, between 15% and 75%, between 20% and 75%, between 25% and 75%, between 30% and 75%, between 35% and 75%, between 40% and 75%, between 45% and 75%, between 50% and 75%, between 55% and 75%, between 60% and 75%, between 65% and 75%, or between 70% and 75%, of that of a control plant grown under comparable conditions.

According to another aspect of the present disclosure, a modified, transgenic, or genome edited/mutated corn plant provided herein comprises a height that is between 2% and 70%, between 5% and 65%, between 10% and 60%, between 15% and 55%, between 20% and 50%, between 25% and 45%, or between 30% and 40%, of that of a control plant grown under comparable conditions.

According to another aspect of the present disclosure, a modified, transgenic, or genome edited/mutated corn plant provided herein comprises a height that is between 1% and 10%, between 10% and 20%, between 20% and 30%, between 30% and 40%, between 40% and 50%, between 50% and 60%, between 60% and 70%, or between 70% and 80%, of that of a control plant grown under comparable conditions.

In an aspect, the stalk or stem diameter of a transgenic corn plant or genome edited/mutated corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plan grown under comparable conditions.

According to another aspect of the present disclosure, a modified, transgenic, or genome edited/mutated corn plant provided herein comprises a stalk or stem diameter that is between 0.1% and 100%, between 0.2% and 100%, between 0.5% and 100%, between 1% and 100%, between 1.5% and 100%, between 2% and 100%, between 2.5% and 100%, between 3% and 100%, between 3.5% and 100%, between 4% and 100%, between 4.5% and 100%, between 5% and 100%, between 6% and 100%, between 7% and 100%, between 8% and 100%, between 9% and 100%, between 10% and 100%, between 15% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100%, greater than that of a control corn plan grown under comparable conditions.

According to another aspect of the present disclosure, a modified, transgenic, or genome edited/mutated corn plant provided herein comprises a stalk or stem diameter that is between 0.1% and 95%, between 0.1% and 90%, between 0.1% and 85%, between 0.1% and 80%, between 0.1% and 75%, between 0.1% and 70%, between 0.1% and 65%, between 0.1% and 60%, between 0.1% and 55%, between 0.1% and 50%, between 0.1% and 45%, between 0.1% and 40%, between 0.1% and 35%, between 0.1% and 30%, between 0.1% and 25%, between 0.1% and 20%, between 0.1% and 15%, between 0.1% and 10%, between 0.1% and 9%, between 0.1% and 8%, between 0.1% and 7%, between 0.1% and 6%, between 0.1% and 5%, between 0.1% and 4.5%, between 0.1% and 4%, between 0.1% and 3.5%, between 0.1% and 3%, between 0.1% and 2.5%, between 0.1% and 2%, between 0.1% and 1.5%, between 0.1% and 1%, between 0.1% and 0.5%, or between 0.1% and 0.2%, greater than that that of a control corn plan grown under comparable conditions.

According to another aspect of the present disclosure, a modified, transgenic, or genome edited/mutated corn plant provided herein comprises a stalk or stem diameter that is between 0.2% and 95%, between 0.5% and 90%, between 1% and 85%, between 1.5% and 80%, between 2% and 75%, between 2.5% and 70%, between 3% and 65%, between 3.5% and 60%, between 4% and 55%, between 4.5% and 50%, between 5% and 45%, between 6% and 40%, between 7% and 35%, between 8% and 30%, between 9% and 25%, or between 10% and 20%, greater than that that of a control corn plan grown under comparable conditions.

According to another aspect of the present disclosure, a modified, transgenic, or genome edited/mutated corn plant provided herein comprises a stalk or stem diameter that is between 0.1% and 1%, between 1% and 5%, between 6% and 10%, between 20% and 30%, between 30% and 40%, between 40% and 50%, between 50% and 60%, between 60% and 70%, between 70% and 80%, between 80% and 90%, between 90% and 100%, greater than that that of a control corn plan grown under comparable conditions.

In another aspect, the yield of a modified, transgenic, or genome edited/mutated exhibiting semi-dwarf phenotype is equal to or more then the yield of a control plant grown under comparable conditions.

In another aspect, a modified, transgenic, or genome edited/mutated corn plant exhibiting semi-dwarf phenotype requires about 5%, 10%, 15%, 20%, or 25% fewer heat units than a control plant to reach anthesis.

In yet another aspect, a modified, transgenic, or genome edited/mutated corn plant exhibiting semi-dwarf phenotype has a relative maturity of about 10%, 15%, 20%, 25%, 30%, 35%, 40%, or 45% fewer days than the relative maturity of a control plant grown under comparable conditions.

According to an aspect of the present disclosure, a modified, transgenic, or genome edited/mutated corn plant provided herein comprises a height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm and an average stem diameter of at least 17.5 mm, at least 18 mm, at least 18.5 mm, at least 19 mm, at least 19.5 mm, at least 20 mm, at least 20.5 mm, at least 21 mm, at least 21.5 mm, or at least 22 mm. According to another aspect the modified corn plant further comprises at least one ear that is substantially free of mature male reproductive tissue.

According to aspects of the present disclosure, modified, transgenic, or genome edited/mutated corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant can be substantially free of off-types, such as male reproductive tissues or structures in one or more ears of the modified corn plant.

According to an aspect of the present disclosure a modified, transgenic, or genome edited/mutated corn plant provided herein comprises a height of between 1000 mm and 1600 mm, 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, or between 1000 mm and 1300 mm, and an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. According to another aspect the modified corn plant further comprises at least one ear that is substantially free of mature male reproductive tissue.

According to an aspect of the present disclosure, a modified, transgenic, or genome edited/mutated corn plant provided herein comprises a height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a control plant and a stalk or stem diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of a control plant.

According to an aspect of the present disclosure, a modified, transgenic, or genome edited/mutated corn plant provided herein comprises a fresh ear weight that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the fresh ear weight of a control plant.

According to an aspect of the present disclosure, a population of modified, transgenic, or genome edited/mutated corn plants provided herein comprises a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% lower as compared to a population of unmodified control plants. According to another aspect of the present disclosure, a population of modified corn plants provided herein comprises a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% lower as compared to a population of control plants.

According to an aspect of the present disclosure, modified, transgenic, or genome edited/mutated corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a control plant.

The "minus-2 internode" of a corn plant refers to the second internode below the ear of the plant, and the "minus-4 internode" of a corn plant refers to the fourth internode below the ear of the plant. According to many aspects, modified, transgenic, or genome edited/mutated corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a control plant.

A modified, transgenic, or genome edited/mutated corn plant can have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant can have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a control plant.

According to an aspect of the present disclosure, modified, transgenic, or genome edited/mutated corn plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant can have an increase in harvestable yield between 1 and 10, between 1 and 8, between 2 and 8, between 2 and 6, between 2 and 5, between 2.5 and 4.5, or between 3 and 4 bushels per acre. A modified corn plant can have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant can have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a control plant.

According to an aspect, the present disclosure provides a population of a modified, transgenic, or genome edited/mutated corn plants, where the population of a modified, transgenic, or genome edited/mutated corn plants shares ancestry with a single a modified, transgenic, or genome edited/mutated corn plant, where the population of a modified, transgenic, or genome edited/mutated corn plants comprises an average height of 1500 mm or less, wherein the population of a modified, transgenic, or genome edited/mutated corn plants comprises an average stalk or stem diameter of 18 mm or more, wherein less than 5%, less than 10%, less than 15%, less than 20%, or less than 25% of the population of modified, transgenic, or genome edited/mutated corn plants comprises a height of greater than 1500 mm, and where less than 5%, less than 10%, less than 15%, less than 20%, or less than 25% of the population of a modified, transgenic, or genome edited/mutated corn plants comprises at least one ear comprising mature male reproductive tissue. In another aspect the population of a modified, transgenic, or genome edited/mutated corn plants comprises an average height of 1200 mm or less.

According to an aspect, the present disclosure provides a population of a modified, transgenic, or genome edited/mutated corn plants, where the population of a modified, transgenic, or genome edited/mutated corn plants share ancestry with a single modified corn plant, where the population of a modified, transgenic, or genome edited/mutated corn plants comprises an average height of 1500 mm or less, where less than 5%, less than 10%, less than 15%, less than 20%, or less than 25% of the population of modified corn plants comprises a height of greater than 1500 mm, and where the population of a modified, transgenic, or genome edited/mutated corn plants comprises a lodging frequency that is at least 5%, at least 10%, at least 20%, at least 30%, at least 40%, at least 50%, at least 60%, at least 70% at least 80%, at least 90%, or 100% lower as compared to a population of control corn plants.

According to an aspect, the present disclosure provides a modified, transgenic, or genome edited/mutated corn plant comprising a height of 1500 mm or less, where the a modified, transgenic, or genome edited/mutated corn plant further comprises a stalk or stem diameter of 18 mm or more, and where at least one ear of the a modified, transgenic, or genome edited/mutated corn plant is substantially free of mature male reproductive tissue.

According to an aspect, the present disclosure provides a modified, transgenic, or genome edited/mutated corn plant comprising a height of 1500 mm or less, wherein the a modified, transgenic, or genome edited/mutated corn plant further comprises a harvest index of at least 0.58, and where the a modified, transgenic, or genome edited/mutated corn plant further comprises at least one ear that is substantially free of mature male reproductive tissue.

According to an aspect of the present disclosure, modified, transgenic, or genome edited/mutated corn plants are provided having a significantly reduced or eliminated expression level of one or more GA3 oxidase and/or GA20 oxidase gene transcript(s) and/or protein(s) in one or more tissue(s), such as one or more stem, internode, leaf and/or vascular tissue(s), of the modified, transgenic, or genome edited/mutated plants, as compared to the same tissue(s) of wild-type or control plants. In an aspect, the level of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant can be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a control corn or cereal plant.

According to an aspect of the present disclosure, modified, transgenic, or genome edited/mutated cereal or corn plants are provided that have at least one beneficial agronomic trait and at least one female reproductive organ or ear that is substantially or completely free of off-types. The beneficial agronomic trait can include, for example, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. A modified, transgenic, or genome edited/mutated cereal or corn plant can have a female reproductive organ or ear that appears normal relative to a control or wild-type plant. Indeed, modified, transgenic, or genome edited/mutated cereal or corn plants are provided that comprise at least one reproductive organ or ear that does not have or exhibit, or is substantially or completely free of, off-types including male sterility, reduced kernel or seed number, and/or masculinized structure(s) in one or more female organs or ears.

A modified, transgenic, or genome edited/mutated cereal or corn plant is provided herein that lacks significant off-types in the reproductive tissues of the plant. Off-types can include male (tassel or anther) sterility, reduced kernel or seed number, and/or the presence of one or more masculinized or male (or male-like) reproductive structures in the female organ or ear (e.g., anther ear) of the plant.

As used herein, a female organ or ear of a plant, such as corn, is "substantially free" of male reproductive structures if male reproductive structures are absent or nearly absent in the female organ or ear of the plant based on visual inspection of the female organ or ear at later reproductive stages.

A female organ or ear of a plant, such as corn, is "completely free" of mature male reproductive structures if male reproductive structures are absent or not observed or observable in the female organ or ear of the plant, such as a corn plant, by visual inspection of the female organ or ear at later reproductive stages.

In an aspect, a modified, transgenic, or genome edited/mutated corn plant exhibits increased ear area relative to a control corn plant.

According to an aspect of the present disclosure, a modified, transgenic, or genome edited/mutated corn plant exhibits an increase in ear area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear area that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear area that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear area that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear area that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased ear volume relative to a control corn plant grown under comparable conditions.

According to an aspect of the present disclosure, a modified, transgenic, or genome edited/mutated corn plant exhibits an increase in ear volume by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear volume that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear volume that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear volume that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear volume that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased ear diameter relative to a control corn plant grown under comparable conditions.

According to an aspect of the present disclosure, a modified, transgenic, or genome edited/mutated corn plant exhibits an ear diameter that is at least 0.2%, at least 0.4%, at least 0.6%, at least 0.8%, at least 1.0%, at least 1.2%, at least 1.4%, at least 1.6%, at least 1.8%, at least 2.0%, at least 2.2%, at least 2.4%, at least 2.6%, at least 2.8%, at least 3.0%, at least 3.2%, at least 3.4%, at least 3.6%, at least 3.8%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, at least 9.5%, at least 10.0%, relative to a control corn plant.

According to an aspect of the present disclosure, a modified, transgenic, or genome edited/mutated corn plant exhibits an ear diameter that is between 0.2% and 10.0%, between 0.4% and 10.0%, between 0.6% and 10.0%, between 0.8% and 10.0%, between 1.0% and 10.0%, between 1.2% and 10.0%, between 1.4% and 10.0%, between 1.6% and 10.0%, between 1.8% and 10.0%, between 2.0% and 10.0%, between 2.2% and 10.0%, between 2.4% and 10.0%, between 2.6% and 10.0%, between 2.8% and 10.0%, between 3.0% and 10.0%, between 3.2% and 10.0%, between 3.4% and 10.0%, between 3.6% and 10.0%, between 3.8% and 10.0%, between 4.0% and 10.0%, between 4.5% and 10.0%, between 5.0% and 10.0%, between 5.5% and 10.0%, between 6.0% and 10.0%, between 6.5% and 10.0%, between 7.0% and 10.0%, between 7.5% and 10.0%, between 8.0% and 10.0%, between 8.5% and 10.0%, between 9.0% and 10.0%, or between 9.5% and 10.0%, greater than that of a control corn plant grown under comparable conditions.

According to an aspect of the present disclosure, a modified, transgenic, or genome edited/mutated corn plant exhibits an ear diameter that is between 0.2% and 9.5%, between 0.2% and 9.0%, between 0.2% and 8.5%, between 0.2% and 8.0%, between 0.2% and 7.5%, between 0.2% and 7.0%, between 0.2% and 6.5%, between 0.2% and 6.0%, between 0.2% and 5.5%, between 0.2% and 5.0%, between 0.2% and 4.5%, between 0.2% and 4.0%, between 0.2% and 3.8%, between 0.2% and 3.6%, between 0.2% and 3.4%, between 0.2% and 3.2%, between 0.2% and 3.0%, between 0.2% and 2.8%, between 0.2% and 2.6%, between 0.2% and 2.4%, between 0.2% and 2.2%, between 0.2% and 2.0%, between 0.2% and 1.8%, between 0.2% and 1.6%, between 0.2% and 1.4%, between 0.2% and 1.2%, between 0.2% and 1.0%, between 0.2% and 0.8%, between 0.2% and 0.6%, or between 0.2% and 0.4%, greater than that of a control corn plant grown under comparable conditions.

According to an aspect of the present disclosure, a modified, transgenic, or genome edited/mutated corn plant exhibits an ear diameter that is between 0.4% and 9.5%, between 0.6% and 9.0%, between 0.8% and 8.5%, between 1.0% and 8.0%, between 1.2% and 7.5%, between 1.4% and 7.0%, between 1.6% and 6.5%, between 1.8% and 6.0%, between 2.0% and 5.5%, between 2.2% and 5.0%, between 2.4% and 4.5%, between 2.6% and 4.0%, between 2.8% and 3.8%, between 3.0% and 3.6%, or between 3.2% and 3.4%, greater than that of a control corn plant grown under comparable conditions.

According to an aspect of the present disclosure, a modified, transgenic, or genome edited/mutated corn plant exhibits an ear diameter that is between 0.2% and 0.6%, between 0.6% and 1.0%, between 1.0% and 1.4%, between 1.4% and 1.8%, between 1.8% and 2.2%, between 2.2% and 2.6%, between 2.6% and 3.0%, between 3.0% and 3.5%, between 3.5% and 4.0%, between 4.0% and 4.5%, between 4.5% and 5.0%, between 5.0% and 5.5%, between 5.5% and 6.0%, between 6.0% and 6.5%, between 6.5% and 7.0%, between 7.0% and 7.5%, between 7.5% and 8.0%, between 8.0% and 8.5%, between 8.5% and 9.0%, between 9.0% and 9.5%, or between 9.5% and 10.0%, greater than that of a control corn plant grown under comparable conditions.

In an aspect, a modified, transgenic, or genome edited/mutated corn plant exhibits increased ear length relative to a control corn plant grown under comparable conditions.

According to an aspect of the present disclosure, a modified, transgenic, or genome edited/mutated corn plant exhibits an increase in ear length by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear length that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a corn plant grown under comparable conditions.

According to an aspect of the present disclosure, a modified, transgenic, or genome edited/mutated corn plant exhibits an ear length that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear length that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear length that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits decreased ear tip void relative to a control corn plant grown under comparable conditions.

According to an aspect of the present disclosure, a modified, transgenic, or genome edited/mutated corn plant exhibits an decrease in ear tip void by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear tip void that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% less than that of a control corn plant grown under comparable conditions.

According to an aspect of the present disclosure, a modified, transgenic, or genome edited/mutated corn plant exhibits an ear tip void that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% less than that of a control corn plant grown under comparable conditions.

According to an aspect of the present disclosure, a modified, transgenic, or genome edited/mutated corn plant exhibits an ear tip void that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% less than that of a control corn plant grown under comparable conditions.

According to an aspect of the present disclosure, a modified, transgenic, or genome edited/mutated corn plant exhibits an ear tip void that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% less than that of a control corn plant grown under comparable conditions.

In an aspect, a modified, transgenic, or genome edited/mutated corn plant exhibits an increased number of kernels per ear relative to a control corn plant grown under comparable conditions.

According to an aspect of the present disclosure, a modified, transgenic, or genome edited/mutated corn plant exhibits an increase in number of kernels per ear by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits kernels per ear that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits kernels per ear that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits kernels per ear that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits kernels per ear that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased single kernel weight relative to a control corn plant grown under comparable conditions.

According to an aspect of the present disclosure, a modified, transgenic, or genome edited/mutated corn plant exhibits an increase in single kernel weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a single kernel weight that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a single kernel weight that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a single kernel weight that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a single kernel weight that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a single kernel weight that is between 1% and 2%, between 2% and 3%, between 3% and 4%, between 4% and 5%, between 5% and 6%, between 6% and 7%, between 7% and 8%, between 8% and 9%, or between 9% and 10% greater than that of a control corn plant grown under comparable conditions.

In an aspect, a modified, transgenic, or genome edited/mutated corn plant exhibits increased ear fresh weight relative to a control corn plant.

According to an aspect of the present disclosure, a modified, transgenic, or genome edited/mutated corn plant exhibits an increased ear fresh weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control corn plant grown under comparable conditions.

According to an aspect of the present disclosure, a modified, transgenic, or genome edited/mutated corn plant exhibits an ear fresh weight that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear fresh weight that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear fresh weight that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear fresh weight that is between 1% and 5%, between 5% and 10%, between 10% and 15%, between 15% and 20%, between 20% and 25%, between 25% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits an ear fresh weight that is between 1% and 2%, between 2% and 3%, between 3% and 4%, between 4% and 5%, between 5% and 6%, between 6% and 7%, between 7% and 8%, between 8% and 9%, between 9% and 10%, between 10% and 11%, between 11% and 12%, between 12% and 13%, between 13% and 14%, between 14% and 15%, between 15% and 16%, between 16% and 17%, between 17% and 18%, between 18% and 19%, between 19% and 20%, between 20% and 21%, between 21% and 22%, between 22% and 23%, between 23% and 24%, between 24% and 25%, between 25% and 26%, between 26% and 27%, between 27% and 28%, between 28% and 29%, between 29% and 30%, greater than that of a control corn plant grown under comparable conditions.

In an aspect, a modified, transgenic, or genome edited/mutated corn plant exhibits an increased yield relative to a control corn plant.

According to an aspect of the present disclosure, a modified, transgenic, or genome edited/mutated corn plant exhibits an increased yield by at least 1%, at least 3%, at least 5%, at least 7%, at least 9%, at least 11%, at least 13%, at least 15%, at least 17%, at least 19%, at least 21%, at least 23%, at least 25%, at least 27%, at least 29%, at least 31%, at least 33%, at least 35%, at least 37%, at least 39%, at least 41%, at least 43%, at least 45%, at least 47%, at least 49%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a yield that is between 1% and 100%, between 3% and 100%, between 5% and 100%, between 7% and 100%, between 9% and 100%, between 11% and 100%, between 13% and 100%, between 15% and 100%, between 17% and 100%, between 19% and 100%, between 21% and 100%, between 23% and 100%, between 25% and 100%, between 27% and 100%, between 29% and 100%, between 31% and 100%, between 33% and 100%, between 35% and 100%, between 37% and 100%, between 39% and 100%, between 41% and 100%, between 43% and 100%, between 45% and 100%, between 47% and 100%, between 49% and 100%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, greater than that of a control corn plant grown under comparable conditions.

According to an aspect of the present disclosure, a modified, transgenic, or genome edited/mutated corn plant exhibits a yield that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 49%, between 1% and 47%, between 1% and 45%, between 1% and 43%, between 1% and 41%, between 1% and 39%, between 1% and 37%, between 1% and 35%, between 1% and 33%, between 1% and 31%, between 1% and 29%, between 1% and 27%, between 1% and 25%, between 1% and 23%, between 1% and 21%, between 1% and 19%, between 1% and 17%, between 1% and 15%, between 1% and 13%, between 1% and 11%, between 1% and 9%, between 1% and 7%, between 1% and 5%, or between 1% and 3%, greater than that of a control corn plant grown under comparable conditions.

According to an aspect of the present disclosure, a modified, transgenic, or genome edited/mutated corn plant exhibits a yield that is between 3% and 95%, between 5% and 90%, between 7% and 85%, between 9% and 80%, between 11% and 75%, between 13% and 70%, between 15% and 65%, between 17% and 60%, between 19% and 55%, between 21% and 50%, between 23% and 49%, between 25% and 47%, between 27% and 45%, between 29% and 43%, between 31% and 41%, between 33% and 39%, or between 35% and 37%, greater than that of a control corn plant grown under comparable conditions.

According to an aspect of the present disclosure, a modified, transgenic, or genome edited/mutated corn plant exhibits a yield that is between 1% and 7%, between 7% and 13%, between 13% and 19%, between 19% and 25%, between 25% and 31%, between 31% and 37%, between 37% and 43%, between 43% and 49%, between 49% and 55%, between 55% and 60%, between 60% and 65%, between 65% and 70%, between 70% and 75%, between 75% and 80%, between 80% and 85%, between 85% and 90%, between 90% and 95%, or between 95% and 100%, greater than that of a control corn plant grown under comparable conditions.

In an aspect, modified, transgenic, or genome edited/mutated corn plants exhibit increased kernels per field area relative to control corn plants.

According to an aspect of the present disclosure, modified, transgenic, or genome edited/mutated corn plants exhibit increased kernels per field area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to control corn plants.

According to an aspect of the present disclosure, modified, transgenic, or genome edited/mutated corn plants exhibit kernels per field area that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of control corn plants grown under comparable conditions.

According to an aspect of the present disclosure, modified, transgenic, or genome edited/mutated corn plants exhibit kernels per field area that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of control corn plants grown under comparable conditions.

According to an aspect of the present disclosure, modified, transgenic, or genome edited/mutated corn plants exhibit kernels per field area that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of control corn plants grown under comparable conditions.

According to an aspect of the present disclosure, modified, transgenic, or genome edited/mutated corn plants exhibit kernels per field area that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of control corn plants grown under comparable conditions.

According to an aspect of the present disclosure, modified, transgenic, or genome edited/mutated corn plants exhibit kernels per field area that is between 1% and 3%, between 3% and 5%, between 5% and 7%, between 7% and 9%, between 9% and 11%, between 11% and 13%, between 13% and 15%, between 15% and 17%, between 17% and 19%, between 19% and 21%, between 21% and 23%, between 23% and 25%, between 25% and 27%, between 27% and 29%, or between 29% and 30% greater than that of control corn plants grown under comparable conditions.

In an aspect, a modified, transgenic, or genome edited/mutated corn plant disclosed in the present disclosure can exhibit one or more improved root traits relative to a control corn plant grown under comparable conditions.

In an aspect, a modified, transgenic, or genome edited/mutated corn plant exhibits increased crown root lateral root density rating at the V12 stage relative to a control corn plant grown under comparable conditions.

According to an aspect of the present disclosure, a modified, transgenic, or genome edited/mutated corn plant exhibits an increased crown root lateral root density rating at the V12 stage by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control corn plant grown under comparable conditions.

According to an aspect of the present disclosure, a modified, transgenic, or genome edited/mutated corn plant exhibits crown root lateral root density rating at the V12 stage that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits crown root lateral root density rating at the V12 stage that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits crown root lateral root density rating at the V12 stage that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits crown root lateral root density rating at the V12 stage that is between 1% and 5%, between 5% and 10%, between 10% and 15%, between 15% and 20%, between 20% and 25%, between 25% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits crown root lateral root density rating at the V12 stage that is between 1% and 2%, between 2% and 3%, between 3% and 4%, between 4% and 5%, between 5% and 6%, between 6% and 7%, between 7% and 8%, between 8% and 9%, between 9% and 10%, between 10% and 11%, between 11% and 12%, between 12% and 13%, between 13% and 14%, between 14% and 15%, between 15% and 16%, between 16% and 17%, between 17% and 18%, between 18% and 19%, between 19% and 20%, between 20% and 21%, between 21% and 22%, between 22% and 23%, between 23% and 24%, between 24% and 25%, between 25% and 26%, between 26% and 27%, between 27% and 28%, between 28% and 29%, between 29% and 30%, greater than that of a control corn plant grown under comparable conditions.

In an aspect, a modified, transgenic, or genome edited/mutated corn plant exhibits increased root dry weight at the V12 stage relative to a control corn plant grown under comparable conditions.

According to an aspect of the present disclosure, a modified, transgenic, or genome edited/mutated corn plant exhibits an increase in root dry weight at the V12 stage by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a root dry weight at the V12 stage that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a root dry weight at the V12 stage that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a root dry weight at the V12 stage that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a root dry weight at the V12 stage that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a root dry weight at the V12 stage that is between 1% and 2%, between 2% and 3%, between 3% and 4%, between 4% and 5%, between 5% and 6%, between 6% and 7%, between 7% and 8%, between 8% and 9%, or between 9% and 10% greater than that of a control corn plant grown under comparable conditions.

In an aspect, a modified, transgenic, or genome edited/mutated corn plant exhibits increased number of florets relative to a control corn plant.

According to an aspect of the present disclosure, a modified, transgenic, or genome edited/mutated corn plant exhibits increased number of florets by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant.

According to an aspect of the present disclosure, a modified, transgenic, or genome edited/mutated corn plant exhibits a number of florets that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a number of florets that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a number of florets that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a number of florets that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a number of florets that is between 1% and 3%, between 3% and 5%, between 5% and 7%, between 7% and 9%, between 9% and 11%, between 11% and 13%, between 13% and 15%, between 15% and 17%, between 17% and 19%, between 19% and 21%, between 21% and 23%, between 23% and 25%, between 25% and 27%, between 27% and 29%, or between 29% and 30% greater than that of a control corn plant grown under comparable conditions.

A modified, transgenic, or genome edited/mutated corn plant disclosed in the present disclosure can display a positive trait interaction in which a trait, such as a positive or negative trait, attributable to a transgene (or mutation or edit) can be enhanced, out-performed, neutralized, offset or mitigated due to the presence of a second transgene (or mutation or edit). Such a transgenic and/or genome edited/mutated corn plant can exhibit improved ear traits as compared to a control corn plant comprising only one transgene (or mutation or edit). For example, GA20Ox_SUP/ZMM19 stack plants may have enhanced traits and/or positive trait interactions relative to ZMM19 single and/or GA20Ox_SUP single plants, in terms of increased ear diameter, single kernel weight, ear fresh weight, ear area, ear volume, ear length, kernels per ear, and/or yield.

In another aspect, a modified, transgenic, or genome edited/mutated corn plant of the present disclosure exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

In yet another aspect, a modified, transgenic, or genome edited/mutated corn plant of the present disclosure does not have any significant off-types in at least one female organ or ear.

According to an aspect of the present disclosure, a modified, transgenic, or genome edited/mutated corn plant has no or reduced adverse effect over a trait or phenotype selected from the group consisting of senescence, delayed flowering, fungal infection, and a combination thereof, relative to a control corn plant.

Short stature or semi-dwarf corn plants can also have one or more additional traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

According to an aspect of the present disclosure, a modified, transgenic, or genome edited/mutated corn plant provided herein comprises a harvest index of at least 0.57, at least 0.58, at least 0.59, at least 0.60, at least 0.61, at least 0.62, at least 0.63, at least 0.64, or at least 0.65. According to another aspect of the present disclosure a modified, transgenic, or genome edited/mutated corn plant provided herein comprises a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. According to yet another aspect of the present disclosure, a modified, transgenic, or genome edited/mutated corn plant provided herein comprises a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater as compared to an unmodified control plant. According to still another aspect of the present disclosure, a modified, transgenic, or genome edited/mutated corn plant provided herein comprises a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater as compared to a control plant.

According to another aspect of the present disclosure, methods are provided for planting a modified or transgenic plant(s) provided herein at a normal/standard or high density in field. According to some aspects, the yield of a crop plant per acre (or per land area) can be increased by planting a modified or transgenic plant(s) of the present disclosure at a higher density in the field. As described herein, modified or transgenic plants expressing a transcribable DNA sequence that encodes a non-coding RNA molecule targeting one or more endogenous GA20 and/or GA3 oxidase gene for suppression and a transgene encoding one or more MADS-box polypeptide, can have reduced plant height, shorter internode(s), increased stalk/stem diameter, and/or increased lodging resistance. Modified or transgenic plants described herein can tolerate high density planting conditions since an increase in stem diameter can resist lodging and the shorter plant height can allow for increased light penetrance to the lower leaves under high density planting conditions. Thus, modified or transgenic plants provided herein can be planted at a higher density to increase the yield per acre (or land area) in the field. For row crops, higher density can be achieved by planting a greater number of seeds/plants per row length and/or by decreasing the spacing between rows. In an aspect, the row spacing for high density planting of the modified, transgenic, or genome edited/mutated corn plants is less than or equal to 40 inches. In an aspect, the row spacing for high density planting of the modified, transgenic, or genome edited/mutated corn plants is less than or equal to 30 inches. In another aspect, the row spacing for high density planting of the modified, transgenic, or genome edited/mutated corn plants is less than or equal to 20 inches.

According to an aspect, seeds of a modified or transgenic crop plants can be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified or transgenic crop plant can be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre.

As an example, seeds of corn plants can be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

EXEMPLARY EMBODIMENTS

1. A modified corn plant or a plant part thereof comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a MADS-box polypeptide.
2. The modified corn plant of embodiment 1, wherein the first and second recombinant expression cassettes are stably integrated into the genome of the corn plant or plant part thereof.
3. The modified corn plant or plant part thereof of embodiment 1, wherein the modified corn plant further exhibits one or more improved root traits, relative to a control corn plant that does not have the first or second recombinant expression cassette.

4. The modified corn plant or plant part thereof of embodiment 1, wherein the modified corn plant is semi-dwarf and has one or more improved ear traits, relative to a control corn plant that does not have the first or second recombinant expression cassette.

5. The modified corn plant or plant part thereof of embodiments 1 to 4, wherein the transcribable DNA sequence encodes a non-coding RNA for suppression of a GA3 oxidase gene.

6. The modified corn plant or plant part thereof of embodiment 5, wherein the transcribable DNA sequence encodes a non-coding RNA for suppression of a GA3 oxidase_1 gene, a GA3 oxidase_2 gene, or both.

7. The modified corn plant or plant part thereof of embodiment 6, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

8. The modified corn plant or plant part thereof of embodiment 6, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

9. The modified corn plant or plant part thereof of embodiments 1 to 4, wherein the transcribable DNA sequence encodes a non-coding RNA for suppression of a GA20 oxidase gene.

10. The modified corn plant or plant part thereof of embodiment 9, wherein the transcribable DNA sequence encodes a non-coding RNA for suppression of a GA20 oxidase_3 gene, a GA20 oxidase_4 gene, a GA20 oxidase_5 gene, or a combination thereof.

11. The modified corn plant or plant part thereof of embodiment 9, wherein the transcribable DNA sequence encodes a non-coding RNA for suppression of a GA20 oxidase_3 gene, a GA20 oxidase_5 gene, or both.

12. The modified corn plant or plant part thereof of embodiment 11, wherein the transcribable DNA sequence comprises a sequence that is at least 60% identical or complementary to at least 15 consecutive nucleotides of SEQ ID NO: 39, 53, or 55.

13. The modified corn plant or plant part thereof of embodiment 11, wherein the transcribable DNA sequence encodes a sequence that is at least 60% identical or complementary to at least 15 consecutive nucleotides of SEQ ID NO: 40, 54, or 56.

14. The modified corn plant or plant part thereof of any one of embodiments 5 to 11, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

15. The modified corn plant or plant part thereof of any one of embodiments 5 to 11, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

16. The modified corn plant or plant part thereof of embodiment 1, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 168.

17. The modified corn plant or plant part thereof of embodiment 1, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

18. The modified corn plant or plant part thereof of any one of embodiments 1 to 4, wherein the MADS-box polypeptide comprises a maize ZMM19 polypeptide.

19. The modified corn plant or plant part thereof of any one of embodiments 1 to 17, wherein the DNA sequence of the second recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

20. The modified corn plant or plant part thereof of embodiment 1 or 4, wherein the expression level of an endogenous GA20 oxidase or GA3 oxidase gene is reduced or eliminated in the modified corn plant or plant part thereof.

21. The modified corn plant or plant part thereof of embodiment 1 or 4, wherein the transcribable DNA sequence is operably linked to a heterologous plant-expressible promoter.

22. The modified corn plant or plant part thereof of embodiment 21, wherein the heterologous plant-expressible promoter is a vascular promoter.

23. The modified corn plant or plant part thereof of embodiment 22, wherein the vascular promoter is selected from the group consisting of a sucrose synthase promoter, a sucrose transporter promoter, a Sh1 promoter, Commelina yellow mottle virus (CoYMV)

promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, a rice yellow stripe 2 (OsYSL2) promoter, and a combination thereof.

24. The modified corn plant or plant part thereof of embodiment 23, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70 or SEQ ID NO: 71, or a functional portion thereof.

25. The modified corn plant or plant part thereof of embodiment 21, wherein the heterologous plant-expressible promoter is a rice tungro bacilliform virus (RTBV) promoter.

26. The modified corn plant or plant part thereof of embodiment 25, wherein RTBV promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

27. The modified corn plant or plant part thereof of embodiment 21, wherein the heterologous plant-expressible promoter is a leaf promoter.

28. The modified corn plant or plant part thereof of embodiment 27, wherein the leaf promoter is selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, a Myb gene promoter, and a combination thereof.

29. The modified corn plant or plant part thereof of embodiment 28, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

30. The modified corn plant or plant part thereof of embodiment 21, wherein the heterologous plant-expressible promoter is a constitutive promoter.

31. The modified corn plant or plant part thereof of embodiment 30, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

32. The modified corn plant or plant part thereof of embodiment 31, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

33. The modified corn plant or plant part thereof of embodiment 1 or 4, wherein the non-coding RNA is a precursor miRNA or siRNA capable of being processed or cleaved to form a mature miRNA or siRNA.

34. The modified corn plant or plant part thereof of embodiment 1 or 4, wherein the DNA sequence comprised in the second recombinant expression cassette is operably linked to a heterologous plant-expressible promoter.

35. The modified corn plant or plant part thereof of embodiment 34, wherein the heterologous plant-expressible promoter is a constitutive promoter.

36. The modified corn plant or plant part thereof of embodiment 35, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

37. The modified corn plant or plant part thereof of embodiment 35, wherein the heterologous plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

38. The modified corn plant or plant part thereof of embodiment 35, wherein the heterologous plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 174 or a functional portion thereof.

39. The modified corn plant or plant part thereof of embodiment 35, wherein the heterologous plant-expressible promoter is selected from the group consisting of a meristem promoter, a root promoter, a seed or kernel promoter, and a combination thereof.

40. The modified corn plant or plant part thereof of any one of embodiments 1 to 36, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

41. The modified corn plant or plant part thereof of any one of embodiments 1 to 40, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

42. The modified corn plant or plant part thereof of any one of embodiments 1 to 41, wherein the modified corn plant exhibits improved lodging resistance, reduced green snap, or both, relative to a control corn plant.

43. The modified corn plant or plant part thereof of embodiments 1 to 42, wherein the modified corn plant exhibits increased ear diameter relative to the control corn plant.

44. The modified corn plant or plant part thereof of embodiment 43, wherein the modified corn plant exhibits an increase in ear diameter by at least 0.2%, at least 0.4%, at least 0.6%, at least 0.8%, at least 1.0%, at least 1.2%, at least 1.4%, at least 1.6%, at least 1.8%, at least 2.0%, at least 2.2%, at least 2.4%, at least 2.6%, at least 2.8%, at least 3.0%, at least 3.2%, at least 3.4%, at least 3.6%, at least 3.8%, or at least 4.0%, relative to the control corn plant.

45. The modified corn plant or plant part thereof of embodiments 1 to 44, wherein the modified corn plant exhibits increased single kernel weight relative to the control corn plant.

46. The modified corn plant or plant part thereof of embodiment 45, wherein the modified corn plant exhibits an increase in singe kernel weight by at least at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

47. The modified corn plant or plant part thereof of any one of embodiments 1 to 46, wherein the modified corn plant exhibits increased ear fresh weight relative to the control corn plant.

48. The modified corn plant or plant part thereof of embodiment 47, wherein the modified corn plant exhibits increased ear fresh weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, relative to the control corn plant.

49. The modified corn plant or plant part thereof of any one of embodiments 1 to 48, wherein the modified corn plant exhibits increased ear area relative to the control corn plant.

50. The modified corn plant or plant part thereof of embodiment 49, wherein the modified corn plant exhibits an increase in ear area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

51. The modified corn plant or plant part thereof of any one of embodiments 1 to 50, wherein the modified corn plant exhibits increased ear volume relative to the control corn plant.

52. The modified corn plant or plant part thereof of embodiment 51, wherein the modified corn plant exhibits an increase in ear volume by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

53. The modified corn plant or plant part thereof of any one of embodiments 1 to 52, wherein the modified corn plant exhibits increased ear length relative to the control corn plant.

54. The modified corn plant or plant part thereof of embodiment 53, wherein the modified corn plant exhibits an increase in ear length by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%, at least 16%, at least 17%, at least 18%, at least 19%, or at least 20%, relative to the control corn plant.

55. The modified corn plant or plant part thereof of any one of embodiments 1 to 54, wherein the modified corn plant exhibits increased number of kernels per ear relative to the control corn plant.

56. The modified corn plant or plant part thereof of embodiment 55, wherein the modified corn plant exhibits an increase in number of kernels per ear by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%, at least 16%, at least 17%, at least 18%, at least 19%, or at least 20%, relative to the control corn plant.

57. The modified corn plant or plant part thereof of any one of embodiments 1 to 56, wherein the modified corn plant exhibits increased yield relative to the control corn plant.

58. The modified corn plant or plant part thereof of embodiment 57, wherein the modified corn plant exhibits an increase in yield by at least 1%, at least 3%, at least 5%, at least 7%, at least 9%, at least 11%, at least 13%, at least 15%, at least 17%, at least 19%, at least 21%, at least 23%, at least 25%, at least 27%, at least 29%, at least 31%, at least 33%, at least 35%, at least 37%, at least 39%, at least 41%, at least 43%, or at least 45%, relative to the control corn plant.

59. The modified corn plant or plant part thereof of any one of embodiments 1 to 58, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to the control corn plant.

60. The modified corn plant or plant part thereof of any one of embodiments 1 to 59, wherein the modified corn plant exhibits increased crown root lateral root density rating at the V12 stage relative to the control corn plant.

61. The modified corn plant or plant part thereof of embodiment 60, wherein the modified corn plant exhibits an increase in crown root lateral root density rating at the V12 stage by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, relative to the control corn plant.

62. The modified corn plant or plant part thereof of any one of embodiments 1 to 61, wherein the modified corn plant exhibits increased root dry weight at the V12 stage relative to the control corn plant.
63. The modified corn plant or plant part thereof of embodiment 62, wherein the modified corn plant exhibits an increase in root dry weight at the V12 stage by at least at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.
64. The modified corn plant or plant part thereof of any one of embodiments 1 to 59, wherein the modified corn plant does not have any significant off-types in at least one female organ or ear.
65. A seed of the modified corn plant of any one of embodiments 1 to 64, wherein the seed comprises the first and second recombinant expression cassettes.
66. The seed of embodiment 65, wherein a progeny plant grown from the seed is semi-dwarf and has one or more improved ear traits, relative to a control corn plant that does not comprise the first or second recombinant expression cassette.
67. The seed of embodiment 66, wherein a progeny plant grown from the seed has one or more improved root traits, relative to the control corn plant.
68. A commodity or commodity product produced from the seed of embodiment 65, comprising the first and second DNA sequence recombinant expression cassettes.
69. A method comprising planting the seed of embodiment 65 in a growth medium or soil.
70. The method of embodiment 69, further comprising planting a plurality of the seeds with a row spacing of less than or equal to 40 inches.
71. The method of embodiment 69, further comprising planting a plurality of the seeds with a row spacing of less than or equal to 30 inches.
72. The method of embodiment 71, wherein the row spacing is less than or equal to 20 inches.
73. The method of embodiment 69, further comprising growing a corn plant from the seed.
74. The method of embodiment 73, further comprising harvesting a seed from the corn plant.
75. The method of any one of embodiments 71 to 74, wherein the seed is planted at a density selected from the group consisting of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, and at least 56,000 plants per acre.
76. A plurality of modified corn plants in a field, each modified corn plant comprising
   1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and
   2) a second recombinant expression cassette comprising a DNA sequence encoding a MADS-box polypeptide.
77. The plurality of modified corn plants of embodiment 76, wherein the modified corn plants have increased yield relative to control corn plants.
78. The plurality of modified corn plants of embodiment 76 or 77, wherein the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.
79. A method for producing a modified corn plant, the method comprising:
   a. introducing into a corn cell a first recombinant expression cassette comprising a DNA sequence encoding a MADS-box polypeptide, wherein the corn cell comprises a second recombinant expression cassette comprising a transcribable DNA sequence encoding a non-coding RNA for suppression of one or more GA3 oxidase genes and/or one or more GA20 oxidase genes; and
   b. regenerating or developing a modified corn plant from the corn cell, wherein the modified corn plant comprises the first and second recombinant expression cassettes.
80. The method of embodiment 79, wherein the introducing is via site-directed integration using a site-specific nuclease.
81. The method of embodiment 80, wherein the site-specific nuclease is selected from the group consisting of a RNA-guided endonuclease, a meganuclease, a zinc-finger nuclease (ZFN), a TALE-endonuclease (TALEN), a recombinase, and a transposase.
82. The method of embodiment 79, wherein the introducing is via *Agrobacterium*-mediated transformation.
83. The method of embodiment 79, wherein the introducing is via particle bombardment.
84. The method of any one of embodiments 79 to 83, wherein the transcribable DNA sequence encodes a non-coding RNA for suppression of a GA3 oxidase_1 gene, a GA3 oxidase_2 gene, or both.
85. The method of embodiment 84, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.
86. The method of embodiment 84, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.
87. The method of any one of embodiments 79 to 83, wherein the transcribable DNA sequence encodes a non-coding RNA for suppression of a GA20 oxidase gene.
88. The method of embodiment 87, wherein the transcribable DNA sequence encodes a non-coding RNA for suppression of a GA20 oxidase_3 gene, a GA20 oxidase_4 gene, a GA20 oxidase_5 gene, or a combination thereof.

89. The method of embodiment 88, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

90. The method of embodiment 88, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

91. The method of any one of embodiments 79 to 90, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

92. The method of any one of embodiments 79 to 90, wherein the MADS-box polypeptide comprises a maize ZMM19 polypeptide.

93. The method of any one of embodiments 79 to 90, wherein the DNA sequence comprised in the first recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

94. The method of any one of embodiments 79 to 90, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

95. The modified corn plant of embodiment 79, wherein the first and second recombinant expression cassettes are stably integrated into the genome of the corn cell.

96. The method of embodiment 79, further comprising selecting a modified corn plant having a desired trait.

97. The method of embodiment 96, wherein the selected modified corn plant is semi-dwarf and has one or more improved ear traits, relative to a control corn plant not having the first or the second recombinant expression cassettes.

98. The method of embodiment 97, wherein the selected modified corn plant has one or more improved root traits, relative to the control corn plant.

99. The method of embodiment 96 or 97, wherein the selecting a modified corn plant having a desired trait comprises the use of one or more molecular techniques.

100. The method of embodiment 99, wherein the one or more molecular techniques are selected from the group consisting of Southern analysis, polymerase chain reaction (PCR) amplification, Northern blots, RNase protection, primer extension, reverse transcription PCR (RT-PCR), Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

101. The method of any one of embodiments 79 to 100, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

102. The method of any one of embodiments 79 to 101, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

103. The method of any one of embodiments 79 to 101, wherein the modified corn plant exhibit an ear trait selected from the group consisting of increased ear diameter, increased single kernel weight, increased ear fresh weight, increased ear area, increased ear volume, increased ear length, increased number of kernels per ear, increased yield, and a combination thereof, relative to a control corn plant.

104. The method of any one of embodiments 79 to 101, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

105. A method for producing a modified corn plant, the method comprising:

106. introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a MADS-box polypeptide; and 107. regenerating or developing a modified corn plant from the corn cell, wherein the modified corn plant comprises the first and second recombinant expression cassettes.
108. The method of embodiment 105, wherein the introducing is via site-directed integration using a site-specific nuclease.
109. The method of embodiment 108, wherein the site-specific nuclease is selected from the group consisting of a RNA-guided endonuclease, a meganuclease, a zinc-finger nuclease (ZFN), a TALE-endonuclease (TALEN), a recombinase, and a transposase.
110. The method of embodiment 105, wherein the introducing is via Agrobacterium-mediated transformation.
111. The method of embodiment 105, wherein the introducing is via particle bombardment.
112. The method of any one of embodiments 105 to 111, wherein the transcribable DNA sequence encodes a non-coding RNA for suppression of a GA3 oxidase_1 gene, a GA3 oxidase_2 gene, or both.
113. The method of embodiment 112, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.
114. The method of embodiment 112, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.
115. The method of any one of embodiments 105 to 111, wherein the transcribable DNA sequence encodes a non-coding RNA for suppression of a GA20 oxidase gene.
116. The method of embodiment 115, wherein the transcribable DNA sequence encodes a non-coding RNA for suppression of a GA20 oxidase_3 gene, a GA20 oxidase_4 gene, a GA20 oxidase_5 gene, or a combination thereof.
117. The method of embodiment 116, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.
118. The method of embodiment 116, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.
119. The method of any one of embodiments 105 to 118, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.
120. The method of any one of embodiments 105 to 118, wherein the MADS-box polypeptide comprises a maize ZMM19 polypeptide.
121. The method of any one of embodiments 105 to 118, wherein the DNA sequence comprised in the second recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.
122. The method of any one of embodiments 105 to 118, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.
123. The modified corn plant of embodiment 105, wherein the first and second recombinant expression cassettes are stably integrated into the genome of the corn cell.
124. The method of embodiment 105, further comprising selecting a modified corn plant having a desired trait.
125. The method of embodiment 124, wherein the selected modified corn plant is semi-dwarf and has one or more improved ear traits, relative to a control corn plant not having the first or the second recombinant expression cassette.
126. The method of embodiment 125, wherein the selected modified corn plant has one or more improved root traits, relative to the control corn plant.
127. The method of embodiment 124 or 125, wherein the selecting a modified corn plant having a desired trait comprises the use of one or more molecular techniques.
128. The method of embodiment 127, wherein the one or more molecular techniques are selected from the group consisting of Southern analysis, PCR amplification, Northern blots, RNase protection, primer extension, RT-PCR, Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.
129. The method of any one of embodiments 105 to 128, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.
130. The method of any one of embodiments 105 to 129, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.
131. The method of any one of embodiments 105 to 130, wherein the modified corn plant exhibit an ear trait selected from the group consisting of increased ear diameter, increased single kernel weight, increased ear fresh weight, increased ear area, increased ear volume, increased ear length, increased number of kernels per ear, increased yield, and a combination thereof, relative to a control corn plant.
132. The method of any one of embodiments 105 to 131, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.
133. A method for producing a modified corn plant, the method comprising
  a. introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a MADS-box polypeptide; and
  b. regenerating or developing a modified corn plant from the corn cell, wherein the modified corn plant comprises the first and second recombinant expression cassettes.
134. A method for producing a modified corn plant, the method comprising
  a. introducing into a corn cell a first recombinant expression cassette comprising a transcribable DNA sequence encoding a non-coding RNA for suppression of one or more GA3 oxidase genes and/or GA20 oxidase genes;
  b. introducing into the corn cell of step (a) a second recombinant expression cassette comprising a DNA sequence encoding a MADS-box polypeptide to create a modified corn cell; and
  c. regenerating or developing a modified corn plant from the modified corn cell of step (b), wherein the modified corn plant comprises the first and second recombinant expression cassettes.
135. A method for producing a modified corn plant, the method comprising
  a. introducing into a corn cell a first recombinant expression cassette comprising a DNA sequence encoding a MADS-box polypeptide;
  b. introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and
  c. regenerating or developing a modified corn plant from the modified corn cell of step (b), wherein the modified corn plant comprises the first and second recombinant expression cassettes.
136. A method for producing a modified corn plant, the method comprising:
  a. crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a MADS-box polypeptide; and
  b. producing a progeny corn plant comprising the recombinant expression cassette and has the reduced expression of the one or more endogenous GA3 oxidase genes and/or GA20 oxidase genes.
137. The method of embodiment 136, wherein the first and second modified corn plants are obtained via site-directed integration using a site-specific nuclease.
138. The method of embodiment 137, wherein the site-specific nuclease is selected from the group consisting of a RNA-guided endonuclease, a meganuclease, a zinc-finger nuclease (ZFN), a TALE-endonuclease (TALEN), a recombinase, and a transposase.
139. The method of embodiment 136, wherein the first and second modified corn plants are obtained via Agrobacterium-mediated transformation.
140. The method of embodiment 136, wherein the first and second modified corn plants are obtained via particle bombardment.
141. The method of embodiment 136 to 140, wherein the first modified corn plant and the progeny corn plant comprise a transcribable DNA sequence encoding a non-coding RNA for suppression of a GA3 oxidase_1 gene, a GA3 oxidase_2 gene, or both.
142. The method of embodiment 141, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.
143. The method of embodiment 141, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.
144. The method of any one of embodiments 136 to 140, wherein the transcribable DNA sequence encodes a non-coding RNA for suppression of a GA20 oxidase gene.
145. The method of embodiment 144, wherein the transcribable DNA sequence encodes a non-coding RNA for suppression of a GA20 oxidase_3 gene, a GA20 oxidase_4 gene, a GA20 oxidase_5 gene, or a combination thereof.
146. The method of embodiment 145, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.
147. The method of embodiment 145, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.
148. The method of any one of embodiments 136 to 147, wherein the second modified corn plant and the progeny corn plant comprise a recombinant expression cassette comprising a DNA sequence encoding a MADS-box polypeptide.
149. The method of embodiment 148, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.
150. The method of any one of embodiments 136 to 147, wherein the MADS-box polypeptide comprises a maize ZMM19 polypeptide.
151. The method of any one of embodiments 136 to 147, wherein the DNA sequence comprised in the second modified corn plant comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.
152. The method of any one of embodiments 136 to 147, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.
153. The method of embodiment 136, further comprising selecting a progeny corn plant having a desired trait.
154. The method of embodiment 153, wherein the selected progeny corn plant is semi-dwarf and has one or more improved ear traits, relative to a control corn plant.
155. The method of embodiment 154, wherein the selected progeny corn plant has one or more improved root traits, relative to the control corn plant
156. The method of embodiment 153 or 154, wherein the selecting a progeny corn plant having a desired trait comprises the use of one or more molecular techniques.
157. The method of embodiment 156, wherein the one or more molecular techniques are selected from the group consisting of Southern analysis, PCR amplification, Northern blots, RNase protection, primer extension, RT-PCR, Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.
158. The method of any one of embodiments 136 to 157, wherein the height at maturity of the progeny corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.
159. The method of any one of embodiments 136 to 158, wherein the stalk or stem diameter of the progeny corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.
160. The method of any one of embodiments 136 to 159, wherein the progeny corn plant exhibit an ear trait selected from the group consisting of increased ear diameter, increased single kernel weight, increased ear fresh weight, increased ear area, increased ear volume, increased ear length, increased number of kernels per ear, increased yield, and a combination thereof, relative to a control corn plant.
161. The method of any one of embodiments 136 to 160, wherein the progeny corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.
162. A method for producing a modified corn plant, the method comprising:
a. introducing into a corn cell a recombinant expression cassette comprising a DNA sequence encoding a MADS-box polypeptide, wherein the DNA sequence is operably linked to a plant-expressible promoter, and wherein the corn cell comprises one or more mutations and/or edits in one or more endogenous GA3 oxidase and/or GA20 oxidase genes; and b. regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

163. The method of embodiment 162, further comprising introducing a recombinant DNA construct encoding a guide RNA that targets the one or more endogenous GA3 oxidase and/or GA20 oxidase genes.

164. The method of embodiment 163, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

165. The method of embodiment 164, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto.

166. The method of any one of embodiments 163 to 165, wherein the guide RNA is a CRISPR RNA (crRNA) or a single-chain guide RNA (sgRNA).

167. The method of any one of embodiments 163 to 166, wherein the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

168. The method of any one of embodiments 163 to 167, wherein the one or more endogenous GA3 oxidase and/or GA20 oxidase genes encode a protein that is at least 80%, at least 85%, at least 90%, at least 95%, at least 96%, at least 97%, at least 98%, at least 99%, at least 99.5%, or 100% identical to SEQ ID NO: 9, 12, 15, 30, or 33.

169. The method of embodiment 162, wherein the introducing is via Agrobacterium-mediated transformation or particle bombardment.

170. The method of embodiment 169, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

171. The method of embodiment 169, wherein the MADS-box polypeptide comprises a maize ZMM19 polypeptide.

172. The method of any one of embodiments 162 to 171, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

173. The method of any one of embodiments 162 to 171, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

174. A method for producing a modified corn plant, the method comprising:
  a. mutating or editing one or more endogenous GA3 oxidase genes and/or one or more GA20 oxidase genes in a corn cell, wherein the corn cell comprises a recombinant expression cassette encoding a MADS-box polypeptide, wherein the DNA sequence is operably linked to a plant-expressible promoter; and
  b. regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

175. The method of embodiment 174, wherein the mutating or editing is obtained by using a site-specific nuclease selected from the group consisting of a RNA-guided endonuclease, a meganuclease, a zinc-finger nuclease (ZFN), a TALE-endonuclease (TALEN), a recombinase, and a transposase.

176. The method of embodiment 174 or 175, further comprising introducing a recombinant DNA construct encoding a guide RNA that targets the one or more endogenous GA3 oxidase and/or GA20 oxidase genes.

177. The method of embodiment 176, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

178. The method of embodiment 177, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto.

179. The method of any one of embodiments 176 to 178, wherein the guide RNA is a CRISPR RNA (crRNA) or a single-chain guide RNA (sgRNA).

180. The method of any one of embodiments 176 to 179, wherein the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.
181. The method of any one of embodiments 176 to 180, wherein the one or more endogenous GA3 oxidase and/or GA20 oxidase genes encode a protein that is at least 80%, at least 85%, at least 90%, at least 95%, at least 96%, at least 97%, at least 98%, at least 99%, at least 99.5%, or 100% identical to SEQ ID NO: 9, 12, 15, 30, or 33.
182. The method of embodiment 174, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.
183. The method of embodiment 174, wherein the recombinant expression cassette encodes a maize ZMM19 polypeptide.
184. The method of embodiment 174, wherein the recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.
185. The method of embodiment 174, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.
186. The method of any one of embodiments 174 to 185, further comprising selecting a modified corn plant having a desired trait.
187. The method of embodiment 186, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.
188. The method of embodiment 187, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.
189. The method of any one of embodiments 186 to 188, wherein the modified corn plant exhibit an ear trait selected from the group consisting of increased ear diameter, increased single kernel weight, increased ear fresh weight, increased ear area, increased ear volume, increased ear length, increased number of kernels per ear, increased yield, and a combination thereof, relative to a control corn plant.
190. The method of any one of embodiments 186 to 189, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.
191. A modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a MADS-box polypeptide, wherein the DNA sequence is operably linked to a plant-expressible promoter.
192. The modified corn plant of embodiment 191, wherein the modified corn plant is semi-dwarf and has one or more improved ear traits, relative to a control corn plant that does not comprise both the one or more mutations or edits and the recombinant expression cassette.
193. The modified corn plant of embodiment 192, wherein the modified corn plant has one or more improved root traits, relative to the control corn plant
194. The modified corn plant of embodiment 191 or 192, wherein the one or more mutations or edits are selected from the group consisting of an insertion, a substitution, an inversion, a deletion, a duplication, and a combination thereof.
195. The modified corn plant of any one of embodiments 191 to 194, wherein the one or more mutations or edits are introduced using a meganuclease, a zinc-finger nuclease (ZFN), a RNA-guided endonuclease, a TALE-endonuclease (TALEN), a recombinase, or a transposase.
196. The modified corn plant of any one of embodiments 191 to 195, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.
197. The modified corn plant of any one of embodiments 191 to 195, wherein MADS-box polypeptide comprises a maize ZMM19 polypeptide.
198. The modified corn plant of any one of embodiments 191 to 195, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.
199. The modified corn plant of any one of embodiments 191 to 195, the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.
200. The modified corn plant of any one of embodiments 191 to 199, wherein the recombinant expression cassette is stably integrated into the genome of the modified corn plant.
201. The modified corn plant of any one of embodiments 191 to 200, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.
202. The modified corn plant of any one of embodiments 191 to 201, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.
203. The modified corn plant of any one of embodiments 191 to 202, wherein the modified corn plant exhibits improved lodging resistance, reduced green snap, or both, relative to the control corn plant.
204. The modified corn plant of any one of embodiments 191 to 203, wherein the modified corn plant exhibits increased ear diameter relative to a control corn plant.
205. The modified corn plant of any one of embodiments 191 to 204, wherein the modified corn plant exhibits increased single kernel weight relative to a control corn plant.
206. The modified corn plant of any one of embodiments 191 to 205, wherein the modified corn plant exhibits increased ear fresh weight relative to a control corn plant.
207. The modified corn plant of any one of embodiments 191 to 206, wherein the modified corn plant exhibits increased ear area relative to a control corn plant.
208. The modified corn plant of any one of embodiments 191 to 207, wherein the modified corn plant exhibits increased ear volume relative to a control corn plant.
209. The modified corn plant of any one of embodiments 191 to 208, wherein the modified corn plant exhibits increased ear length relative to a control corn plant.
210. The modified corn plant of any one of embodiments 191 to 209, wherein the modified corn plant exhibits increased number of kernels per ear relative to a control corn plant.
211. The modified corn plant of any one of embodiments 191 to 210, wherein the modified corn plant exhibits increased yield relative to a control corn plant.
212. The modified corn plant of any one of embodiments 191 to 211, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.
213. The modified corn plant of any one of embodiments 191 to 212, wherein the modified corn plant does not have any significant off-types in at least one female organ or ear.
214. A plurality of modified corn plants in a field, each modified corn plant comprising
1) one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and
2) a recombinant expression cassette comprising a DNA sequence encoding a MADS-box polypeptide, wherein the DNA sequence is operably linked to a plant-expressible promoter.
215. The plurality of modified corn plants of embodiment 214, wherein the modified corn plants have increased yield relative to control corn plants.
216. The plurality of modified corn plants of embodiment 214 or 215, wherein the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.
217. A recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a MADS-box polypeptide, wherein the DNA sequence is operably linked to a plant-expressible promoter.
218. The recombinant DNA construct of embodiment 217, wherein the first and second expression cassettes are in a single T-DNA segment of a transformation vector.
219. The recombinant DNA construct of embodiment 217, wherein the first and second expression cassettes are in two different T-DNA segments of a transformation vector.
220. The recombinant DNA construct of any one of embodiments 217 to 219, wherein the transcribable DNA sequence encodes a non-coding RNA for suppression of a GA3 oxidase gene.
221. The recombinant DNA construct of embodiment 220, wherein the transcribable DNA sequence encodes a non-coding RNA for suppression of a GA3 oxidase_1 gene, a GA3 oxidase_2 gene, or both.

222. The recombinant DNA construct of embodiment 221, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

223. The recombinant DNA construct of embodiment 221, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

224. The recombinant DNA construct of embodiment 220, wherein the transcribable DNA sequence encodes a non-coding RNA for suppression of a GA20 oxidase gene.

225. The recombinant DNA construct of embodiment 224, wherein the transcribable DNA sequence encodes a non-coding RNA for suppression of a GA20 oxidase_3 gene, a GA20 oxidase_4 gene, a GA20 oxidase_5 gene, or a combination thereof.

226. The recombinant DNA construct of embodiment 224, wherein the transcribable DNA sequence encodes a non-coding RNA for suppression of a GA20 oxidase_3 gene, a GA20 oxidase_5 gene, or both.

227. The recombinant DNA construct of embodiment 226, wherein the transcribable DNA sequence comprises a sequence that is at least 80% identical or complementary to at least 15 consecutive nucleotides of SEQ ID NO: 39, 53, or 55.

228. The recombinant DNA construct of embodiment 227, wherein the transcribable DNA sequence encodes a sequence that is at least 80% complementary to at least 15 consecutive nucleotides of SEQ ID NO: 40, 54, or 56.

229. The recombinant DNA construct of any one of embodiments 217 to 228, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

230. The recombinant DNA construct of any one of embodiments to 217 to 229, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

231. The recombinant DNA construct of any one of embodiments 217 to 230, wherein the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

232. The recombinant DNA construct of any one of embodiments 217 to 230, wherein the DNA sequence comprised in the second expression cassette encodes a maize ZMM19 polypeptide.

233. The recombinant DNA construct of any one of embodiments 217 to 230, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

234. The recombinant DNA construct of any one of embodiments 217 to 230, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

235. The recombinant DNA construct of any one of embodiments 217 to 232, the plant-expressible promoter is a vascular promoter.

236. The recombinant DNA construct of embodiment 235, wherein the vascular promoter is selected from the group consisting of a sucrose synthase promoter, a sucrose transporter promoter, a Sh1 promoter, CoYMV promoter, a WDV large intergenic region (LIR) promoter, a MSV coat polypeptide (CP) promoter, a rice yellow stripe 1 (YS1)-like promoter, a rice yellow stripe 2 (OsYSL2) promoter, and a combination thereof.

237. The recombinant DNA construct of any one of embodiments 217 to 232, wherein the plant-expressible promoter is an RTBV promoter.

238. The recombinant DNA construct of any one of embodiments 217 to 232, wherein the plant-expressible promoter is a leaf promoter.

239. The recombinant DNA construct of embodiment 238, wherein the leaf promoter is selected from the group consisting of a RuBisCO promoter, a PPDK promoter, a FDA promoter, a Nadh-Gogat promoter, a chlorophyll a/b binding polypeptide gene promoter, a PEPC promoter, a Myb gene promoter, and a combination thereof.

240. The recombinant DNA construct of any one of embodiments 217 to 232, wherein the plant-expressible promoter is a constitutive promoter.

241. The recombinant DNA construct of embodiment 240, wherein the constitutive promoter is selected from the group consisting of an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

242. The recombinant DNA construct of any one of embodiments 217 to 232, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

243. The recombinant DNA construct of any one of embodiments 217 to 232, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 174 or a functional portion thereof.

244. The recombinant DNA construct of any one of embodiments 217 to 232, wherein the plant-expressible promoter is selected from the group consisting of a meristem promoter, a root promoter, a seed or kernel promoter, and a combination thereof.

245. The recombinant DNA construct of embodiment 217, wherein the non-coding RNA is a precursor miRNA or siRNA capable of being processed or cleaved to form a mature miRNA or siRNA.

246. A transformation vector comprising the recombinant DNA construct of any one of embodiments 217 to 245.

247. A modified corn plant or a plant part thereof comprising the recombinant DNA construct of embodiment 246.

248. The modified corn plant of embodiment 247, wherein the modified corn plant is semi-dwarf and has one or more improved ear traits, relative to a control corn plant not having both the first and second expression cassettes.

249. The modified corn plant of embodiment 248, wherein the modified corn plant has one or more improved root traits, relative to the control corn plant 250. The modified corn plant of embodiment 248, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to the control corn plant.

251. The modified corn plant of embodiment 248, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to the control corn plant.

252. The modified corn plant of embodiment 248, wherein the modified corn plant exhibits improved lodging resistance, reduced green snap, or both, relative to the control corn plant.

253. The modified corn plant of embodiment 248, wherein the modified corn plant exhibits increased ear diameter relative to the control corn plant.

254. The modified corn plant of embodiment 248, wherein the modified corn plant exhibits increased single kernel weight relative to the control corn plant.

255. The modified corn plant of embodiment 248, wherein the modified corn plant exhibits increased ear fresh weight relative to the control corn plant.

256. The modified corn plant of embodiment 248, wherein the modified corn plant exhibits increased ear area relative to the control corn plant.

257. The modified corn plant of embodiment 248, wherein the modified corn plant exhibits increased ear volume relative to the control corn plant.

258. The modified corn plant of embodiment 248, wherein the modified corn plant exhibits increased ear length relative to the control corn plant.

259. The modified corn plant of embodiment 248, wherein the modified corn plant exhibits increased number of kernels per ear relative to the control corn plant.

260. The modified corn plant of embodiment 248, wherein the modified corn plant exhibits increased yield relative to the control corn plant.

261. The modified corn plant of embodiment 248, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to the control corn plant.

262. The modified corn plant of embodiment 248, wherein the modified corn plant does not have any significant off-types in at least one female organ or ear.

263. A recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a MADS-box polypeptide, wherein the DNA sequence is operably linked to a plant-expressible promoter.

264. The recombinant DNA donor template molecule of embodiment 263, comprising two of the homology sequences, wherein the two homology sequences flank the insertion sequence.

265. The recombinant DNA donor template molecule of embodiment 263 or 264, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

266. The recombinant DNA donor template molecule of embodiment 263 or 264, wherein the MADS-box polypeptide comprises a maize ZMM19 polypeptide.

267. The recombinant DNA donor template molecule of embodiment 263 or 264, wherein the DNA sequence comprised in the expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

268. The recombinant DNA donor template molecule of embodiment 263 or 264, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

269. The recombinant DNA donor template molecule of any one of embodiments 263 to 268, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

270. The recombinant DNA donor template molecule of any one of embodiments 263 to 268, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 174 or a functional portion thereof.

271. The recombinant DNA donor template molecule of any one of embodiments 263 to 268, wherein the plant-expressible promoter is selected from the group consisting of a meristem promoter, a root promoter, a seed or kernel promoter, and a combination thereof.

272. The recombinant DNA donor template molecule of any one of embodiments 263 to 269, further comprising a transcribable DNA sequence encoding a non-coding RNA for suppression of one or more GA20 oxidase genes and/or one or more GA3 oxidase genes, wherein the transcribable DNA sequence is operably linked to a promoter.

273. The recombinant DNA donor template molecule of embodiment 271, wherein the promoter is a vascular promoter.

274. The recombinant DNA donor template molecule of embodiment 272, wherein the vascular promoter is selected from the group consisting of a sucrose synthase promoter, a sucrose transporter promoter, a Sh1 promoter, Commelina yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, a rice yellow stripe 2 (OsYSL2) promoter, and a combination thereof.

275. The recombinant DNA donor template molecule of embodiment 273, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70, or SEQ ID NO: 71, or a functional portion thereof.

276. The recombinant DNA donor template molecule of any one of embodiments 263 to 268, wherein the promoter is a rice tungro bacilliform virus (RTBV) promoter.

277. The recombinant DNA donor template molecule of embodiment 275, wherein the RTBV promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

278. The recombinant DNA donor template molecule of any one of embodiments 263 to 268, wherein the promoter is a leaf promoter.

279. The recombinant DNA donor template molecule of embodiment 277, wherein the leaf promoter is selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, a Myb gene promoter, and a combination thereof.

280. The recombinant DNA donor template molecule of embodiment 278, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

281. The recombinant DNA donor template molecule of any one of embodiments 263 to 268, wherein the promoter is a constitutive promoter.

282. The recombinant DNA donor template molecule of embodiment 280, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a *mirabilis* mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

283. The recombinant DNA donor template molecule of embodiment 281, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

284. The modified corn plant of embodiment 1, wherein the first recombinant expression cassette comprises SEQ ID NO: 39, and the second recombinant expression cassette comprises SEQ ID NO: 169.

285. The modified corn plant of embodiment 284, wherein the modified corn plant is semi-dwarf and exhibits one or more improved ear traits, relative to a control plant that does not comprise the first or second recombinant expression cassette.

286. The modified corn plant of embodiment 285, wherein the one or more improved ear traits are selected from the group consisting of broad acreage yield, ear area, ear dry weight, ear tip void, single kernel weight, kernels per ear, ear fresh weight, and a combination thereof.

287. A modified corn plant or a plant part thereof comprising 1) a first transcribable DNA sequence comprising SEQ ID NO: 39, and 2) a second transcribable DNA sequence comprising SEQ ID NO: 169.

288. The modified corn plant of embodiment 287, wherein the modified corn plant is semi-dwarf and has one or more improved ear traits, relative to a control corn plant that does not have the first or second transcribable DNA sequence.

289. The modified corn plant of embodiment 288, wherein the one or more improved ear traits are selected from the group consisting of broad acreage yield, ear area, ear dry weight, ear tip void, single kernel weight, kernels per ear, ear fresh weight, and a combination thereof.

290. A method for producing a modified corn plant, the method comprising
  a. introducing into a corn cell a recombinant expression cassette comprising a first transcribable DNA sequence comprising SEQ ID NO: 39, and a second transcribable DNA sequence comprising SEQ ID NO: 169;
  b. regenerating or developing a modified corn plant from the corn cell, wherein the modified corn plant comprises the first and second transcribable DNA sequences.

291. The method of embodiment 290, wherein the modified corn plant is semi-dwarf and has one or more improved ear traits, relative to a control corn plant that does not have the first or second transcribable DNA sequence.

292. The method of embodiment 291, wherein the one or more improved ear traits are selected from the group consisting of broad acreage yield, ear area, ear dry weight, ear tip void, single kernel weight, kernels per ear, ear fresh weight, and a combination thereof.

293. A recombinant expression cassette comprising 1) a first transcribable DNA sequence comprising SEQ ID NO: 39, and 2) a second transcribable DNA sequence comprising SEQ ID NO: 169.

EXAMPLES

Example 1. Generation of the GA20Ox_SUP/ZMM19 Stack Plants

An inbred corn plant line was transformed via *Agrobacterium*-mediated transformation with a transformation vector having an expression construct comprising a miRNA-encoding DNA sequence (SEQ ID NO: 39) encoding a targeting sequence (SEQ ID NO: 40) under the control of a rice tungro baciliform virus (RTBV) promoter (SEQ ID NO: 65) known to cause expression in vascular tissues of plants. The miRNA encoded by the construct comprises an RNA sequence that targets the GA20 oxidase_3 and GA20 oxidase_5 genes in corn plants. Several transformation events were generated therefrom. The resulting transformed/transgenic inbred line is herein referred to as GA20Ox_SUP or GA20Ox_SUP single.

Plant height was measured up to the uppermost ligulated leaf at the R3 stage. As shown in FIG. 1, statistically significant reductions in plant height between 35% and 45% are consistently observed in GA20Ox_SUP single plants relative to control plants (p-value≤0.2).

Similarly, an inbred corn plant line was transformed via *Agrobacterium*-mediated transformation with a transformation vector having an expression construct comprising an *Oryza sativa* Rcc3 gene promoter region (SEQ ID NO: 170), a leader sequence thereof (SEQ ID NO: 171), a *Zea mays* intron sequence (SEQ ID NO: 172), and an *Oryza sativa* UP2 terminator region (SEQ ID NO: 173), operably linked to a polynucleotide sequence (SEQ ID NO: 169) encoding maize ZMM19 polypeptide (SEQ ID NO: 168). Several transformation events were generated therefrom. The resulting transformed/transgenic inbred line is herein referred to as ZMM19, ZMM19 transgenic plant, or ZMM19 single.

Parental GA20Ox_SUP and ZMM19 singles were crossed to create a stacked transgenic progeny plant comprising both the ZMM19 transgene and the miRNA-encoding DNA sequence for the suppression of GA20 oxidase_3 and GA20 oxidase_5 genes. The stacked combination may be referred to as a breeding or crossing stack since the transgenes are brought together through crossing of two parental plants. The resulting stacked transgenic line is herein referred to as GA20Ox_SUP/ZMM19 stack. The GA20Ox_SUP/ZMM19 stack can be an inbred stack if the parental lines are of the same inbred line origin, or a hybrid when the parental lines are of different inbreds.

For each type of transgenic single and stack plants, the corresponding control plants were also produced for comparison having the same inbred line or same parental line combination, but without the transgenic GA20Ox_SUP and ZMM19 constructs.

Example 2. Reduced Height of the GA20Ox_SUP/ZMM19 Stack Plants

GA20Ox_SUP/ZMM19 stack plants were grown to maturity in a field under standard agronomic practice and their heights were measured. Plant height was measured as the plot average from the soil line to the base of highest collared leaf at the R3 stage. A sufficient number of plants were measured to meet statistical significance with p-value≤0.2. Control plants of the same parental inbred lines but without the GA20Ox_SUP and ZMM19 transgenic constructs were also grown under similar conditions.

Figure 2:
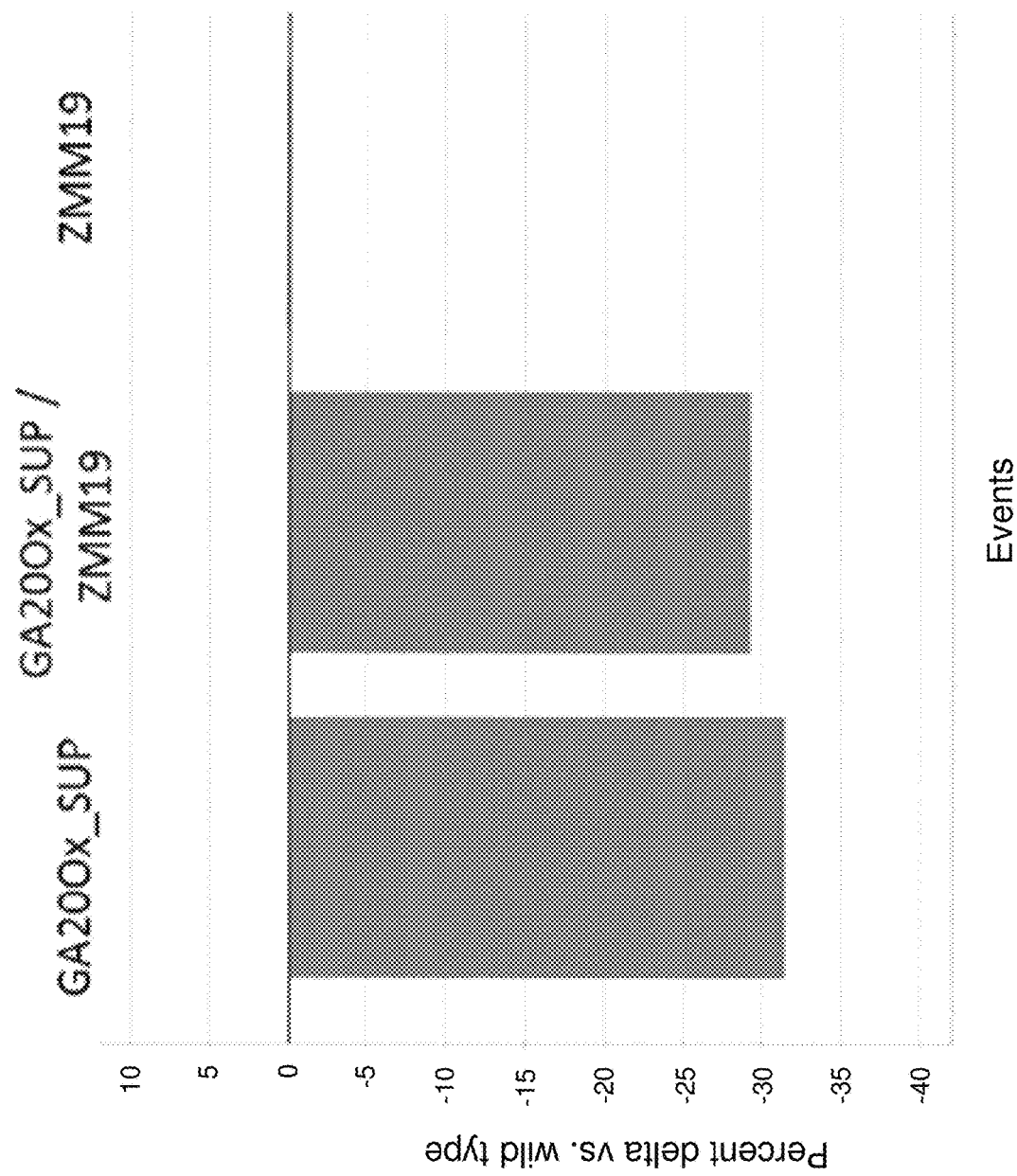
FIG. 2 shows plant heights of stacked transgenic corn plants comprising a DNA sequence encoding a miRNA for suppression of GA20 oxidase genes and a transgene encoding maize ZMM19 polypeptide ("GA20Ox_SUP/ZMM19 stack"), along with GA20Ox_SUP single corn plants, and ZMM19 single corn plants, each relative to control corn plants.

Average plant height reduction for the GA20Ox_SUP/ZMM19 stack, as well as the GA20Ox_SUP single and ZMM19 single, are shown in FIG. 2, each relative to control plants. As shown in FIG. 2, a statistically significant reduction in plant height averaging between 25 to 30% was consistently observed in GA20Ox_SUP/ZMM19 stack plants relative to control plants. In contrast, the plant height of ZMM19 single plants were relatively unchanged in comparison to control plants.

Example 3. Enhanced Root Traits and Ear Traits with Expression of the ZMM19 Gene The transgenic single and stack plants and control plants described in Example 1 were grown under standard agronomic practice. Several root traits were measured for the ZMM19 single plants. Crown lateral root density rating at the V12 stage (CLRV12) is measured as an average of two plants per plot, using a visual rating system score from 1-9, with 1 being the least complex looking root system and 9 being the most complex looking root system. Root dry weight at the V12 (RDWV12) stage is measured as the plot average (based on two plants) of root dry weight at the V12 stage.

Corn ear traits were measured for the ZMM19 single plants at the R6 stage. Ear area is measured as the plot average of the area of an ear from a two-dimensional view by imaging the ear and including kernels and tip void in the area measurement. Typically, 10 representative ears were measured per plot. Ear diameter is a measure of the plot average of the ear diameter measured as the maximal "wide" axis of an ear over its widest section. Ear length is a measure of the plot average of the length of an ear measured from the tip of the ear in a straight line to the base of the ear node. Ear volume is measured as the plot average of the volume of an ear calculated by measuring the diameter and estimating the resulting volume along the length of the ear (one row at a time), accounting for the shape/contour of the ear, but assuming that the ear is a perfect circle for each row.

Grain yield estimate is a conversion from the hand-harvested grain weight per area measurement, collected from a small section of a plot, to the equivalent number of bushels per acre, including adjustment to a standard moisture level. Number of kernels per ear is a measure of the plot average of the number of kernels divided by the number of ears.

Single kernel weight is measured as the plot average of weight per kernel, calculated as the sample kernel weight (adjusted to a standard moisture level)/sample kernel number. The sample kernel number can range from 350 to 850.

Figure 3A:
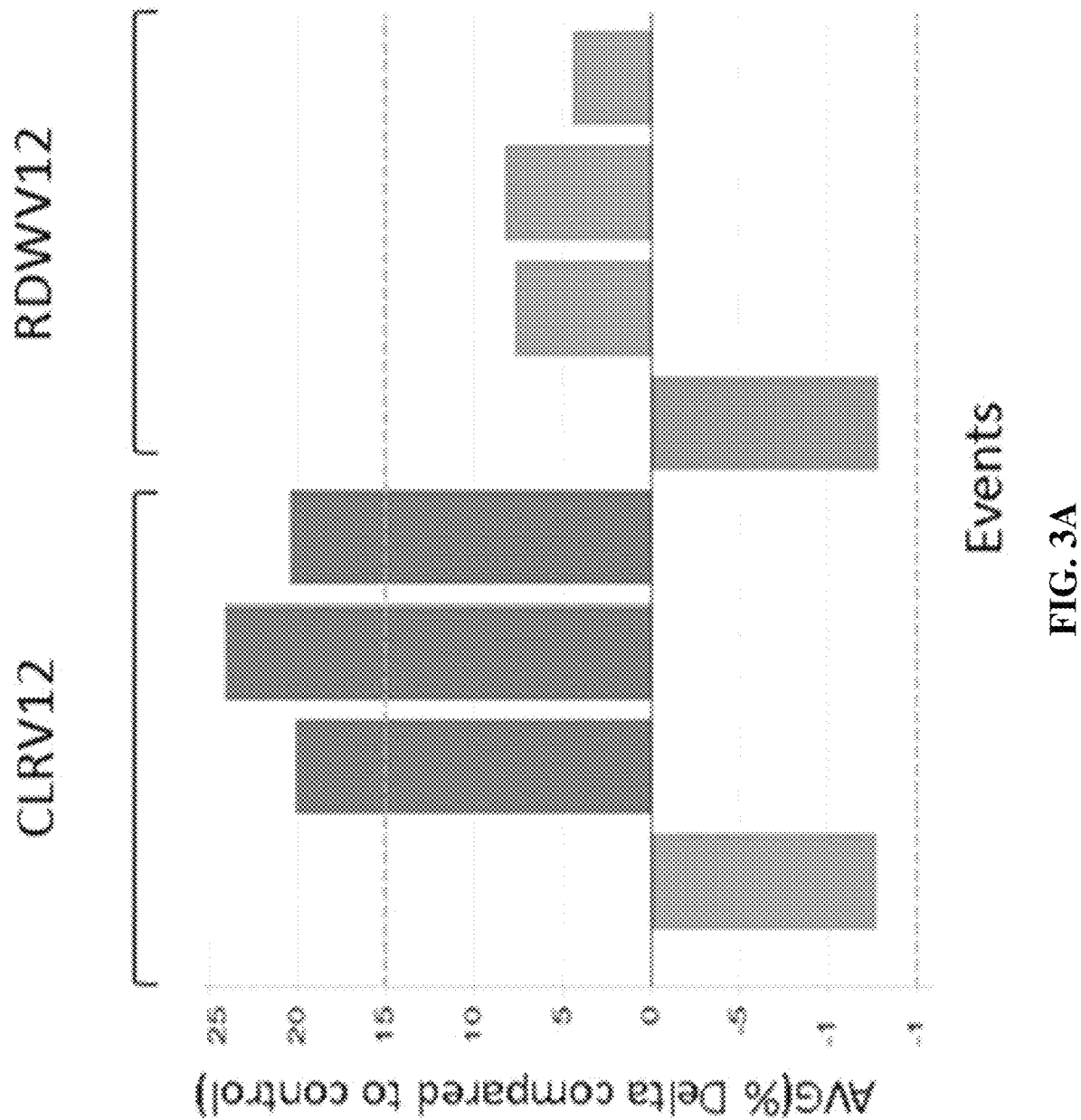
FIG. 3A shows root traits of transgenic corn plants comprising a transgene encoding maize ZMM19 polypeptide ("ZMM19 single") relative to control corn plants.

FIG. 3A shows root trait results for ZMM19 single plants. Results are shown as percent difference (delta) between ZMM19 single plants and control plants of the same inbred without the ZMM19 transgenic construct. Dark grey bars indicate statistically significant changes as compared to control plants (p-value≤0.2). As shown in FIG. 3A, in comparison to controls, ZMM19 single plants exhibited statistically significant increase in crown root lateral root density rating at the V12 stage (CLRV12) by about 20 to 25% across most events. ZMM19 single plants also exhibited numerical increase in root dry weight at the V12 stage (RDWV12) in comparison to controls.

Figure 3B:
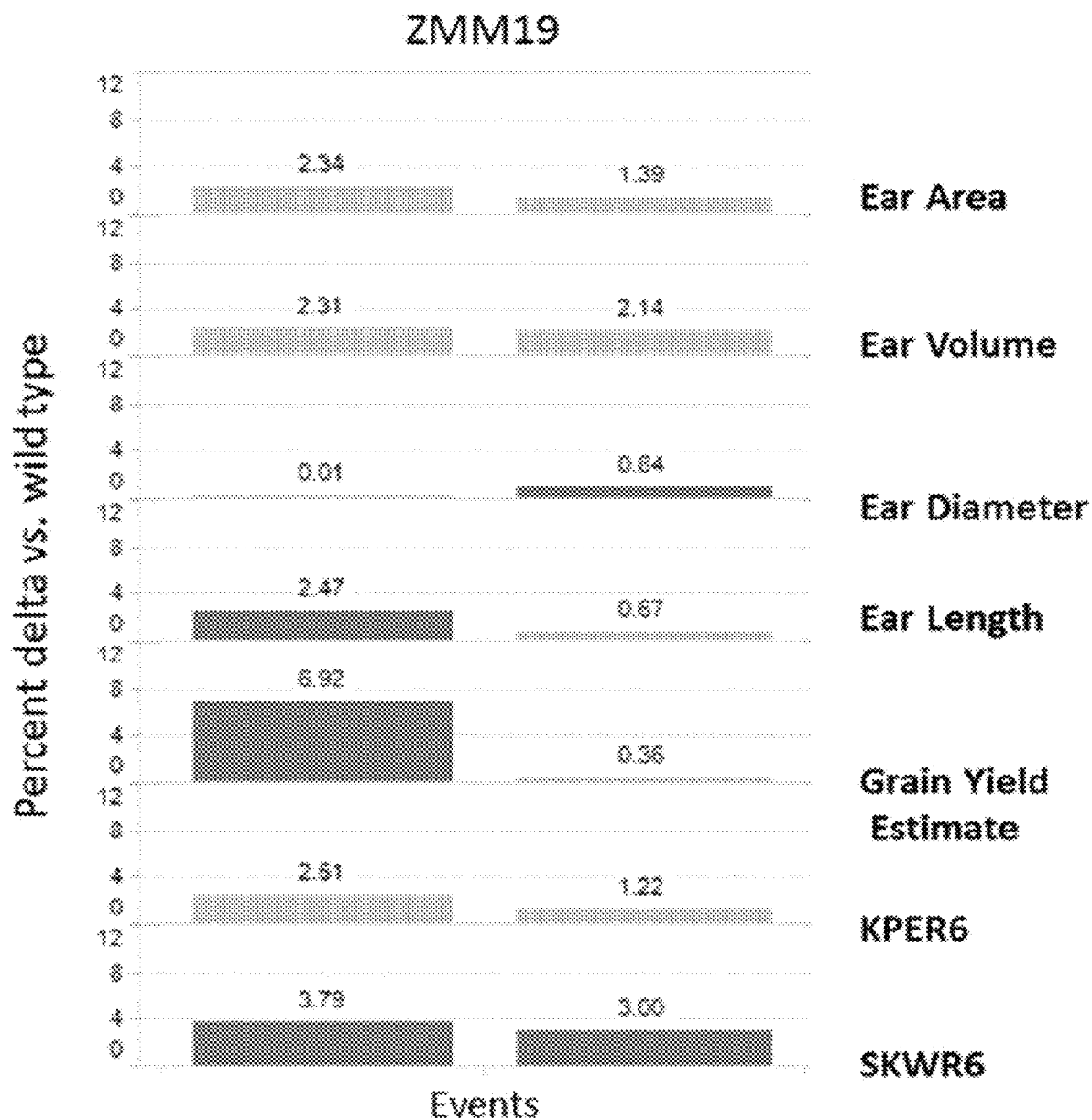
FIG. 3B shows ear traits of ZMM19 single plants relative to control corn plants.

FIG. 3B shows ear trait results for ZMM19 single plants. Results are shown as percent difference (delta) between ZMM19 single plants and control plants of the same inbred without the ZMM19 transgenic construct. Dark grey bars indicate statistically significant changes (positive or negative) as compared to control plants (p-value≤0.2). As shown in FIG. 3B, in comparison to controls, ZMM19 single plants exhibited statistically significant improvement in a number of ear traits, including increased ear diameter, increased ear length, increased grain yield estimate, and increased single kernel weight (SKWR6) depending on the transformation event. ZMM19 single plants also exhibited numerical increases in ear area, ear volume, and number of kernels per ear (KPER6) in comparison to control plants.

Figure 3C:
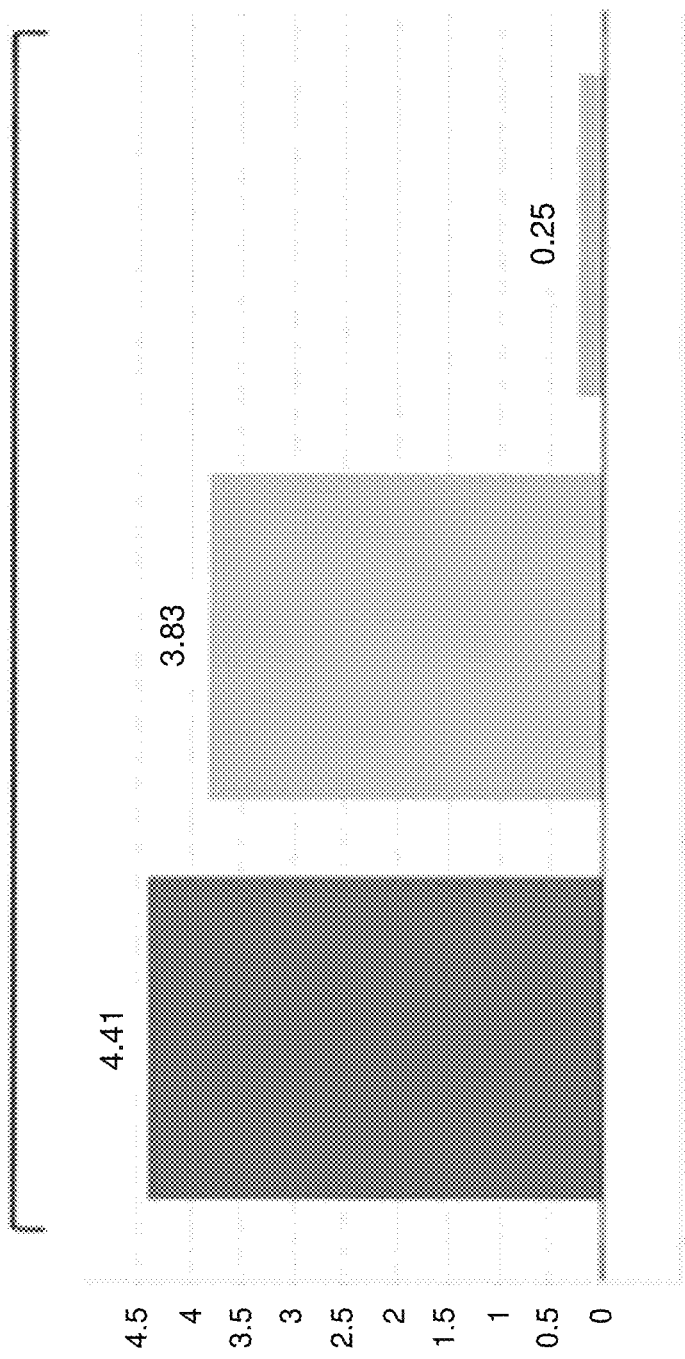
FIG. 3C shows yield of ZMM19 single plants relative to control corn plants.

As shown in FIG. 3C, ZMM19 single plants showed a slight to modest increase in yield (in bushels/acre) by as much as 4.5 bushels/acre in comparison to control plants. However, as shown below, GA20Ox_SUP/ZMM19 stack plants surprisingly exhibited statistically significant increase in yield of at least 8 bushels/acre in comparison to control plants depending on event and germplasm.

Example 4. Enhanced Ear Traits of the GA20Ox_SUP/ZMM19 Stack Plants

Figure 4A:
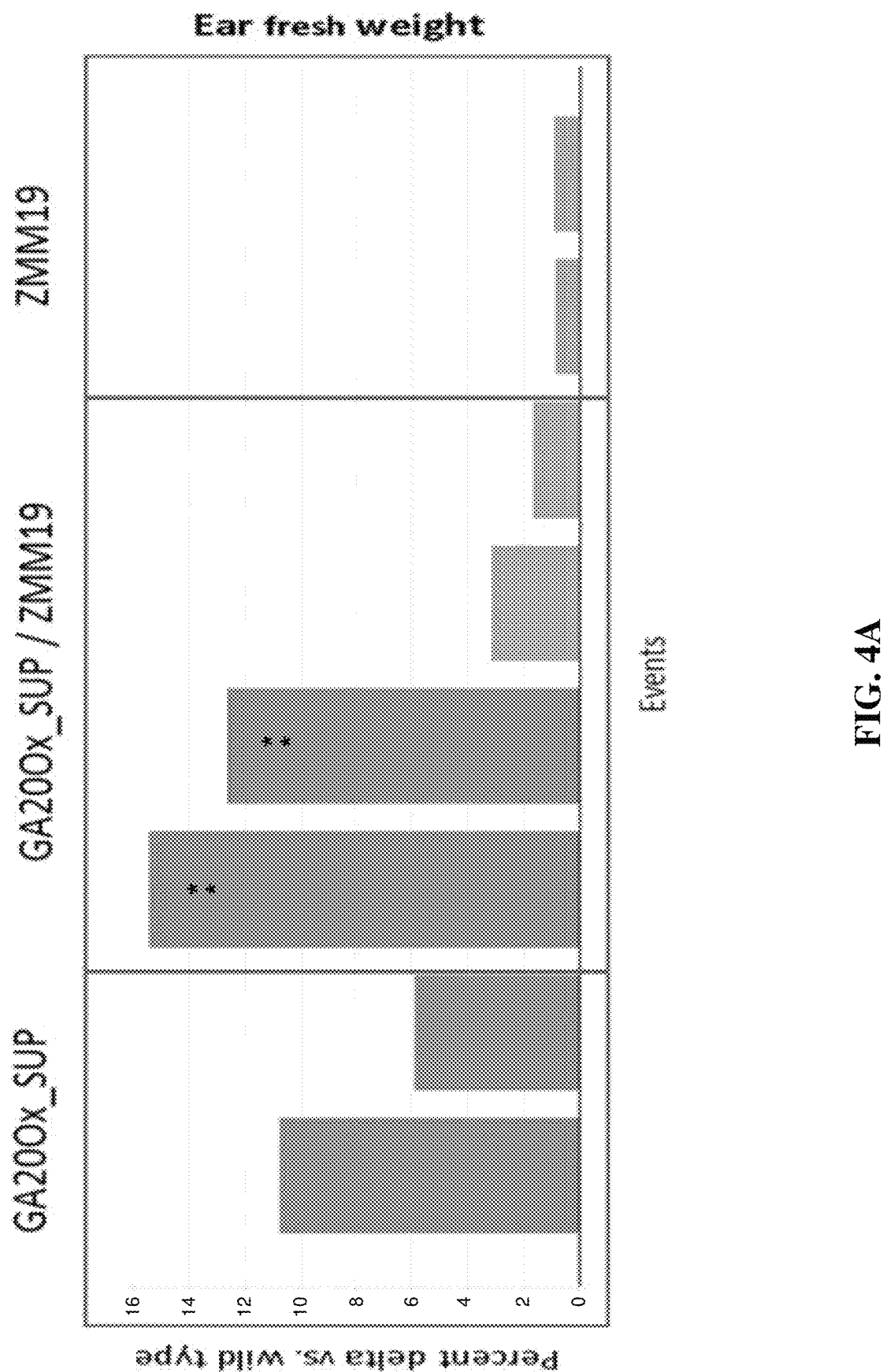
FIGS. 4A-4C show ear traits of GA20Ox_SUP/ZMM19 stack corn plants across four transformation events, GA20Ox_SUP single corn plants across two transformation events, and ZMM19 single corn plants across two transformation events, including ear fresh weight, ear area, ear volume, ear diameter, ear length, number of kernels per ear at the R6 stage, and single kernel weight at the R6 stage, under standard agronomic conditions in the field, relative to control corn plants.
Figure 4B:
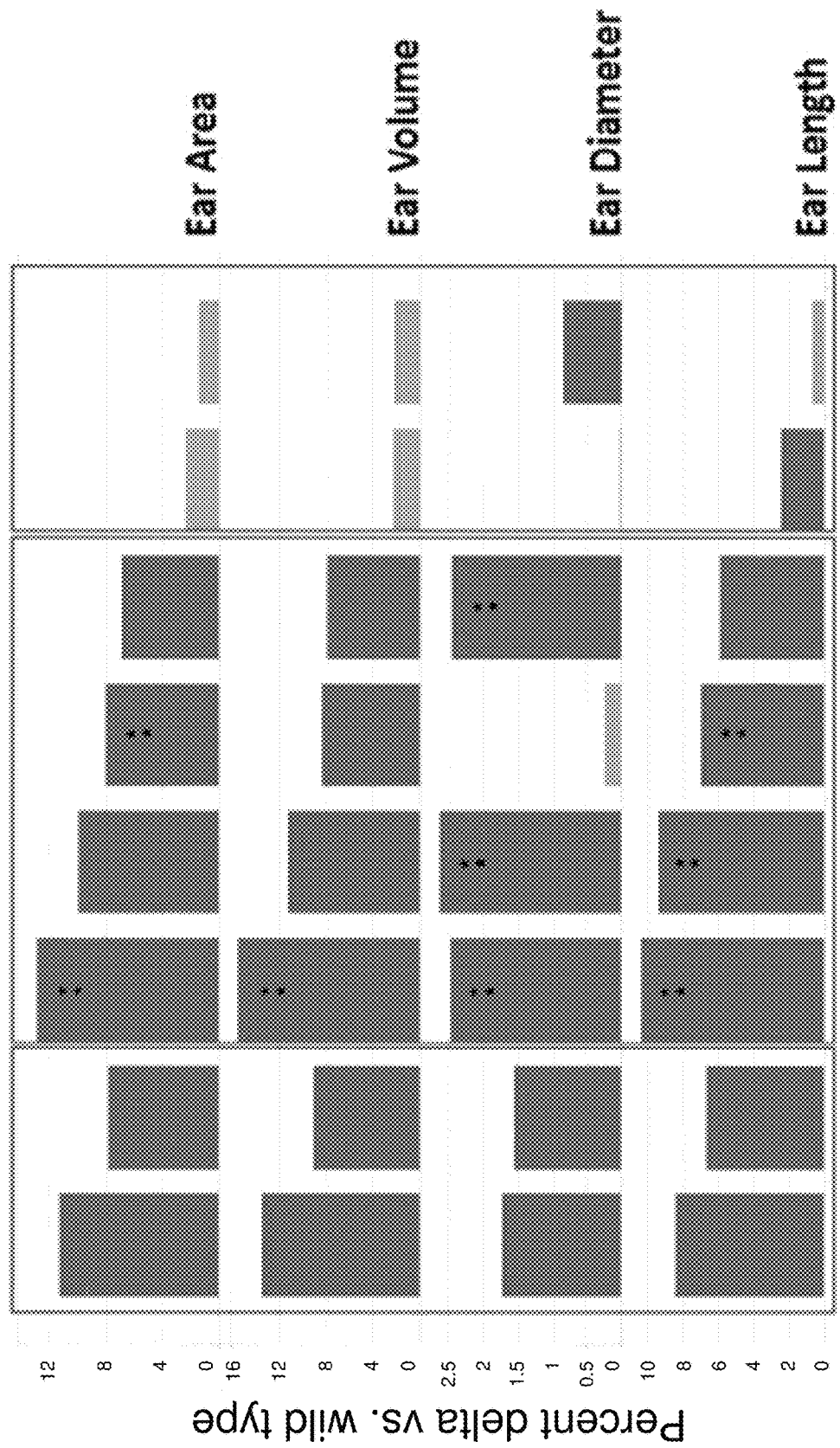
Figure 4C:
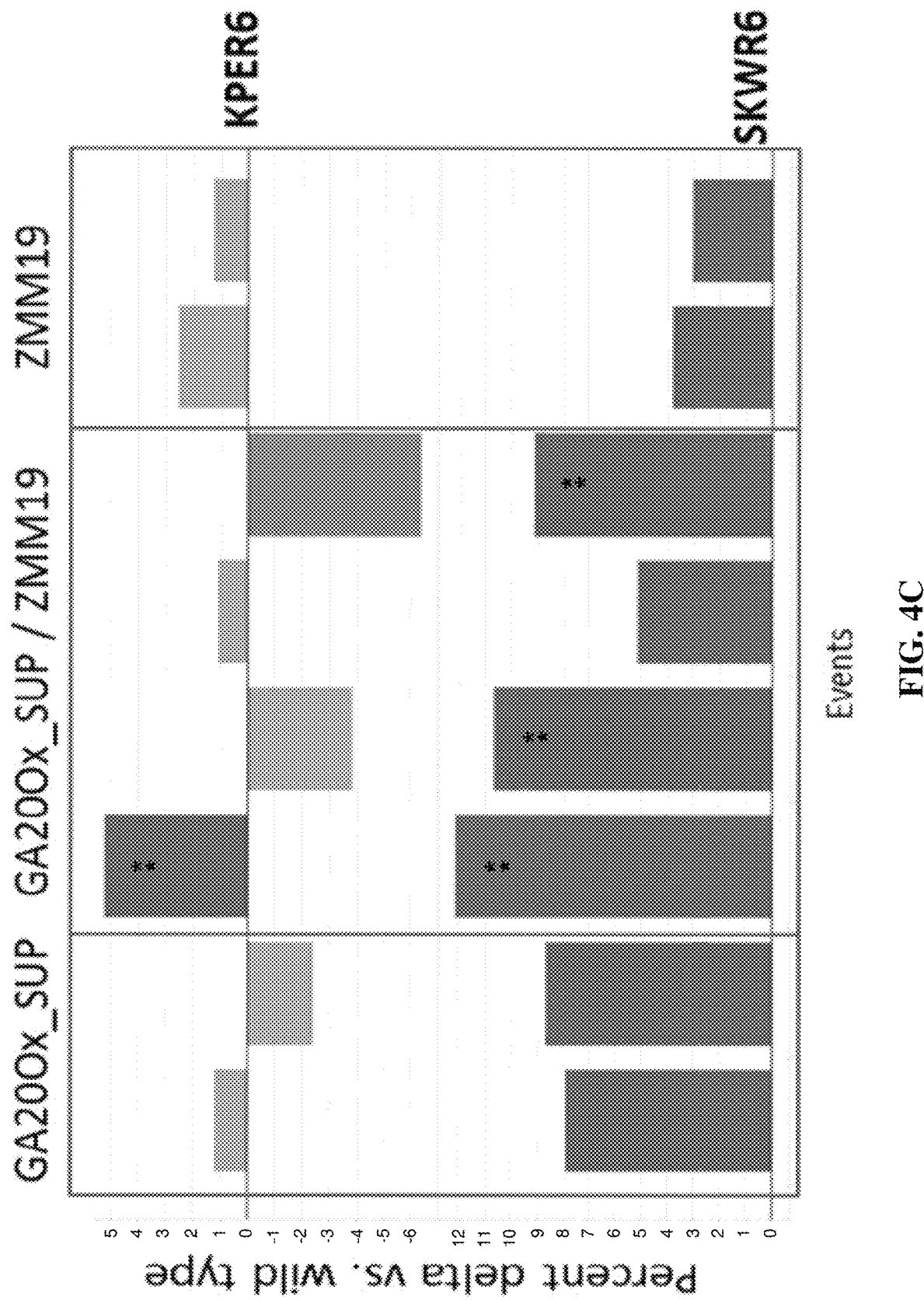

Positive trait interactions with regard to ear traits were observed when both the GA20Ox_SUP and ZMM19 constructs were present in the same plants. As shown in FIG. 4A-4C, ear traits such as ear fresh weight, ear area, ear volume, ear diameter, ear length, kernels per ear, and single kernel weight were measured in two events of GA20OX_SUP single, two events of ZMM19 single, and four event combinations of GA20Ox_SUP/ZMM19 stack plants grown in a single growing season. The definitions for ear area, ear volume, ear diameter, ear length, kernels per ear, and single kernel weight are provided above. Ear fresh weight is measured as the plot average of the weight of a fresh ear at the R6 stage. Each bar in FIG. 4A-4C indicates one transformation event (or stacked event combination). Bars with double asterisks (**) for stacked event combinations indicate a statistically significant change (increase) as compared to both GA20Ox_SUP and ZMM19 single plants.

Results in FIG. 4A-4C show that while GA20Ox_SUP and ZMM19 single events can have moderately improved ear fresh weight, ear area, ear volume, ear diameter, ear length, kernels per ear (KPER6), and/or single kernel weight (SKWR6) relative to control plants, GA20Ox_SUP/ZMM19 stack plants had a statistically significant increase in all seven ear traits relative to control plants. The average increase in all seven ear traits in GA20Ox_SUP/ZMM19 stack plants was numerically greater than that of the ZMM19 and GA20Ox_SUP single plants, with statistically significant increases in these ear traits over one or both of the ZMM19 and GA20Ox_SUP single plants with some events.

Figure 4D:
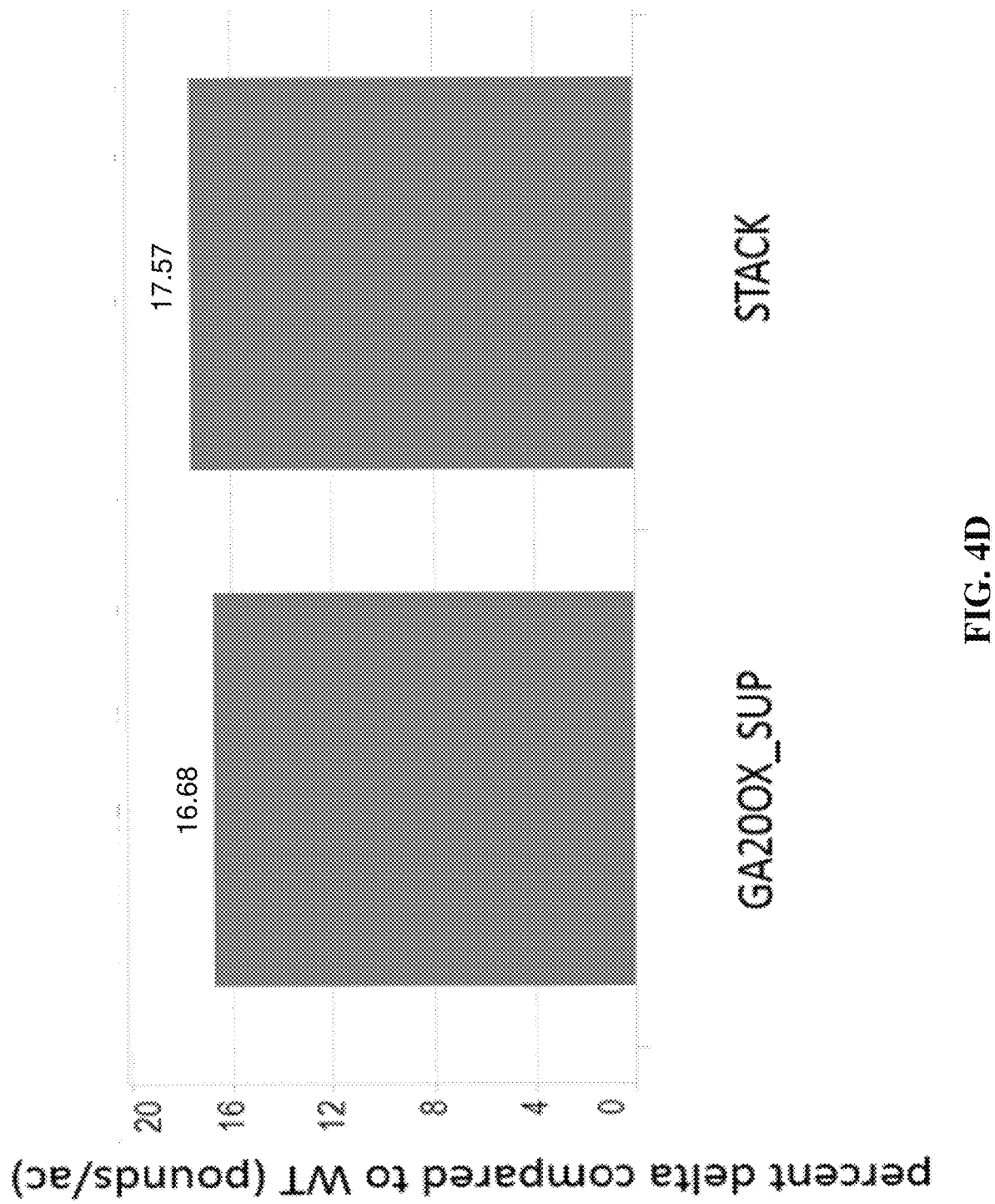
FIG. 4D shows grain yield estimate of GA20Ox_SUP single and GA20Ox_SUP/ZMM19 stack plants, relative to control corn plants.

FIG. 4D shows grain yield estimate as measured for plants grown in a single growing season having one event of the GA20Ox_SUP single, or one event combination for the GA20Ox_SUP/ZMM19 transgene stack, relative to control plants. The data in FIG. 4D is presented as the percentage difference between the grain yield estimate of GA20Ox_SUP single or GA20Ox_SUP/ZMM19 stack plants, relative to wildtype control plants. Dark gray bars indicate statistically significant positive changes (p-value≤0.2). As shown in FIG. 4D, GA20Ox_SUP/ZMM19 stack plants showed a statistically significant increase in grain yield estimate relative to control plants, with an average increase greater than that of GA20Ox_SUP single plants.

Figure 4E:
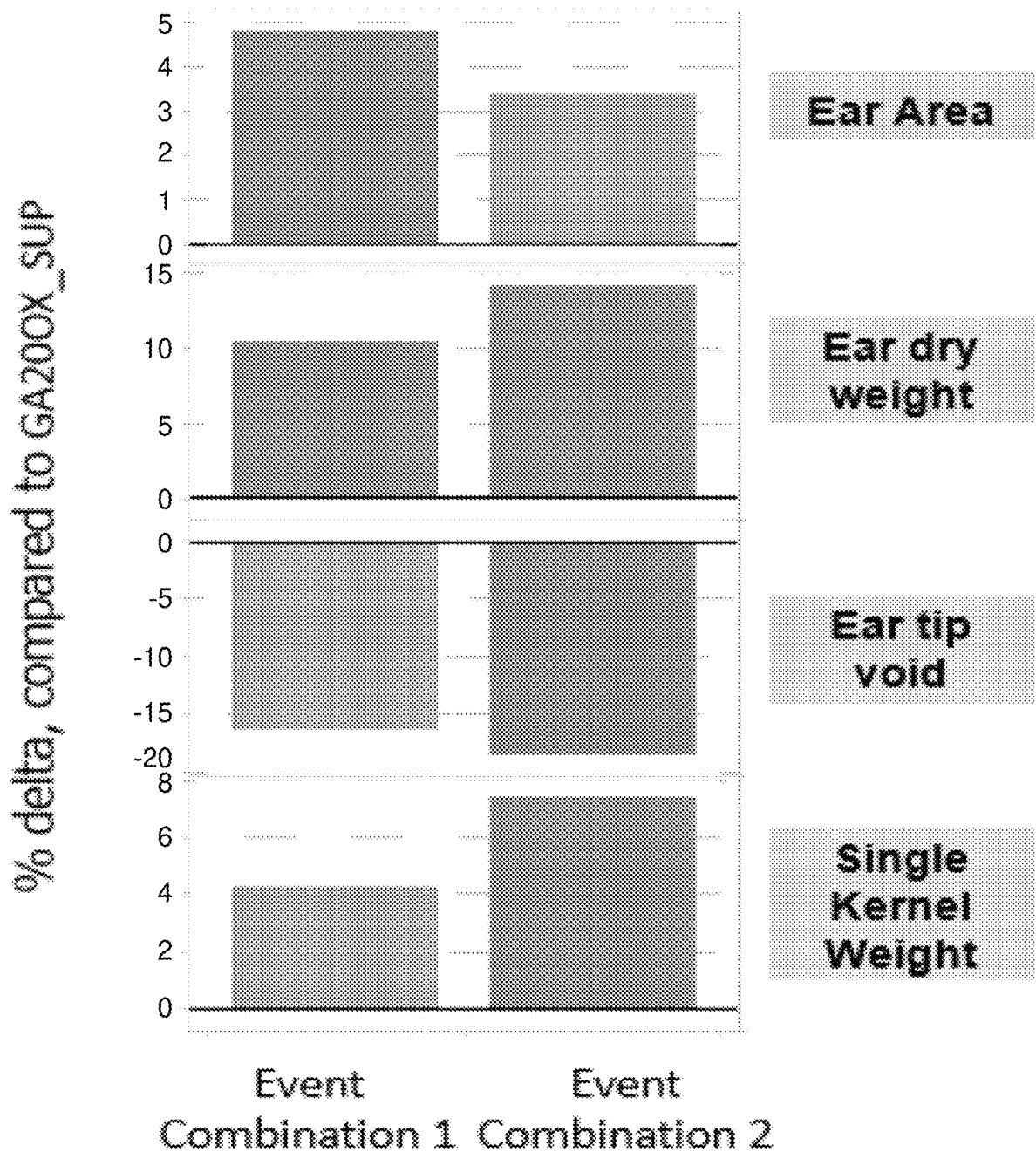
FIG. 4E shows ear area, ear dry weight, ear tip void, and single kernel weight of GA20Ox_SUP/ZMM19 stack plants in a drought reproductive assay, relative to GA20Ox_SUP single plants.

FIG. 4E shows ear area, ear dry weight, ear tip void, and single kernel weight with two event combinations of GA20Ox_SUP/ZMM19 stack plants in a drought reproductive assay in which drought stress was applied from the V8 to R1 developmental stages. The data in FIG. 4E is presented as the percentage difference between each of the above ear traits of GA20Ox_SUP/ZMM19 stack plants and that of GA20Ox_SUP single plants. Dark gray bars indicate statistically significant positive or negative changes (p-value≤0.1), and light gray bars indicate numerically positive or negative changes. As shown in FIG. 4E, GA20Ox_SUP/ZMM19 stack plants showed statistically significant increase in ear area, ear dry weight, and single kernel weight, relative to GA20Ox_SUP single plants. Further, GA20Ox_SUP/ZMM19 stack plants showed statistically significant decrease in ear tip void relative to GA20Ox_SUP single plants.

These results show that GA20Ox_SUP/ZMM19 stack plants have enhanced ear traits, such as ear fresh weight, ear area, ear dry weight, ear tip void, ear volume, ear diameter, ear length, kernels per ear, and single kernel weight, as compared to control plants and ZMM19 and/or GA20Ox_SUP single plants with statistically significant improvement in these traits in GA20Ox_SUP/ZMM19 stack plants depending on the particular event combinations.

Example 5. Increased Yield of GA20Ox_SUP/ZMM19 Stack Plants

Figure 5:
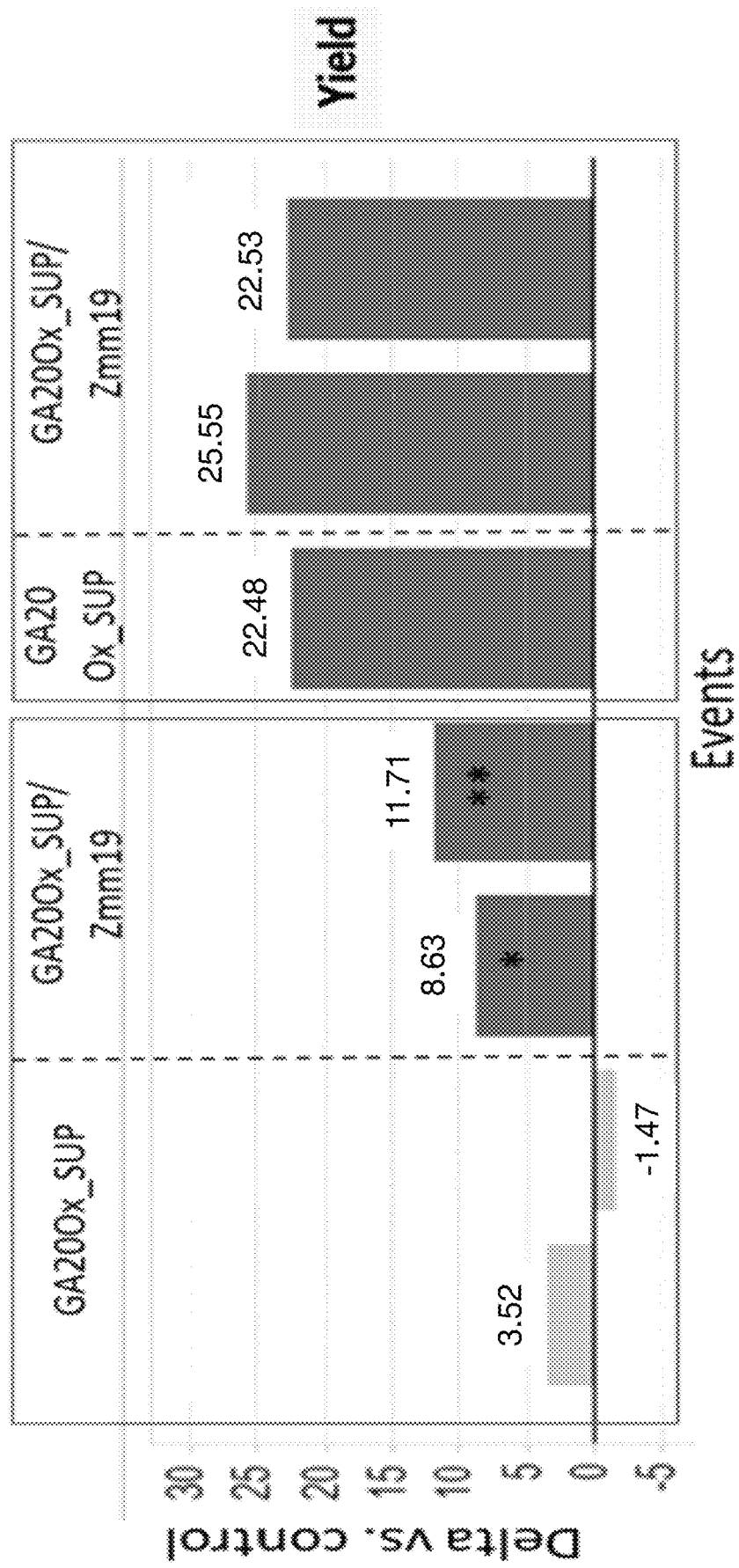
FIG. 5 shows yield of GA20Ox_SUP/ZMM19 stack corn plants and GA20Ox_SUP single corn plants under standard agronomic conditions in the field, relative to control corn plants.

FIG. 5 shows broad acre yield results in a field trial for GA20Ox_SUP single plants and GA20Ox_SUP/ZMM19 stack plants. Results are shown as the difference (delta) in yield (bushels/acre) as compared to control plants. Dark grey bars indicate values significantly different (increased) from control plants (p-value≤0.2). Bars with two asterisks (**) indicate values statistically different (increased) from GA20Ox_SUP single plants (p-value≤0.1), and bars with one asterisk (*) indicate values numerically different (increased) from GA20Ox_SUP single plants.

As shown in FIG. 5, statistically significant increases in yield for GA20Ox_SUP/ZMM19 stack plants were observed relative to control plants, and the average numerical increase was greater than that of GA20Ox_SUP single plants, although the amount of the increase was dependent on the particular corn hybrid germplasm (each box in FIG. 5 represents a different corn hybrid plant cross involving the same female parent but different male testers). Some of these yield results for GA20Ox_SUP/ZMM19 stack plants are surprising given the relatively modest increase in yield in ZMM19 single plants (shown in FIG. 3C above to be about 4.5 bushels per acre or less).

These results suggest that the positive ear traits described above in GA20Ox_SUP/ZMM19 stack plants may cause, or allow for, an increase in yield in GA20Ox_SUP/ZMM19 stack plants over control plants that can be greater than that of GA20Ox_SUP and/or ZMM19 singles.

Example 6. Identification of MADS-Box Gene Homologs

Twenty-five MADS-box homologs were identified from the following species: bread wheat, domesticated barley, Indian rice, Japanese rice, maize, perennial ryegrass, sorghum, and tall fescue. The *Zea mays* ZMM19 protein sequences were further searched in Genbank® to identify additional MADS-box homologs from various plant species using BlastP (e-value cutoff of 1e-10). Preliminary search results were then filtered to identify those having a full amino acid sequence with a starting methionine and SRF-TF and K-box Pfam domains having at least 70% sequence identity to *Zea mays* ZMM19 protein. Compiled results of these searches include proteins having amino acid sequences as set forth in SEQ ID NOs: 175-199.

Example 7. Generation of GA20Ox_SUP/ZMM19 Vector Stack Plants Using a Single Vector Constructs and vectors were created via molecular cloning each having an expression cassette comprising a DNA sequence encoding a miRNA that targets the GA20 oxidase_3 and GA20 oxidase_5 genes in corn plants and another expression cassette comprising a DNA sequence encoding a maize ZMM19 polypeptide. Two vectors (Vector 1 and Vector 2) were constructed comprising in order a miRNA-encoding DNA sequence (SEQ ID NO: 39) encoding a miRNA having a targeting sequence (SEQ ID NO: 40) for the GA20 oxidase_3 and GA20 oxidase_5 genes and a gene sequence encoding a maize ZMM19 polypeptide (SEQ ID NO: 169), wherein the two coding sequences are each operably linked to a promoter and a terminator sequence and are separated from each other by an intergenic sequence. A third vector (Vector 3) was constructed comprising in order a gene sequence encoding a maize ZMM19 polypeptide (SEQ ID NO: 169) and a miRNA-encoding DNA sequence (SEQ ID NO: 39) encoding a miRNA having a targeting sequence (SEQ ID NO: 40) for the GA20 oxidase_3 and GA20 oxidase_5 genes, wherein the two coding sequences are each operably linked to a promoter and a terminator sequence and are separated from each other by an intergenic sequence. The order of elements for each expression cassette is as provided above in Example 1.

Corn plants were transformed via *Agrobacterium*-mediated transformation with one of Vector 1, Vector 2, or Vector 3 to create transgenic corn plants. Transgenic corn plants transformed with Vector 1, Vector 2, or Vector 3 were then crossed as females to different male tester corn lines to create progeny plants comprising both the ZMM19 transgene and the miRNA-encoding DNA sequence for the suppression of the GA20 oxidase_3 and GA20 oxidase_5 genes. The resulting stacked transgenic progeny plants are herein referred to as GA20Ox_SUP/ZMM19 vector stack plants, as opposed to breeding or crossing stack plants where the transgenes are from different parents and are brought together in progeny plants by crossing the parents together.

Example 8. Increased Yield of GA20Ox_SUP/ZMM19 Vector Stack Plants Compared to Control Transgenic corn plants transformed with Vector 1 were crossed as females to two male tester corn lines ("Tester 1" or "Tester 2") to produce progeny GA20Ox_SUP/ZMM19 vector stack plants. Six transformation events were tested for broad acre yield (BAY) with two tester lines.

Figure 6:
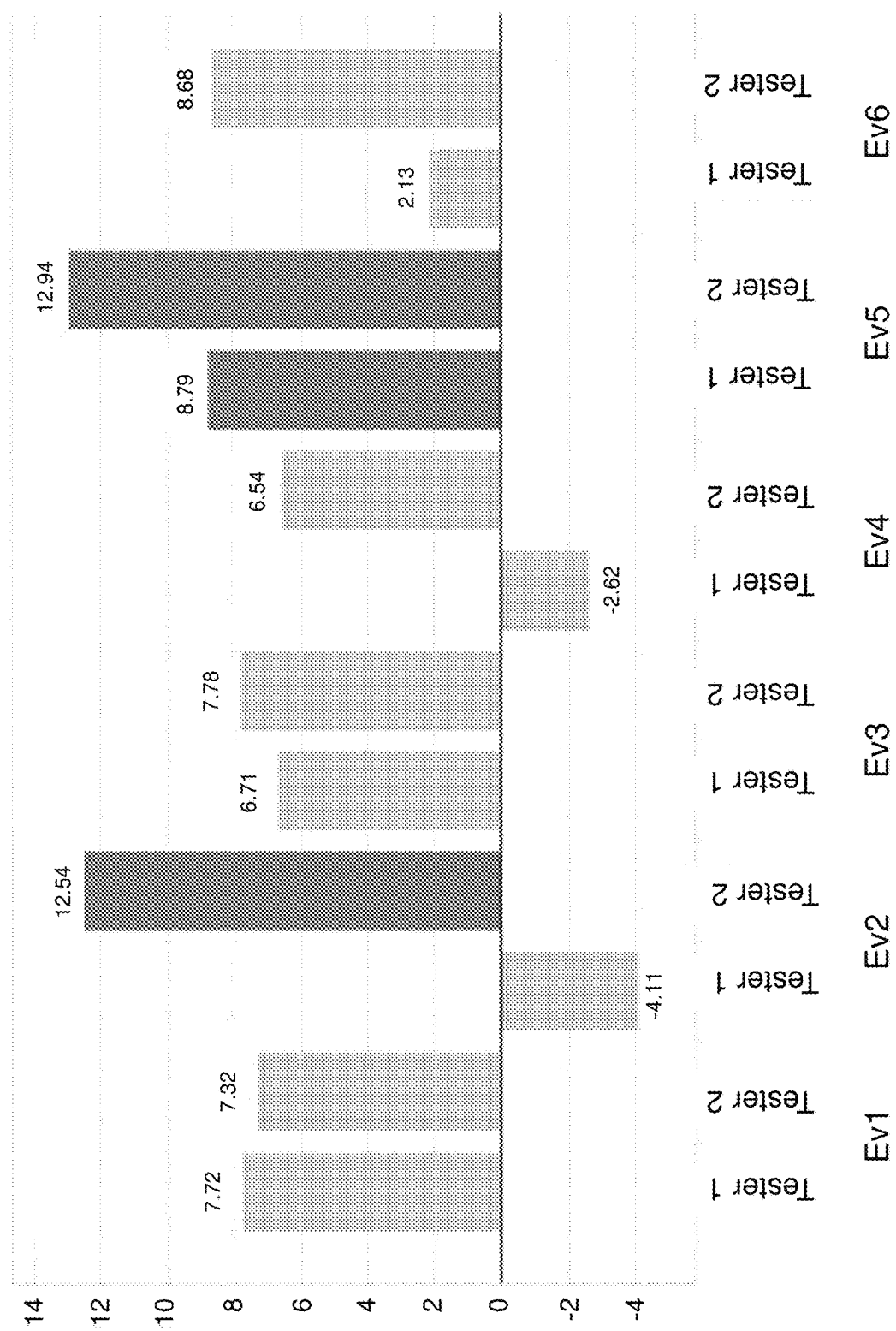
FIG. 6 shows broad acreage yield from six events of GA20Ox_SUP/ZMM19 vector stack plants, relative to control corn plants.

FIG. 6 shows BAY results in one growing season across 15 locations from six events of GA20Ox_SUP/ZMM19 vector stack plants containing a transformation event from Vector 1. BAY results are shown as the mean difference in bushels/acre between GA20Ox_SUP/ZMM19 vector stack plants and wildtype control plants. Each bar in FIG. 6 represents a transformation event. Dark gray bars in FIG. 6 are indicative of statistically significant positive changes (p-value≤0.1), and light gray bars are indicative of numerically positive or negative changes.

As shown in FIG. 6, two out of six events of GA20Ox_SUP/ZMM19 vector stack plants containing a transformation event from Vector 1 showed statistically significant increase in BAY relative to control plants (with at least one of the two testers), with an average increase of about 6 bushels/acre. The other four events of GA20Ox_SUP/ZMM19 vector stack plants containing a transformation event from Vector 1 showed a numerical increase in BAY relative to control plants, although two of these other four events showed a numerical decrease in BAY relative to control plants with one of the two male tester lines.

Figure 7:
FIG. 7 shows ear fresh weight per plant of GA20Ox_SUP/ZMM19 vector stack plants, relative to GA20Ox_SUP single plants.

Example 9. Increased Ear Fresh Weight of the GA20Ox_SUP/ZMM19 Vector Stack Plants Compared to GA20Ox_SUP Single FIG. 7 shows ear fresh weight per plant for plants containing one of six events of the GA20Ox_SUP/ZMM19 vector stack made using Vector 1, one of six events of GA20Ox_SUP/ZMM19 vector stack made using Vector 2, or one of three events of GA20Ox_SUP/ZMM19 vector stack made using Vector 3. Results are shown as the percentage difference in ear fresh weight per plant between GA20Ox_SUP/ZMM19 vector stack plants and that of GA20Ox_SUP single plants. Each bar in FIG. 7 represents a single vector stack transformation event. Dark gray bars in FIG. 7 are indicative of statistically significant positive changes (p-value≤0.1), and light gray bars are indicative of numerically positive or negative changes.

As shown in the left panel of FIG. 7, plants containing one of three events of GA20Ox_SUP/ZMM19 vector stack made using Vector 1 showed a statistically significant increase in ear fresh weight per plant relative to GA20Ox_SUP single plants, and plants containing another event of GA20Ox_SUP/ZMM19 vector stack made from Vector 1 showed a numerical increase in ear fresh weight per plant relative to GA20Ox_SUP single plants, although plants containing one of two other events from Vector 1 showed a numerical (but not statistically significant) decrease in ear fresh weight per plant relative to GA20Ox_SUP single plants.

As shown in the middle panel of FIG. 7, plants containing any one of the six events of GA20Ox_SUP/ZMM19 vector stack from Vector 2 showed a statistically significant increase in ear fresh weight per plant relative to GA20Ox_SUP single plants.

As shown in the right panel of FIG. 7, plants containing one of two events of GA20Ox_SUP/ZMM19 vector stack plants made using Vector 3 showed a statistically significant increase in ear fresh weight per plant relative to GA20Ox_SUP single plants, and the other event of the GA20Ox_SUP/ZMM19 vector stack made from Vector 3 showed a numerical increase in ear fresh weight per plant relative to GA20Ox_SUP single plants.

Figure 8:
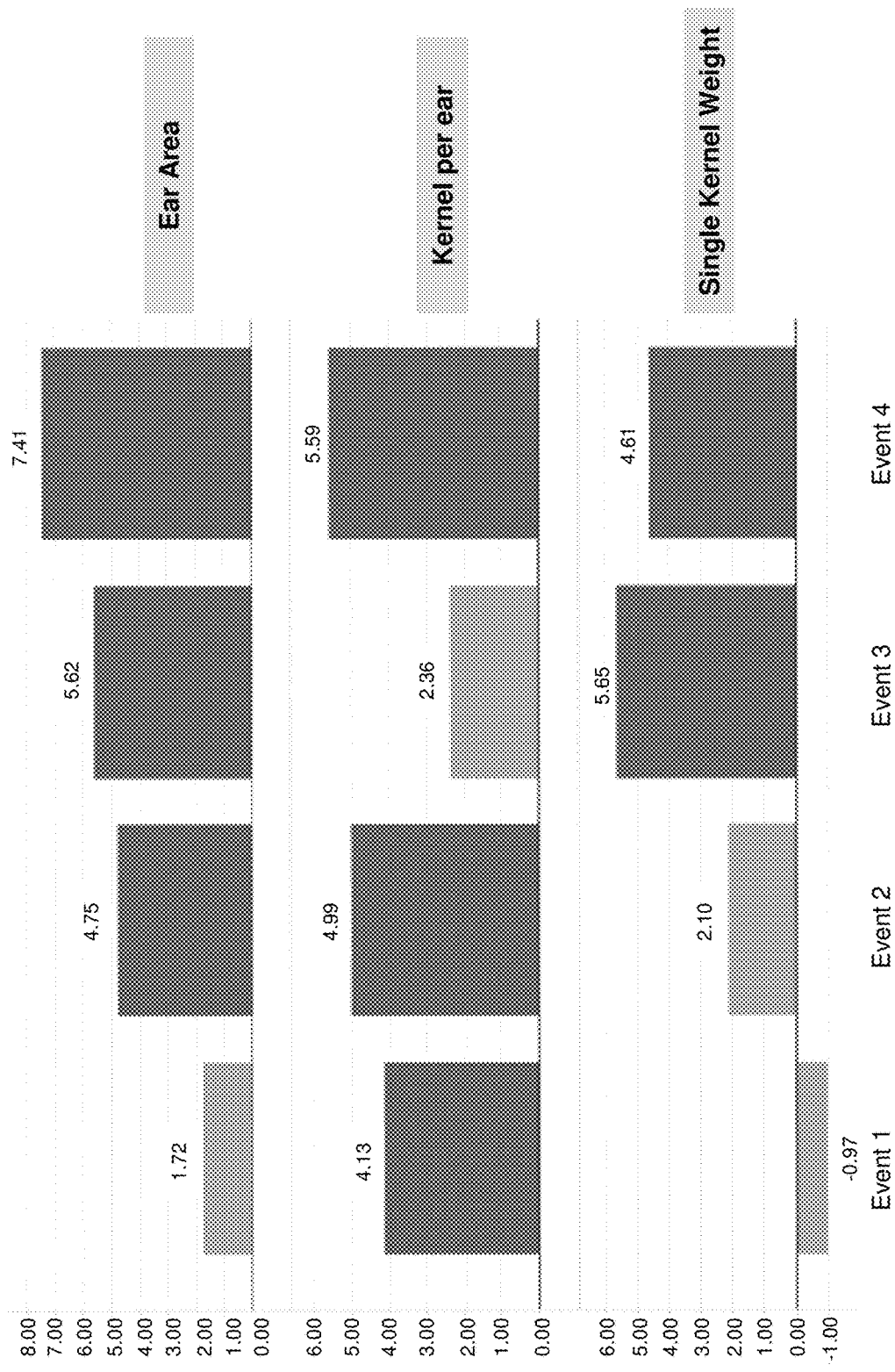
FIG. 8 shows ear area, kernels per ear, and single kernel weight of GA20Ox_SUP/ZMM19 vector stack plants, relative to GA20Ox_SUP single plants.

Example 10. Increased Ear Traits of the GA20Ox_SUP/ZMM19 Vector Stack Plants Compared to GA20Ox_SUP Single FIG. 8 shows ear area, kernels per ear, and single kernel weight traits, as measured with GA20Ox_SUP/ZMM19 vector stack plants containing one of four transformation events made using Vector 1 described above. Results are shown as the percentage difference between the ear area, kernels per ear, or single kernel weight of GA20Ox_SUP/ZMM19 vector stack plants and that of GA20Ox_SUP single plants. Each bar in FIG. 8 represents a single vector stack transformation event. Dark gray bars in FIG. 8 are indicative of statistically significant positive changes (p-value≤0.1), and light gray bars are indicative of numerically positive or negative changes.

As shown in the top panel of FIG. 8, plants containing one of three events of the GA20Ox_SUP/ZMM19 vector stack from Vector 1 showed a statistically significant increase in ear area relative to GA20Ox_SUP single plants, and plants containing the other event of the GA20Ox_SUP/ZMM19 vector stack from Vector 1 showed a numerical increase in ear area relative to GA20Ox_SUP single plants.

As shown in the middle panel of FIG. 8, plants containing one of three events of the GA20Ox_SUP/ZMM19 vector stack from Vector 1 showed a statistically significant increase in kernels per ear relative to GA20Ox_SUP single plants, and plants containing the other event of the GA20Ox_SUP/ZMM19 vector stack from Vector 1 showed a numerical increase in kernels per ear relative to GA20Ox_SUP single plants.

As shown in the bottom panel of FIG. 8, plants containing one of two (out of four) events of the GA20Ox_SUP/ZMM19 vector stack made from Vector 1 showed a statistically significant increase in single kernel weight relative to GA20Ox_SUP single plants, whereas one of the other events of the GA20Ox_SUP/ZMM19 vector stack made using Vector 1 showed a numerical increase in single kernel weight relative to GA20Ox_SUP single plants, and another event of the GA20Ox_SUP/ZMM19 vector stack made using Vector 1 showed a numerical decrease in single kernel weight relative to GA20Ox_SUP single plants.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples.

The invention claimed is:

1. A method for producing a transgenic corn plant, the method comprising:
   (I) introducing into a corn cell (i) a first recombinant expression cassette comprising a first heterologous plant-expressible promoter operably linked to a transcribable DNA sequence encoding a non-coding RNA for suppression of one or more gibberellic acid 20 (GA20) oxidase genes, wherein the non-coding RNA comprises a targeting sequence that is (a) at least 95% complementary to at least 19 consecutive nucleotides of a first mRNA molecule encoding a first endogenous GA20 oxidase protein that has at least 95% amino acid sequence identity to the amino acid sequence as set forth in SEQ ID NO: 9, and (b) at least 95% complementary to at least 19 consecutive nucleotides of a second mRNA molecule encoding a second endogenous GA20 oxidase protein that has at least 95% amino acid sequence identity to the amino acid sequence as set forth in SEQ ID NO: 15, and (ii) a second recombinant expression cassette comprising a DNA sequence encoding a MADS-box polypeptide that has at least 95% amino acid sequence identity to the amino acid sequence as set forth in SEQ ID NO: 168; and
   (II) regenerating or developing a transgenic corn plant from the corn cell, wherein the transgenic corn plant comprises the first and second recombinant expression cassettes, and wherein expression of said non-coding RNA and said MADS-box polypeptide in said transgenic corn plant results in a semi-dwarf phenotype, and an increase in one or more improved ear trait selected from the group consisting of ear diameter, single kernel weight, ear fresh weight, ear area, ear volume, ear length, kernels per ear, yield, grain yield estimate, broad acreage yield, ear dry weight, and ear tip void, as compared to a control wild-type corn plant grown under comparable conditions.

2. The method of claim 1, wherein the transcribable DNA sequence encoding said non-coding RNA comprises a nucleotide sequence that is 100% identical or complementary to at least 15 consecutive nucleotides of SEQ ID NO: 39.

3. A method for producing a transgenic corn plant, the method comprising:
   (I) crossing a first transgenic corn plant with a second transgenic corn plant, wherein the first transgenic corn plant comprises a first recombinant expression cassette comprising a first heterologous plant-expressible promoter operably linked to a transcribable DNA sequence encoding a non-coding RNA for suppression of one or more gibberellic acid 20 (GA20) oxidase genes, wherein the non-coding RNA comprises a targeting sequence that is (a) at least 95% complementary to at least 19 consecutive nucleotides of a first mRNA molecule encoding a first endogenous GA20 oxidase protein that has at least 95% amino acid sequence identity to the amino acid sequence as set forth in SEQ ID NO: 9, and (b) at least 95% complementary to at least 19 consecutive nucleotides of a second mRNA molecule encoding a second endogenous GA20 oxidase protein that has at least 95% amino acid sequence identity to the amino acid sequence as set forth in SEQ ID NO: 15, and wherein the expression of one or more endogenous GA20 oxidase genes is reduced in the first transgenic corn plant as compared to a control wild-type corn plant grown under comparable conditions, and wherein the second transgenic corn plant comprises a second recombinant expression cassette comprising a DNA sequence encoding a MADS-box polypeptide that has at least 95% amino acid sequence identity to the amino acid sequence as set forth in SEQ ID NO: 168; and
   (II) producing a transgenic progeny corn plant comprising the first and second recombinant expression cassettes and that has the reduced expression of the one or more endogenous GA20 oxidase genes, and increased expression of said MADS-box polypeptide as compared to a control wild-type corn plant grown under comparable conditions, and wherein expression of said non-coding RNA and said MADS-box polypeptide in said transgenic progeny corn plant results in a semi-dwarf phenotype, and an increase in one or more improved ear trait selected from the group consisting of ear diameter, single kernel weight, ear fresh weight, ear area, ear volume, ear length, kernels per ear, yield, grain yield estimate, broad acreage yield, ear dry weight, and ear tip void, as compared to a control wild-type corn plant grown under comparable conditions.

4. The method of claim 3, wherein the first transgenic corn plant and the transgenic progeny corn plant comprise a transcribable DNA sequence encoding said non-coding RNA comprising a nucleotide sequence that is 100% identical or complementary to at least 15 consecutive nucleotides of SEQ ID NO: 39.

5. The method of claim 1, wherein the transcribable DNA sequence comprised in the first recombinant expression cassette or the DNA sequence comprised in the second recombinant expression cassette is operably linked to a heterologous plant-expressible promoter selected from the group consisting of a vascular promoter, a rice tungro bacilliform virus (RTBV) promoter, a leaf promoter, and a constitutive promoter.

6. The method of claim 1, wherein the introducing is via site-directed integration using a site-specific nuclease, *Agrobacterium*-mediated transformation, or particle bombardment.

7. The method of claim 1, wherein the first and second recombinant expression cassettes are stably integrated into the genome of the transgenic corn plant produced in step (II).

8. The method of claim 3, wherein the first or the second recombinant expression cassette is operably linked to a heterologous plant-expressible promoter selected from the group consisting of a vascular promoter, a rice tungro bacilliform virus (RTBV) promoter, a leaf promoter, and a constitutive promoter.

9. The method of claim 3, wherein the first and the second transgenic corn plants are obtained via site-directed integration using a site-specific nuclease, *Agrobacterium*-mediated transformation, or particle bombardment.

10. The method of claim 1, further comprising selecting a transgenic progeny corn plant of said transgenic corn plant of step (II) that is semi-dwarf and has increased crown root lateral root density rating at the V12 stage and increased root dry weight as compared to a control wild-type corn plant grown under comparable conditions.

11. The method of claim 3, further comprising selecting a transgenic progeny corn plant that is semi-dwarf and has increased crown root lateral root density rating at the V12 stage and increased root dry weight as compared to a control wild-type corn plant grown under comparable conditions.

* * * * *

SEQUENCE LISTING

```
Sequence total quantity: 217
SEQ ID NO: 1            moltype = DNA  length = 1741
FEATURE                 Location/Qualifiers
source                  1..1741
                        mol_type = unassigned DNA
                        organism = Zea mays
SEQUENCE: 1
gacggtagtt ttcatctaaa gtttattctt cgtcacatgg gatggccgtt tgcttgtttg   60
ttgcttccgg gaggcggtgg tgaattgaag cagatcgaca agcatggctg cccactggtc  120
tcgatcgatc ggcctgccat gccatgccat gccactagag tccgtcctga ctggccgccc  180
gttccccgt  ataaaaaggc aggcaggcag gcagagcggg gacgagcaag caagcagttg  240
cagttgcagc ggcctcctcc tctgcttcct ccctcctcct cctcaccatg gtgctggctg  300
cgcacgatcc ccctcccctt gtgttcgacg ctgcccgcct gagcggcctc tccgacatcc  360
cgcagcagtt catctggccg gcggacgaga gccccacccc ggactccgcc gaggagctgg  420
ccgtgccgct catcgacctc tccggggacg ccgccgaggt ggtccggcag gtccggcgcg  480
cctgcgacct gcacggcttc ttccaggtgg tggggcacgg catcgacgcg gcgctgacgg  540
cggaggccca ccgctgcatg gacgccttct tcacgctgcc gctcccggac aagcagcgcg  600
cgcagcgccg ccagggggac agctgcggct acgccagcag cttcacgggc cggttcgcgt  660
ccaagctgcc ctggaaggag acgctgtcgt tccgctacac cgacgacgac gacgcgaca   720
agtccaagga cgtcgtggcg tcctacttcg tggacaagct gggcgagggg taccggcacc  780
acggggaggt gtacggcgcg tactgctctg agatgagccg tctgtcgctg gagctcatgg  840
aggtgctagg cgagagcctg ggcgtgggcc ggcgccactt ccggcgcttc ttccagggga  900
acgactccat catgcgcctc aactactacc cgccgtgcca gcggccctac gacacgctgg  960
```

```
gcacggggcc gcattgcgac cccacgtcgc tcaccatcct gcaccaggac gacgtgggcg  1020
gactccaggt gttcgacgcc gccacgctcg cgtggcgctc catcaggccc cgccgggcg   1080
ccttcgtcgt caacatcggc gacaccttca tggcgctctc caacgggcgc tacaggagct  1140
gcctccaccg cgccgtcgtc aacagccggg tggcacgccg ctcgctcgcc ttcttcctgt  1200
gcccggagat ggacaaggtg gtcaggccgc ccaaggacgt ggtggacgac gccaacccga  1260
gggcgtaccc ggacttcacg tggaggacgc tgctggactt caccatgagg cactacaggt  1320
cggacatgag gacgctcgag gccttctcca actggctcag caccagtagc aatggcggac  1380
agcacctgct ggagaagaag taggcatgct atttgggtat ggaagatggt ggatgtaagc  1440
aaacaaagcc aaattaagca gagtaggtta attaaggttg gctgatgatc catttaggga  1500
aggagctgat ctccctgact ccctcctcca attttctcaa ccaaatttat atagtataat  1560
aataataata aaatagcaag taatagttgt atcgtattat tattaattaa tttattagct  1620
ggtaggcaag tagtattaaa taccatttgt agtacgatgg gcgtatttct attttggcgt  1680
tttgctctgt gttttttgac gtttcctttg gatttggggg gacctcagat cagctcggcc  1740
t                                                                  1741

SEQ ID NO: 2         moltype = DNA  length = 1116
FEATURE              Location/Qualifiers
source               1..1116
                     mol_type = unassigned DNA
                     organism = Zea mays
SEQUENCE: 2
atggtgctgg ctgcgcacga tcccccctccc cttgtgttcg acgctgcccg cctgagcggc  60
ctctccgaca tcccgcagca gttcatctgg ccggcggacg agagcccac cccggactcc    120
gccgaggagc tggccgtgcc gctcatcgac ctctccgggg acgccgccga ggtggtccgg   180
caggtccggc gcgcctgcga cctgcacggc ttcttccagg tggtgggca cggcatcgac    240
gcggcgctga cggcggaggc ccaccgctgc atggacgcct tcttcacgct gccgctcccg   300
gacaagcagc gcgcgcagcg ccgccagggg gacagctgcg gctacgccag cagcttcacg   360
ggccggttcg cgtccaagct gccctggaag gagacgctgt cgttccgcta caccgacgac   420
gacgacggcg acaagtccaa ggacgtcgtg gcgtcctact tcgtggacaa gctgggcgag   480
gggtaccggc accacggggga ggtgtacggg cgctactgcc tgagatgag ccgtctgtcg    540
ctggagctca tggaggtgct aggcgagagc ctgggcgtgg gccggcgcca cttccgcgc    600
ttcttccagg ggaacgactc catcatgcgc ctcaactact acccgccgtg ccagcggccc   660
tacgacacgc tgggcacggg gccgcattgc gaccccacgt cgctcaccat cctgcaccag   720
gacgacgtgg gcggactcca ggtgttcgac gccgccacgc tcgcctggcg ctccatcagg   780
ccccgcccg gcgccttcgt cgtcaacatc ggcgacacct tcatgcgct ctccaacggg    840
cgctacagga gctgcctcca ccgcgccgtc gtcaacagcc gggtggcacg ccgctcgctc   900
gccttcttcc tgtgcccgga gatggacaag gtggtcaggc cgcccaagga gctggtggac   960
gacgccaacc cgagggcgta cccggacttc acgtggagga gctgctgga cttcaccatg   1020
aggcactaca ggtcggacat gaggacgctc gaggccttct ccaactggct cagcaccagt  1080
agcaatggcg gacagcacct gctggagaag aagtag                            1116

SEQ ID NO: 3         moltype = AA  length = 371
FEATURE              Location/Qualifiers
source               1..371
                     mol_type = protein
                     organism = Zea mays
SEQUENCE: 3
MVLAAHDPPP LVFDAARLSG LSDIPQQFIW PADESPTPDS AEELAVPLID LSGDAAEVVR    60
QVRRACDLHG FFQVVGHGID AALTAEAHRC MDAFFTLPLP DKQRAQRRQG DSCGYASSFT   120
GRFASKLPWK ETLSFRYTDD DDGDKSKDVV ASYFVDKLGE GYRHHGEVYG RYCSEMSRLS   180
LELMEVLGES LGVGRRHFRR FFQGNDSIMR LNYYPPCQRP YDTLGTGPHC DPTSLTILHQ   240
DDVGGLQVFD AATLAWRSIR PRPGAFVVNI GDTFMALSNG RYRSCLHRAV VNSRVARRSL   300
AFFLCPEMDK VVRPPKELVD DANPRAYPDF TWRTLLDFTM RHYRSDMRTL EAFSNWLSTS   360
SNGGQHLLEK K                                                       371

SEQ ID NO: 4         moltype = DNA  length = 1517
FEATURE              Location/Qualifiers
source               1..1517
                     mol_type = unassigned DNA
                     organism = Zea mays
SEQUENCE: 4
caggaataaa ataagcctcc gcccggcttc gttgcatcca cgcacgcagc aagcgatcgg    60
atttcgccag catggcggcg gcggccgtgg tgttcgacgc cgaggcgctg agccgggagg   120
agcacatccc ggcgcagttc gtgtggccca ccgaggacgg ggcgcagttc ggggccgtgc   180
aggaggtcgc catcccgtgt gtcgacctcg gcgagttcct ccgccgcggg gtgctcccgc   240
gcggcgtggc ggaggcgtgc gagcgccacg cgtcttcca ggtggtgaac cacggcgtg    300
gcgccgcgct gctcgccgag gcctaccgct gttgcgacgc cttttacgcg ctcccgctcg   360
cggacaagca gcgcgcgcag cgccggcacg gggagaacca cggctacgcc agcagcttca   420
cggggccgct tccactgctgc ctgccgtgga aggaacgct gtcctccaac tgcccccgca   480
gtgccgggac tgcgcgcgcc gtcgtcggct acttcgtcga cgtcctcggc gaggactacc   540
gccacatggg ggaggtgtac caggagtact gcgacgcgat gacgcgtctg cgctggacg   600
tgacggaggt gctggcggca gcgctggggc tggaccgcgg cgcactgcgc ggcttcttcg   660
agggcggcga ctccgtcatg cggctgaacc actaccggg tgccggcag ccgcacctga     720
cgctgggac gggccgcac cggaccgaca gtcgctgcc caggacgagg                780
tgggcggggt gcaggtgcgc gccgcggcgg ggcgtggcgc gcggtgcgg cccgcgcgg    840
acgcgttcgt ggtcaacatt ggcgacacct tcgccgcgct caccgacggg gtcacacca   900
gctgcctgca ccgcgccgtg gtgaccgcg cgggctccg ccggtcgctc gccttcttcc  960
tcaacccgc gctggaccgc gtcgtccgcc cgccgggcgc gctcctccag gagaacaagc  1020
aggcgggcc ccgcgcgcg ttcccggact tcacgtggcg cgagttcctc gagttcacgc   1080
```

```
agaagcacta ccggtcggac gcgggcacca tggacgcctt cgtgtcgtgg atcgcgggag    1140
gccgccgcca ccatggcgga caggaggagg gcaactgaga tcgatgcatc tctagctgta    1200
ggcagcagcg cagcagctac caagaataat ggccggcgac ggagatgcag ctacgacgca    1260
caaataaatt gagtgtttgt ggtacaataa ggacgaggac gatcaatggc gacctgtaac    1320
cggtgcagtt ttagttaatc tttcatggcc atatggcatt aaccaatcgt tggtgtaaaa    1380
tgcgtgcatg cttttgcatgc caatgttggc catgtgatgg cacagcgtga gtgtagctca    1440
cccaccgtga caacgtgcta atttcgtgtg gtcctagata ccaaggtcgt ctaatgaact    1500
tgatggattg atgattt                                                   1517

SEQ ID NO: 5            moltype = DNA  length = 1107
FEATURE                 Location/Qualifiers
source                  1..1107
                        mol_type = unassigned DNA
                        organism = Zea mays
SEQUENCE: 5
atggcggcgg cggccgtggt gttcgacgcc gaggcgctga gccggaggga gcacatcccg    60
gcgcagttcg tgtggcccac cgaggagcgg gcgccggcgg gcggcgtgga ggaggtcgcc    120
atcccgtggt cgacctcgg cgagttcctc cgccgcgtgg tgctcccgcg cggcgtgcg    180
gaggcgtgcg agcgccacgg cgtcttccag gtggtgaacc acggcgtggg cgccgcgctg    240
ctcgccgagg cctaccgctg ttgcgacgcc ttttacgcgc tcccgctcgc ggacaagcag    300
cgcgcgcagc gccggcacgg ggagaaccac ggctacgcca gcagcttcac gggccgcttc    360
cactgctgcc tgccgtggaa ggagacgctg tccttcaact gccccgccgg tgccgggact    420
gcgcgcgccg tcgtcggcta cttcgtcgac gtcctcggcg aggactaccg ccacatgggg    480
gaggtgtacc aggagtactg cgacgcgatg acgcgtctgg cgctggacgt gacggaggtg    540
ctggcggcag cgctggggct ggaccgcggc gcactgcgcg gcttcttcga gggcggcgac    600
tccgtcatgc ggctgaacca ctacccggcg tgccggcagc cgcacctgac gctgggacg    660
ggcccgcacc gggacccgac gtcgctgacg ctgctgcacc aggacgacgt gggcgggctg    720
caggtgcgcg ccggcggcgg gccgtggcgc gcggtgcggc cccgcgcgga cgcgttcgtg    780
gtcaacattg gcgacacctt cgccgcgctc accgacgggc gtcacaccag ctgcctgcac    840
cgcgcggtgg tgaccggcgg cggctcccgc cggtcgctcg ccttcttcct caacccgccg    900
ctggaccgcg tcgtccgccc gccggggcgcg ctcctccagg agaacaagca ggccgggccgc    960
ccgcgcgcgt tccggacttt cacgtggcgc gagttcctcg agttcacgca gaagcactac    1020
cggtcggacg cgggcaccat ggacgccttc gtgtcgtgga tcgcgggagg ccgccgccac    1080
catggcggac aggaggaggg caactga                                        1107

SEQ ID NO: 6            moltype = AA  length = 368
FEATURE                 Location/Qualifiers
source                  1..368
                        mol_type = protein
                        organism = Zea mays
SEQUENCE: 6
MAAAAVVFDA EALSREEHIP AQFVWPTEER APAGGVEEVA IPVVDLGEFL RRGVLPRGVA    60
EACERHGVFQ VVNHGVGAAL LAEAYRCCDA FYALPLADKQ RAQRRHGENH GYASSFTGRF    120
HCCLPWKETL SFNCPAGAGT ARAVVGYFVD VLGEDYRHMG EVYQEYCDAM TRLALDVTEV    180
LAAALGLDRG ALRGFFEGGD SVMRLNHYPA CRQPHLTLGT GPHRDPTSLT LLHQDDVGGL    240
QVRAGGGPWR AVRPRADAFV VNIGDTFAAL TDGRHTSCLH RAVVTGGGSR RSLAFFLNPP    300
LDRVVRPPGA LLQENKQAGR PRAFPDFTWR EFLEFTQKHY RSDAGTMDAF VSWIAGGRRH    360
HGGQEEGN                                                             368

SEQ ID NO: 7            moltype = DNA  length = 1522
FEATURE                 Location/Qualifiers
source                  1..1522
                        mol_type = unassigned DNA
                        organism = Zea mays
SEQUENCE: 7
gcacactcgc agctcgcaca tctcatggtg tcctaagaac ggcaagagcc agctctgcct    60
agcagcagcg cacagccaca tccatggacg ccagcccgac cccaccgctc cccctccgcg    120
ccccaactcc cagcattgac ctcccccgctg caaggacag ggccgacgcg gcggctaaca    180
aggccgcggc tgtgttcgac ctgcgccggg agcccaagat cccggagcca ttcctgtggc    240
cgcacgaaga ggcgcgccg acctccgccg cggagtcgga ggtgccggtg gtggacgttg    300
gcgtgctgcg caatgcgac ggcgcggggc tccgccggc cgccgcgcaa gtggcggcgg    360
cgtgcgcgac gcacgggttc ttccaggtgt gcgggcacgg cgtggacgcg cgctggggc    420
gcgccgcgct ggacggcgcc agcgacttct tccggctgcc gctggctgag aagcagcggg    480
cccggcgcgt cccccggcacc gtgtccgggt acacgacggc gcacgccgac cggttcgcgt    540
ccaagctccc ctggaaggag accctgtcct tcggcttcca cgacggcgcc cgggcgcccg    600
tcgtcgtgga ctacttcacc ggcacccctcg gccaagattt cgagccagtg gggcgggtgt    660
accagaggta ctgcgaggag atgaaggagc tgtcgctgac gatcatggag ctgctggagc    720
tgagcctggg cgtggagcgc ggctactacc gggagttctt cgaggacagc cgctccatca    780
tgcggtgcaa ctactacccg ccgtgccctc tgccggacgc cacgctcggc acggcccgg    840
actgcgaccc cacggcgctg accatcctcc tgcaggacga cgtcggcggg ctggaggtcc    900
tggtggacgg cgagtggcgc cccgtccggc ccgtccagg cgccatggtc atcaacatcg    960
gcgacacctt catggcgctg tccaacggcc ggtacaagag ctgcctgcac cgcgcggtgg    1020
tgaaccggcc gcaggagcgg caatcgctgg ccttcttcct gtgcccgcgc gaggaccggg    1080
tggtcccgcc gccggccagc gccgccgcgg cgcagtaccc ggacttcacg tggcggac    1140
tcatgcgctt cacgcagcgc cactaccgcg ccgacacccg cacgctgac gccttcaccc    1200
gctggctctc ccacgcccg gcggccggcg ctccctgcac ctaacgagcc ggccgtctct    1260
ttcgccgggg cccgcgcggg gttcgcccac gtggtgatca ggtggcagac atgtggccca    1320
cgggccccgc gccgccttcc ccattttggg acgacctac tgctactact actagtgtac    1380
atatgcaaaa aaatacatat atatataggt actttctcta atattttat ataaagcaa    1440
```

```
ggcggcctgg tgttcttttc tttgttttgt cgacaactgt ttgatcccat cctatggacg   1500
atggatagtt caatgtttgt ac                                            1522

SEQ ID NO: 8            moltype = DNA  length = 1161
FEATURE                 Location/Qualifiers
source                  1..1161
                        mol_type = unassigned DNA
                        organism = Zea mays
SEQUENCE: 8
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg gcggcggcgc agggttcttc    300
caggtgtgcg gcacggcgt ggacgcggcg ctggggcgcg ccgcgctgga cggcgccagc    360
gacttcttcc ggctgccgct ggctgagaag cagcgggccc ggcgcgtccc ggcaccgtg    420
tccgggtaca cgagcgcgca cgccgaccgg ttcgcgtcca agctcccctg gaaggagacc    480
ctgtccttcg gcttccacga cggcgccgcg ccgcccgtcg tcgtggacta cttcaccggc    540
accctcggcc aagatttcga gccagtgggg cgggtgtacc agaggtactg cgaggagatg    600
aaggagctgt cgctgacgat catggagctg ctggagctga gcctgggcgt ggagcgcggc    660
tactaccggg agttcttcga ggacagccgc tccatcatgc ggtgcaacta ctacccgccg    720
tgcccggtgc cggagccgca gctggcacg gccccgcact cgcgacccac gcgcgctgac    780
atcctcctgc aggacgacgt cggcgggctg gaggtcctgg tggacggcga gtggcgcccc    840
gtccggcccg tccaggcgc catggtcatc aacatcggcg acaccttcat ggcgctgtcc    900
aacgggcggt acaagagctg cctgcaccgc gcggtggtga accggcggca ggagcggcaa    960
tcgctggcct tcttcctgtg cccgcgcgag gaccggttgg tgcgccgcc ggccagcgcc   1020
gcgccgcggc agtacccgga cttcacctgg gccgacctca tgcgcttcac cagcgcac    1080
taccgcgccg acacccgcac gctggacgcc ttcacccgct ggctctccca cggcccggcg   1140
gcggcggctc cctgcaccta a                                             1161

SEQ ID NO: 9            moltype = AA  length = 386
FEATURE                 Location/Qualifiers
source                  1..386
                        mol_type = protein
                        organism = Zea mays
SEQUENCE: 9
MDASPTPPLP LRAPTPSIDL PAGKDRADAA ANKAAAVFDL RREPKIPEPF LWPHEEARPT     60
SAAELEVPVV DVGVLRNGDG AGLRRAAAQV AAACATHGFF QVCGHGVDAA LGRAALDGAS    120
DFFRLPLAEK QRARRVPGTV SGYTSAHADR FASKLPWKET LSFGFHDGAA APVVVDYFTG    180
TLGQDFEPVG RVYQRYCEEM KELSLTIMEL LELSLGVERG YYREFFEDSR SIMRCNYYPP    240
CPVPERTLGT GPHCDPTALT ILLQDDVGGL EVLVDGEWRP VRPVPGAMVI NIGDTFMALS    300
NGRYKSCLHR AVVNRRQERQ SLAFFLCPRE DRVVRPPASA APRQYPDFTW ADLMRFTQRH    360
YRADTRTLDA FTRWLSHGPA AAAPCT                                        386

SEQ ID NO: 10           moltype = DNA  length = 1457
FEATURE                 Location/Qualifiers
source                  1..1457
                        mol_type = unassigned DNA
                        organism = Zea mays
SEQUENCE: 10
taatcacctc atcacaggtc cccccagcct cactctcgcg ccggctcaag gtacattgcg     60
tgtcctagcc aagacacgca gctcatctca gcctcacacg cacagcaaga gcgaggcgtg    120
attcgccatg gcggcctca ctatggacca ggccttcgtg caggccccg agcaccgccc    180
caagcccatc gtcaccgagg ccaccggcat ccctctcatc gacctctcgc tctggccgc    240
cagcgcggc gccgtggacg cgctggccgc cgaggtgggc cgaggtgggc gggactgggg    300
cttcttcgtg gtcgtgggcc acggcgtgcc cgcagagacc gtggcgcgcg cgacggaggc    360
gcagcgagcg ttcttcgcgc tgccggcaga gcggaaggcc gccgtgcgga ggaacgaggc    420
ggagccgctc gggtactacg agtcggagca caccaagaac gtgagggact ggaaggaggt    480
gtacgacctc gtgccgcgcg agccgccgcc gccggcagcc gtggccgacg gcgagcttgg    540
gttcgataac aagtggcccc aggatctacc gggcttcaga gaggcgctgg aggagtacgc    600
gaaagcgatg gaagagctgg cgttcaagct gctggagctg atcgcccgga gcctgaagct    660
gaggcccgac cggctgcacg gcttcttcaa ggaccagacg accttcatcc ggctgaacca    720
ctaccctcct tgcccgagcc ccgacctggc cctcggcgtg gggcggcaca aggacgccgg    780
cgccctgacc atcctgtacc aggacgacgt cgggggcgcc ggtccgcc ggctccagc    840
cggcgagtgg gtccgcgtca ggccgtgcc cgactcgttc atcatcaacg tcggcgacct    900
catccaggta cgagagcgcg gagcaccggg tgtcggtgaa ctcgcgagg gagaggttct    960
ccatgcccta cttcttcaac ccggcgacct acaccatggt ggagccggtg gaggagctgg   1020
tgagcaagga cgatccgccc aggtacgacg cctacaactg gggcgacttc ttcagcacca   1080
ggaagaacag caacttcaag aagctcaacg tggagaacat tcagatcgcg catttcaaga   1140
agagcctcgt cctcgcctaa ctactgctac tgctaggatc catgccattg ccatgtcgtc   1200
ttcagattca gagcacgcca tgtcgtcgct agcttcgtgg tagaacaaat aatgatgtgc   1260
gtgctgtgtg taagcatgga tatggatgtg aatatgtaat atgatgagca ctcctacttt   1320
ggtatgtttg ggaataacag acttgtgttg gtctggttca ttatttgtaa gaaaatcaaa   1380
aagagttagt agggcaggag gctaaccaca gtcatgctgc accacatccc tggtggaaag   1440
ctggccgggt tacgcta                                                  1457

SEQ ID NO: 11           moltype = DNA  length = 1116
FEATURE                 Location/Qualifiers
source                  1..1116
```

```
                        mol_type = unassigned DNA
                        organism = Zea mays
SEQUENCE: 11
atgggcggcc tcactatgga ccaggccttc gtgcaggccc ccgagcaccg ccccaagccc    60
atcgtcaccg aggccaccgg catccctctc atcgacctct cgcctctggc cgccagcggc   120
ggcgccgtgg acgcgctggc cgccgaggtg ggcgcggcga gccgggactg gggcttcttc   180
gtggtcgtgg ccacggcgt gcccgcagag accgtggccgc gcgcgacgga ggcgcagcga   240
gcgttcttcg cgctgccggc agagcggaag gccgccgtgc ggaggaacga ggcggagccg   300
ctcgggtact acgagtcgga gcacaccaag aacgtgaggg actggaagga ggtgtacgac   360
ctcgtgccgc gcgagccgcc gccgccggca gccgtgccgc acggcgagct tgtcgttcgat   420
aacaagtggc cccaggatct accgggcttc agagaggcgc tggaggagta cgcgaaagcg   480
atggaagagc tggcgttcaa gctgctggag ctgatcgccc ggagcctgaa gctgaggccc   540
gaccggctgc acggcttctt caaggaccag acgaccttca tccggctgaa ccactaccct   600
ccttgcccga gccccgacct ggccctcggc gtgggcggca caaggacgc cggcgccctc   660
accatcctgt accaggacga cgtcgggggg ctcgacgtcc ggcggcgctc cgacggcgag   720
tgggtccgcg tcaggcccgt gcccgactcg ttcatcatca cgtcggcga cctcatccag   780
gtacgagagc gcggagcacc gggtgtcggt gaactcggcg agggagaggt tctccatgcc   840
ctacttcttc aacccggcga cctacaccat ggtggagcg gtggaggac tggtgagcaa   900
ggacgatccg cccaggtacg acgcctacaa ctgggcgac ttcttcagca ccaggaagaa   960
cagcaacttc aagaagctca acgtggagaa cattcagatc gcgcatttca agaagagcct  1020
cgtcctcgcc taactactgc tactgctagg atccatgcca ttgccatgtc gtcttcagat  1080
tcagagcacg ccatgtcgtc gctagcttcg tggtag                            1116

SEQ ID NO: 12           moltype = AA    length = 371
FEATURE                 Location/Qualifiers
source                  1..371
                        mol_type = protein
                        organism = Zea mays
SEQUENCE: 12
MGGLTMDQAF VQAPEHRPKP IVTEATGIPL IDLSPLAASG GAVDALAAEV GAASRDWGFF    60
VVVGHGVPAE TVARATEAQR AFFALPAERK AAVRRNEAEP LGYYESEHTK NVRDWKEVYD   120
LVPREPPPPA AVADGELVFD NKWPQDLPGF REALEEYAKA MEELAFKLLE LIARSLKLRP   180
DRLHGFFKDQ TTFIRLNHYP PCPSPDLALG VGRHKDAGAL TILYQDDVGG LDVRRRSDGE   240
WVRVRPVPDS FIINVGDLIQ VRERGAPGVG ELGEGEVLHA LLLQPGDLHH GGAGGGAGEQ   300
GRSAQVRRLQ LGRLLQHQEE QQLQEAQRGE HSDRAFQEEP RPRLTTATAR IHAIAMSSSD   360
SEHAMSSLAS W                                                        371

SEQ ID NO: 13           moltype = DNA    length = 1733
FEATURE                 Location/Qualifiers
source                  1..1733
                        mol_type = unassigned DNA
                        organism = Zea mays
SEQUENCE: 13
atgaggccgc gcctccctcc aaatgttccc tccctgcctt cgtctttgtc gttgctcgca    60
aactccctgt cctcccctgt tacaaatacc ccacccgcc cggacagctt ccctgcatac   120
ttgcagctcg cacatctcat ggtgtcgcag gaacgacaag agccagctgt gcctagcagc   180
agcagcagca gcgccaagcg cgcagccacg tccatgacg ccagcccgc gcgcctgctc   240
ctcctccgcg cccccactcc cagccccagc attgacctcc ccgctggcaa ggacaaggcc   300
gacgcggcgg ccagcaaggc cggcgcggcc gtgttcgacc tgcgccggga gcccaagatc   360
cccgcgccat tcctgtggcc gcaggaagag gcgcggccgt cctcggccgc ggagctggag   420
gtgccgatgg tggacgtggg cgtgctgcgc aatggcgacc gcgccgacga gcggcggagg   480
gcggcgcagg tggccgcggc gtgcgcgacg cacgggttct tccaggtgtg cgggcacggc   540
gtggacgcgg cgctggggcg cgccgcgctg gacggcgcca gcgacttctt ccggctgccg   600
ctcgccgaga agcagcgcgc ccggcgcgtc ccggcaccg tgtccgggta cacgagcgcg   660
cacgccgccc ggttcgcggc caagctcccc tggaaggaga ccctgtcgtt cggctaccac   720
gacggcgccc gtcgcctgt cgtcgtggac tacttcgtcg gcaccctcgg ccaggatttc   780
gagccaatgg ggtgggtgta ccagaggtac tgcgaggaga tgaaggagct gtcgctgacg   840
atcatggagc tgctggagct gagcctgggc gtggagctgc gcggctacta ccgggagttc   900
ttcgaggaca gccggtccat catgcggtgc aactactacc cgctcgtgccc ggagccggag   960
cgcacgctgg gcacggcgcc cgactcgac cccacgacgg tcaccatcct cctgcaggac  1020
gacgtgggcg ggctggaggt gctggtggac gtgagtggc gccccgtccg gcccgtcccg  1080
ggcgccatgt catcaacat cggcgacacc ttcatgcgc tgtcgaacgg gagtacaag   1140
agctgcctgc accgcgcgt ggtgaaccag cggcgggcgc ggcggtcgct ggccttcttc   1200
ctgtgccgc gcgaggaccg ggtggtgccgc cgcggacgcg gtgctgcgcc ggcgctac   1260
ccggacttca cctgggccga cctcatgcgc ttcacgcagc gccactaccg cgccgacacc   1320
cgcacgctgg acgccttcac ccgctggctc tcccacggcc cggcccaggc ggcggcgcct   1380
ccctgcacct agcgagccgg gccaaggcgg tctctttcgc cccacgtgcg cgcccagctg   1440
ggcaggtggc cagacacgcg gcccgcgggc cccgcgcgc cttgccattt tttgacgctg   1500
gccctactgc tgtgctacta gtgtacatat gcaagagtac atatatatat atatatatac   1560
gtattttcta tatattatat ataaaagcaa ggcggcccgg tgcccttctc ttgttttgtc   1620
cacaactgtt tgatcccatt atttctatgga ccatggatac ttcaatgtt gtactaagac   1680
cgtgaacgtg ggattcttt ccttcctctg tgtttttct gagaaaaatt aaa            1733

SEQ ID NO: 14           moltype = DNA    length = 1392
FEATURE                 Location/Qualifiers
source                  1..1392
                        mol_type = unassigned DNA
                        organism = Zea mays
SEQUENCE: 14
```

```
atgaggccgc gcctccctcc aaatgttccc tccctgcctt cgtctttgtc gttgctcgca    60
aactccctgt cctcccctgt tacaaatacc cccaccgcc cggacagctt ccctgcatac    120
ttgcagctcg cacatctcat ggtgtcgcag aacgacaag agccagctgt gcctagcagc    180
agcagcagca gcgccaagcg cgcagccacg tccatggacg ccagcccggc cccgccgctc    240
ctcctccgcg cccccactcc cagccccagc attgacctcc ccgctggcaa ggacaaggcc    300
gacgcggcgg ccagcaaggc cggcgcggc gtgttcgacc tgcgccggga gcccaagatc    360
cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
gcggcgcagg tggccgcggc gtgcgcgacg cacgggttct tccaggtgtg cgggcacggc    540
gtggacgcgg cgctggggcg cgccgcgctg gacggcgcca gcgactttt ccggctgccg    600
ctcgccgaga agcagcgcgc ccggcgcgtc cccggcaccg tgtccgggta cacgagcgcg    660
cacgccgacc ggttcgcggc caagctcccc tggaaggaga ccctgtcgtt cggctaccac    720
gacggcgccg cgtcgcctgt cgtcgtggac tacttcgtcg gcaccctcgg ccaggatttc    780
gagccaatgg ggtgggtgta ccagaggtac tgcgaggaag tgaaggagct gtcgctgacg    840
atcatggagc tgctggagct gagcctgggc gtggagctgc gcggctacta ccgggagttc    900
ttcgaggaca gccggtccat catgcggtgc aactactacc cgccgtgccc ggagccggag    960
cgcacgctgg gcacgggccc cgactgcgac cccacgcgc tcaccatcct cctgcaggac   1020
gacgtgggcg gcctggaggt gctggtggac ggtgagtggc gccccgtccg gcccgtcccg   1080
ggcgccatgg tcatcaacat cggcgacacc ttcatggccc tgtcgaacgg gaggtacaag   1140
agctgcctgc accgcgcggt ggtgaaccag cggcgggcgc ggcggtcgct ggccttcttc   1200
ctgtgcccgc gcgaggaccg ggtggtgcgc ccgccgccca gtgctgcgcc gcggcgctac   1260
ccggacttca cctgggccga cctcatgcgc ttcacgcagc gccactaccg cgccgacacc   1320
cgcacgctgg acgccttcac ccgctggctc tcccacggcc cggcccaggc ggcggcgcct   1380
ccctgcacct ag                                                       1392

SEQ ID NO: 15          moltype = AA    length = 463
FEATURE                Location/Qualifiers
source                 1..463
                       mol_type = protein
                       organism = Zea mays
SEQUENCE: 15
MRPRLPPNVP SLPSSLSLLA NSLSSPVTNT PTRPDSFPAY LQLAHLMVSQ ERQEPAVPSS    60
SSSSAKRAAT SMDASPAPPL LLRAPTPSPS IDLPAGKDKA DAAASKAGAA VFDLRREPKI   120
PAPFLWPQEE ARPSSAAELE VPMVDVGVLR NGDRAGLRRA AAQVAAACAT HGFFQVCGHG   180
VDAALGRAAL DGASDFFRLP LAEKQRARRV PGTVSGYTSA HADRFAAKLP WKETLSFGYH   240
DGAASPVVVD YFVGTLGQDF EPMGWVYQRY CEEMKELSLT IMELLELSLG VELRGYYREF   300
FEDSRSIMRC NYYPPCPEPE RTLGTGPHCD PTALTILLQD DVGGLEVLVD GEWRPVRPVP   360
GAMVINIGDT FMALSNGRYK SCLHRAVVNQ RRARRSLAFF LCPREDRVVR PPASAAPRRY   420
PDFTWADLMR FTQRHYRADT RTLDAFTRWL SHGPAQAAAP PCT                     463

SEQ ID NO: 16          moltype = DNA   length = 1510
FEATURE                Location/Qualifiers
source                 1..1510
                       mol_type = unassigned DNA
                       organism = Zea mays
SEQUENCE: 16
aaagagcgcg cgacggcggc ccctgggaga gccatgcgag actggaggcg gaaccgcgca    60
cgacaccaag ctgccgcgcc ggactgctgc acgcaagcgc agcgcaggac cgaccgacct   120
ccgtaggcac gcacgcgcc ggcggcatgg cggagcacct cctgtcgacg gccgtgcacg   180
acacgctgcc ggggagctac gtgccggccg agccggagcg cccgcgcctc gcggaggtcg   240
tgaccggccg gcgcatcccc gtcgtggacc tgggcagccc cgaccgcgcc ggggtcggcg   300
ccgccgtcgg cgacgcctgc cgctcgcacg gcttcttcca ggtcgtcaac acgggatcc   360
acgccgccct ggtcgcggcg gtgatggccg cggggcgcgg cttcttccgg ctgccccccg   420
aggagaaggc caagctctac tccgacacc ccgccaggaa gatccggctg tccaccagct   480
tcaacgtgcg caaggagacg gtgcacaact ggcgcgcta cctccgcctg cactgccatc   540
ccctcgacga gttcctgccc gattggccgt ccaacccgcc cgatttcaag gagaccatgg   600
gcacctactg caaggaggtc cgggagctcg ggttcaggct gtacgccgcg atctcggaga   660
gcctgggcct agaggcgagc tacatgaagg aagcgctggg ggagcaggag cagcacatgg   720
cggtcaactt ctaccgccg tgcccggagc cggagctcac ctacggcctc ccggcgcaca   780
ccgaccccaa cgcgctcacc atcctgctca tggaccccga cgtcgccgg ctgcaggtgc   840
tccacgccgg ccagtgggtc gccgtcaacc cgcagcccgg cgcgctcatc atcaacatcg   900
gcgaccagct gcaggcgctg agcaacggc agtaccggag cgtgtggcac cgcgcggtgg   960
tgaactcgga ccggagcgc atgtccgtgg cgtcgttcct gtgcccgtgc aaccacgtcg  1020
tgctcggccc cgcgcggaag ctcgtcaccg aggacaccgg ccgtgtac aggaactaca  1080
cgtacgacaa gtactacgcc aagttctgga gcaggaacct ggaccaggag cactgcctcg  1140
agctcttcag aacctagcga atcggatacg gatggatgga tacattacat acgcgccctc  1200
tgttttctc catgacgtta aagaacacg ttctgcaatg tttgtccatt caaggtggta  1260
tcaatcaagg ctgtcggtcg tgcaattctt ccgctccata tacatagtta aatgctttga  1320
aagaaaaga aaaaaaagaa acacaagtat tatggcacta ctagtgtttt taggaacaag  1380
gaaagagggg ttgcccctgc tggctatata tattaaatat aaataaaggt aaggctgtag  1440
acattggtga ataagagaaa gtatttgagt ttctctattg tcactccaga acagactcct  1500
ttgcctcgat                                                        1510

SEQ ID NO: 17          moltype = DNA   length = 1011
FEATURE                Location/Qualifiers
source                 1..1011
                       mol_type = unassigned DNA
                       organism = Zea mays
SEQUENCE: 17
```

```
atggcggagc acctcctgtc gacggccgtg cacgacacgc tgccggggag ctacgtgcgg    60
ccggagccgg agcgcccgcg cctcgcggag gtcgtgaccg gcgcgcgcat ccccgtcgtg   120
gacctgggca gccccgaccg cggcgcggtc gtggccgccg tcggcgacgc ctgccgctcg   180
cacggcttct tccaggtcgt caaccacggg atacacgccg ccctggtcgc ggcggtgatg   240
gccgcggggc gcggcttctt ccggctgccc ccgaggaga aggccaagct ctactccgac   300
gaccccgcca ggaagatccg gctgtccacc agcttcaacg tgcgcaagga gacggtgcac   360
aactggcgcg actaccctcc cctgcactgc catcccctcg acgagttcct gcccgattgg   420
ccgtccaacc cgcccgattt caaggagacc atgggcacct actgcaagga ggtccgggag   480
ctcgggttca ggctgtacgc cgcgatctcg gagagcctgg gcctagaggc gagctacatg   540
aaggaagcgc tggggagca ggagcagcac atggcggtca acttctaccc gccgtgcccg   600
gagccggagc tcacctacgg cctcccggcg cacaccgacc caacgcgct caccatcctg   660
ctcatggacc cggacgtcgc cggcctgcag gtgctccacg ccggccagtg ggtcgccgtc   720
aacccgcagc ccggcgcgct catcatcaac atcggcgacc agctgcaggc gctgagcaac   780
gggcagtacc ggagcgtgtg gcacagggcg gtggtgaact cggaccggga gcgcatgtcc   840
gtggcgtcgt tcctgtgccc gtgcaaccac gtcgtgctcg gccccgcgcg gaagctcgtc   900
accgaggaca ccccggccgt gtacaggaac tacacgtacg acaagtacta cgccaagttc   960
tggagcagga acctggacca ggagcactgc ctcgagctct cagaaccta g           1011

SEQ ID NO: 18          moltype = AA  length = 336
FEATURE                Location/Qualifiers
source                 1..336
                       mol_type = protein
                       organism = Zea mays
SEQUENCE: 18
MAEHLLSTAV HDTLPGSYVR PEPERPRLAE VVTGARIPVV DLGSPDRGAV VAAVGDACRS    60
HGFFQVVNHG IHAALVAAVM AAGRGFFRLP PEEKAKLYSD DPARKIRLST SFNVRKETVH   120
NWRDYLRLHC HPLDEFLPDW PSNPPDFKET MGTYCKEVRE LGFRLYAAIS ESLGLEASYM   180
KEALGEQEQH MAVNFYPPCP EPELTYGLPA HTDPNALTIL LMDPDVAGLQ VLHAGQWVAV   240
NPQPGALIIN IGDQLQALSN GQYRSVWHRA VVNSDRERMS VASFLCPCNH VVLGPARKLV   300
TEDTPAVYRN YTYDKYYAKF WSRNLDQEHC LELFRT                            336

SEQ ID NO: 19          moltype = DNA  length = 1387
FEATURE                Location/Qualifiers
source                 1..1387
                       mol_type = unassigned DNA
                       organism = Zea mays
SEQUENCE: 19
gttttctttt tgaacgtaac tgacagaagc tatctgccta gctacggcgt gtcggttgct    60
tgtctcacca aagcagcgac atggaagcct gacagctcgt cgcgtcgcgc catttccacc   120
caacaaagcg gcggcgccag cacgcactgc ttctgcttgt gcgtgctcct ccgttccggg   180
cacgcctcta aagtctatac agcctcgaat ccatcccggc cgccgctcct gggggatact   240
acagcgagcc gaagcgggga tggcggagat ccctgtgatc gacctgcgcg tcgccggctc   300
ggcggccgag gagtccgcgc ggctgcgggc cgcgtcgggc cgcctgggct gcttccgggt   360
gaccggccac ggcgtgccct cggtgctcct ggcagagatg aaggccgccg tgcgcgcgct   420
cttcgacctc cccgacgacg ccaagcgccg caacgccgac gtcatcaccg gcagcggcta   480
cgtcgccccc agcccgacca acccgctcta cgaggccttc gggctcctcg acgccgccgt   540
gcccaccgac gtcgacgcct tttgcgcgct cctcgacgcg ccgcccaaca tcagggagac   600
cgtcaaggcc tacgcggaga agatgcacga tgtgatcgtt ggcgtcgccc gcgagctggc   660
gtctagcctg gggctagtcg aggagcactc gttccaggac tggccgtgcc agttccgcat   720
caacaggtac aactacacgc gggagacggt gggctcctcc ggcgtgcaga cccacacgga   780
ctcgggcttc ctcaccgtgc tccatgagga cgagtgtgtc ggcggcctc aggtcctgga   840
cccgggcacc ggcagttcg tgccgtgga ccccgtcgcg ggctccttc tcgtaaacat   900
cggcgacgtc ggcacggcgt ggagcaacgg gaggctgcac aacgtgaagc accgggtgcg   960
gtgcgtcgca cccgtgccgc gcatctccat cgccatgttc ctgctcgcac ccaaggacga  1020
cagcgtgagc gcaccggcgg cgttcgtgga cgcggaccac ccgcgcaggt acaaggtgtt  1080
caactacaac gactatcgga ggctcagact gtccaccggc gagcacgcag gcgaggcgct  1140
cgcacggatg gcggcgtgac gtggctggag ctgcaaattg gattggaagc cgagacaagc  1200
cgttagttat ttaccatgcc cgtgcgttca ccgcacacaa tcatattcaa aagccataaa  1260
ataaaaaata attttaatat cagtcaacat atggtttaaa tatcatatgg agtacaatat  1320
tccgaatttt tttttgtaat ttagtctgtc ttttgaaaaa aatgcacatc tagacctccg  1380
gatgact                                                           1387

SEQ ID NO: 20          moltype = DNA  length = 900
FEATURE                Location/Qualifiers
source                 1..900
                       mol_type = unassigned DNA
                       organism = Zea mays
SEQUENCE: 20
atggcggaga tccctgtgat cgacctgcgc gtcgccggct cggcggccga ggagtccgcg    60
cggctgcggg ccgcgtgcga gcgcctgggc tgcttccggg tgaccggcca cggcgtgccc   120
tcggtgctcc tggcagagat gaaggccgcc gtgcgcgcgc tcttcgacct ccccgacgac   180
gccaagcgcc gcaacgccga cgtcatcacc ggcagcggct acgtcgcccc cagcccgacc   240
aacccgctct acgaggcctt cgggctcctc gacgccgccg tgcccaccga cgtcgacgcc   300
ttttgcgcgc tcctcgacgc gccgcccaac atcagggaga ccgtcaaggc ctacgcggag   360
aagatgcacg atgtgatcgt tggcgtcgcc cgcgagctgg cgtctagcct ggggctagtc   420
gaggagcact cgttccagga ctggccgtgc cagttccgca tcaacaggta caactacacg   480
cgggagacgg tgggctcctc cggcgtgcag acccacacgg actcgggctt cctcaccgtg   540
ctccatgagg acgagtgtgt cggcggcctc aggtcctgga cccgggcac cggcgagttc   600
gtgcccgtgg acccgtcgc gggctccttt tcgtaaaca tcggcgacgt cggcacggcg   660
```

```
tggagcaacg ggaggctgca caacgtgaag caccgggtgc ggtgcgtcgc acccgtgccg    720
cgcatctcca tcgccatgtt cctgctcgca cccaaggacg acagcgtgag cgcaccggcg    780
gcgttcgtgg acgcggacca cccgcgcagg tacaaggtgt tcaactacaa cgactatcgg    840
aggctcagac tgtccaccgg cgagcacgca ggcgaggcgc tcgcacggat ggcggcgtga    900

SEQ ID NO: 21           moltype = AA  length = 299
FEATURE                 Location/Qualifiers
source                  1..299
                        mol_type = protein
                        organism = Zea mays
SEQUENCE: 21
MAEIPVIDLR VAGSAAEESA RLRAACERLG CFRVTGHGVP SVLLAEMKAA VRALFDLPDD     60
AKRRNADVIT GSGYVAPSPT NPLYEAFGLL DAAVPTDVDA FCALLDAPPN IRETVKAYAE    120
KMHDVIVGVA RELASSLGLV EEHSFQDWPC QFRINRYNYT RETVGSSGVQ THTDSGFLTV    180
LHEDECVGGL EVLDPGTGEF VPVDPVAGSF LVNIGDVGTA WSNGRLHNVK HRVRCVAPVP    240
RISIAMFLLA PKDDSVSAPA AFVDADHPRR YKVFNYNDYR RLRLSTGEHA GEALARMAA     299

SEQ ID NO: 22           moltype = DNA  length = 1496
FEATURE                 Location/Qualifiers
source                  1..1496
                        mol_type = unassigned DNA
                        organism = Zea mays
SEQUENCE: 22
gtcggtctct tgtctcacca aaccggcgac atggtacatg gaggccagcc cgtcgcttgg     60
cgccacaagt ctcggtgccg tccgtccgac aagcggcgcc agcgcacgct ggctgctcgt    120
gcacgcctct aaatacggcc ccggacccgc caccaagcga aggccatcgc cgtccgccgc    180
cccccaccaa ccacgaaacca cgcaagcgaa cccggccggc gcggggcagc ggcgatggcg    240
gagatcccgg tgatcgacct gcgcctcgcc ggctcgtcgc ccgacgagtc ggcgcggctg    300
cgcgacgcgt gcgagcgcct gggctgcttt cgggtgaccg ccacggcgc gcccgcgggg    360
ctcctggccg acatgaaggc cgccgtgcgc gcgctcttcg acctccccga cgacgccaag    420
cgccgcaacg ccgacgtcat ccccggcagc ggctacgtcg cgccctgccc cgccaacccg    480
ctctacgagg ccttcgggct cctcgacgcc gccgcgcccg ccgacgtcga cgccttctgc    540
gcgcgcctcg acgcgccgcc caaagtcagg gagaccgtca agacctacgc ggagaagatg    600
cacgacgtga tcgtcggcgt gccggcgag ctggccacca gcctgggcgc gggcctggag    660
gagcactcgt tccaggactg gccgtgccag ttccgcatca acaggtacaa ctacacggg    720
gagacggtgg gctcctccgg cgtgcagacc cacacggact cgggcttcct caccgtgctc    780
caggaggacg agtgcgtcgg cggcctcgag gtgctggacc ccgccgccgg tgagttcgtg    840
cccgtggacc ccgtcgccgg ctccttcctc gtcaacatcg gcgacgtcgg cacggcgtgg    900
agcaacggga ggctccacaa cgtgaagcac cgggtgcggt gcgtggcgc cgtgccgcgc    960
atctccatcg ccatgttcct gctggcgccc aaggacgacc gcgtgagcgc cccggaggcg   1020
ttggtcgacg cgggccaccc gcgtcggtac aagccgttca actacgacga ctaccggagg   1080
ctccggctgt ccaccggcga gcgcgcaggc gaggcgctcg cgcggatggc ggcgtgatgt   1140
cgtcacgcac gtgcaagccg ttaattatag gctcgcgcat gcatacgcct acacgagagg   1200
ttgtctcgtt aagccgttct attaaaatgt gtggggaga aagatgacta ccgtggtgcc   1260
atgtggattg ctatcgggtc tgatcaataa aatcttgcaa cacttgcacg tgcgattcca   1320
tatcctagca cgggtgggcg ccacgctagt aggtagagac cggagcggcc aaaaaatggc   1380
tacagcacca gtaggtgaac tctcaagcaa cactggctat cccacttctg acgttgtctc   1440
tctcatcact atgtatgacc agcgaatgaa gtgtttaaaa atctgacgcc gtgaaa       1496

SEQ ID NO: 23           moltype = DNA  length = 903
FEATURE                 Location/Qualifiers
source                  1..903
                        mol_type = unassigned DNA
                        organism = Zea mays
SEQUENCE: 23
atggcggaga tcccggtgat cgacctgcgc ctcgccggct cgtcgcccga cgagtcggcg     60
cggctgcgcg acgcgtgcga gcgcctgggc tgctttcggg tgaccggcca cggcgcgccc    120
gcggggctcc tggccgacat gaaggccgcc gtgcgcgcgc tcttcgacct ccccgacgac    180
gccaagcgcc gcaacgccga cgtcatcccc ggcagcggct acgtcgcgcc ctgccccgcc    240
aacccgctct acgaggcctt cgggctcctc gacgccgccg cgcccgccga cgtcgacgcc    300
ttctgcgcgc gcctcgacgc gccgcccaaa gtcagggaga ccgtcaagac ctacgcggag    360
aagatgcacg acgtgatcgt cggcgtcgcc ggcgagctgg ccaccagcct ggggctgggc    420
ctggaggagc actcgttcca ggactggccg tgccagttcc gcatcaacag gtacaactac    480
acgcaggaga cggtgggctc ctccggcgtg cagacccaca cggactcggg cttcctcacc    540
gtgctccagg aggacgagtg cgtcggcggc ctcgaggtgc tggaccccgc cgccggtgag    600
ttcgtgcccg tggaccccgt cgccggctcc ttcctcgtca acatcggcga cgtcggcacg    660
gcgtggagca acgggaggct ccacaacgtg aagcaccggg tgcggtgcgt cgcgcccgtg    720
ccgcgcatct ccatcgccat gttcctgctg gcgcccaagg acgaccgcgt gagcgccccg    780
gaggcgttgg tcgacgcggg ccacccgcgt cggtacaagc cgttcaacta cgacgactac    840
cggaggctcc ggctgtccac cggcgagcgc gcaggcgagg cgctcgcgcg gatggcggcg    900
tga                                                                  903

SEQ ID NO: 24           moltype = AA  length = 300
FEATURE                 Location/Qualifiers
source                  1..300
                        mol_type = protein
                        organism = Zea mays
SEQUENCE: 24
MAEIPVIDLR LAGSSPDESA RLRDACERLG CFRVTGHGAP AGLLADMKAA VRALFDLPDD     60
```

```
AKRRNADVIP GSGYVAPCPA NPLYEAFGLL DAAAPADVDA FCARLDAPPK VRETVKTYAE    120
KMHDVIVGVA GELATSLGLG LEEHSFQDWP CQFRINRYNY TQETVGSSGV QTHTDSGFLT    180
VLQEDECVGG LEVLDPAAGE FVPVDPVAGS FLVNIGDVGT AWSNGRLHNV KHRVRCVAPV    240
PRISIAMFLL APKDDRVSAP EALVDAGHPR RYKPFNYDDY RRLRLSTGER AGEALARMAA    300

SEQ ID NO: 25           moltype = DNA   length = 1614
FEATURE                 Location/Qualifiers
source                  1..1614
                        mol_type = unassigned DNA
                        organism = Zea mays
SEQUENCE: 25
accacacgaa ttgcacatct ccacagctca cgattccaac actagctaca tatatatgta      60
gctttctagg ctactatata cactcaccac caagtgtgaa gtgtgtatat atagtgacag     120
ctactgcaat atatacatac gcgtcaccta tatattagcc aagtagctca tatgagcttg     180
gttgcggcgc caatggcgat cgtcgacgtg gccaacgccc agctgcagca agcagcagca     240
gcagctgcca agaaagacga ggacggccat gagcagcagg agtcgtccta cgactacggc     300
gcgctgatga aaggcgtgag gcacctgtcg acagcggca ttaccaggct gcccgacagg      360
tacgtcctgc ccgcgtccga ccgccccggc gtccttgccg tctcgtcgtc cgtggcgggc     420
agcggcaggg tcaagctccc tgtcgtcaac ctcgccggcc tccgcgaccc ctgccagcgc     480
gccgccgtgc tggccacgct cgacgccgcg tgccgggagt acggcttctt tcaggtggta     540
aaccacgggt tcgggagcga cgtgagcggc gggatgctgg acgtggcgca gcgcttcttc     600
gagctgccgc tggccgagcg agcgcggcac atgtcggcgg acgtgcgggc gccggtgcgc     660
tacggcacca gcttcaacca ggccaaggac gacgtgctct gctggcgcga cttcctcaag     720
ctcgtctgcc agccgctgca ggcggtgctc ccgtactggc cccagcagcc ggcggacctc     780
agggacgtgg ccaccaggta cgccacggcg agccaccggc tgttcatgga ggtcatggag     840
gcggcgctgg aggccctggg catccccacg gccggcggta cgtcgggga gctggcagcg     900
tcgtcgtcgc acatgatgac ggtgaactgc tacccggctg gcccgcagcc tgagctcacg     960
ctggggatgc cctcgcactc ggactacggc ctcttcacgt tcgtcctgca ggaccacgtc    1020
gagggcctcc aggtcatgca cgacggccgc tggctcacca tcgacccat cccgggatcg     1080
ttcgtcgtca acgtcggcga ccacctagag atctacagca acgggcggta caagagcgcg    1140
ctgcaccggg tgcacgtgaa ctccacgcgc ccgcgcatct cggtggcgtc gttccacagc    1200
ctgccggcgg agcgagtgat cgggccggcc cggagctggt ggacgacga ggccggcaac     1260
ccgcggcggt acatggacac cgacttcgct accttcctcg cctacctcgc atccgcggac    1320
ggcaagaaca agaccttcct ccagtcaagg aagctgcctg ctgctgatcc tccatgcctc    1380
tagctaacta gatagctgct tattaatctg acagaataag attaatcagt tcagcgcaca    1440
attccacaag cgaaaacaaa cctggatttg ttttaattag ctctgccctt cattattaca    1500
ttcaagctag ctcttggtca acgcatgcac acaagcttga gcattgactg gtccctttc     1560
aatcggttgc attgtactcc ctccgtacca aaattggttg tcgctatagt attt          1614

SEQ ID NO: 26           moltype = DNA   length = 1212
FEATURE                 Location/Qualifiers
source                  1..1212
                        mol_type = unassigned DNA
                        organism = Zea mays
SEQUENCE: 26
atgagcttgg ttgcggcgcc aatggcgatc gtcgacgtgg ccaacgccca gctgcagcaa      60
gcagcagcag cagctgccaa gaaagacgag gacggccatg agcagcagga gtcgtcctac     120
gactacggcg cgctgatgaa aggcgtgagg cacctgtcgg acagcggcat taccaggctg     180
cccgacaggt acgtcctgcc cgcgtccgac cgccccggcg tccttgccgt ctcgtcgtcc     240
gtggcgggca gcggcagggt caagctccct gtcgtcaacc tcgccggcct ccgcgacccc     300
tgccagcgcg ccgccgtgct ggccacgctc gacgccgcg tgccgggagta cggcttctt      360
caggtggtaa accacgggtt cgggagcgac gtgagcggcg ggatgctgga cgtggcgcag     420
cgcttcttcg agctgccgct ggccgagcga gcgcggcaca tgtcggcgga cgtgcgggcg     480
ccggtgcgct acggcaccag cttcaaccag gccaaggacg acgtgctctg ctggcgcgac     540
ttcctcaagc tcgtctgcca gccgctgcag gcggtgctcc cgtactggcc ccagcagccg     600
gcggacctca gggacgtggc caccaggtac gccacggcga gccaccggct gttcatggag     660
gtcatggagg cggcgctgga ggccctgggc atccccacgg ccggcggtgt gctcggggag     720
ctggcagcgt cgtcgtcgca catgatgacg gtgaactgct acccggctgc ccgcagcct      780
gagctcacgc tggggatgcc ctcgcactcg gactacggcc tcttcacgtt cgtcctgcag     840
gaccacgtcg agggcctcca ggtcatgcac gacggccgct ggctcaccat cgacccatc     900
ccgggatcgt tcgtcgtcaa cgtcggcgac caccttagaga tctacagcaa cgggcggtac    960
aagagcgcgc tgcaccgggt gcacgtgaac tccacgcggc cgcgcatctc ggtggcgtcg    1020
ttccacagcc tgccggcgga gcgagtgatc gggccggcgc ggagctggtg gacgacgag     1080
gccggcaacc cgcggcggta catggacacc gacttcgcta ccttcctcgc ctacctcgca    1140
tccgcggacg gcaagaacaa gaccttcctc cagtcaagga agctgcctgc tgctgctcct    1200
ccatgcctct ag                                                        1212

SEQ ID NO: 27           moltype = AA    length = 403
FEATURE                 Location/Qualifiers
source                  1..403
                        mol_type = protein
                        organism = Zea mays
SEQUENCE: 27
MSLVAAPMAI VDVANAQLQQ AAAAAAKKDE DGHEQQESSY DYGALMKGVR HLSDSGITRL      60
PDRYVLPASD RPGVLAVSSS VAGSGRVKLP VVNLAGLRDP CQRAAVLATL DAACREYGFF    120
QVVNHGFGSD VSGGMLDVAQ RFFELPLAER ARHMSADVRA PVRYGTSFNQ AKDDVLCWRD    180
FLKLVCQPLQ AVLPYWPQQP ADLRDVATRY ATASHRLFME VMEAALEALG IPTAGGVLGE    240
LAASSSHMMT VNCYPACPQP ELTLGMPSHS DYGLFTFVLQ DHVEGLQVMH DGRWLTIDPI    300
PGSFVVNVGD HLEIYSNGRY KSALHRVHVN STRPRISVAS FHSLPAERVI GPAPELVDDE    360
```

```
AGNPRRYMDT DFATFLAYLA SADGKNKTFL QSRKLPAAAP PCL                           403

SEQ ID NO: 28              moltype = DNA   length = 1863
FEATURE                    Location/Qualifiers
source                     1..1863
                           mol_type = unassigned DNA
                           organism = Zea mays
SEQUENCE: 28
tgccaccata ccactagtgc aaggtcctag atttacactt ggtgctacac cttgcttcgc    60
ccccttcctt ccttccttcc ttccttccct ccttccttgg tctctaggca gctagcagtg   120
tggtgctgct gccggccgcc tattggccgc tgggactgga gatccattaa ttactgcgcg   180
cgcgcggcta accaaccaat cccagcgtgc gtaatctatt gcccacatgc cgacgccgtc   240
gcacctcaac aagaacccgc gctacctgga cttccgggcg gcgcggcggg tgccggagtc   300
gcacgcctgg ccgggcctgc acgaccaccc cgtcgtggac ggcggcgcgc cgggccccga   360
cgccgtgccg gtggtggacc tgggcgccgc ggaccgggcg ccggcgccgg cggcggcggt   420
ggcccgcgcc gccgagcaat ggggcgcgtt cctgctcacg ggccacggcg tccccgcgga   480
cctgctggcc cgcgtggagg accggatcgc caccatgttc gcgctgccgg ccgacgacaa   540
gatgcgcgcc gtgcgcgggc ccggcgacgc ctgcggctac ggctcccgcc ccatctcctc   600
cttcttctcc aagtgcatgt ggtccgaggg ctacaccttc tcgccggcct ccctccgcgc   660
cgacctccgc aagctctggc ccaaggccgg cgacgactac accagcttct gtgatgtgat   720
ggaggagttc cacaagcaca tgcgcgccct cgcggacaag ctgctggagc tgttcctcat   780
ggcgctgggg ctcaccacga gcaggccag cgccgtcgag gccgagcgga ggatcgccga   840
gacgatgacc gccaccatgc atctcaactg gtacccgagg tgcccggacc cgcggcgcgc   900
gctgggcctg atcgcgcaca ccgactcggg cttcttcacc ttcgtgatgc agagcctcgt   960
gcccgggctg cagctcttcc gccacgcccc ggaccggtgg gtggcggtgc cggccgtgcc  1020
gggcgccttc gtcgtcaacg tgggcgacct tttccacatc ctcaccaacg gccggttcca  1080
cagcgtgtac caccgcgcgc tcgtgaaccg ggacctcgac aggatctcgc tcggctactt  1140
cctcggcccg ccgccgcacg ccaaggtggc ggcctgcgc gaggccgtgc cgcccggccg  1200
ggccccgcg taccgcgccg tcacgtggcc cgagtacatg ggcgtccgca agaaggcctt  1260
caccaccggc gcctccgcc tcaagatggt ggccctcgcc gccgccgcg acctcgacga  1320
cgacggcgac gccgccgtcg tccatcagca gcagcagcta gtcgtctcgt cgtagccgag  1380
accgatcgcc ggagactgat gctgatgatg atgcatatat acatgagaga atcgtcgag  1440
tagactagcc gattgcaaaa gcaacccag ctgccgaaac ctggcatatc gatcccattc  1500
tctgctgcgc acatgtatgc atgcatcgc ttcgtccgtt cgactcgtgt gtgcttgctt  1560
gcttgcgcgt gcagcagaac taattccgtt ccgcagctag ctgctctgct ctgctctgct  1620
ggaatgtaat taagtagtag tatatggtag tagagaaaag attagctagg gcatcgatat  1680
agatgacggg ccggggaaga agacgaatta attaagatcg atcgacgacg acgagctgtg  1740
cgtggctggc tgtgttcttc tctagcctag ttacagaggc cggctgctgc tgcttccaat  1800
cgggctgctt gtcgctactg acgatcgtta gtggatccat taactaatct ggaattctgg  1860
att                                                                1863

SEQ ID NO: 29              moltype = DNA   length = 1149
FEATURE                    Location/Qualifiers
source                     1..1149
                           mol_type = unassigned DNA
                           organism = Zea mays
SEQUENCE: 29
atgccgacgc cgtcgcacct caacaagaac ccgcgctacc tggacttccg ggcggcgcgg    60
cgggtgccgg agtcgcacgc ctggccgggc ctgcacgacc accccgtcgt ggacggcggc   120
gcgcggggcc ccgacgccgt gccggtggtg gacctgggcg ccgcggaccc ggcgccggcg   180
ccggcggcg cggtggcccg cgccgccgag caatggggcg cgttcctgct cacggggcca   240
ggcgtccccg cggacctgct ggcgcgcgtg gaggaccgga tcgccaccat gttcgcgctg   300
ccggccgacg acaagatgcg cgccgtgcgc gggcccggcg acgcctgcgg ctacggctcc   360
cgcccatct cctccttctt ctccaagtgc atgtggtccg agggctacac cttctcgccg   420
gcctccctcc gcgccgacct ccgcaagctc tggcccaagg ccggcgacga ctacaccagc   480
ttctgtgatg tgatggagga gttccacaag cacatgcgcg ccctcgcgga caagctgctg   540
gagctgttcc tcatggcgct ggggctcacc gacgagcagg ccagcgccgt cgaggccgag   600
cggaggatcg ccgagacgat gaccgccacc atgcatctca actggtaccc gaggtgcccg   660
gaccgcggg gcgcgctggg cgtgatcgcg cacaccgact cgggcttctt caccttcgtg   720
atgcagagcc tcgtgccggg gctgcagctc ttccgccacg ccccggaccg gtgggtgcg   780
gtgccggccg tgccgggcgc cttcgtcgtc aacgtgggcg acctcttcca catcctcacc   840
aacggccggt tccacagcgt gtaccaccgc gccgtcgtga accgggacct cgacaggatc   900
tcgctcggct acttcctcgg cccgccgccg cacgccaagg tggcggcgct gcgcgaggcc   960
gtgccgcccg gccgggcccc gcgtaccgc gccgtcgtcg gccgtggcca tgccccgagta  1020
cgcaagaagg ccttcaccac cggcgcctcc gcgctcaaga tggtcgccct cgccgccgcc  1080
gccgacctcg acgacgacgg cgacgccgcc gtcgtccatc agcagcagca gctagtcgtc  1140
tcgtcgtag                                                          1149

SEQ ID NO: 30              moltype = AA   length = 382
FEATURE                    Location/Qualifiers
source                     1..382
                           mol_type = protein
                           organism = Zea mays
SEQUENCE: 30
MPTPSHLNKN PRYLDFRAAR RVPESHAWPG LHDHPVVDGG APGPDAVPVV DLGAADPAPA     60
PAAAVARAAE QWGAFLLTGH GVPADLLARV EDRIATMFAL PADDKMRAVR GPGDACGYGS    120
PPISSFFSKC MWSEGYTFSP ASLRADLRKL WPKAGDDYTS FCDVMEEFHK HMRALADKLL   180
ELFLMALGLT DEQASAVEAE RRIAETMTAT MHLNWYPRCP DPRRALGLIA HTDSGFFTFV   240
MQSLVPGLQL FRHAPDRWVA VPAVPGAFVV NVGDLFHILT NGRFHSVYHR AVVNRDLDRI   300
```

```
SLGYFLGPPP HAKVAPLREA VPPGRAPAYR AVTWPEYMGV RKKAFTTGAS ALKMVALAAA  360
ADLDDDGDAA VVHQQQQLVV SS                                          382

SEQ ID NO: 31            moltype = DNA  length = 1439
FEATURE                  Location/Qualifiers
source                   1..1439
                         mol_type = unassigned DNA
                         organism = Zea mays
SEQUENCE: 31
gacctccatt ttgattatct ctatcctgta cgtgccgaga gtccttcaaa gccgacgacg   60
agacgacgat gcagtcgtcg tcgtcatcag cctcgacgcc ggctgccgct tccggcctcg  120
tcttcgatct cgggtctgcg gcgggcgtgc cggagacaca cgcgtggccg ggggtgaacg  180
agtacccgtc ggtggagtcc gctggccgcg acgtggtccc ggtggtggac atgggggtgg  240
cctgcccgga cgcgacgcgg cgttggcgc gccgcagga cgagtggggt gtgtttctga    300
tcgtcggcca cggcgtgccc cggaagtgg cggcgcgtgc cgaggagcag gtcgcgcgcc   360
tgttcgtgct cccggctcct gacaaggccc gcgcggggcg ccgccccggg gagcccacgg   420
ccaccggcta cggcaggccg cccctggcac tccgcttctc caagctcatg tggtccgagg   480
ggtacacgtt ccgcgccgcc accgtccgcg aagagttccg cccgacgggg               540
gcgacgacta cctccgcttc tgcgacgtga tggaggagta cgacagagag atgagggctc    600
tcggtggcag gctgctcgac ctcttcttca tggcgctcgg cctcaccgac gtccagttcg    660
ccaccggcga gacggagcgg aggatccgcg agacctggac ggcgacgatg cacccaatcc    720
tgtgtccgga accggagcgg gccatcggge tgacggcaga cacggactcg ggcttcatca    780
cgctcatcat gcagagcccc gtgcccggge tgcagctgct ccgccgcggg ccggaccggt    840
gggtgacggt gccggcgccg ccgggcgcgc tcatcgtcat gctcggcgac ctgttccagg    900
tgctcacgaa cggccgcttc cggagcccta tccaccgcgc cgtcgtaagc cgagagcgcg    960
agcggatctc cgtgccctac ttcctctgcc cgccggaaga catgacggtg gcgccgctcg   1020
cgtccgctct gctgccgggg aggaaggccg tgttccggge cgtgacgtgg ccagagtaca   1080
tggaggtcaa gcacaaggtg ttcggcacgg atgcgccggc cctggagatg ctgcagctgc   1140
aggtggatga ggaagaacaa ggtgaaaggg ccgccaccac ctaagcccta aggaactact   1200
agctgaatcc ataaactaat aaagaattcg tgaataaggg cgttggaaga ctggacacaa   1260
cacaagagag ttgctatata tcgtatttct gaaatttaag gcaaatatct tagttaaaaa   1320
actggtatat ttaaatagac aatatatatc taaaataaag atagttcacc atttttacgg   1380
tcgaacaatg ataaagttat atattgtctg aatagtaaca aattaaagat ttccaggag    1439

SEQ ID NO: 32            moltype = DNA  length = 1116
FEATURE                  Location/Qualifiers
source                   1..1116
                         mol_type = unassigned DNA
                         organism = Zea mays
SEQUENCE: 32
atgcagtcgt cgtcgtcatc agcctcgacg ccggctgccg cttccggcct cgtcttcgat    60
ctcgggtctg cggcgggcgt gccggagaca cacgcgtggc cggggggtgaa cgagtacccg  120
tcggtggagt ccgctggccg cgacgtggtc ccggtggtgg acatggggt gccgtgcccg    180
gacgcgacgc gggcgttggc gcgcgccgca gacgagtggg gcgtgtttct gctcgtcggc  240
cacggcgtgc ccgggaagtg gcggcgcgct gccgaggagc aggtcgcgcg cctgttcgtg  300
ctcccggctc tgacaaggc ccgcgcgggg cgccgccccg gggagcccac ggccaccggc    360
tacggcaggc cgccctgc actccgcttc tccaagctca tgtggtccga ggggtacacg    420
ttccgcgccg ccaccgtccg cgaagagttc cgccgcgtct ggcccgacgg cggcgacgac   480
tacctccgct tctgcgacgt gatggaggag tacgacagag atgagggc tctcggtggc     540
aggctgctcg acctcttctt catggcgctc ggcctcaccg acgtccagtt cgccaccggc   600
gagacggagc ggaggatccg cgagacctgg acggcgacga tgcacccaat cctgtgtccg   660
gaaccggagc gcgccatcgg gctgacggc cacacggact cgggcttcat cacgctcatc   720
atgcagagcc ccgtgcccgg gctgcagctg ctccgccgcg gccggaccg gtgggtgacg  780
gtgccggcgc cgccgggcgc gctcatcgtc atgctcggcg acctgttcca ggtgctcacg   840
aacggccgct tccggagccc tatccaccgc gccgtcgtaa gccgagagcg cgagcggatc   900
tccgtgccct acttcctctg cccgccggag acatgacgt ggcgccgct cgcgtccgct    960
ctgctgccgg ggaggaaggc cgtgttccgg gccgtgacgt ggccagagta catggaggtc  1020
aagcacaagg tgttcggcac ggatgcgccg gccctggaga tgctgcagct gcaggtggat  1080
gaggaagaac aaggtgaaag gccgccacc acctaa                              1116

SEQ ID NO: 33            moltype = AA  length = 371
FEATURE                  Location/Qualifiers
source                   1..371
                         mol_type = protein
                         organism = Zea mays
SEQUENCE: 33
MQSSSSSAST PAAASGLVFD LGSAAGVPET HAWPGVNEYP SVESAGRDVV PVVDMGVACP    60
DATRALARAA DEWGVPLLVG HGVPREVAAR AEEQVARLFV LPAPDKARAG RRPGEPTATG   120
YGRPPLALRF SKLMWSEGYT FRAATVREEF RRVWPDGGDD YLRFCDVMEE YDREMRALGG   180
RLLDLFFMAL GLTDVQFATG ETERRIRETW TATMHPILCP EPERAIGLTA HTDSGFITLI   240
MQSPVPGLQL LRRGPDRWVT VPAPPGALIV MLGDLFQVLT NGRFRSPIHR AVVSRERERI   300
SVPYFLCPPE DMTVAPLASA LLPGRKAVFR AVTWPEYMEV KHKVFGTDAP ALEMLQLQVD   360
EEEQGERAAT T                                                        371

SEQ ID NO: 34            moltype = DNA  length = 4095
FEATURE                  Location/Qualifiers
source                   1..4095
                         mol_type = unassigned DNA
                         organism = Zea mays
```

SEQUENCE: 34
```
taaatttgtg atccttgtga agttgttata tcatgaattg tgaacttgtt gcatttgtga    60
tcttttgtca actttgttgt attgtgaagt ttgatatgtt taccgatcgt attttagatt   120
tcgatcgtta ccgtgtatt ttccgcacca aacttttgtt tccgatgttt tcgaaatacc   180
gatatcgttt ccgtttctat agttacccct ttcaatttta tttccgatta aaaatatgaa   240
aacggtaatg gttttagtgt ttatcgaccg ttttcatctc taatcatccc tgccggtgaa   300
gtttaattt tcccttggct aaagagatgc aagctgctgt aaaatacgtt aaaacaggca   360
aggcagcccc agcagccagc atcgcgtgcc cgtctatgta catcagtgga tacgtagcat   420
ctctagtgag taatataacg attgcatttg gctggaggac gtatgttata taagtatgtc   480
atttaccagt tgcattagta tcttccctaa ctccctataat aactctcttc gtggaatgga   540
cgtagacgta tgctatataa gtattaaaaa atagttttt aagctggtgt cctcaatttt   600
gctattgttc tcgtttttat ctttagttgt gtcacaaatt taatccgtac aacaaatcaa   660
aaataccata cccttcttat attaattttc taacataaca tttgtttaga tattttcagt   720
cgtgaaaata caattctaat tctaacgtcg tagtatcaaa tcaaaccatc cagaatttga   780
ccaagcttaa ttataaaaaa tataaaattt atgatactga atagatagca ttagatttgt   840
tatataaat attttataa aataccattt ttatggtata aatattggta ctcctttact   900
ttaaactata gatagttttg actaaggatg caactagaat tgcatcctct tttcactgca   960
ccttcattag ttttaatatt tatttagatg ggcccttgca aactgtagat atcatctctt  1020
gcaacattct ttctatagca ccacgaaaat gtattgcggc tttgaaatta taattgaatt  1080
agttgtatca tttctttcac cgatgcgtta aattcaaaat taagtgttat atttcttcat  1140
aatttgttaa atatatagac cctataatcc accattattt actataatag catacattaa  1200
cattggtttt agcctacact acgacactcg aggcattgaa ttttcctcta tcaaagaatt  1260
atatgtgtag tagtattgtt cttgacaaaa aggggatta aaattaaact accaatattg  1320
atacttatct tatcacatcc atgaatacaa tcaacactct tacaaaagat aagatacaag  1380
attaaaaagt accatgataa tacattaaga ttattagcaa tgcattaaat taaataaatg  1440
tgcaagtgaa tcatgatttt agttttatct attttacttt taaaatatga tattctgtga  1500
ctacttctaa gcataaatgt gattctaagt catgaccgat cgtgcttatt cagaaaaatg  1560
aaggagacac agatttctat aaaaaaaggt tgtcatggga ctattgggtc aaccatctta  1620
ttcatttggg aaaataagtt tagaacacat caacccattt tagatgttga gtttggccct  1680
aatggtccat tgaccttact tttgtgggtt gacatagacc atctatccca agttattgtt  1740
gtgtcacatt ccctgatatc atgaatctat atttttagctt tccgttttca tattttagt  1800
cgttacatat tttttatccg cgtactagat taaaactcta gttgttgcaa tacattttgt  1860
tcattttttt ctatttcttc tttactaaca acatattcta gttcctagct acattcttaa  1920
gtaccatagt gctataaaca tttttatcc tacattattc cacttaagaa attgaatttt  1980
ctgcataaaa aaattatatg tccagtagtg ttgtcttata aaagcataaa gtgattaaaa  2040
ttaaaaccat tattgatatc ttattttca aaaaaaata taagcttata gaaagtgaat  2100
taatttcatg gtaaattaat atagtttaaa ttgaattatt agtgttatta ctatgtttat  2160
tatcaatgaa acatttttca tggttgatat aacttagtgt tacttatttt agtatttttt  2220
atataattct agttaactt tagttttga tttaaaaaaa cgagaattgt gtcctttgt  2280
ggagtgagta taaagaaagt aatatctgtt catcataatt tggttttta aggtacgtta  2340
aacttgcttt atatttggac tcaagctatg tctaaataca tagtaaaaaa gcaatatttc  2400
tagaaaagac aaaacatctt ataatttaga atcaaggaaa tatatagatt ttatgtgcag  2460
tgagaagcca tttacaatgg aacgttcaac gttgggccaa tagatatttt gcgatatgat  2520
gatgggcata ttttttgcatg gttgtccctc cactagctat agtttgatga tacgatacgc  2580
tgcacacacc attgggttgt accatgttag tgtagcaaca gtagaaaccc aattgtggcc  2640
gtgaaccatg ataatactag gtagagtgct agctagaggt ttcaggctat tgatgcgtga  2700
attaacttt ctgttgtgtt gcgaggaaac gagtattgtg aaatatttga aacggttttt  2760
tttgtgaaag atttgaaacg gtattttgt tgtgaaataa agatcaaggc taaataaatt  2820
caaactaata aaacatatta attgacggcc tgaagccccc gcccccatgg ccccatgcca  2880
tagcatcagg tcccacatga catgaggccg cgcctccctc tatgttggct ccctgccttc  2940
gccgttgtcg tcgctcccga actccctctc ctccccctgtt acaaataccc ccaccccgcc  3000
ggacagcttc cctgcacact cgcagctcgc acatctcatg gtgtcctaag aacggcaaga  3060
gccagctctg cctagcagca gcgcacagcc acatccatgg acgccagccc gacccccaccg  3120
ctcccccctcc gcgccccaac tcccagcatt gacctcccccg ctggcaagga cagggccgac  3180
gcggcggcta acaaggccgc ggctgtgttc gacctgccgg gggagcccaa gatcccggag  3240
ccattcctgt ggccgcacga agaggcgcgg ccgacctcgg ccgcggagct ggaggtgccg  3300
gtggtggacg tgggcgtgct gcgcaatggc gacggcgcgg ggctccgccg cgccgcggcg  3360
caagtggcgg cggcgtgcgc gacgcacggg ttcttccagg tgtgcgggca cggcgtggac  3420
gcggcgctgg ggcgcgcgc gctggacggc gccagcgact tcttccggct gccgctggct  3480
gagaagcagc gggcccggcg cgtcccccggc accgtgtccg ggtacacgag cgcgcacgcg  3540
gaccggttcg cgtccaagct cccctggaag gagaccctgt ccttcggctt ccacgacggc  3600
gccgcggcgc ccgtcgtcgt ggactacttc accggcaccc tcggccaaga tttcgagcca  3660
gtggggtgag taaagaagaa gatggcgccg aatttacatt tataagtagg accagcagaa  3720
gccccctgccc ctgggggcct tagcattgca ttcgactgat gaatacgcat ggcaggcggg  3780
tgtaccagag gtactgcgag gagatgaagg agctgtcgct gacgatcatg gagctgctgg  3840
agctgagcct gggcgtggag gcggctact accgggagtt cttcgaggac agccgctcca  3900
tcatgcggtt caactactac ccgccgtgcc cggtgccgga gcgcacgctg gcacgggcc  3960
cgcactgcga ccccacggcg ctgaccatcc tcctgcagga cgacgtcggc gggctggagg  4020
tcctggtgga cggcgagtgg cgccccgtcc ggcccgtccc aggcgccatg gtcatcaaca  4080
tcggcgacac cttca                                                   4095
```

| SEQ ID NO: 35 | moltype = DNA length = 7404 |
|---|---|
| FEATURE | Location/Qualifiers |
| source | 1..7404 |
| | mol_type = unassigned DNA |
| | organism = Zea mays |

SEQUENCE: 35
```
cctatttgt gtctaatact cttcttatat taattgtttg gtcaaacttt agataaattt    60
gactaatgat gcaattaaaa ctgcatcacc tttactaagg tactgcttta tatgtttcga   120
```

```
caaaattttc aattattctc tatgtgtttt aatctttgcg ctacacctcc attgatttaa    180
atactcattt attttaaacc ataacttaaa ttatatcgga tctttgcatc ctttctatgg    240
caccatacat gaatcgatat tttggctgca aatttttaat catgttagtt ttagcatttt    300
ttcatatcca tgtgttaagt ttgaatcatg tgttgttttt atataattta ttgaaaatat    360
agatcctaaa cttcactaat acttacaaca atagcatcat catgtgtttt aatccacgcc    420
acaacactca aggcattgaa ttttcttcta ccaaagagtt gtatgtgtgt attgttcttt    480
aaaaaataga gtgattataa ttaaactacc agtattcata tgtaaaatgt atagacatct    540
aaaataaaat ttgcaaaaaa cattgttgca gactttcaat ataattaaga atgggtttta    600
gggtcatgat atatggtttg ttaaagaaac ttgttttttt ttgcaattga taaactataa    660
aatacatttt cactattgtg tgcatatgta cttggtatac atagtggcat atatcatttt    720
tgtttacttt gaggtttgaa ttatctatgt taaaattgga taacatagat acattggtgt    780
gcgtcctttg gcccatttac ttgactgagg agcaatacta taaagtaaaa catatttgga    840
tattttatct taaactccta gcataatatt gatttaatta tgaacaaata tatgtttagg    900
tgatagtttc atgggtggta aactatataa gaaggcttac catgatcttt gcaaactcta    960
ggctatgaaa gagttccatg atttgtctta gaagcataga caaaacagtg ataatgatct   1020
aaatcacact tatggcactg atgaccatat atgcaaagct aaatgcatgt taagttgtat   1080
tatatcatat gtttacaatg actatcgcat ataacgagga atacattgtc tatatagata   1140
gctattactg tagtagtgcc aaatgttgga caacatgaat cataatcttc aaacctagag   1200
aaattgtagt cagtcgtaca catatcgtct agtaagttgt ctatactttt tatttattgt   1260
atcaaatttt attgttatct tgcttgcttg tttgtttgta ccatagacac aatatggtca   1320
aaaagtggtc aatcgattcg aagaagattg caattgacga gtgctaacag ttgatccttt   1380
tgttgtgcac gctagcggag tagcatgaaa agagtaaaat atgaaattag cgttctaaac   1440
tgtttgtgct ataggtactt cgtatttaat ggagtgacta actataggaa ggtgagagct   1500
cagaagtcag caccctcaca cagagttcta gagttagtgg tcatcgaacc acgacaaact   1560
acatgatgag cagaagaggc aacatcaaga ctatgatcaa tagtttcggg tcaatgaatg   1620
acatcgtgat gagtatttat ctaactatat agaacaacaa cacatgatgt ttttaagtaag   1680
ttcaactgat cttctattgc tatctttaag tatttaacgt agcgaataat gttttatcta   1740
tttcattcat aaataatgtt gtgacaaaag gggataacca tcacttttac catgttctag   1800
ataccacaac catctccacc atcataatgg gttcttcatt ggtgcttgga cctcaaataa   1860
tcatatctat agccaactta gctcaattct aataaaatta ggcaacttgg cttcattgta   1920
gcaaaaatag ccaacttagc tcaattttat ctaaacttag ctaatctagc acaacttaga   1980
tcaatattag gaaaaactaa tcaatctaat ctagctcaac tatagcgaaa gatagatatt   2040
gtagcataac ttagtagatc tatctcaaat tttagcaaaa actaatcaat ttagataaac   2100
tctataaaat tttaatcatt atgacttatt tccaactaat tgtaacttgc atgattttta   2160
tgttccttct ttataattag caacacctaa agacacgaat gatgagggt ctaacgcatt   2220
cattaaccag ttgttaaata atactctagg tagatgataa gaactctaat tattctatga   2280
atctaagcta aaagatgttt aatatttaag tattggtgtt tattatgtta tttagaacga   2340
ttcatgttac ttaaagattt gttatgattt ttaaaatatga ttatgataat ttatgtggtg   2400
tggattaact tgtgaacata tgtgatgtag atgaatatgt atgttgtgga tggaaccata   2460
tgaatatata tacacactca tatactattc gttggtgtag gtaaagcttc atccatcggt   2520
aattactaaa tggtcttcag tcattaccac taggtgaagc ttcacacgac cgataattat   2580
tgaagaacgc tcattaattt ccggtaatgg cttattggcc ttcactagtc ggtgaaaatt   2640
agcttttttt ataccaataa aaattagcta atatatgtga accaggtcta atttttatgg   2700
gcctcttacc gaccaaaatt gattagatta ttgttacaat agtttttagtc aaaagctagc   2760
tatgctataa aaattttgaa ttaaagtgag tttcgtaata aaaattgcat acttttaaaa   2820
taaaataatt aaaaaaacagt tttagaaat acaatcaaac accttatgct ataaaaaaat   2880
tgtaatgtac ctacaaaat ataatacttt acttttaaaat aggcctgtgc cttctcggct   2940
ctatatgggc tgcctccaac gaagcgccat ggccatgggc tccactgtgt cgggtcccac   3000
atgaggccgc gcctccctcc aaatgttccc tccctgcctt cgtctttgtc gttgctcgca   3060
aactccctgt cctcccctgt tacaaatacc cccaccgcc cggacagctt ccctgcatac   3120
ttgcagctcg cacatctcat ggtgtcgcag gaacgacaag agccagctgt gcctagcagc   3180
agcagcagca gcgccaagcg cgcagccacg tccatggacg ccagcccggc ccgccgctc   3240
ctcctccgcg cccccactcc cagccccagc attgacctcc ccgctggcaa ggacaaggcc   3300
gacgcggcgc ccagcaaggc cggcgcggcc gtgttcgacc tgcgccggga gcccaagatc   3360
cccgcgccat tcctgtggcc gcaggaagga gcgcggccgt cctcggccgc ggagctggag   3420
gtgccgatgg tggacgtggg cgtgctgcgc aatggcgaac gcgcgggggct gcgggcgcgcc   3480
gcggcgcagg tggccgcggc gtgcgcgacg cacgggttct tccaggtgtg cgggcacggc   3540
gtggacgcgg cgctggggcg cgccgcgctg acggcgccag cgacttcttc ccggctgccg   3600
ctcgccgaga agcagcgcgc ccggcgcgtc cccgccaccg tgtccgggta cagcagccgg   3660
cacgccgacc ggttccgcgg caagctcccc tggaaggaga ccctgtcgtt cggctaccac   3720
gacggcgccg cgtcgcctgt cgtcgtggac tacttcgtcg gcaccctcgg ccaggatttc   3780
gagccaatgg ggtaagtaag gtagtaagaa ggagcgccgg tttacattta ccgcacgtcg   3840
gcgtgcggtc gagtcgggac tcgggagacg tatgaacccc cgtcccgtcc catgcatgtg   3900
tggcaggtgg gtgtaccaga ggtactgcga ggagatgaag tgtgtcgc tgacgatcat   3960
ggagctgctg gagctgagcc tgggcgtgga gctgcgcggc tactaccggg agttcttcga   4020
ggacagccgg tccatcatgc ggtgaactca ctacccgccg tgcccggagc ggagcgcac   4080
gctgggcacg ggcccgcact cgaccccac ggcgctcacc atcctcctgc aggacgacgt   4140
gggcgggctg gaggtgctgg tggacggtga gtggcgcccc gtccgggccg tccgggcgc   4200
catggtcatc aacatcggcg acaccttcat ggtaacgaaa cgaaagcgct cgctcctctg   4260
ttttccttgg ccgctcttgt cctgtgtgta tattcagttg agctctctct gtgctgttat   4320
ttcccgaatc ctagtggacc taaacggca ggttattaca gcacgcacac gtaggcatgt   4380
catgtagcta gtacatacat agcgatgccg atgcaaatgc aatagagaca tgcgttcgag   4440
ttggttccta tctcggcggg ctacggcagg tacacgcggc cgcggcgcgc tctctctagt   4500
ctatccgcgg ccgcgcccag gccgatcgag gcttccggg agagtgcgg acaagagaac   4560
ggaccgaggg ggtcggctag cggtagcaag ttccctgttg gtttgtgcg ttggagcgtt   4620
gcggagagc ttgcgcgggcg gcggggacgt cgacgggac gtggcggga gacgatacga   4680
tgggtgccgg gcaggtttcc gaattccaaa cgttttgtg gcgtgcgtcc atggggcgcc   4740
cccaaacttc ggacgtttcc ggcgctcaa caaatcttct cgcttcacac gtcaccgtcg   4800
tcccggattc atttgcctcg tcgctccacc attcgctgct ctcctctcca cgtactctta   4860
```

```
ccctgacctt tgggaaagaa ctgaacattc gagatgcaca acagttcaaa tataacatat  4920
gcagcacaag atcgttcgac tgctatccga caagccaaca acgtgcccag tagaactgaa  4980
tgtacctgtg atttccagca ctaacttaca gcaacgttgt gaaaaaacaa aaacgaaaac  5040
aaacggcaga aaaacagat gtattgttct acagttacac caaatatttt ctggtccttt  5100
cagcaccaac aagagccata cgcatatcta gaagacaaaa ttcctctaat ttcaccccta  5160
cgtggtagca gttcctcctc aacacagttc acgtgctagc gtcgagttct ttgggccgcc  5220
acatcgactt ctcgacgcag agcaggccct cgctgccctt ggtgtaggtc atccgcacct  5280
cccactgcac ggacttggcc atgctctcca gctcatttat cgtgtccgcg gtgtccctca  5340
cgatcagctt gccctgtggc ctcagtacac ggtcgacctc ggcgaaaact gcagccagtt  5400
tgcatctgta aacaggcaac acagatttt agtatctaaa acactgcagg caaacgccac  5460
aggttttagt cgcaagaagc aataaaagca tgcaaacaat gctacgtgta cgtatcaaag  5520
gaacatgtca aaactcgttg catgaacgat cattgatgtt tccttgctga actagtcaca  5580
tcagtctgct tcaacttctg ggtttcacta gtagatatac cagaagggta gaataatgtg  5640
aagagcaaga aatacagacc tcttctgag ctttgagaac agatggtccg cgtgcagaag  5700
gtcatacgtt cttgggtaag tgctgaaaga ctcgcaccag tcatggtaca tgccaaacaa  5760
accgcgctcg tagatgatgg gcagcgtgtc tggtgaatcg atcggcacga tattcatgac  5820
ccagaccttt tggtccctca gagctgcagc aaaactgcca tgcaacaatg taaagcatta  5880
gtcaagaaga aggtgtacag tgcatttctc cttgtcaaca gtcttcagta acaaaaaaaa  5940
agtgttatgc ttgactgaat cttcaaaga aatatgcttg atgacttatg gtggacaagt  6000
tgcctgttat agtgttatgt tttaattaac tatgtgccag cttgggtaac tagtagttat  6060
gtagtgtgat ctgaattacc aaaatataaa taaataata aacatgccca agaaactacg  6120
aaaaccattt acttaccctc catagacagc tctcatgtcc atgacatttc tcactttgga  6180
ccagtcaatt cccatgccat tcacatacga tttacttaca acccgtttcc agtgggcatt  6240
atctgcctca aaatcttcat ttgcaggctt tccatagaca ccaacttgg aaccatcaat  6300
ccagaaaggg gtcttctcaa gcctttgcgg ccataactct ggccattttg atcctcggac  6360
ttttgagcca ccaggcagtt tgtgcatgca tgcttccaac ggtacattcc tgcaaatcaa  6420
aaggctgtgt aagcaaagca gagaagcact tttctccatt gaaaatatac tcttctcaaa  6480
gaaccgaaac cataccaagc agcatctgca tcatcgagatt ccttgcacaa tggcgggctg  6540
ttttcagatc tttctcata gcaaatattg tccattggtt tctgatatat gaccatacca  6600
acttggttta acttatccett agtcttgttg accatcttcc agcacatgga ctttgtcaaa  6660
gtagacatgg ctgaaaaggg tatgtgccca catgttatgt tagaaataaa attcaatttt  6720
gaacagttgg tccatagcat gtattttgaa caaatgcaat ccttctccat ccatgaaaga  6780
agttgaccct tcatacttag gattattcag tactttcact catgtctgct gaatttgttc  6840
tcttggtagt tgctatacaa gaaagggga agtacagagt agctaaactt atacaagcta  6900
tagtctgata tttgtatgaa acataaattt tggtatggat gtcttattaa aatgggaggt  6960
tgtataatat ttttctagcc tacctcaact tgcttgagac taaaaggctt tgttgttgtt  7020
gttgaggctg tatggtgctt tgactttaca aatcaagtta tcagctaccc tacttatgga  7080
tatacaccte tcataaaatg atggtaagaa gtttcgatat gtcacattaa cataagaact  7140
tcattcagtt agggtacaac gaagttaagt agttacggaa ataccattcc aaatctcaac  7200
atcctctggg agcttttggt aaacaggagt ggcagaccag acaaagtaac caccagggcg  7260
taacaagcgg ttcaattcca gcaaaagcat gccacctaaa agtagcgagc cagcaataag  7320
attcagttct atagcaaatc aataaatgaa aggaggacat gtcaatatgt aaccagcagg  7380
acaaaccttc gatgtgccaa ggga                                          7404
```

```
SEQ ID NO: 36           moltype = DNA   length = 1788
FEATURE                 Location/Qualifiers
source                  1..1788
                        mol_type = unassigned DNA
                        organism = Zea mays
SEQUENCE: 36
aatcccagcg tgcgtaatct attgcccaca tgccgacgcc gtcgcacctc aacaagaacc    60
cgcgctacct ggacttccgg gcggcgcggc gggtgccgga gtcgcacgcc tggccgggcc   120
tgcacgacca ccccgtcgtg gacgcgcgcg cgccggccc cgacgccgtg ccggtggtgg   180
acctgggcgc gcggacccg gcgccggcgc cggcggcggc ggtggcccgc gccgccgagc   240
aatgggggcg gttcctgctc acgggccacg gcgtccccgc ggacctgctg gcgcgcgtgg   300
aggaccggat cgccaccatg ttcgcgctgc cggccgacga caagatgcgc gccgtgcgcg   360
ggcccggcga cgcctgcggc tacggctccc gccccatctc ctccttcttc tccaagtgca   420
tgtggtccga gggctacacc ttctcgccgg cctccctccg cgccgacctc cgcaagctct   480
ggcccaaggc cggcgacgac tacaccagct tctggtacgt tgcgttgcgt gcttgtgtgc   540
gcgcacacct gccgaccgcg gccacaccgt acgcaaccca cgctacgta cgtgcgctag   600
ctacctgctt cgctcgcttc gctcctctcg cctcgccatg catatgcacg tacggccgta   660
caggtacagc agcaggtcac acgcacgaac gcacgcacgc accagcaccg atatgataca   720
tcatcgacgt gtcgtccccc cgtctaaggc catgcatgca tgcaagcacg cctagctagc   780
ccttttggct tgctagctga cgaggggagc taggacgagc atacttactg tcgcgcgtcat   840
gctcaattgc tcacactata ctactacttg ttactacagt gatgtgatgg aggagttcca   900
caagcacatg cgcgccctcg cggacaagct gctggagctg ttcctcatgg cgctggggct   960
caccgacgag caggccagcg ccgtcgaggc cgagcggagg atcgccgaga cgatgaccgc  1020
caccatgcat ctcaactggt gggtatatat tattgtctgt catgttgtcg tcgtcgtacg  1080
cgttgcggtt gggtgtacat gtatataaca caaacaacaa aaaactaacg ccgtgccgac  1140
gacgacgacg atcatcaggt acccgaggtg cccggacccg cggcgcgcgc tgggggctgat  1200
cgcgcacacc gactcgggct tcttcacctt cgtgatgcag agcctcgtgc ccgggctgca  1260
gctcttccgc cacgccccgg accggtgggt ggcggtgccg gccgtgccgg gcgccttcgt  1320
cgtcaacgtg gcgacctct tccacatcct caccaacggc cggttccaca gcgtgtacca  1380
ccgcgcgggc gtgaacgggg acctcgacag gatctcgctc ggctacttcc tcggcccgag  1440
gccgcacgcg aaggtggcgc gctgcgcga ggccgtgccg cccggccggg ccccgcgta  1500
ccgcgccgtc acgtggcccg agtacatggg cgtccgcaag aaggccttca ccaccggcgc  1560
ctccgcgctc aagatggtcg ccctcgccgc cgccgcgac ctcgacgacg acggcgacgc  1620
cgccgtcgtc catcagcagc agcagctagt cgtctcgtcg tagccgagac cgatcgccgg  1680
agactgatgc tgatgatgat gcatatatac atgagagaaa tcgtcgagta gactagccga  1740
```

```
ttgcaaaagc aaccccagct gccgaaacct ggcatatcga tcccattc           1788

SEQ ID NO: 37           moltype = DNA   length = 1698
FEATURE                 Location/Qualifiers
source                  1..1698
                        mol_type = unassigned DNA
                        organism = Zea mays
SEQUENCE: 37
cgtgccgaga gtccttcaaa gccgacgacg agacgacgat gcagtcgtcg tcgtcatcag   60
cctcgacgcc ggctgccgct tccggcctcg tcttcgatct cgggtctgcg gcgggcgtgc  120
cggagacaca cgcgtggccg ggggtgaacg agtacccgtc ggtggagtcc gctgccgcg   180
acgtggtccc ggtggtggac atgggggtgg cctgcccgga cgcgacgcgg gcgttggcgc  240
gcgccgcaga cgagtgggc gtgtttctgc tcgtcggcca cggcgtgccc cgggaagtgg   300
cggcgcgtgc cgaggagcag gtcgcgcgcc tgttcgtgcc cccggctcct gacaaggccg  360
gcgcggggcg ccgccccggg gagcccacgg ccaccggcta cggcaggccg cccctggcac  420
tccgcttctc caagctcatg tggtccgagg ggtacacgtt ccgcgccgcc accgtccgcg  480
aagagttccg ccgcgtctgg cccgacgcg gcgacgacta cctccgcttc tggtacgtac   540
gagcgccatg tcacgtgctt gtgctttcat gcctcgtacc gtcgtcgtgc tgtacgtgtt  600
atgtttatcg gccggtacgt cacgcgtgct acactggtta acgacgtgag cgtgcccacg   660
ttgactgcat gcatgtgcat gcgcgcgccc agcgacgtga tggaggagta cgacagagag  720
atgagggctc tcggtggcag gctgctcgac ctcttcttca tggcgctcgg cctcaccgac  780
gtccagttcg ccaccggcga gacggacgg aggatccggc agacctggac ggcgacgatg   840
cacccaatcc tgtacgtacg tcaaaaacga atatctgacc aatgcaaacg ttttttctgca  900
atgccagtca tccactcatc ctgtacgtac ctctggactc tgcttgtcca tctactgatg   960
acacgtatgg taggtacccc aggtgtccgg aaccggagcg cgccatcggg ctgacggcgc  1020
acacggactc gggcttcatc acgctcatca tgcagagccc cgtgcccggg tcgcagctgc  1080
tccgccgcgg gccggaccgg tgggtgacgg tgccggcgcc gccgggcgcg ctcatcgtca   1140
tgctcggcga cctgttccag gtgctcacga acggccgctt ccggagccct atccaccgcg   1200
ccgtcgtaag ccgagagcgc gagcggatct ccgtgcccta cttcctctgc ccgccggagg   1260
acatgacggt ggcgccgctc gcgtccgctc tgctgccggg gaggaaggcc gtgttccggg   1320
ccgtgacgtg gccagagtac atggaggtca agcacaaggt gttcggcacg gatgcgccgg   1380
ccctggagat gctgcagctg caggtggatg aggaagaaca aggtgaaagg gccgccacca   1440
cctaagccct aaggaactac tagctgaatc cataaactaa taagaattc gtgaataagg    1500
gcgttggaag actggacaca acacaagaga gttgctatat atcgtatttc tgaaatttaaa  1560
ggcaaatatc ttagttaaaa aactggtata tttaaataga caatatatat ctaaaataaa  1620
gatagttcac cattttttacg gtcgaacaat gataaagtta tatattgtct gaatagtaac  1680
aaattaaaga tttccagg                                                 1698

SEQ ID NO: 38           moltype = DNA   length = 4095
FEATURE                 Location/Qualifiers
source                  1..4095
                        mol_type = unassigned DNA
                        organism = Zea mays
SEQUENCE: 38
cggtctaagt gaccgtttga gagaggaaaa gggttgaaag agacccggtc tttgtgacca    60
cctcaacggg gagtaggttt ataagaaccg aacctcggta aaacgaatca ccgtgtcatc   120
cgccttattt gcttgtgatt tgttttcgcc ctctcttttcg gactcgttta tatttctaac  180
gctaaccccg acttgtagtt gtgcttaaag tttgtaaatt tcagattcgc cctattcacc   240
ccctctaggc gactttcata taaatattgg gagaaatatg aaaaacaaat gaaggtcgaa   300
cgagtcagag acaccataaa aaagaggtcg tcttaactag ggtgctaaac ctcaacattg   360
tagtagatct tagtactgag tttgacatct ttgacaccaa caagatggtg atacgttcat  420
ttctacgtta acttgggtag gtatatcgac tatagtggcc tataacacta ggctatgtaa   480
tatgatattg tgttgagtct ttataaacat gattttttt aaaaaaaaga gctaaaataa   540
aaaatagaaa tcgacggtac gatgcaagtt cttctcaaga caaccaaacg cacccttgcc   600
cctttattga aattgaagta tgtgcttat caaatgttta aatactaatt ataagtatta   660
aatataattt aattataata ctaattatat agataaagac taaataacaa gacaaattta  720
ttaaatataa ttaattcatt attaacaaat acttaatgta gcacgatcga atcatggact  780
aattagtctt gatagactcg tcttaccatt taatcataat tagttttgta tactgtttat  840
aatatttcta actagtagt attaaactttt tgatgtaacc taactaaaagt ttagtcacgc  900
caatacataa ggactcggat cgttcgatca cccatgacat cacgtatact aagagcatct  960
ccaaaagctc tccagaagtc tcccctaaat ctatttttt gggaaaaaca caaaaacatg  1020
tctccaacag ttcccttaaa gcgcccccaa cttttttcata gcccttaaaa ctccctcatt  1080
tgtagctaca aatgaggggt ttttgggct ccccagaaac aaaactgttga tttaagggat  1140
ctgttggaga aaggattaaa atttaccctc acttattatt tagatgtccc ttaaaactga  1200
ttttgaggag tcgttttatg tagagctctt ggagatgctc taacacaccg agcacaacccg  1260
catcatcaat caaaacaacc caaagtttgt tcggtacaag tcatcagcct gtgtacacac  1320
atcagcctcg gccccgggag aagcgctagc aaacaaggtt cacctaaaaa tccatccaga  1380
ttcattgaat ccaaccagca caaacgtccc atttattaat cacctcatca caggtccccc  1440
cagcctcact ctcgcgccgg ctcaaggtac attgcgtcc ctagccaaga cacgcagtc   1500
atctcagcct cacacgcaca gcaagagcga ggcgtgattc gccatgggcg gcctcactat  1560
ggaccaggcc ttcgtgcagg ccccccagca ccgccccaag cccatcgtca ccgaggccac  1620
cggcatccct ctcatcgacc tctcgcctct ggccgccagc ggcggcgccg tggacgcgct  1680
ggccgccgag gtgggcgcgg cgagccggga ctggggcttc ttcgtggtcg tgggccacgg  1740
cgtgcccgca gagcgctggg cgcgcgcgac ggcagcgcgg cagcgttct tcgcgctgcc   1800
ggcagagcgg aagccgccgc tgcggaggaa cgaggcggag ccgctcgggt actacgagtc  1860
ggagcacacc aagaacgtga gggactggaa ggaggtgtac gacctcgtgc cgcgcgagcc  1920
gccgccgccg gcagccgtgg ccgacggcga gcttgtgttc gataacaagt ggcccccagga  1980
tctaccgggc ttcaggtgac gaaattaact atatatccct ttcgatcata gttgcgttaa  2040
taaattaagg gaatcgtgag cgtacgtacg taagtttccg cagagaggcg ctggaggagt  2100
```

```
acgcgaaagc gatggaagag ctggcgttca agctgctgga gctgatcgcc cggagcctga   2160
agctgaggcc cgaccggctg cacggcttct tcaaggacca gacgaccttc atccggctga   2220
accactaccc tccttgcccg agccccgacc tggccctcgg cgtggggcgg cacaaggacg   2280
ccggcgccct gaccatcctg taccaggacg acgtcggggg gctcgacgtc cggcggcgct   2340
ccgacggcga gtgggtccgc gtcaggcccg tgcccgactc gttcatcatc aacgtcggcg   2400
acctcatcca ggtacgtgcc cacctgatga actgagctga acgtaggttg catgcactgc   2460
atgtgtatag gcttctcaga tcgcttcgtg tggcgtaagg tgtggagcaa cgacaggtac   2520
gagagcgcgg agcaccgggt gtcggtgaac tcggcgaggg agaggttctc catgccctac   2580
ttcttcaacc cggcgaccta caccatggtg gagccggtgg aggagctggt gagcaaggac   2640
gatccgccca ggtacgacgc ctacaactgg ggcgacttct tcagcaccag gaagaacagc   2700
aacttcaaga agctcaacgt ggagaacatt cagatcgcgc atttcaagaa gagcctcgtc   2760
ctcgcctaac tactgctact gctaggatcc atgccattgc catgtcgtct tcagattcag   2820
agcacgccat gtcgtcgcta gcttcgtggt agaacaaata atgatgtgcg tgctgtgtgt   2880
aagcatggat atggatgtga atatgtaata tgatgagcac tcctactttg gtatgttttgg   2940
gaataacaga cttgtgttgg tctggttcat tatttgtaag aaaatcaaaa agagttagta   3000
gggcaggagg ctaaccacag tcatgctgca ccacatccct ggtggaaagc tggccgggtt   3060
acgctacgct cgtgcagcca gattactgca gggccggat atgcttccgg tggaaggaag   3120
gggacggtgg ctgaggacca tggggctgga gcctgggaga gaggtcgagc tagaagaaag   3180
ggggagagag aagacgcaca acgaagatgg gtcagccagg gatttcgacc caaggggag    3240
ctagtggatt ttgggagaaa acagaaaaga gaaaagagaa aagaagaaaa atttgttggt   3300
gtgaacacaa ggttgatttg tcttttctta tttggattga tgatgagtcg tggactaacc   3360
gacccgtgag ctattgtgtc gtataatcat gtctctcggt ttctggtgtg caggtttgaa   3420
gcacagagac ggtggtcgac gcaaaggtga acgtcatgca ggttcgtgcc gatggaccgg   3480
gagcagtgaa agacgagcgt tgggacttga acaagggacc agagtcgccg gatgactagc   3540
cgcagtggct gacgcctgga acacgcatag acgtgaggac gtggtagagc aggtgaaaat   3600
cgcctagagg ggggggggt gaatagacaa aacctaaaa ttataaactt tgaacacaaa    3660
ctttacctga ggttaccgtt agaacgagta ttaatgaaat cggagtgcgg aaggcaagtt   3720
cttcttgcta cgagttgctt aatcaatatt gataactttg ggagtcaact caaaatgatc   3780
acaagcaaaa gaactagaga gagaggagag gaagaatcaa ctcgcaaagt aatgatcaac   3840
acaaatgaac acaatgattt atttctcgag gtttggttcc gaagaaccta ctccccgttc   3900
aggagtccac ataggacatg tctctttcaa ccctttctct ctctcaaatg gtcacataga   3960
ctggttcagt tgagagcacc taggggggg tgaataggtg atcttgtaaa atcaaacact   4020
aatagccaca aaacttagtt taaagtgtta gtacggctaa gtagctttga agcgagttat   4080
tgtgaacaca acaat                                                   4095

SEQ ID NO: 39         moltype = DNA    length = 21
FEATURE               Location/Qualifiers
misc_feature          1..21
                      note = suppression oligo
source                1..21
                      mol_type = other DNA
                      organism = synthetic construct
SEQUENCE: 39
ctccatcatg cggtgcaact a                                            21

SEQ ID NO: 40         moltype = RNA    length = 21
FEATURE               Location/Qualifiers
misc_feature          1..21
                      note = suppression oligo
source                1..21
                      mol_type = other RNA
                      organism = synthetic construct
SEQUENCE: 40
tagttgcacc gcatgatgga g                                            21

SEQ ID NO: 41         moltype = DNA    length = 19
FEATURE               Location/Qualifiers
misc_feature          1..19
                      note = suppression oligo
source                1..19
                      mol_type = other DNA
                      organism = synthetic construct
SEQUENCE: 41
ggtactgcga ggagatgaa                                               19

SEQ ID NO: 42         moltype = RNA    length = 21
FEATURE               Location/Qualifiers
misc_feature          1..21
                      note = suppression oligo
source                1..21
                      mol_type = other RNA
                      organism = synthetic construct
SEQUENCE: 42
ttcatctcct cgcagtacct a                                            21

SEQ ID NO: 43         moltype = DNA    length = 19
FEATURE               Location/Qualifiers
misc_feature          1..19
                      note = suppression oligo
```

```
source                   1..19
                         mol_type = other DNA
                         organism = synthetic construct
SEQUENCE: 43
caggcgccat ggtcatcaa                                                     19

SEQ ID NO: 44            moltype = RNA   length = 21
FEATURE                  Location/Qualifiers
misc_feature             1..21
                         note = suppression oligo
source                   1..21
                         mol_type = other RNA
                         organism = synthetic construct
SEQUENCE: 44
ttgatgacca tggcgcctgg a                                                  21

SEQ ID NO: 45            moltype = DNA   length = 19
FEATURE                  Location/Qualifiers
misc_feature             1..19
                         note = suppression oligo
source                   1..19
                         mol_type = other DNA
                         organism = synthetic construct
SEQUENCE: 45
tcatgcggtg caactacta                                                     19

SEQ ID NO: 46            moltype = RNA   length = 21
FEATURE                  Location/Qualifiers
misc_feature             1..21
                         note = suppression oligo
source                   1..21
                         mol_type = other RNA
                         organism = synthetic construct
SEQUENCE: 46
tagtagttgc accgcatgat a                                                  21

SEQ ID NO: 47            moltype = DNA   length = 19
FEATURE                  Location/Qualifiers
misc_feature             1..19
                         note = suppression oligo
source                   1..19
                         mol_type = other DNA
                         organism = synthetic construct
SEQUENCE: 47
tcgctcgcct tcttcctca                                                     19

SEQ ID NO: 48            moltype = RNA   length = 21
FEATURE                  Location/Qualifiers
misc_feature             1..21
                         note = suppression oligo
source                   1..21
                         mol_type = other RNA
                         organism = synthetic construct
SEQUENCE: 48
tgaggaagaa ggcgagcgac a                                                  21

SEQ ID NO: 49            moltype = DNA   length = 19
FEATURE                  Location/Qualifiers
misc_feature             1..19
                         note = suppression oligo
source                   1..19
                         mol_type = other DNA
                         organism = synthetic construct
SEQUENCE: 49
tccaacgggc ggtacaaga                                                     19

SEQ ID NO: 50            moltype = RNA   length = 21
FEATURE                  Location/Qualifiers
misc_feature             1..21
                         note = suppression oligo
source                   1..21
                         mol_type = other RNA
                         organism = synthetic construct
SEQUENCE: 50
tcttgtaccg cccgttggac c                                                  21

SEQ ID NO: 51            moltype = DNA   length = 19
FEATURE                  Location/Qualifiers
misc_feature             1..19
```

```
                        note = suppression oligo
source                  1..19
                        mol_type = other DNA
                        organism = synthetic construct
SEQUENCE: 51
gcatcaacag gtacaacta                                                    19

SEQ ID NO: 52           moltype = RNA  length = 21
FEATURE                 Location/Qualifiers
misc_feature            1..21
                        note = suppression oligo
source                  1..21
                        mol_type = other RNA
                        organism = synthetic construct
SEQUENCE: 52
tagttgtacc tgttgatgcg a                                                 21

SEQ ID NO: 53           moltype = DNA  length = 19
FEATURE                 Location/Qualifiers
misc_feature            1..19
                        note = suppression oligo
source                  1..19
                        mol_type = other DNA
                        organism = synthetic construct
SEQUENCE: 53
tggacgatgg atagttcaa                                                    19

SEQ ID NO: 54           moltype = RNA  length = 21
FEATURE                 Location/Qualifiers
misc_feature            1..21
                        note = suppression oligo
source                  1..21
                        mol_type = other RNA
                        organism = synthetic construct
SEQUENCE: 54
ttgaactatc catcgtccat c                                                 21

SEQ ID NO: 55           moltype = DNA  length = 19
FEATURE                 Location/Qualifiers
misc_feature            1..19
                        note = suppression oligo
source                  1..19
                        mol_type = other DNA
                        organism = synthetic construct
SEQUENCE: 55
tggaccatgg atacttcaa                                                    19

SEQ ID NO: 56           moltype = RNA  length = 21
FEATURE                 Location/Qualifiers
misc_feature            1..21
                        note = suppression oligo
source                  1..21
                        mol_type = other RNA
                        organism = synthetic construct
SEQUENCE: 56
ttgaagtatc catggtccat c                                                 21

SEQ ID NO: 57           moltype = DNA  length = 19
FEATURE                 Location/Qualifiers
misc_feature            1..19
                        note = suppression oligo
source                  1..19
                        mol_type = other DNA
                        organism = synthetic construct
SEQUENCE: 57
gcaaggtcct agatttaca                                                    19

SEQ ID NO: 58           moltype = RNA  length = 21
FEATURE                 Location/Qualifiers
misc_feature            1..21
                        note = suppression oligo
source                  1..21
                        mol_type = other RNA
                        organism = synthetic construct
SEQUENCE: 58
tgtaaatcta ggaccttgca a                                                 21

SEQ ID NO: 59           moltype = DNA  length = 19
FEATURE                 Location/Qualifiers
```

```
misc_feature         1..19
                     note = suppression oligo
source               1..19
                     mol_type = other DNA
                     organism = synthetic construct
SEQUENCE: 59
cagagtacat ggaggtcaa                                             19

SEQ ID NO: 60        moltype = RNA   length = 21
FEATURE              Location/Qualifiers
misc_feature         1..21
                     note = suppression oligo
source               1..21
                     mol_type = other RNA
                     organism = synthetic construct
SEQUENCE: 60
ttgacctcca tgtactctgg a                                          21

SEQ ID NO: 61        moltype = DNA   length = 19
FEATURE              Location/Qualifiers
misc_feature         1..19
                     note = suppression oligo
source               1..19
                     mol_type = other DNA
                     organism = synthetic construct
SEQUENCE: 61
ccatgcccta cttcttcaa                                             19

SEQ ID NO: 62        moltype = RNA   length = 21
FEATURE              Location/Qualifiers
misc_feature         1..21
                     note = suppression oligo
source               1..21
                     mol_type = other RNA
                     organism = synthetic construct
SEQUENCE: 62
ttgaagaagt agggcatgga a                                          21

SEQ ID NO: 63        moltype = DNA   length = 19
FEATURE              Location/Qualifiers
misc_feature         1..19
                     note = suppression oligo
source               1..19
                     mol_type = other DNA
                     organism = synthetic construct
SEQUENCE: 63
acatggcggt caacttcta                                             19

SEQ ID NO: 64        moltype = RNA   length = 21
FEATURE              Location/Qualifiers
misc_feature         1..21
                     note = suppression oligo
source               1..21
                     mol_type = other RNA
                     organism = synthetic construct
SEQUENCE: 64
tagaagttga ccgccatgtg a                                          21

SEQ ID NO: 65        moltype = DNA   length = 726
FEATURE              Location/Qualifiers
source               1..726
                     mol_type = unassigned DNA
                     organism = Rice tungro bacilliform virus
SEQUENCE: 65
tcctacaaaa gggagtagta atatttaatg agcttgaagg aggatatcaa ctctctccaa   60
ggtttattgg agacctttat gctcatggtt ttattaaaca aataaacttc acaaccaagg  120
ttcctgaagg gctaccgcca atcatagcgg aaaaacttca agactataag ttccctggat  180
caaataccgt cttaatagaa cgagagattc ctcgctggaa cttcaatgaa atgaaaagag  240
aaacacagat gaggaccaac ttatatatct tcaagaatta tcgctgtttc tatggctatt  300
caccattaag gccatacgaa cctataactc ctgaagaatt tgggtttgat tactacagtt  360
gggaaaatat ggttgatgaa gacgaaggag aagttgtata catctccaag tatactaaga  420
ttatcaaagt cactaaagag catgcatggg cttggccaga acatgatgga gacacaatgt  480
cctgcaccac atcaatagaa gatgaatgga tccatcgtat ggacaatgct taagaagct  540
ttatcaaaag caactttaag tacgaatcaa taaagaagga ccagaagata taaagcggga  600
acatcttcac atgctaccac atggctagca tctttacttt agcatctcta ttattgtaag  660
agtgtataat gaccagtgtg ccctggact ccagtatata aggagcacca gagtagtgta  720
atagat                                                            726

SEQ ID NO: 66        moltype = DNA   length = 165
```

```
FEATURE              Location/Qualifiers
source               1..165
                     mol_type = unassigned DNA
                     organism = Rice tungro bacilliform virus
SEQUENCE: 66
acgaatcaat aaagaaggac cagaagatat aaagctggaa catcttcaca tgctaccaca   60
tggctagcat ctttacttta gcatctctat tattgtaaga gtgtataatg accagtgtgc  120
ccctggactc cagtatataa ggagcaccag agtagtgtaa tagat                 165

SEQ ID NO: 67        moltype = DNA   length = 2000
FEATURE              Location/Qualifiers
source               1..2000
                     mol_type = unassigned DNA
                     organism = Zea mays
SEQUENCE: 67
ctgcaatata tacaccaaaa gtattataaa ctgtcatata tatgaccaaa acctttttat   60
tttagaaaag tatattaatc atggtatatt aatcaaagtt gttgttgggg ctgcaaaaat  120
catcccttc ttccacaagc tgttccttga actgcaggta ctcaggaact ctcagctcct  180
caacagcgag ctcactgacg ttgaccctca catactccca gacaccaggc ctagggcgga  240
tggcaagtgc aacccatggg gggatgacaa tcgcctcctg taagataata gagctagaat  300
gattaaagaa ggtgcacact acaaaaggaa cagtgctgtc cagcgagatc tgaatctgat  360
gcaaacctga gctgccctca ggacatcctc aaaagcacta tccttgagct tctcgcgctc  420
agcctcaggg atcgcattgt tgtactcggc aatgatctgg tggggctgca gcataccctt  480
tccaaggttt ttcagcctgc gcaaaacgat gtgccaaata acatcagact atgccagatc  540
tataaactca tcaaacatat acaatttcaa gaaatagttt agacgtatga tcagcagtca  600
gtagcgtggg aacatatgca acatagcgaa gaggcacaac agcaaattca ttcgaaaaaa  660
tgaaaacaaa gattcctctc ttttaactga acttctcgaa accccttttca tgcctacaca  720
tccgatctag tcagatgcct atgcgttcat gctgaacaga acgtgtcaga actaagcata  780
aactggttag caagcattat cgtattcgat agaccctta gtaacaagct atacattggg  840
taagttcaga ctccaatcat tctgttcaga aacatcgtat tgaatataaa actaaagaac  900
acacatgcag gtgcagccag atctaacagc agtttacagt cggtactaaa aaaagcatgg  960
tgtatgtatg tatcatcagt atccagtact aggtttcgac aaaatcctgg atgctaatta 1020
aatactcatc ttattaggga acacaggaac attatgtcta cagcattgaa tgatggccac 1080
atcatgctag atctaacaat acataaatg atggaactgg tcttaaaaag tcgcattcgc 1140
tcaaataata cccgtagcaa aataaatgta aacttgcaga cgaagcgggg gaaatgaggg 1200
cagacctggt gaagacggcg acaagctcat tggggtgggc agagagtgag tcgccaatgc 1260
gctccctgac gctgtggagg cggctcagga cacggtcacc tgcaccttcc cccattgctg 1320
tcctcttcct ggatcctcag gcctgcacag cgaaaccgaa acggaagcgg aagcttcagt 1380
cagcagagaa aactgaaacc gaaaaacggt tcagatccgt tgacataaaa gctgcgatga 1440
catcctaaaa ctaaaacccc tccagcaaga cataaaccca actgccaaca accagtcttt 1500
taagtctcga cacaccttg acgctgcgcc acgaaactat attgcaggca agaaaccaac 1560
agaacctaac tctggaaggg gggaaagaaa cggcagacag gagcaagacc caaaaaaaaa 1620
cgactcagat cctggtacta tagtcctagt acctagacca gaaagaagaa acaaccaata 1680
caacaagagg catacaagaa ctgaatcgat gaactgaaac gcttcagagg accgaggaat 1740
ggcggagaag ggaggcgcct atttatacag atctgacgag agaaccgaac aaaaacacat 1800
cgatgggaac catggagaag aaaagggctg ccgcatggc accaatggcc tcggcctcca 1860
aaaagccgtt gaatccaaag caggcgagga cgaagcgtga cgcggcaggg tacttctcta 1920
gaaaagcacg gcatcagcaa ggtggggggg ctggggttcc ttattgcagg caatcacgag 1980
gtgattagca caaacggaag                                             2000

SEQ ID NO: 68        moltype = DNA   length = 2000
FEATURE              Location/Qualifiers
source               1..2000
                     mol_type = unassigned DNA
                     organism = Oryza sativa
SEQUENCE: 68
ctgaaatata catcagagat attacaatga catatatatc gataaaagaa aaataataaa   60
attaagtttt aaattttaag aatatatgtt tttagtatcc caattatgca gatttcatac  120
ccttcttcca caagctgttc cttgaactgc aagtactcgg ggactgtcag caactcaaca  180
gcgagctcgc tcacattgac cctcacatac tcccagacac cgggcctcgg gcggatggca  240
agggcaaccc atggggagat aacaatcccc tcctgcatga taaaaaacaa ttacaagtta  300
agttagagca agcggtagag taaagatgga tctctgtgat gcaatgaaat ctgaatctga  360
ttcaaacctg tgcactcctc aggacatcct caaaagcacc gtccttcagc ttctcacgat  420
cagcctcaga gattgcgttg ttgtactcag caatgatctg gagggcctga agcattccct  480
ttccgaggtt aaccagcctg cgcaaataac agtgtcaaca aaaatatcag gccagatcta  540
tcaactcagc ctataaatat ctcaataaga taattttagc acttgagcat ttgcgcataa  600
taagaaaatt tgctattagc cacttaaaaa gaccatatat gatctgtttg cattgagatg  660
aattaaaaat ttcattgtag atatgaaatg attagtttg accatttaat tggacttaat  720
gaaatatgcg cgataatcag atctacgcgc tcgcgccaat agatctagta agatgtaggt  780
ttttttatttt ttttgtgaaa ctttgctacc acaacaagca tctgtaccag tgcagaattc  840
attacttgta ttcagtttgt aaaccgtata tataatataa ataacatgca catgcagtca  900
gatctagcac taccagtcca cagtaatcca aaactacatt tgtatatttc atcattattc  960
agtagtacta ggtttgtaca aaatcttggc tgcagaaggc cgcacttaaa tattcattct 1020
aatcagaaac ttaaaaaaaa agtactaaaa aatgattgc atccaattca gtaaatatga 1080
gccattcctg gccagatcta acaatctcaa caacaaagat cctatatgaa catctccttc 1140
taaaagaaaa tacagtaaca tctgaaggca gtagactaga aaccaacaaa atctaatgct 1200
gggaaatcac taaatcagca cgaacctggt gaagacggcg acgagctcat tggggtgggc 1260
ggagagggag tcgccgatgc gctccctgac gctgtggagg cggctcagga cgcggtcgcc 1320
ggcagcttcc cccattgctc tcctcttcct cttggctcct caagcctgcg tgcacaacca 1380
```

```
accaccatca tcagatacat ccagacccag tcaacacaat cactccagga aaaaaaaaag   1440
tcaagccata aacccaacc aaaaaccacg cctttgacaa acactggaag aaaaagaaaa    1500
tcgcagcttt ttcacaagca atctagaaga aagaaaaag aaaagactac atagcagcta   1560
taattgactg agaagcatac aggaatcaaa caatggagaa ggggagggag gaagaacaat  1620
gatgctccag gctgaggacc gaggaactgg gtgaagcgga gtaggcgcgt attatgcag    1680
atctgaggag agaaaccacc aaaacaatcc gatggtttca acgaaaaaga tcgtcgcttc  1740
ttgctgcacc agctcaccca tagccgttga gatcgaagct aagctagcag cagcaaagct  1800
ggaacgaaga gtgacgcatt caagctcctc tcctctcctc tcctctcctc cggagcacga  1860
ggccagcatg ggatggattg gggtttcttg ttggccatgg caaggagga ggtcattaac   1920
gttgacacgg cgtaatttaa ttaaatctta tcttaaaata tgatttaagt ggtagtaaca  1980
aggaagatta atactatgaa                                               2000

SEQ ID NO: 69         moltype = DNA  length = 2000
FEATURE               Location/Qualifiers
source                1..2000
                      mol_type = unassigned DNA
                      organism = Oryza sativa
SEQUENCE: 69
gctgtttaag aaaaacagaa gtaaaattca gtcactgtta ttttgcttca gttataatct   60
gcaaatcgtc gttctggtac ttactgtcca tcaacaagct gttccttgaa tgccaagtac  120
tcagaaacac tcagctcttc cactgccaac tcacttacat tcacccgaat gtagtcccag  180
acaccaggcc ttggcctgat ggccagtgca acccagggcg gagcacaat ggcttcctac   240
atacagtcaa ggaagtaagt tagaaagact ggtatttgac tttgagttga ctatcataac  300
catcctggct cattgccaaa tttacctgag cagcccggag aatgtcttca aagggagcat  360
atttctcttt gtcagcttcg atcaaggcat cgaactccgc aagcagctgg tgacgctgga  420
gcattccctt tccctggtta acatacctgc atagagtgat atttaagaaa tagaaccaat  480
gcttagatct cacatccttt ctgcggctga actatgttaa tggcactacc acataaacct  540
gatttttact tcttatttt aagaccacat gatctgtact taatctagct atgaacaaac  600
aatatttcaa catcatctaa gattcatgac tcaagacaaa atgttagag ctcatcacag   660
attattatag ataccatcat taaaactaaa gagatgcata accttgtcag ctaagaattt  720
gtaacatact aacatgttat cgtttcacat ctgggttgac taagaactaa ccaactgtat  780
ggataaaatc attgaaaact caaaacaatt agtagcaggt tccaagaaga cacaagatat  840
tatattgaga tcttcaccta gaagagtg caatcaactc attgggatga acgagaagg     900
tggcaccgag gcgttcgcgg agactgtgga ggcgagctag cttggcagcc atgactcaat  960
ttcaggaact gcaaagaaag gttacacta gcaacacgta ccaaaaccac tcacttgcac  1020
aagaataatt agtcaacagc catcactaag cattgcaaga ctatctctga acaggaaagc  1080
catgctaaat caacactaat aacatcacac aaaagcattg gaagatcaaa acataactaa  1140
aaacagctgt ttcatcataca caactgaaag catctatggt ttacaagca gagtgcgagt  1200
actgattcaa aataaatcaa cctgaaccaa tatactctga caatgttttc aaagggataa  1260
aagaaccagc tttatcaaat ggatttgttg ggtttttagta agtatcattg agataccgat 1320
ggcatatctc aaactttgca aaattataat ggcatggttc caaattaccc tttagtatta  1380
gcaccagtta gatcctaatt cctaaatccg ataggacaga gcgaaagatc cctggagata  1440
tgaagatttg gctacagatt aagcagagcc aacatgaagt tccgaatatt atgaatccgc  1500
aagcggggag atcaaagaga agaatacgga aggtcgcgac tccatgaaag aatccaacca  1560
aaaacccaaa gattttctc agttcaaaaa aaaaaaaccc ttcatttttg gttcgccatc   1620
caccgacagg caccaagaca ttcctcagga agcaaaaaag attaagcaga acaagtgata  1680
agcaagacac agtatcaacg gactacgagt cgagaaaatc actgaggcgc gattcttact  1740
gcaccaagta aaaaaaatt tgggggcaaa aagaactctg caatgggcg gagcaacgtg    1800
gcagcaaaac taaggtcga ggatttgagg ttttttgccg gttttcctcg aaaccccgaa   1860
tccgctcata gtaaacccac taaactgcag cagaaacccc cctcttggtt cagatttacc  1920
gaaagcagta aacccaagaa catgtcagca aaaactcctg caagattcag ctgacgaccc  1980
accaaagaat cgcaagaaat                                               2000

SEQ ID NO: 70         moltype = DNA  length = 2000
FEATURE               Location/Qualifiers
source                1..2000
                      mol_type = unassigned DNA
                      organism = Oryza sativa
SEQUENCE: 70
tggcggacgc gccacgcaca aacacaaacc tgcacacccc tgtgtcagag gaggagaggc   60
caagaaagga aatcgagtgg aggaagtgag gagcggcgga gacgtaggag gaggagggg   120
agatggaaat ggaaagccgc gcgagagagg aggcgcgtgc tggatgggag gaggaggagg  180
aggtggtggg tttgtgtttg gagagacgag cgagagaggc gaagcattta agggaggaa   240
gaggggagag gagagagaga gagagagaga gagagagaga gagaggaatat             300
aataaagggt ggtgcacctg ccaactgcta tgctcaccaa cactttgtac acacccagtt  360
acacccccct gcctttatta tttccagtgc agtaataact tcaacaatta ttgaaatgaa  420
aatgaattaa atggagttag tatcggatta gcgacacgct tgccgagctt ctagacggtg  480
cgattatttc agcgggaacg actttctgta ggtgaattta atagaggagt gttttaaatc  540
cactcgacgt tgtaatagct ggtttaattc gtttgtactg tcgagtgatt atccaaaatc  600
aattttggat atttaaaaga aaaaaaaaca gatccgaagt attggaccta ctggcaaata  660
ggaattttgc tatatatagg tgtgcgttca tttataatgg agtagcatgg agttttatta  720
atccagtaaa tgttttcatt gatttaatta atataacgaa tttcgcttga ggccatattt  780
gttaaacgct tttatctcta tcatcattca tcctaccagt aaagagcacc ggagatcgca  840
cttcatttaa atatatgtcc atgttggata aaccatagtt tattatagtg ttcttttata  900
tgtttttgtgg ggaatttaga ttgtttaata tggcatacat atccatccat cattattata 960
ttctaacaca actggataag tgttctaaac tattgtagaa taactttgta gtatgatcga  1020
tcttgtggaa taaaaaagt ctgacaataa cctttcataa aggaatatga ataccgtaa    1080
tcaacgcatc aaatcattca cggtgtacgc ctagcgaatt cgttggcgag tgctcgtgcg  1140
gccgtgggct cgctgtgatg catgcatggc tctctggcta cgtcgagata gcgattagta  1200
```

-continued

```
gcaaaattaa gcaagccact tattaattaa tctttggaga tatcatatga ttaaggcatt    1260
aattcgtacg tactcgtcgt cagcgttttc tgcaaagtcc actacagttt tttctttctt    1320
tgctgaaaat gctgatgtgt tggagatgga gtgacgtgca caacctgccg ccacgtggat    1380
ggttgctgga gcctacgtgt catcttaatt tgaacaaaaa aaaagagga ataatacatc     1440
aatacatttt cgaatttcag ttctgccatt gaccagtaat acacatgtcg gcctcacatt    1500
ttaccctgat cttagtaacg ggtggtcgcc tggtcggtca ctgaaaaaag ttcaggaaat    1560
tatagtcaaa ctgaaacgaa catattcact ccttaaaaaa actaaatctt tttatatatt    1620
tgtgatattg taaaatagct acgggataat gatatagata tatatagtga taagggatag    1680
atggatcgag atatggagtt gtgctttctt taatttccac tacttgggct accatattat    1740
ggtagttggt atgaaaagat acacagcagt atagtgatgt gatcaatgac atgtatatct    1800
cacatgctcc catgttggag tcaaattttg ctagactaaa atccaattcc aagcagtccc    1860
tagccaagaa caaacaaaat tcagtgaggt cactgctgca ccaaggactg catgcatgca    1920
ggagaagggc attttctctt ttttcttttg gagactcgat tcaattcggt cggtcggtcg    1980
caatggtcag cttaattaaa                                                 2000

SEQ ID NO: 71          moltype = DNA   length = 2000
FEATURE                Location/Qualifiers
source                 1..2000
                       mol_type = unassigned DNA
                       organism = Oryza sativa
SEQUENCE: 71
tgtgaaaggt ggcggcacca gcttagccgc agcttctctc gtcgtctccc tgaaacgaga    60
gggaggaagt tggtagcgtg atatatttag gcatgtcatc tcttgtataa gaagtcttat    120
ctgtgctaat tcacacggtt ctctaatctc tctccattct gtttttgtaa attggttcag    180
tagatagcgt agggttatgc ttatatatac tccgtgaagt atatatttaa aaattagtca    240
cacgtaaagt actatacatg tttttatcgtc taataacaat aaaaacacta atcataaaat    300
ttttttaaat aatacgaatg gttaaacgtt gaatatgaac cgtgcaaaac tatatttatt    360
ttgtaacaga gaaaatattt cacattaatt agattgttgt tttatggaag gttggagagc    420
tgcgccgccg ttgcgcagac ctaggaggct gcttataagt tataatcaat caattcacgg    480
atgccggctg ggacgcggcc catcgtccgg gaagacgaca actcaacgca aaaagccgat    540
atgcctccaa attgccattg ccacctctac ggctgtttat actgctccaa atcaaaagcg    600
tccatggaag aatctagtat ttcccgcaaa gacgatgatg atatgcagga ttggatatat    660
agggggttgt tgcatgattg ctagaactcc cgtttccgaa gttgttcgtc cattttttaaa   720
gctgccaaat aggaatttat tttgttttca agtgtaatag agttctgtcc agatgagtga    780
attataattt ggttcacatt ttatttgcta agtttcagtt tgaacattct caaataactt    840
ttttcttcac ttttttaaccg agtaacttag ttattttttc cgtttggacc acccaacaat   900
ttgttgctaa gtgcatctca cccgtcaaat aattcctttg aatccaaatt caattatatc    960
ccaaaaataa aaaacttctg aattccacat caattcacac cccaaccatt ttaatttctc    1020
tccatatttt ccatttctct attttttacct ttctctcttt tccatctatt tattttttc    1080
cttttctatt tctttcttc tccttccttt tctgtttcc ttcttcttct cctcggctag     1140
gcccgagcca gccgctgccg cctcgcgcca acctgtgcc gccttacgcc gcgcttgcgt     1200
gcgctcgcgc ccacctcgtg cccaacccgc gcacgccaca cgcacacacg aggacgatcg    1260
acggacgaat gcaatcatat ccccttcctt aactcagctag aaggctcaag aaccgcaact   1320
ttgatctctt ccaccctctc aaatccgccc caacccctgc tgactcaatc gccattaccg    1380
gaggaaaaat ccccgaaacc ctattaccgg cgccactaac agagctccaa aattcgtcgc    1440
ataattcgaa aatattctga aattgaaggt aaaaatggaa tctacatgcg aagtactccc    1500
tttccctcc aatccgtcac tggaacgccg ccggcgcgcc ctcccgctgc cactgccctg    1560
tttggccgcc gacagccgca cggcgcgccg ctgctccagg ccgccctagc ttcaaccacc   1620
gccacctttg gctccgcctc cctcctctta tgctcaccaa gcccgcctcc ctcgccggag   1680
atcgccggaa ccaccgccgc catggccgcc accgcctcct gcttctggcc gccgcgcca    1740
gcctcggcac cggcgcctat gccaccgccg accacgcgaaa cggagtccct acaccttggg  1800
gaccacaaaa ccggcggcat ccctcccaaa accggcctcc tccaccgccg gcgttcgtgg   1860
gattccggcc agttctgtgc agagcgagag aagaagagga aaaatagatt ttcctattga    1920
aagataaatc agaaaattcc ttttttctttt cctatcaagt tgaccatccg tttgacctca   1980
aaatcaaaat ctgagaccta                                                 2000

SEQ ID NO: 72          moltype = DNA   length = 786
FEATURE                Location/Qualifiers
source                 1..786
                       mol_type = unassigned DNA
                       organism = Zea mays
SEQUENCE: 72
gacatggagg tggaaggcct gacgtagata gagaagatgc tcttagcttt cattgtcttt    60
cttttgtagt catctgattt acctctctcg tttatacaac tggttttta aacactcctt     120
aacttttcaa attgtctctt tcttaccct agactagata attttaatgg tgattttgct    180
aatgtggcgc catgttagat agaggtaaaa tgaactagtt aaaagctcag agtgataaat    240
caggctctca aaaattcata aactgttttt taaatatcca aatatttta catggaaaat    300
aataaatttt agtttagtat taaaaaattc agttgaatat agttttgtct tcaaaaatta   360
tgaaactgat cttaattatt tttccttaaa accgtgctct atctttgatg tctagtttga   420
gacgattata taattttttt tgtgcttaac tacgacgagc tgaagtacgt agaaatacta    480
gtggagtcgt gccgcgtgtg cctgtagcca ctcgtacgct acagcccaag cgctagagcc    540
caagaggccg gaggtggaag gcgtcgcggc actatagcca ctcgccgcaa gagcccaaga   600
gaccggagct ggaaggatga gggtctgggt gttcacgaat gcctggagg caggaggctc    660
gtcgtccgga gccacaggcg tggagacgtc cgggataagg tgagcagccg ctgcgatagg   720
ggcgcgtgtg aaccccgtcg cgcccacgg atggtataag aataaaggca ttccgcgtgc    780
aggatt                                                                786

SEQ ID NO: 73          moltype = DNA   length = 1160
FEATURE                Location/Qualifiers
```

```
source                  1..1160
                        mol_type = unassigned DNA
                        organism = Zea mays
SEQUENCE: 73
atgtgctggt gccccataag gtaggcacct aggtctgtgt ttgaagcatc gacagatttg    60
taaacatgtt cctatgaacc tatttctgat tgataatttg tcaaaactca tcatttgtct   120
tcatccttgc ctgcttgcgt tcacgtgaca aagtacgtgt atgtcttcgg cctttgctgt   180
gtatgtttcg cattgcttag atgtggtgaa agaacatcag aagatgcatt gatggcgtgc   240
ttaaaccagt gatgtgctcc aggtgttcct gcagtctgca gagatattta ctcttgtagt   300
cttgttgaca gcacagttgt atgtgatttc ttggatgtaa tgtaaaccaa atgaaagata   360
ggaacagttc gtcctcttcc gtatacgaag gtcactgtat catttgtcgt ggcacaagat   420
gatctgcagg caggactgca acatggtttc ttggactgtc ctgaatgccc gttcttgttc   480
tttagttgag ccagagcagc agcctggtgt cggtgcctga gacctgacga agcacacggc   540
aaacaaacaa gtcgcagcag ctagcagggg cgttgccatc gccacaagcc cccaagagac   600
ccgccgagga aaagaaaaaa aaactacggc cgccgttgcc aagccgagcg tgcgaaccga   660
tccacggatg gagatcaga  gatcacccac cgcaggcggg cggcagtggc tggcgaggtg   720
cgtccacaga acctgctgca ggtccctgtc cgtcccggcg accccttttc taggcgagca   780
actccccatg gcagagctgc acgcagcagg gcccgtcgtt ggttgcagct ttaaccctt   840
ttgttttaac catacaatgc agagtcgcag aggtgaaaca ggacggaaat tacagaaaag   900
atggtggtgt gccagcagcc ccagcatgaa gaagatcagg acaaaagaaa agcttgtgat   960
tggtgacagc aacaggattg gattggagcc aagctaggca gtgagaggca ggcagcaaga  1020
cgcgtcagcc actgaaatcc agagggcaac ctcggcctca caactcatat ccccttgtgc  1080
tgttgcgcgc cgtggttagc caggtgtgct gcaggcctcc tccttgttta tatatgggag  1140
atgctctcac cctctaaggt                                              1160

SEQ ID NO: 74           moltype = DNA  length = 1532
FEATURE                 Location/Qualifiers
source                  1..1532
                        mol_type = unassigned DNA
                        organism = Oryza sativa
SEQUENCE: 74
tagtcctcta atatatgaaa ttttgatata ggtaaagaag ggtattgcaa ggataagaat    60
gtaaaaagaa ataagagtaa tccttaccga taatagtatt cctctctac  cgttaaaagt   120
taaacctgtg cgtgtagcat tttaatccag gatctatcga atccgtccct cgttggcgtg   180
ggcgacgaac acgtgcagaa gaagcttcc  ccagaaagca cctcaccgtc tcgccgtctg   240
gcagactggc acgcggggcc ctaccctcgc tgccgcctggg cccgtccgcc ttctgcacac   300
tgtcacgccc ccacccgctc gccgcctcgc gcctctctct ccgcctccgc cgcggccgcc   360
cgacgtgata gcgacgtagta ggactcgcca aacacaaaa atccatcgcg attttttggaa   420
ttttgttaca aaccaaatcc cgcattagag atttaatttg atttaattta attacgtagg   480
agtaccagat aaggagatcg agttaaaaaa gctaacggcg cggcgtggtt atctccgaat   540
cggctgtggc tccccgcgtc ggcgtcggcg cggcggcggc gcgccggccg aaccctggcc   600
gtcggatcgg gcgtcgtcct gggccccacg cgccacgggc ggctgtcgtt tgctcctcgg   660
agcggggtgg gcccaccatg gccaccacca caggtcggtg tcgcggctga cctggcggtg   720
gtcccgtgct cgcggtgttt tttttttttc actctctttc tctcggtgga cagtagcggg   780
ggccgcggcc cgcgggggca gagattgcaa aaacagcgga aacggaagat tgcaaaattg   840
caactgcttt cctgttttta attcgggatc aaaaagattc tttcgtcggg gtccccgtgc   900
cattgttgta ttgcgcgtag gtccttgctt gtaaaagata atctccttaa tttttttcttt   960
gtactactag tgtatatgca gtaagaatat accatgagta aaatgaacca caaactaat   1020
tacgatatac cattctcatg tagacgttct cttttctttt gctagtcata cgtgcatata  1080
taaccaaaca aaaaaatgtt tgaagtactc ctatccaatt tattactcca gtagacaaca  1140
aaagaaaatg tttgaagtaa taactgatcc atggtacagt agggttgtcg tcaatcttgt  1200
gtttctttca ttccattgta cttacaatcg tactccagct agcacagcac aatgggctta  1260
agctttggac cccaaattct gatcttgtcg ggaccccgta cgaaaatact cccgtagaga  1320
tgcagatacc gtcacaacct acaaccaacg aatgttaaga aaacaaggg  aaaaaaaaag  1380
aggcgaattc ggaggagaaa aaacggttgg  taaaatatag tgcgggtgtg gggacgcgac  1440
gcgagcgacg aaagaggaga gaggatgggt tggcctgccc ccccctcccc tgtctataaa  1500
tgcagaggcg ccgagtgccc tagtcgccgc tc                                1532

SEQ ID NO: 75           moltype = DNA  length = 841
FEATURE                 Location/Qualifiers
source                  1..841
                        mol_type = unassigned DNA
                        organism = Oryza sativa
SEQUENCE: 75
tcgaggtcat tcatatgctt gagaagagag tcgggatagt ccaaaataaa acaaggtaa     60
gattacctgg tcaaaagtga aaacatcagt taaaaggtgg tataaagtaa aatatccggta   120
ataaaaggtg gcccaaagtg aaatttactc ttttctacta ttataaaaat tgaggatgtt   180
tttgtcggta ctttgatacg tcatttttgt atgaattggt ttttaagttt attcgctttt   240
ggaaatgcat atctgtattt gagtcgggtt ttagttcgtt ttgcttttgt aaatacagag   300
ggatttgtat aagaaatatc tttagaaaaa cccatatgct aatttgacat aattttttgag   360
aaaaatatat attcaggcga attctcacaa tgaacaataa taagattaaa atagctttcc   420
cccgttgcag cgcatgggta ttttttctag taaaaataaa agataaactt agactcaaaa   480
catttacaaa aacaacccct aaagttccta agcccaaagt tgctatccac gatccatagc   540
aagccgcaaa caacccaacc caaccaaccc caccccaagtc cagccaactg gacaatagtc   600
tccacacccc cccactatca ccgtgagttg tccgcacgca ccgcacgtct cgcagccaaa   660
aaaaaaaaga aagaaaaaaa agaaaaagaa aaaacagcag gtgggtccgg gtcgtggggg   720
ccggaaacgc gaggaggatc gcgagccagc gacgaggccg ccctccctc cgcttccaaa   780
gaaacgcccc ccatcgccac tatatacata ccccccctc tcctcccatc cccccaaccc   840
t                                                                   841
```

```
SEQ ID NO: 76          moltype = DNA  length = 1392
FEATURE                Location/Qualifiers
source                 1..1392
                       mol_type = unassigned DNA
                       organism = Oryza sativa
SEQUENCE: 76
ctcgaggtca ttcatatgct tgagaagaga gtcgggatag tccaaaataa aacaaaggta   60
agattacctg gtcaaaagtg aaaacatcag ttaaaaggtg gtataagtaa aatatcggta  120
ataaaaggtg gcccaaagtg aaatttactc ttttctacta ttataaaaat tgaggatgtt  180
ttgtcggtac tttgatacgt catttttgta tgaattggtt tttaagttta ttcgcgattt  240
tggaaatgca tatctgtatt tgagtcgggt tttaagttcg tttgcttttg taaatacaga  300
gggatttgta taagaaatat cttaaaaaa acccatatgc taatttgaca taattttga   360
gaaaaatata tattcaggcg aattctcaca atgaacaata ataagattaa aatagcttga  420
ccccgttgca gcgatgggta tttttttctag taaaataaaa gataaactta gactcaaaac  480
atttacaaaa acaaccccta aagtcctaaa gcccaaagtg ctatgcacga tccatagcaa  540
gcccagccca acccaaccca acccagtgca gccaactggc aaatagtctc  600
cacaccccgg cactatcacc gtgagttgtc cgcaccaccg cacgtctcgc agccaaaaaa  660
aaaaaaagaa agaaaaaaaa gaaaagaaa aaacagcagg tgggtccggg tcgtgggggc  720
cggaaaagcg aggaggatcg cgagcagcga cgaggccggc cctccctccg cttccaaaga  780
aacgcccccc atcgccacta tatcatacc cccccctctc ctcccatccc cccaaccta   840
ccaccaccac caccaccacc tcctccccc tcgctgccga acgacgagct cctccccct   900
cccccctccgc cgccgccggt aaccacccg cgtccctc ctctttcttt ctccgttttt  960
tttttccgtc tcgtctcgat cttttggcctt ggtagtttgg gggcgagagg cggcttcgtc 1020
gcccagatcg gtgcgcggga ggggcgggat ctcgcggctg ggtctcggcg tgcggccgga 1080
tcctcgcggg gaatgggct ctcggatgta gatctgactg gccgttgttg ggggagatga 1140
tgggcgttt aaaatttcgc catgctaaac aagatcagga agaggggaaa agggcactat 1200
ggtttatatt tttatatatt tctgctgctg ctcgtcaggc ttagatgtgc tagatctttc 1260
tttcttcttt ttgtgggtag aatttgaatc cctcagcatt gttcatcggt agttttcttt 1320
ttcatgattt gtgacaaatg cagcctcgtg cggagctttt ttgtaggtag aagatggctg 1380
acgccgagga ta                                                     1392

SEQ ID NO: 77          moltype = DNA  length = 743
FEATURE                Location/Qualifiers
source                 1..743
                       mol_type = unassigned DNA
                       organism = Oryza sativa
SEQUENCE: 77
gaattcccgg acctccatgc ctacatcaac taatttgatt ccttgagttt acgtttagtg   60
atatgtctat ttttagagct tgttggggct tcggcctcag ctctagccag ccaaacatgt  120
tctaccaagt acccctatgtt ggcatgatat agtgatgcat tataacaata aatgagcgag  180
ggattgctgg ctgaaaaagc tatactagct gcatttggtt atagttaacc gaactattaa  240
ttgcgtgtac aacaaaataa aaaaaatgca tgttgcaat tctttcatta acattatgtt  300
ttggtagtgt gaattagaaa tttgattgac agtagatcga caaacatagt ttcaatatgc  360
ttaagttagt tatgacttta acatatcagt ctccttgata ttttcgtttt agattcgtct  420
ctctactagt gtgtatgtcc accttccata gcagtgaagg gttccattcc atccctggta  480
aaaaaaatc aaccactact aatttatttcc taaaagcaaa aatgataaaa tatcattttt  540
ttaataaaaa taaaaaaatt tgggggtaca taattgatgt tgcccccttgg gattaaccttt  600
aaaaaagggc gaattttcta gggtttggcc aagttttgca atgcaccaaa ttattcccct  660
tgggccggcc gccacccaa aaaaaccccc aaccccccaac tttccattga aggccgggcc  720
cccttaaatc ctcatccccc caa                                          743

SEQ ID NO: 78          moltype = DNA  length = 144
FEATURE                Location/Qualifiers
source                 1..144
                       mol_type = unassigned DNA
                       organism = Oryza sativa
SEQUENCE: 78
taaaaaaggg cgaattttct agggtttggc caagttttgc aatgcaccaa attattcccc   60
ttgggccggc cgccacccca aaaaaaaccc caacccccaa ctttccattg aaggccgggc  120
cccttaaat cctcatcccc ccaa                                         144

SEQ ID NO: 79          moltype = DNA  length = 612
FEATURE                Location/Qualifiers
source                 1..612
                       mol_type = unassigned DNA
                       organism = Cauliflower mosaic virus
SEQUENCE: 79
ggtccgattg agacttttca acaaagggta atatccggaa acctcctcgg attccattgc   60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gaccctcct ctatataagg aagttcattt  600
catttggaga gg                                                      612
```

```
SEQ ID NO: 80            moltype = DNA  length = 837
FEATURE                  Location/Qualifiers
source                   1..837
                         mol_type = unassigned DNA
                         organism = Coix lacryma-jobi
SEQUENCE: 80
agcagactcg cattatcgat ggagctctac caaactggcc ctaggcatta acctaccatg   60
gatcacatcg taaaaaaaaa accctaccat ggatcctatc tgtttctctt ttgccctgaa  120
agagtgaagt catcatcata tttaccatgg cgcgcgtagg agcgcttcgt cgaagaccca  180
tagggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaattttt gcgtattcga   360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggcctcct ctcacacggc acggaaccgt   720
cacgagctca cggcaccggc agcacggcgg ggattccttc cccaccaccg ctccttcct   780
ttcccttcct cgcccgccat cataaatagc caccctccc agcttcttc gccacat       837

SEQ ID NO: 81            moltype = DNA  length = 947
FEATURE                  Location/Qualifiers
source                   1..947
                         mol_type = unassigned DNA
                         organism = Oryza sativa
SEQUENCE: 81
aatccgaaaa gtttctgcac cgttttcacg tcctaactaa caatataggg aacgtgtgct   60
aaatataaaa tgagacctta tatatgtagc gctgataact agaactatgt aagaaaaact  120
catccaccta ctttagtggc aatcgggcta aataaaaaag agtcgctaca ctagtttcgt  180
tttccttagt aattaagtgg gaaaatgaaa tcattattgc ttagaatata cgttcacatc  240
tctgtcatga agttaaatta ttcgaggtag ccataattgt catcaaactc ttcttgaata  300
aaaaaatctt tctagctgaa ctcaatgggt aaagagagat atttttttt aaaaaaaaat   360
agaatgaaga tattctgaac gtatcggcaa agatttaaac ataataattat ataatttat  420
agtttgtgca ttcgttatat cgcacgtcat taaggacatg tcttactcca tctcaatttt  480
tatttagtaa ttaaagacaa ttgacttatt tttattattt atctttttc gattagatgc   540
aaggtactta cgcacacact ttgtgctcat gtgcatgtgt gagtgcacct cctcaataca  600
cgttcaacta gcgacacatc tccaatatca ctcgcctatt taatacattt aggtagcaat  660
atctgaattc aagcactcca ccatcaccag accactttta ataatatcta aaatacaaaa  720
aataatttta cagaatagca tgaaaagtat gaaacgaact atttaggttt ttcacataca  780
aaaaaaaaaa gaatttgct cgtgcgcgag cgccaatctc ccatattggg cacacaggca    840
acaacagagt ggctgcccac agaacaaccc acaaaaaacg atgatctaac ggaggacagc  900
aagtccgcaa caaccttta acagcaggct ttgcggccag gagagag                 947

SEQ ID NO: 82            moltype = DNA  length = 721
FEATURE                  Location/Qualifiers
source                   1..721
                         mol_type = unassigned DNA
                         organism = Mirabilis mosaic caulimovirus
SEQUENCE: 82
tggagattca gaaaaatctc catcaacaaa taatccaagt aaggattaat ggattgatca   60
acatccttac cgctatgggt aagattgatg aaaagtcaaa aacaaaaatc aattatgcac  120
accagcatgt gttgatcacc agctattgtg ggacaccaat ttcgtccaca gacatcaaca  180
tcttatcgtc ctttgaagat aagataataa tgttgaagat aagagtggga gccaccacta  240
aaacattgct ttgtcaaaag ctaaaaaaga tgatgcccga cagccacttg tgtgaagcat  300
gtgaagccgg tccctccact aagaaaatta gtgaagcatc ttccagtggt ccctccactc  360
acagctcaat cagtgagcaa caggacgaag gaaatgacgt aagccatgac gtctaatccc  420
acaagaattt ccttatataa ggaacacaaa tcagaaggaa gagatcaatc gaaatcaaaa  480
tcggaatcga aatcaaaatc ggaatcgaaa tctctcatct ctctctacct tctctctaaa  540
aaacacttag atgtgtgagt aatcacccac ttggggttgt aatatgtagt agtaaataag  600
ggaaccttag ggtataccat tgttgtaata ttatttcag tatcaataaa ataatctttc    660
agtttatctt atattcattt gtgtgacacc gtattcccat aaaaccgatc ctaatctctc  720
c                                                                  721

SEQ ID NO: 83            moltype = DNA  length = 352
FEATURE                  Location/Qualifiers
source                   1..352
                         mol_type = unassigned DNA
                         organism = Peanut chlorotic streak caulimovirus
SEQUENCE: 83
acagagggat ttctctgaag atcatgtttg ccagctatgc gaacaatcat cgggagatct   60
tgagccaatc aaagaggagt gatgtagacc taaagcaata atggagccat gacgtaaggg  120
cttacgccat tacgaaataa ttaaaggctg atgtgacctg tcggtctctc agaaccttta  180
ctttttatat ttggcgtgta ttttttaaatt tccacggcaa tgacgatgtg acctgtgcat  240
ccgcttgcc tataaataag ttttagtttg tattgatcga cacgatcgag aagacacggc    300
catttggacg atcatttgag agtctaaaag aacgagtctt gtaatatgtt tt           352

SEQ ID NO: 84            moltype = DNA  length = 1648
```

```
FEATURE              Location/Qualifiers
source               1..1648
                     mol_type = unassigned DNA
                     organism = Sorghum bicolor
SEQUENCE: 84
cactcgcaca tctcatggtg tcccaagaac ggcaagagcc agcactgcct ctgcctagca   60
acagcagcag cgccaagcga gcagccgcgt ccatggacgc cagcagcccg gccccgccgc  120
tcctcctccg cgcccccact cccagtccca gcattgacct ccccgctgcc gctggcaagg  180
ccgcggccgt gttcgacctg cggcgggagc ccaagatccc ggccgcattc ctgtggccgc  240
acgaggaggc gcgcccgacc tcggccgcgg agctggaggt tccggtggtg gacgtgggcg  300
tgctgcgcaa tggcgaccgc gcggggctgc ggcgcgccgc ggccgcaggtg gcctcggcgt  360
gcgcgacgca cggggttcttc caggtgtgcg ggcacggcgt ggacgcggcc ctggggcgcg  420
ccgcgctgga cggcgccagc gacttcttcc ggctgccgct ggccgacaag cagcgcgccc  480
ggcgcgtccc cggcaccgtg tccgggtaca cgagcgcgca cgccgaccgg ttcgcgtcca  540
agctcccctg gaaggagacc ctgtccttcg gcttccacga cggcgccgcg tcgcccgtcg  600
tcgtggacta cttcaccggc accctcggcc aagatttcga gccaatgggg cgggtgtacc  660
agaggtactg cgagaagatg aaggagctgt cgctgacgat catggagctg ctggagctga  720
gcctgggcgt ggagcgcggc tactaccggg agttcttcga ggacagccgc tccatcatgc  780
ggtgcaacta ctacccgccg tgcccggagc cggagcgcac gctgggcacg ggcccgcact  840
gcgaccctac ggcgctgacc atcctcctgc aggacgacgt cggcgggctg gaggtgctgg  900
tggacggcga gtggcgcccc gtccggcccg tccaggcgc catggtcatc aacatcggcg  960
acaccttcat ggcgctgtcg aacggcgggt acaagagctg cctgcaccgc gcggtggtga 1020
accagcggca ggagcggcgg tcgctggcct tcttcctgtg cccgcgcgag gacccgggtgg 1080
tgcggccgcc ggccagcagc gccaccgccg ggcagtaccc ggacttcacc tgggccgacc 1140
tcatgcgctt cacgcagcgc cactaccgcg ccgacacccg cacgctggac gccttcaccc 1200
gctggctctc ccacgcccca gtcccagccc aggaggcggc ggctccctgc acctagcgag 1260
cgagcgagcc gggccaaaca aacaaggggc aaaggccatc tctttcgccg ggcccgcgc 1320
gcggggttcg cccacgtgcg cgcccaggtg ggcgctggcc gcgggcaggt ggcggacatg 1380
tggcctgcgg gccccgcgcc gccttccat ttttggacgc tgccgcgcat gccgcatgcg 1440
tgcgtcgacg gccctactac ttctactact gctactgcca ctactagtgt acatacgcaa 1500
aaatacatat atacgtattt tctatatata tatatataag caaggcggcc ccccggtgac 1560
cttttctttg tttttgtcga caactgtgtt ttgatcccat tctagctgtt ctatggacca 1620
tggatggttc gttcaatgtt tgtacgta                                    1648

SEQ ID NO: 85        moltype = DNA   length = 1242
FEATURE              Location/Qualifiers
source               1..1242
                     mol_type = unassigned DNA
                     organism = Sorghum bicolor
SEQUENCE: 85
atggtgtccc aagaacggca agagccagca ctgcctctgc ctagcaacag cagcagcgcc   60
aagcgagcag ccgcgtccat ggacgccagc agccgggccc cgccgctcct cctccgcgcc  120
cccactccca gtcccagcat tgacctcccc gctgccgctg gcaaggccgc cgtgttcc   180
gacctgcggc gggagcccaa gatcccggcc ccattcctgt ggccgcacga ggaggcgcgc  240
ccgacctcgg ccgcggagct ggaggttccg gtggtgaacg tgggcgtgct gcgcaatggc  300
gaccgcgcgg ggctgcggcg cgccgcggcg caggtggcct cggcgtgcgc gacgcacggg  360
ttcttccagg tgtgcgggca cggcgtggac gcggccctgg ggcgtgacgc gctggacggc  420
gccagcgact tcttccggct gccgctggcc gacaagcagc gcgcccgcg cgtccccggc  480
accgtgtccg gtacacgag cgcgcacgcc gaccggttcg cgtccaagct ccctggaag  540
gagaccctgt ccttcggctt ccacgacggc gccgcgtcgc cgtcgtcgt ggactacttc  600
accggcaccc tcggccaaga tttcgagcca atggggcgtg taccagag gtactgcgag  660
aagatgaagg agctgtcgct gacgatcatg gagctgctgg agctgagcct gggcgtggag  720
cgcggctact accgggagtt cttcgaggac agccgctcca tcatgcggtg caactactac  780
ccgccgtgcc cggagccgga gcgcacgctg ggcacgggcc gcactgcga ccctacggcg  840
ctgaccatcc tcctgcagga cgacgtcggc gggctggagg tgctggtgga cggcgagtgg  900
cgccccgtcc ggcccgtccc aggcgccatg gtcatcaaca tcggcgacac cttcatggcg  960
ctgtcgaacg gcgggtacaa gagctgcctg caccgcgcgg tggtgaacca gcggcaggag 1020
cggcggtcgc tggccttctt cctgtgcccg cgcgaggac gggtggtgcg gccgccggcc 1080
agcagcgcca cgccgcggca gtaccggac ttcacctggg ccgacctcat gcgcttcacg 1140
cagcgccact accgcgccga caccgcacg ctggacgcct tcaccgctg gctctcccac 1200
gcccagtcc cagcccagga ggcggcggct ccctgcacct ag                     1242

SEQ ID NO: 86        moltype = AA    length = 413
FEATURE              Location/Qualifiers
source               1..413
                     mol_type = protein
                     organism = Sorghum bicolor
SEQUENCE: 86
MVSQERQEPA LPLPSNSSSA KRAAASMDAS SPAPPLLLRA PTPSPSIDLP AAAGKAAAVF   60
DLRREPKIPA PFLWPHEEAR PTSAAELEVP VVDVGVLRNG DRAGLRRAAA QVASACATHG  120
FFQVCGHGVD AALGRAALDG ASDFFRLPLA DKQRARRVPG TVSGYTSAHA DRFASKLPWK  180
ETLSFGFHDG AASPVVVDYF TGTLGQDFEP MGRVYQRYCE KMKELSLTIM ELLELSLGVE  240
RGYYREFFED SRSIMRCNYY PPCPEPERTL GTGPHCDPTA LTILLQDDVG GLEVLVDGEW  300
RPVRPVPGAM VINIGDTFMA LSNGRYKSCL HRAVVNQRQE RRSLAFFLCP REDRVVRPPA  360
SSATPRQYPD FTWADLMRFT QRHYRADTRT LDAFTRWLSH GPVPAQEAAA PCT         413

SEQ ID NO: 87        moltype = DNA   length = 12906
FEATURE              Location/Qualifiers
source               1..12906
``` mol_type = unassigned DNA
organism = Sorghum bicolor

SEQUENCE: 87

```
cactcgcaca tctcatggtg tcccaagaac ggcaagagcc agcactgcct ctgcctagca    60
acagcagcag cgccaagcga gcagccgcgt ccatggcgca cagcagcccg gccccgccgc   120
tcctcctccg cgcccccact cccagtccca gcattgacct ccccgctgcc gctggcaagg   180
ccgcggccgt gttcgacctg cggcgggagc ccaagatccc ggcgccattc ctgtggccgc   240
acgaggaggc gcgcccgacc tcggccgcgg agctggaggt tccggtggtg gacgtgggcg   300
tgctgcgcaa tggcgaccgc gcggggctgc ggcgcgccgc ggcgcaggtg gcctcggcgt   360
gcgcgacgca cgggttcttc caggtgtgcg ggcacggcgt ggacgcggcc ctggggcgcg   420
ccgcgctgga cggcgccagc gacttcttcc ggctgccgct ggccgacaag cagcgcgccc   480
ggcgcgtccc cggcaccgtg tccgggtaca cgagcgcgca cgccgaccgg ttcgcgtcca   540
agctcccctg gaaggagacc ctgtccttcg gcttccacga cggcgccgcg tcgcccgtcg   600
tcgtggacta cttcaccggc accctcggcc aagatttcga gccaatgggt taagcgaagc   660
accgatttac atttaccgcg cgtcggcccc tgaggcctgg gtcttagtct tagcactgca   720
tatacggtcg gtagctctgg atatgatacg tatatatgaa accccgttcc aatcccatgc   780
acggtgtaca caggcgggtg taccagaggt actgcgagaa gatgaaggag ctgtcgctga   840
cgatcatgga gctgctggag ctgagcctgg gcgtggagcg cggctactac cgggagttct   900
tcgaggacag ccgctccatc atgcggtgca actactaccc gccgtgcccg gagcggagc    960
gcacgctggg cacgggcccg cactgcgacc ctacggcgct gaccatcctc ctgcaggacg  1020
acgtcggcgg gctggaggtg ctggtggacg gcgagtggcg ccccgtccgg cccgtcccag  1080
gcgccatggt catcaacatc ggcgacacct tcatgtaac ccctgctctg ttttttcttg   1140
tcctcctctt gtcctgtgtg tgtgtatatt cacttctctc tgtttttttg ccccgaatcc  1200
tagtggacct aactgacgg attacagcac gcacacgtag gcatgtcatg tagcagcagt   1260
ctgcagcact gtagtactta gcgatgcaat agagacatgc gttccagtcg gttccatctc  1320
ggtgggctac agctacagtc ctacacggac gcggctcgta gtcgtaggga cgggcgcgtt  1380
ctctgtatcc acacacggct gcgcccaggc cgaggcttcc gccgcgggaa agttgcgaca  1440
acagaacggg gtttgtgccg ttggagcgtt gcggagaggc agaggcttgg gggacgggg   1500
gcgcgatacg ctgcgatggg tgggtgaccg aggcgacgct ttcggcgggg gcccgggcct  1560
gcccaggtgc gcgcggcctc gtcgccttcc cctgttttt tgatgccgcc gctcggtcct  1620
cggtgttctg gctccgcccg cccgctcgct gggtgcccat cccatctgat ccgatccgct  1680
ccgctccgcg gtgcggtcc tatgcgatgc cgccgcacga gcgcggggg ccgcccgtgg    1740
aggagtagaa agtggtacaa ggttggttgg aacttggaat tgtgggggt tactgctgct   1800
ggtggctgct gctttgcaac ttgccaggct gctgcctgtt gcccccgcg ttttctagcc   1860
gtttccgctc gcgatccggc acgcggcgcc cacaccgggg ctccagctcg gccccttggc  1920
cgtgtaggta gcaggcactt gcatctgtcc gttcgacacg atgattcttg tgcactgtgt  1980
acgtatgtac taacccttc tggtatgatg tacgcatggc atgcaggcgc tgtcgaacgg   2040
gcggtacaag agctgcctgc accgcgcggt ggtgaaccag cggcaggagc ggcggtcgct  2100
ggccttcttc ctgtgcccgc gcgaggaccg ggtggtgccg ccgccggcca gcagcgccac  2160
gccgcggcag tacccggact tcacctgggc cgacctcatg cgcttcacgc agcgccacta  2220
ccgcgccgac acccgcacgc tggacgcctt cacccgctgg ctctcccacg gcccagtccc  2280
agcccaggag gcggcggctc cctgcaccta gcgagcgagc gagccgggcc aaacaaacaa  2340
ggggcaaagg ccatctcttt cgccggggcc cgcgcgcggg gttcgcccac gtgcgccca   2400
aggtgggcgc tggccgcggg caggtggcgg acatgtggcc tgcggggccc gcgccgcctt  2460
cccattttg gacgctgccg cgcatgccgc atgcgtgcgt cgacgccct actacttcta   2520
ctactgctac tgcgactact agtgtacata cgcaaaaata catatatacg tattttctat  2580
atatatatat ataagcaagg cggccccccg gtgacctttt ctttgttttt gtcgacaact  2640
gtgtttgat cccattctag ctgttctatg gaccatggat ggttcgttca atgtttgtac   2700
gtactccacg taaccaaact actctagtgg actagtagat cgggctcatg tgatgaaact  2760
ggaccgacg ggacgtcacg tgcgtcaccc gcgtctggta gcggtagcgc acgagcgccg   2820
aatgttttcct gggcccgcaa gagaatcgct tctcatctcc tctcaccatg aatggggaaa  2880
aatgctgcgt cgaaagttcc agacgtttcc aaattccaaa cggttttgtg gcgtccgatc  2940
catgggggcgc cccaaacttc caagacgttt tcaggttcca aatcttcgtg ctccacatca  3000
ccttcttccc agattcattt gcctcgtcgc ttgctctcct gtgttattca cgggtcccac  3060
tgttgccccg tctgcgagaa agaaatttat tagagttgaa gcattcgaca tttcgactga  3120
ctgattgtta gtatcactaa attttgtgca catgtttctt tggtcattca tctctggata  3180
tttttttag ataatggata taaatatcgg gcctctacat ctgaggaagt acacagccaa    3240
ttattttcat ctctggacat gggacgatgg aagaggcaga tagatttagg agaccttca   3300
attcagaatt tcaggtgcac aaggcctgcc tggcttgccc ggattcttgt ttcggacatg  3360
accaactagg ccgcactact tgcactgata gctgagaaa aaacaaaact ttgcaaacag   3420
caggattatc tacaagggaa actccatcca cgtgaaccag catttcaggg agagatgcga  3480
caaaaaaaa gaggcggcaa caaaaaaatc ttactgcaat tttatctctg cattgaacct   3540
cttccaacca tgccgcatcc tgtactgttt tgtatctttc ccggtggtcc gttgcgttct  3600
cacgcagttg ataacatgca gtcacgcacc accgaatcca gtgtactagg gtagtgact   3660
tgtcacgcgg aacaacaggt cggtagcacc aagcaagtcg ctgtagactt gggcgttaa   3720
caacgacttg cacaacagtt caaatatagc atatgcaatt atgcacaaga ttgttcgact  3780
gctatccgac aaactgaaga agctgcccaa ttgaacagaa tgtaccagtg atttccagca  3840
cactatctta cagcagcgtt gagaatgaaa caacaaatgg gggaaaacag atgtgtatta  3900
ttctacagtt acaccaaaga gtttgtcctt tcagcatcaa caagaatcat atgcatatct  3960
agtgacaaaa attcctctaa ttttacccta cttggtaaca gttctcttca acacatatat  4020
ttcacgtgct tgcatcgagt tccttgggcc gccacatcga cttctcgacg caaagcaagc  4080
cctcgttgcc cttggtgtag gtcattcgca cctcccactg cagggacttg gccatgcttt  4140
ccagttcgtt tattgtgtcc gcagtgtccc tcacaatcag tttgccttgg ggcctcagta  4200
cacgatcaac ctcggcaaaa actgccatca atttgcatct gtaaacaagc aacacagatt  4260
tagcatctgt aaacaccaca ggtttcattg caagaagcat aaagcatgca aacatgctac  4320
ttgtacatgt caaagaaaca tgtcaaactc aaacacatga aaatcattat tattgttttc  4380
ttgctgaact gatcacatta gttggttttca atttctgagt tccactagta atctatacca  4440
gaaggataga ataatgtcaa gaacaagaga tacaaacctc tttgtgagct tgagaatag   4500
atggtccgcg tgcagaaggt cataagttct tgggtaagtg ctcaaagact cgcaccagtc  4560
```

```
atggtacata ccaaacaaac cacgctcgta aatgatgggc agtgtgtctg gtgaatcaat 4620
cggcacaata ttcatgaccc agaccttttg gtccctcaga gctgcagcaa aactgccatg 4680
caacgatgta aagcattagt aaaaatattg ggttttttaa accaaaacca agaaagataa 4740
ttcctccagc ttaactgaaa gaaagaaaga aaaaaactgc ttaatgactt atggtggaca 4800
agttgcctgt tatgttttat gatagctatg tgccagcttg gctaactggt agttatgtag 4860
tgtgatctga attaccaaaa aagagaagaa aaaaaaatca tgcccaagaa actgagaaag 4920
acacccattt acttaccctc catacacagc tctcatgtcc attacatttc tcactttgga 4980
ccagtcaatt cccatgccat tcacatacga tttacttaca acccttttcc agtgagcatt 5040
atctgcctcg aaatcttcat ttgcaggctt tccatagacc ccaaccttgg aaccatcaat 5100
ccagaaagga gtcttctcaa gcctttgtgg ccaaaactct ggccattttg accctcgaac 5160
tttcgagcca acaggcagtt tgtgcatgca tgcttccaaa ggtacattcc tgcaaatcaa 5220
aagattgtgt aagcaaagca gaggaagcac ttcgccgcat tgaaaatacg ttcttctcaa 5280
agaaacaaaa ccataccaag ctgcatctgc atcatcagat tccttgcaca atggtgggtt 5340
gttttcggat cttttctcat agcaaatgtt gtccattggt ttctgaaata tgaccatacc 5400
aacttgattt aacttatcct tagtcttgtt gaccatcttc cagcacatgg actttgtcaa 5460
agtggacatc gctgaaaaga ttaagggggtc atatgttatg atagaaataa aattcaattt 5520
tgcactgttg gtacatagca tctgtttttga acaaatgcaa tccttcctta tccatgaaag 5580
aagttaaccc ctgatactta ggattattca gtactttcac tcatgaactg ctgaatttgt 5640
tctgccagta gttgctatac tagaaatgtt cagtgtacca aacataaatt tggtacgggt 5700
tccttattaa agatgggagg ctgtatggta tttcgacgta acaaatcaag ttagcagcta 5760
ccctacttat ggatatacac ttctcaaaat gaatatacat agttttgata ggtgacatta 5820
attaatataa gaacttcatg cagttagggt gaaactaaag taagcagtta cggaaatacc 5880
attccaaatc tcaacatcct ctgggagctt ttggtaaaca ggagtggcag accagacaaa 5940
gtaaccacca gggcgtaaca agcggttcaa ttccagcaaa agcatgccac ctaaaaggag 6000
tcagtaataa gattcagttc tatagcaaat caataaatga aggaagaca tgtcaccaac 6060
aagacaaacc ttcaatgtgc caagggaccc tgcagcgagc gcaatgaatg acatcaaaga 6120
ctctgctggg gtatgaagt ctcttggtgc ccatcacagc tgatattgct ggaattcccc 6180
tttctaatgc aaattgtact tgagcttcat gctcatcttt cggagcaaaa gacatggtaa 6240
gcacatctct atcaaacatg tagcctccaa agctggcaac tccacaaccg acatctagaa 6300
tgacgcggct tcgtttgccc catgcaatat caggcagtgc ctgtgaatga cagtttaatc 6360
agcatatgat gaaagcaagt gtgataatat caagttcaaa gatgcaacat gaaacttttca 6420
taatcatgga cagtactaag cttgcttgat agattaatgt atggatgaga ctaaaaaaaa 6480
ggaaagttga atccatcaga acgagaggct gaaaacacat ggctggctgt gaaagcctga 6540
tgtcgtttag tctagcataa acaaactgtc ctcagcatgt agatttccat agggtggcat 6600
ttgacaaatt atgattgtgg actagcgaat caatcactga ttctcaaaag tgtgagacag 6660
atgagttcaa gtctaagggg tgactaatat gggatgctgg gatgatgatg atgatatata 6720
cctgctgaat agtatcaata tagtggaggg caccattctt gaactgagtc ccaccccag 6780
ggaacaggag gtagtcacct gatactttaa cccaattttg atgtcccttg tactctgcga 6840
gcctagtgtg aggaacattg ctgtaccata cctgcaaaaa gcagcacaag atggtaataa 6900
gtaaacagag atcttggtca gctaaagatg attcagtgtc gtacaattta gaatagacag 6960
aatcaccttg tccctgctcc ttggccactc aattgggcgt ttatatcctt ctgggagtgg 7020
aacaaggcag gtaggaggct cctcagggca atgcctctca cgatgttcat aatgtttagt 7080
agttcgaagc ttcttgatag ccttctcgtt gtcaaggcaa ggtatgtaat ctgtcgcagtg 7140
actgctatta catagtttcc aggaatagct agtcgcatca cctgaagact ttgatgacgc 7200
ttggacttcc ttttcattct tggactctgc agcctgtgtg gggaatgaac cattctgggt 7260
atttgactcc ttcagaagct ctgattgggc cccatcagga aatacctcgt tggagtttga 7320
gctctgatcc ttctctccat ttcttccac ctctatctgaggtt gctcctcctg 7380
agtggcatca ccttcaggct tctcttcttg atcatccttg ctctctccat caggtttttc 7440
atcaccactc tcatttgtga tttcatcatc tttcttctcc ccactcttct ccccgtcacc 7500
atcgttcttc atgtcatctg accgcccttc tgattttcca tttgcatcat caaacatatc 7560
cttggtctca gcttttctctg tcggcacttc cggctcctc tcttcaggct tctccctctg 7620
cttctcagtg aacttctctt ccatcgtggc atccttgtta ttcggctcct ccggcatcgt 7680
ggcatcattg ttgtcggtgt cctcaaattt ctcagaacct tcaccagcat tgtcctgtga 7740
ggcccccaaa ttgacaggcg caggctgctg cttcaccacc ggcttcttat tcgaggagat 7800
ctccagcggg aagacagtgg acgaggtcat catccacagc ccgaccaggc agagcgccac 7860
aaagacgacg accgtggtgg tcgtgcagaa cgacgacgag gtcgaggacg gccggcggcc 7920
gtccatcttc ccacctcggc caaatgccat tagtgcctgg cgaacatgta ccagagcacc 7980
gaccttcacg cgatttatct ccaccaacta ctgctggacc aagaaccccc aaaaaaatcg 8040
cacctttgtc tgcttttgtgc tgctacagcc gcgcggcaac tgaagcaaac cacaaaaaaa 8100
acttaaatcg ccgcggacat aaatcaaggt gctgatcta aagaacaaac gctggatcta 8160
ctcaagcaac aacggaagga agatccgcta ttggtgctag tattagcttc ttgtttccta 8220
gtactacagc ggctcttttcc cagtataaga acacgggaaa acgcggagaa atccccttc 8280
gtggccaaac atggaaagaa aattagtaaa gcgtgtgctt taaaaccccc tcgttctgtt 8340
ccttccgcgg agagctaccg catcttccaa ttgagctggt tctcagctgg gcgcaaaacg 8400
cgcactaatc aatgtccgat tccatccaca aagaaaaaaa agacgggaac agctaatcca 8460
gcagctcgct cgctagctag ctagctcatc ggcggaagga cggaaccagc tttgctggat 8520
ccaggacagc aagagtgtgc aaggagaaag aacgagcag caatgcggat tgcggaggcg 8580
gtggattggt acctcgccgg aaccgaccgg agtggtcgcg gtggccctcc gcgcggatct 8640
cgaagaggag cgaggaaggg gaaggcggat gcgcgtcctt gggttctctg ccaccgcact 8700
gggcctcgcc gcgttataaa ggcgggcggg cgggcgcagt gcgcagtgtg agtggagtgc 8760
aatctgttgt gtagtgtgtg aagaggcgga agccggaagcg gaggagatgg gttcgcatta 8820
gacgaccgta cgtaattata cgctatacta gtacttgggt tagattactc gggagatctt 8880
ggccaaaatg tccggtctga gtgttggta gtttatggaa tttgccctttt taagatgttg 8940
gtatttctcc ggggagcttaa aaagaagaaa tggcagtgct ttaggccttg tttagatgcg 9000
aaaaaaattt ggatttcgct actgtggcat ttttatttgt ttgtagcaaa tattgtccaa 9060
acacggacta actaagattc atctcgcgat ttacagttaa actgtacaat tagttttttat 9120
tttcatttat atttaatgtt tcatggatgt gtcgaaagat acgatatgat agaaaattt 9180
gaaaactttt tagttattga ggttaactaa acaatgcctt aattgagaat ttactcgagc 9240
aaaaagagtt aggtcagtct cagtggagag tttcatggtg ttgtttccaa gactgccata 9300
```

```
tcatgtgaaa tgaaatgaaa cttggttgaa acactcactc tcaatggaga gtttcatttt    9360
atagtttcat gggcatttaa tttcaatact catagagagt tgatatcgtg ccaactcatt    9420
tcttctctct cttcttaaat acacagtcat atcatcaaaa aaaatcctat gtagcaacat    9480
atttaatgca aataaaactc atatggtgga ctgtaggagt agcattaggc caagggcaca    9540
cacacggtca cggtgtgagt gcgacggtgc gagtgggccc gcggcggtag taagtgcgtg    9600
cgcgccggc  gcccccctcc gcggcgacga cgcagcggca gcgcgtcgtc cagtgcaccg    9660
tctgctgttc ggcgctgcgg gtcctccgcg ccacggcgca gtgaaccggg cgcgtgcatc    9720
ccgggagcgg cggcttggca ctcccctgct tgtcggtggc ggccgtcggc atcgctcggc    9780
cccggagcgt cacgaggctg ctgattggga gcgagagcga gtagtggggc tggttgggga    9840
caatcccatt cccacccggc ccaccaggct gggactggcc cactagtcac tagtgggtgg    9900
ctcatgggtg tgggtgggct ggctaatgcc gcctgcccaa caaccaaccc aaccccctgtg    9960
gacgctggta ccggtagttg ccgcgccatg gtggactgct gccgcctgat gcctttgcct   10020
gccacgctcc acgagttgag gcgcaccaaa ctgtgctgtg ctcctgattt gtgctaatcg   10080
gccgacgcgt accattcttt cttctttcg  tctacgcgca gagaggccgg ttgactgttt   10140
cttcgttgga gggccatgtt gactcgtact aataataaaa ataataatac taggttgact   10200
ttttcaattc caacgcagca gtgcaaagct gcccaccttat gagcacaggt cctttttttaa   10260
ctccgttttt gtacgtacac acgtactgtc cagcctgtgt ctaataatct taccaaaaac   10320
ctgtcatctc actatcaacc aatcaggctc tccgcctgtt cgtcgaggaa cagcagttgt   10380
tttccctact ccaacataga gtacactatg gacgcacatt accatgccag cttgagctta   10440
gcattgccca ccgttggata actgccatgc cattctcagg ccctgtttag ttcccatcta   10500
aaaatttttc atccattcca tcgaatcttt ggacacatgc atggaacatt aaatgtagat   10560
aaaaaaataa actaattaca cagtttagtt gagaatcgcg agacgaatct tttaagtcta   10620
gttactccat aattagcctt aagtgctaca gtaatccaca tatactaatg acagattaat   10680
tatgcttaat aaatttgtct tacagtttcc tgacgagcta tgtaatttgt tttttttatta   10740
gtttctaaaa accccctcccg acatccttcc gacatatccg atgtgacaac caaaaaattt   10800
tcatcttcaa tctaaacagg ccctcactct catcatctca tgccgggca aggcgagaga gcaggtccgt   10860
cgtcaggtct gtcgtcccgt cccgtgccgt ctgaagcaac aggcgagaga acgccgttc   10920
catcggtttg ccgagcgtgc agaggataga gctatactcg atccgagag gattgtgaaa   10980
cgaagcacgg ttaagcagtg ccgcgcacgt gctgctctgc tcctgatcc gatccagatc   11040
gactcggggc gtctcggcct cagcggcgat ggcaatcatc gctggagctgg             11100
acgttttcgt cttgcattgc aggaggcgga acagaacgga gaaagccacg gcgcgctttg   11160
ccgacgccac gcgctgacac gagggacccg ttcagcggcc agcacgcagc ctaatcatgc   11220
ctgtcgggg  gagctcatcc gttcctgaat ttgggtcatg ctccagtatc aggtattcag   11280
gtactagtac tcctgagcca tgtgctgcga caaaaaagcg aggctcctgt agtagagcct   11340
tgtttactta caaaattttt tacattctca gttatattaa atttgtgac acatgcataa    11400
agcattaaat atacataaaa gaaataatta tttacacagt tacttataat ttgcgaaacg   11460
aatcttttaa gactggttag tttatgatta gataatattt attaaataca aatgaaagta   11520
atattattta tatttttgcaa aaagtaaata agacctaggt agctaggcca acgtgagcat   11580
gtcggaccg  gaccggttcg ttctacggcg cgtcccgcaa acctgcagcc aggtagtagt   11640
agtacaccgt gcacgggaga ggtgcgccat gcatgctcgg gcaaaagatc atagagaaag   11700
gtgcagcgtt tcagttgcac acctgaccga gtgacgcctc gccttgtttg gctttgttcc   11760
caaaattttt taaaattcct catcacatta aatctttgaa cgaatatatg gagcattaaa   11820
tataaataaa agaaataatt aatcatacaa tttgtctgta atttgcgaga cgaatctttt   11880
gagcctagtt agtttataat taaataatat ttgttaaata caaacgaaaa tgctacgtta   11940
gccaaaacta aaattttttct ccaaacgtga cccagcacct tccgatcaat catcactcag   12000
cgggtcacgt cagaagatca gatggacctt gccgtccggg cctgtctctc ggcctcctcc   12060
ccatctggaa caacagagg  tccagtcctg tttcgagtcg agctgagtcg atcagatggg   12120
cctaaatagg ccgaagacgt aggcaaaggg cccgctgatt tatctgattc ttctaggacc   12180
gtgcatcgc  ggatgggcct aggtggaaac ccaacagatg tgaggcttca aagaggaaga   12240
agtccgttac acatggagag ttagtctata atgggataat atttaccaca aacaaataaa   12300
aatactacag tagcgaaatc caaaattttt cacatctaaa caaggcccta gatgtttttgt   12360
cagtgccaga ccagagaaaa tctcgtcttc tgctgtcaat agcttgatg attcctggcg   12420
gcagaggtaa agcttgcctg ggccttgttt agttccgaaa agtgaaaagt ttcggtact    12480
gtagcacttt tgtttgttcg tgacaaatat catccaatta tggactaact agaattaaaa   12540
gattcgtctc gtgatctaca gctaaactgt gtaattagtt tttgttttcg tctatattta   12600
atgtttcatg catgtgccac aagattcgat gtgacggaga attttgaaaa ttttttggtt   12660
ttcagagtga actaaacaag gcccagatgt aattgaccat gccatcgagc gcgagttgac   12720
tagagtgagt cggccctgat ggttaagtag tgcagactgc caagtggaca accgtctatc   12780
aactttgcag agtggggcga atgcactgag gatgttggag aggggcaagc caaggtaaac   12840
ttgaggaaag atgcttgttg acactgtagt atgtgaacaa tcctgtttaa ttttgtgtcc   12900
tcgacg                                                              12906

SEQ ID NO: 88              moltype = DNA  length = 1790
FEATURE                    Location/Qualifiers
source                     1..1790
                           mol_type = unassigned DNA
                           organism = Setaria italica
SEQUENCE: 88
tctcatggtg tcccaagcac agcaagagcc agctctgcct cacagcagca gcaccgccaa      60
gcgcgcagcc gcgtcactca tggacgcccg cccggcccag cctctcctcc tccgcgcccc     120
gactccagc  attgacctcc ccgcgtccaa gccggacagg gccgccgcgg cggcggcaa      180
ggccgccgcc gcctccgtgt tcgacctgcg gcgggagccc aagatcccgg cgccattcgt     240
gtggccgcac gacgacgcgc ggccggcgtc ggcggcggag ctggacgtgc cgttggtgga     300
cgtggggcgtg ctgcgcaatg gcgaccgcgc ggggctgcgg gcgctgcgg cagggtggt     360
cgcgggcgtgc gcgacgcacg ggttcttcca ggtgtgcggg cacggcgtgg gcgcggacct     420
ggcgcgcgcg gcgctggacg gcgccagtga cttcttccgg ctgccgctgg cggagaagca     480
gcgcgcccgc cgcgtcccgg gaccgtgtc  cgggtacacg agcgcgcacg ccgaccggtt     540
cgcgtccaag ctccccctgga aggagaccct ctccttcggg ttccacgacg gcgccgcgtc     600
gcccgtcgtc gtcgactact tcgccggcac cctcgggcag gacttcgagg cagtggggcg     660
```

```
ggtgtaccag aggtactgcg aggagatgaa ggctctgtcg ctgacgatca tggagctcct   720
ggagctgagc ctgggcgtgg agcgcggcta ctaccgcgac ttcttcgagg acagccgctc   780
catcatgcgg tgcaactact acccgccgtg cccggagccg gagcgcacgc tgggcacggg   840
cccgcactgc gaccccaccg cgctgaccat cctcctccag gacgacgtcg gcgggctcga   900
ggtcctcgtc gacggcgact ggcgccccgt ccgccccgtc cccggcgcca tggtcatcaa   960
catcggcgac accttcatgg ctctgtccaa cgggcggtac aagagctgcc tgcaccgggc  1020
ggtggtgaac cagcggcagg agcggcggtc gctggccttc ttcctgtgcc cgcgcgagga  1080
ccgggtggtg cgcccgccgg ccagcggcgc cgtcggcgag gcgccccgcc gctaccggga  1140
cttcacctgg gccgacctca tgcgcttcac gcagcgccac cgccgccgcg acacccgcac  1200
gctggacgcc ttcacacgct ggctctccca cggcccggcc caggacgcgc cagtggcggc  1260
ggcggcttcc acctagctag cggcgcggat ccgaccgagc ccattgacga cgccgtccct  1320
ttccgccgcc gccggggccc gcgcggggt tcacccacg tgcgcgccca ggtgggcgag  1380
gtggcggcct cgtggcccgc gggccccgcg ccgccttccc attttttggc gctgccgccc  1440
cgcgcgcatg ccggatgcgt gcgtccacgg cctactgcg ctactagtgt acatatacaa  1500
acatacatat atacgtagta taaatatata agcaagcggc ccggtgcccc ttttcgtttt  1560
cttgttttgt cgatcacaat ctctggattc gatggatgga taaatgtttg tacgcatgca  1620
tgtagatggg ctcatgaaat ttcagaatct ggaacggacg aggagctcac gtgcctcttc  1680
cgtgtctggt agcgggtagct gcgtgccaaa tgtctggtgg gcccaaagaa attctagtgc  1740
cacccgtccg gatccggcat ccgaaagttc ccgacggttc gacacccgaa              1790

SEQ ID NO: 89        moltype = DNA   length = 1272
FEATURE              Location/Qualifiers
source               1..1272
                     mol_type = unassigned DNA
                     organism = Setaria italica
SEQUENCE: 89
atggtgtccc aagcacagca agagccagct ctgcctcaca gcagcagcac cgccaagcgc   60
gcagccgcgt cactcatgga cgcccgcccg gcccagcctc tcctcctccg cgccccgact  120
cccagcattg acctccccgc gtccaagccg gacaggccg ccgcggcgg cggcaaggcc  180
gccgccgcct ccgtgttcga cctgcggcgg gagcccaaga tcccgcgcgc attcgtgtgg  240
ccgcacgacg acgcgcggcc ggcgtcggcg gcggagctgg acgtgccgtt ggtggacgtg  300
ggcgtgctgc gcaatggcga ccgcgcgggg ctgcggcgcg ctgcggcgca ggtggccgcg  360
gcgtgcgcga cgcacgggtt cttccaggtg tgcgggcacg gcgtgggcgc ggacctggcg  420
cgcgcggcgc tggacgcggc cagtgacttc ttccggctgc cgctggcgga gaagcagcgc  480
gcccggcgcg tcccggggac cgtgtccggg tacacgagcg cgcacgcgga ccggttcgcg  540
tccaagctcc cctggaagga gaccctctcc ttcgggttcc acgacggcgc cgcgtcgccc  600
gtcgtcgtcg actacttcgc cggcaccctc gggcaggact cgaggcagt ggggcgggtg  660
taccagaggt actgcgagga gatgaaggct ctgtcgctga cgatcatgga gctcctggag  720
ctgagcctgg gcgtggagcg cggctactac cgcgacttct cgaggacag ccgctcgccc  780
atgcggtgca actactaccc gccgtgcccg gagccggagc gcacgctggg cacgggcccg  840
cactgcgacc ccaccgcgct gaccatcctc tccaggacga cgtcggcgg gctcgaggtc  900
ctcgtcgacg gcgactggcg ccccgtccgc ccgtccccg cgccatggt catcaacatc  960
ggcgacacct tcatggctct gtccaacggg cggtacaaga gctgcctgca ccgggcggcg 1020
gtgaaccagc ggcaggagcg gcggtcgctg gccttcttcc tgtgcccgcg cgaggaccgg 1080
gtggtgcgcc cgccggccag cggcgccgtc ggcgaggcgc cccgccgcta cccggacttc 1140
acctgggccg acctcatgcg cttcacgcag cgccactacc gcgccgacac ccgcacgctg 1200
gacgccttca cacgctggct ctcccacggc ccggcccagg acgcgccagt ggcggcggcg 1260
gcttccacct ag                                                    1272

SEQ ID NO: 90        moltype = AA   length = 423
FEATURE              Location/Qualifiers
source               1..423
                     mol_type = protein
                     organism = Setaria italica
SEQUENCE: 90
MVSQAQQEPA LPHSSSTAKR AAASLMDARP AQPLLLRAPT PSIDLPASKP DRAAAAAGKA    60
AAASVFDLRR EPKIPAPFVW PHDDARPASA AELDVPLVDV GVLRNGDRAG LRRAAAQVAA   120
ACATHGFFQV CGHGVGADLA RAALDGASDF FRLPLAEKQR ARRVPGTVSG YTSAHADRFA   180
SKLPWKETLS FGFHDGAASP VVVDYFAGTL GQDFEAVGRV YQRYCEEMKA LSLTIMELLE   240
LSLGVERGYY RDFFEDSRSI MRCNYYPPCP EPERTLGTGP HCDPTALTIL LQDDVGGLEV   300
LVDGDWRPVR PVPGAMVINI GDTFMALSNG RYKSCLHRAV VNQRQERRSL AFFLCPREDR   360
VVRPPASGAV GEAPRRYPDF TWADLMRFTQ RHYRADTRTL DAFTRWLSHG PAQDAPVAAA   420
AST                                                                423

SEQ ID NO: 91        moltype = DNA   length = 2888
FEATURE              Location/Qualifiers
source               1..2888
                     mol_type = unassigned DNA
                     organism = Setaria italica
SEQUENCE: 91
tctcatggtg tccaagcac agcaagagcc agctctgcct cacagcagca gcaccgccaa    60
gcgcgcagcc gcgtcactca tggacgcccg cccgggccag cctctcctcc tccgcgcccc   120
gactcccagc attgacctcc ccgcgtccaa gccggacagg ccgccgcgg cggcggcaa   180
ggccgccgcc gcctccgtgt tcgacctgcg gcgggagccc aagatcccgc gccattcgt   240
gtggccgcac gacgacgcgc ggccggcgtc ggcggcggag ctggacgtgc cgttggtgga   300
cgtgggcgtg ctgcgcaatg cgaccgcgc ggggctgcgg cgctgcgg cgcaggtggc   360
cgcggcgtgc gcgacgcacg ggttcttcca ggtgtgcggg cacggcgtgg gcgcggacct   420
ggcgcgcgcg gcgctggacg gcgccagtga cttcttccgg ctgccgctgg cggagaagca   480
gcgcgcccgg cgcgtccgg ggaccgtgtc cgggtacacg agcgcgcacg ccgaccggtt   540
```

```
cgcgtccaag ctcccctgga aggagaccct ctccttcggg ttccacgacg gcgccgcgtc    600
gcccgtcgtc gtcgactact tcgccggcac cctcgggcag gacttcgagg cagtgggata    660
agtatgtagg aatgaacttg gcacgcattg catccacatg gcgtgctgat cgaacgagct    720
gagccaaccg gcatgcacac atggcgtggc aggcgggtgt accagaggta ctgcgaggag    780
atgaaggctc tgtcgctgac gatcatggag ctcctgagtg tgagcctggg cgtggagcgc    840
ggctactacc gcgacttctt cgaggacagc cgctccatca tgcggtgcaa ctactacccg    900
ccgtgcccgg agcggagcg cacgctgggc acgggcccgc actgcgaccc caccgcgctg    960
accatcctcc tccaggacga cgtcggcggg ctcgaggtcc tcgtcgacgg cgactggcgc   1020
cccgtccgcc ccgtcccgg cgccatggtc atcaacatcg gcgacaccgt catggtacgg   1080
ccgccgctaa tccatccttt tgttgctctt atctcctctg gcgagtgcga gtaacgaaag   1140
cgctagctcc cctgctcctt gtcctgctct gtttcccaag tcctaatgga gctaaccggg   1200
cagactgcaa cacgcacgcg taggcatgtc acgtagccac cacttgcact gtgctgcgca   1260
gcgacgacgc aacgcggacg tgcgttcgag tcggttccat ctcggcgccg ctacacgcgg   1320
ccgcggctcc tagcctccta gggctccctg atccctatcc ccgagccctt ccgcgggaaa   1380
agttcgttgg cgacggcaga ggagagccga cgggtccgtg ccgttggagc gtggcggcag   1440
gagaggccgg gagggtgttt tgttgcgttg cgcggcggcg cggaggatgc gatggcgcgg   1500
gcgggcggcg ctttcggcgg tggccccgc gacccacgtg cgcgcgcggt ctcgtcgcct   1560
tccctgtttt ggtgccacct ctctgtgtcc gggaatgggt tggcttagcg gcgaccgaga   1620
ccgggcggtg gtctgcctg ctcccggcgc ccatccgcc tggtctctca tcctgctcct   1680
cctatgcgcg aggggcctg tagcggctgg agtacaagca gattggttgg gttgggttgc   1740
tgctgcttgg ctgttgcccg cccgcttcct agccgtttcc gctcgccatc cggcacgcgg   1800
cgcccacgcc ggggctccag ctcggccct ttggccgtgg gggtggcagg caccccctgca   1860
tcgtctcgtg cgtccggttt ccgcgcctgg ccccccgcct tgaggtttcc ctgtgctttt   1920
gacaagactt tcgtagatat atgtgtgtgt atgtgtgtgt gtgcgtgcgc gcgtgtgtgt   1980
atatatatat ataaataaat aacatctgtg aatgatggat tacacgtgta gctgaccggc   2040
tgattgtgtt cgcgtgtgtg tcttcgatgc attgcaggct ctgtccaacg ggcggtacaa   2100
gagctgcctg caccgggcgg tggtgaacca gcgcaggag cggcggtcgc tggccttctt   2160
cctgtgcccg cgcgaggacc gggtggtgcg cccgccggcc agcggcgccc tcggcgaggc   2220
gccccgccgc tacccggact tcacctgggc cgacctcatg cgcttcacgc agcgccacta   2280
ccgcgccgac acccgcacgc tggacgcctt cacacgctgg ctctcccacg gcccggccca   2340
ggacgcgcca gtggcggcgg cggcttccac ctagctagcg gcgcggatcc gaccgagccc   2400
attgacgacg ccgtcccttt ccgccgccgc cggggcccgc gcggggttc accccacgtg   2460
cgcgcccagg tgggcgaggt ggcggcctcg tgggcccgcg gccccgcgcc gccttcccat   2520
ttttgggcgc tgccgcccg cgcgcatgcc ggatgcgtgt gtccacggcc tactgctgct   2580
actagtgtac atatacaaac atacatatat acgtagtata aatatataag caagcggccc   2640
ggtgccccttt ttcgttttct tgttttgtcg atcacaatct ctggattcga tggatggata   2700
aatgtttgta cgcatgcatg tagatgggct catgaaattt cagaatctgg aacggacgag   2760
gagctcacgt gcctcttccg tgtctggtag cggtagctgc gtgccaaatg tctggtgggc   2820
ccaaagaaat tctagtgcca cccgtccgga tccggcatcc gaaagttccc gacggttcga   2880
cacccgaa                                                            2888

SEQ ID NO: 92          moltype = DNA  length = 1567
FEATURE                Location/Qualifiers
source                 1..1567
                       mol_type = unassigned DNA
                       organism = Oryza sativa
SEQUENCE: 92
tgcccagaca gctcgccctg cacacacaca cacactcaca ctcacacacg ctctcaactc     60
actcccgctc aacacagcgc tcacttctca tctccaatct catggtggcc gagcacccca    120
cgccaccaca gccgcaccaa ccaccgccca tggactccac cgccggctct ggcattgccg    180
cccccgcggc ggcggcggtg tgcgacctga ggatggacac caagatcccg gagccattcg    240
tgtggccgaa cggcgacgcg aggcggcgt cggcggcgga gctggacatg cccgtggtcg    300
acgtgggcgt gctccgcgac ggcgacgccg aggggctgcg ccgcgccgcg cgcaggtgg    360
ccgccgcgtc cgccacgcac gggttcttcc aggtgtccga gcacggcgtc gacgccgctc    420
tggcgcgcgc ggcgctcgac ggcgcagcg acttcttccg cctcccgctc gccgagaagc    480
gccgcgcgcg ccgcgtcccg ggcaccgtgt ccggctacac cagcgcccac gccgaccgct    540
tcgcctccaa gctcccatgg aaggagaccc tctccttcgg cttccacgac cgcgccgccg    600
cccccgtcgt cgccgactac ttctccagca ccctcggccc cgacttcgcg ccaatgggga    660
gggtgtacca gaagtactgc gaggagatga aggagctgtc gctgacgatc atggaactcc    720
tggagctgag cctgggcgtg gagcgaggct actacgggga gttcttccgc gacagcagct    780
caatcatgcg gtgcaactac tacccgccat gcccggagcc ggagcggacg ctcggcacgg    840
gcccgcactg cgaccccacc gccctcacca tcctcctcca ggacgacgtc ggcggcctcg    900
aggtcctcgt cgacggcgaa tggcgccccg tcagccccgt ccccggcgcc atggtcatca    960
acatccgcga caccttcatg cgctgtcga acgggaggta taagagctgc ctgcacagggg   1020
cggtggtgaa ccagcggcgg gagcggcggt cgctggcgtt cttcctgtgc ccgcgggagg   1080
acagggtggt gcgccgcccg ccgagcgccg ccaccgccga gcactacccg gacttccacct  1140
gggccgacct catgcgcttc acgcagcgcc actaccgcgc cgacacccgc acgctcgacg   1200
ccttcacgcg ctggctcgcg ccgccggcg cccgacgcgc cgcgacggcc caggtcgagg   1260
cggccagctg atcgccgaac ggaacgaaat ggaacgaaca gaagccgatt tttggcgggg   1320
cccacgccca cgtgaggccc acgtggaca gtgggccccgg gcgaggtgg cacccacgtg   1380
gaccgcgggc ccgcgccgc cttccaattt tggaccctac cgctgtacat attcatatat   1440
tgcaagaaga agcaaaacgt acgtgtgggt tgggttgggc ttctctctat tactaaaaaa   1500
aatataatgg aacgacggat gaatggatgc ttatttattt atctaaattg aattcgaatt   1560
cggctca                                                             1567

SEQ ID NO: 93          moltype = DNA  length = 1170
FEATURE                Location/Qualifiers
source                 1..1170
                       mol_type = unassigned DNA
```

```
                        organism = Oryza sativa
SEQUENCE: 93
atggtggccg agcaccccac gccaccacag ccgcaccaac caccgcccat ggactccacc   60
gccggctctg gcattgccgc cccggcggcg gcggcggtgt gcgacctgag gatggagccc  120
aagatcccgg agccattcgt gtggccgaac ggcgacgcga ggccggcgtc ggcggcggag  180
ctggacatgc ccgtggtcga cgtgggcgtg ctccgcgacg gcgacgccga ggggctgcgc  240
cgcgccgcgg cgcaggtggc cgccgcgtgc gccacgcacg gttcttcca ggtgtccgag   300
cacggcgtcg acgccgctct ggcgcgcgcc gcgctcgacg gcgccagcga cttcttccgc  360
ctcccgctcg ccgagaagcg ccgcgcgcgc gcgtcccgg gcaccgtgtc cggctacacc   420
agcgcccacg ccgaccgctt cgcctccaag ctcccatgga aggagaccct ctccttcggc  480
ttccacgacc gcgccgccgc cccgtcgtc gccgactact tctccagcac cctcggcccc   540
gacttcgcgc caatggggag ggtgtaccag aagtactgcg aggagatgaa ggagctgtcg  600
ctgacgatca tggaactcct ggagctgagc ctgggcgtgg agcgaggcta ctacagggag  660
ttcttcgcgg acagcagctc aatcatgcgg tgcaactact acccgccatg cccggagccg  720
gagcggacgc tcggcacggg cccgcactgc gaccccaccg ccctcaccat cctcctccag  780
gacgacgtcg gcggcctcga ggtcctcgtc gacggcgaat ggcgcccgt cagccccgtc   840
cccggcgcca tggtcatcaa catcggcgac accttcatgg cgctgtcgaa cgggaggtat  900
aagagctgcc tgcacagggc ggtggtgaac cagcggcggg agcgcggtc gctggccttc   960
ttcctgtgcc cgcgggagga cagggtggtg cggccgccgc cgagcgccgc cacgccgcag 1020
cactaccccgg acttcacctg gccgacctc atgcgcttca cgcagcgcca ctaccgcgcc  1080
gacacccgca cgctcgacgc cttcacgcgc tggctcgcgc cgccggccgc cgacgccgcc 1140
gcgacggcgc aggtcgaggc ggccagctga                                   1170

SEQ ID NO: 94          moltype = AA  length = 389
FEATURE                Location/Qualifiers
source                 1..389
                       mol_type = protein
                       organism = Oryza sativa
SEQUENCE: 94
MVAEHPTPPQ PHQPPPMDST AGSGIAAPAA AAVCDLRMEP KIPEPFVWPN GDARPASAAE   60
LDMPVVDVGV LRDGDAEGLR RAAAQVAAAC ATHGFFQVSE HGVDAALARA ALDGASDFFR  120
LPLAEKRRAR RVPGTVSGYT SAHADRFASK LPWKETLSFG FHDRAAAPVV ADYFSSTLGP  180
DFAPMGRVYQ KYCEEMKELS LTIMELLELS LGVERGYYRE FFADSSSIMR CNYYPPCPEP  240
ERTLGTGPHC DPTALTILLQ DDVGGLEVLV DGEWRPVSPV PGAMVINIGD TFMALSNGRY  300
KSCLHRAVVN QRRERRSLAF FLCPREDRVV RPPPSAATPQ HYPDFTWADL MRFTQRHYRA  360
DTRTLDAFTR WLAPPAADAA ATAQVEAAS                                    389

SEQ ID NO: 95          moltype = DNA  length = 3140
FEATURE                Location/Qualifiers
source                 1..3140
                       mol_type = unassigned DNA
                       organism = Oryza sativa
SEQUENCE: 95
tgcccagaca gctcgccctg cacacacaca cacactcaca ctcacacacg ctctcaactc   60
actcccgctc aacacagcgc tcacttctca tctccaatct catggtggcc gagcacccca  120
cgccaccaca gccgcaccaa ccaccgccca tggactccac cgccggctct ggcattgccg  180
ccccggcggc ggcggcggtg tgcgacctga ggatggagcc caagatcccg agccattcg   240
tgtggccgaa cggcgacgcg aggccggcgt cggcggcgga gctggacatg cccgtggtcg  300
acgtgggcgt gctccgcgac ggcgacgccg aggggctgcg ccgcgccgcg gcgcaggtgg  360
ccgccgcgtg cgccacgcac gggttcttcc aggtgtccga gcacggcgtc gacgccgctc  420
tggcgcgcgc cgcgctcgac ggcgccagcg acttcttccg cctcccgctc gccgagaagc  480
gccgcgcgcg ccgcgtcccg ggcaccgtgt ccggctacac cagcgcccac gccgaccgct  540
tcgcctccaa gctcccatgg aaggagaccc tctccttcgg cttccacgac cgcgccgccg  600
ccccgtcgt cgccgactac ttctccagca ccctcggccc cgacttcgcg ccaatggggt  660
aattaaaacg atggtggacg acattgcatt tcaaattcaa aacaaattca aaacacaccg  720
accgagatta tgctgaattc aaacgcgttt gtgcgcgcag gagggtgtac cagaagtact  780
gcgaggagat gaaggagctg tcgctgacga tcatggaact cctggagctg agcctgggcg  840
tggagcgagg ctactacagg gagttcttcg cggacagcag ctcaatcatg cggtgcaact  900
actacccgcc atgccccgag ccggagcgga cgctcggcac gggcccgcac tgcgacccca  960
ccgccctcac catcctcctc caggacgacg tcggcggctc cgaggtcctc gtcgacggcg 1020
aatggcgccc cgtcagcccc gtccccggcg ccatggtcat caacatcggc gacaccttca 1080
tggtaaacca tctcctattc tcctctcctc tgttctcctc tgcttcgaag caacagaaca 1140
agtaattcaa gctttttttt ctctctgcg cgaaattgac gagaaaaata agatcgtggt 1200
aggggcgggg cttcagctg aaagcgggaa gaaaccgacc tgacgtgatt tctctgttcc 1260
aatcacaaac aatggaatgc cccactcctc catgtgttat gatttatctc acatcttata 1320
gttaatagga gtaagtaaca agctactttt ttcatattat agttcgtttg atttttttt  1380
tttaaagttt tttagttttt atccaaattt attgaaaaac ttagcaacgt ttataatacc 1440
aaattagtct cattttagttt aatattgtat atatatttgat aatatattta tgttatatta 1500
aaaatattac tataattttc tataaacatt attaaaagcc atttataata taaaatggaa 1560
ggagtaatta atatggatct cccccgacat gagaatattt tccgatggtg tgacgacgcc 1620
atgtaagctt cggtggggcct ggacggccag aggtgccaac agccacgtcc aacacccct  1680
gggtccccc ctaacactcc aaacagtagt gagtagtgtc tcgtcgcgtt ttagtatttg 1740
atgacaaaca aagtgtgagt tgagttagcc accaccaact tgcacacgag cacatacatt 1800
tgtgtccatt ctcgccagtc acttccatct ctagtccta ctcctatcta gcgatgtaag 1860
cggataattt catcatccgt atataaacct gtttgttata gttaatttcc tatataaac   1920
tataacagta tacattttaa aagaaaacaa aattaggata aacaggccct gctcctatcc 1980
atccatggca cttggaagga ccagactcgg tcatgccatg ccaagccaag atatgggtta 2040
tggaagagta gagaagagga gagatgagag ataagcatgc gttctcctcc tcgttggatg 2100
tgtatttgg agggatttgt gtagtagtag cagcggcgcc gcggggacgg atgcggatgg 2160
```

```
tggcgctttc ggtggcgttt tcccgggggg gttttggttt ggcgcttggg ggggatggca  2220
tggcgcggcg tgcggctgca cgccacacac acgcgcgcgc acgcacgtac gtcgtcgtcg  2280
ccgcgggcgg acggtagctt aggtggtgt gttccgcgcg cgggcgcgga ttgttccatg   2340
ccgatcgatt tggcgccacc ctcgccgcgg ctcttgtcgc gtcgtgcgcc tctctcgcgc  2400
ggtttgtcct tgtcgcgttg ctcagccggc gacggggca cggacattgg cgatgtagcc   2460
ctgcacgtgt cggcctctcc gttgatgaat gatgatgtat gtatgtattt ttttttgtct  2520
gaaggaattt gtgggaatt gttgtgtgtg caggcgctgt cgaacgggag gtataagagc   2580
tgcctgcaca gggcggtggt gaaccagcgg cgggagcggc ggtcgctggc gttcttcctg  2640
tgcccgcggg aggacagggt ggtgcggccg ccgccgagcg ccgccactacc gcgcacacc   2700
ccggacttca cctgggccga ccctcatgcgc ttcacggcag gccactaccg cgcgcacacc  2760
cgcacgctcg acgccttcac gcgctggctc gcgccgccgg ccgccgacgc cgccgcgacg  2820
gcgcaggtcg aggcggccag ctgatcgccg aacggaacga aacggaacga acagaagccg  2880
atttttggcg gggcccacgc ccacgtgagg ccccacgtgg acagtgggcc cgggcggagg  2940
tggcacccac gtggaccgcg ggccccgcgc cgccttccaa ttttggaccg taccgctgta  3000
catattcata tattgcaaga agaagcaaaa cgtacgtgtg ggttgggttg ggcttctctc   3060
tattactaaa aaaaatataa tggaacgacg gatgaatgga tgcttattta tttatctaaa  3120
ttgaattcga attcggctca                                                3140

SEQ ID NO: 96          moltype = DNA   length = 1170
FEATURE                Location/Qualifiers
source                 1..1170
                       mol_type = unassigned DNA
                       organism = Triticum aestivum
SEQUENCE: 96
atggacacca gccctgcaac tccctgctc tccagcctc ctgctcccag cattgacccg     60
ttcgccgcca aggcggccgt caacaagggc ggcggccgg caaccgtggt gtacgaccctc  120
cggagggagc cgaagatccc cgccccgttc gtgtggccgc acgccgaggt gcgccccacc  180
acggcccagg agctggccgt gccggtggtg gacgtgggcg tgctgcgcaa tggcgacgcc  240
gcggggctcc gccgcgccgt ggcgcaggtg gccgcgcgcgt cgccacgca cgggttcttc  300
caggtgtccg ggcacggcgt ggacgaggcc ctggccgcgc cggcgcggag cgccgcgaag  360
ggcttcttcc ggctgccgct ggccgagaag cagcgcgcgc ggcgcgtccc ggggaccgtg  420
tccgggtaca cgagcgcgca cgccgaccgg ttcgcctcca agctccctg gaaggagacc   480
ctctccttcg gcttccacga ccgcgccggc gccgcgcccg tcgtggtgga ctacttcacc  540
agcacccctcg ggccggactact cgagccaatg ggagagggtg accaggagta ctgcgggaag 600
atgaaggagc tgtcgctgag gatcatggag ctgctgagc tgagccaggg cgtggagaag  660
cgcgggtact accgggagtt cttcgcggac agcagctcca tcatgcggtg caactactac  720
ccgccgtgcc cggagccgga gcgcacgctg gcacgggcc gcactgcga ccccacggcg   780
ctcaccatcc tactgcagga cgacgtggcc gggctgaggc tcctcgtcga cggcgactgg  840
cgccccgtcc gcccgtccc cggcgccatg gtcatcaaca tcggcgacac cttcatggcc   900
ctgtcgaacg gcggtacaa gagctgcctg caccgcgcgg tggtgaaccg cgggcaggag  960
cggcggtcgc tggccttctt cctgtgcccg gcgaggacc gctggtgcg gccgccgccg  1020
ggcctgagga gccgcggcg gtacccggac ttcacctggg ctgacctcat gcgcttcacg 1080
cagcgccact accgcgccga cacgcgcacc ctcgacgcct tcacccagtg gttctcctcc  1140
tcctcctcct cggcccagga ggcggcctga                                    1170

SEQ ID NO: 97          moltype = AA   length = 389
FEATURE                Location/Qualifiers
source                 1..389
                       mol_type = protein
                       organism = Triticum aestivum
SEQUENCE: 97
MDTSPATPLL LQPPAPSIDP FAAKAAVNKG GGAATAVYDL RREPKIPAPF VWPHAEVRPT     60
TAQELAVPVV DVGVLRNGDA AGLRRAVAQV AAACATHGFF QVSGHGVDEA LARAALDGAS   120
GFFRLPLAEK QRARRVPGTV SGYTSAHADR FASKLPWKET LSFGFHDRAG AAPVVVDYFT   180
STLGPDYEPM GRVYQEYCGK MKELSLRIME LLELSQGVEK RGYYREFFAD SSSIMRCNYY    240
PPCPEPERTL GTGPHCDPTA LTILLQDDVG GLEVLVDGDW RPVRPVPGAM VINIGDTFMA    300
LSNGRYKSCL HRAVVNRRQE RRSLAFFLCP REDRVVRPPP GLRSPRRYPD FTWADLMRFT   360
QRHYRADTRT LDAFTQWFSS SSSSAQEAA                                      389

SEQ ID NO: 98          moltype = DNA   length = 3050
FEATURE                Location/Qualifiers
source                 1..3050
                       mol_type = unassigned DNA
                       organism = Triticum aestivum
SEQUENCE: 98
ctcatggtgc tccagaccgc tcagcaagaa ccatccctga cgcgtccgcc tcactgcagc     60
gtcgccagcg cgcgctcgcc ggcggccatg gacaccagcc ctgcaactcc cctgctcctc   120
cagcctcctg ctcccagcat tgacccgttc gccgccaagg cggccgtcaa caagggcggc   180
ggcggccgcaa ccgcggtgta cgacctccgg agggagccga gatccccgcc ccgttcgtg   240
tggccgcacg ccgaggtgcg ccccaccacg gccaggagc tggccgtgcc ggtggtggac   300
gtgggcgtgc tgcgcaatgg cgacgccgcg gggctccgcc gcgccgtggc gcaggtggcc   360
gcggcgtgcg ccacgcacgg gttcttccag gtgtccgggc acggcgtgga cgaggccctg   420
gcgcgcgcgc gctggacgg cgcgagcggc ttcttccggc tgccgctggc cgagaagcag   480
cgcgcgcggc gcgtcccggg gaccgtgtcc gggtacacga gcgcgcacgc   540
gcctccaagc tcccctggaa ggagaccctc tccttcggct ccacgaccgc cggcgcgc    600
gcgcccgtcg tggtggacta cttcaccagc accctcgggc cggactacga gccaatgggg   660
taatatatcc acccgccac acccctatcc ggcagcacg aatccatccc cgccactgca    720
tttttttcct tttgtttccg cgcgaccgta cgttcgatcg cgcccacgt acgtacgtgc   780
gtacgcagta gcagtacttg aagccgccgt actacgtgct gagtagtgac aactgaacac   840
```

```
gtgcaggagg gtgtaccagg agtactgcgg gaagatgaag gagctgtcgc tgaggatcat   900
ggagctgctg gagctgagcc agggcgtgga gaagcgcggg tactaccggg agttcttcgc   960
ggacagcagc tccatcatgc ggtgcaacta ctaccgccg tgcccggagc cggagcgcac   1020
gctgggcacg ggcccgcact gcgacccac ggcgctcacc atcctactgc aggacgacgt   1080
gggcgggctg gaggtcctcg tcgacggcga ctggcgcccc gtccgccccg tccccggcgc   1140
catggtcatc aacatcggcg acaccttcat ggtaattact cctctctcag cgttgctttc   1200
gctgattaat tgcagaaaca gtagtcaact acccatgctc tgttccgctg tgctctgctt   1260
cccaacgagc gaaccggccc ataaaaactg ccttgctgtc ttggaaccaa gaggaaaggg   1320
accgtgggag cctaccgaca cgacgtgatt gcactctgct tcctaacaag cgagccgccg   1380
gtagggctat caccgtaagg gctcctttga ttcaaaggaa tttcttagga tttctgaagg   1440
attgaaatcc ttaggatttt ttcctatgtt ggtacttcga ttcataggat tgaatcccat   1500
aggatttttt tcctatgaaa tcttctgtac tacatttcat aggaaatcta acatccactc   1560
caacctttttt ttatatttcc tttgtttttc atgtgccatc aaacactcct tgttaatcct   1620
ataggattca agtgggcatg ccactccaat cctatacttt tcccattcct acgttttcaa   1680
aatcctacga atcaaagagg ccctaaagct gctgacatga cgtgattttt tttttctttt   1740
cttctttttct ttctcagctc caatcaacgc tggttattag atcattagag tggacaggtt   1800
gaattaacat gcagtagtta gtagttagca gccacaaacg ggtcccgttc tctgaagtct   1860
gaactgacat aagtcctgat catcgaccat tcttttgcttc ctaggacgat gcctgttgga   1920
acttgcgtcc aatgcccgtt agggagtggt aattgtcatc acttttagac tcgtcgattc   1980
cactgatgaa gacgtagcac atggatgagc caacgtatcc gtttctagtg gtctcgaaaa   2040
gtagggtttc attcattcta tctatctatc cgtccgtcca aaagggctgc gatgcgagca   2100
cttgagtcgg agccaatcag agcgcgagaa aagatagggg ggtagcaag ccatgtcgga   2160
ggggcgtttg cttccggcag gtttggattc ttgtggtagg cgggcggctc tgtacagtag   2220
cggcggtgac ggtgaggtgg cggcgctttc ggtggcgggc caaccaggt gcatgcacgc   2280
gcgctcgtcg ttttccgcc tgaatctgcc gctgcgccca tggcaagggg gtgggtgctg   2340
ccgccgggca atggagtaga tcacggtcgc gtcgggctc ggccagttga tcacggttcg   2400
ttcgtgcggt actaggttcc cccacggcac tgtgactgca tcgttccggc cctcgccatt   2460
ggcgatcggg caatctcctg ttcatccgtc gctgttgatt cctcggccac gatagaccat   2520
gcgcgtgccg gtcgtcgccc cgtcgcgctc gcttcacgtg ctcgtcgcgt ggctcccgtc   2580
ccacacgagg ccgccgcttt ctgacccagt ggagccgcgtg atttacagtt tatatatgtc   2640
gctgcatttt tctttttgtg tgctgctcat tttgcttgga cggagaccgg gaacgattag   2700
ccacggatct aacgcgttgt tgcttgtttt caatgcatgc atgcaggcgc tgtcgaacgg   2760
gcggtacaag agctgcctgc accgcgcggt ggtgaaccgg cggcaggagc ggcggtcgct   2820
ggcttcttc ctgtgcccgc gcgaggaccg cgtggtgcgg ccgccgccgg gcctgaggag   2880
cccgcggcgg tacccggact tcacctgggc tgacctcatg cgcttcacgc agcgccacta   2940
ccgcgccgac acgcgcaccc tcgacgcctt cacccagtgg ttctcctcct cctcctcctc   3000
ggcccaggag gcggcctgat tctgctctgc cacgaaacga tcggtccaca              3050

SEQ ID NO: 99           moltype = DNA   length = 1486
FEATURE                 Location/Qualifiers
source                  1..1486
                        mol_type = unassigned DNA
                        organism = Hordeum vulgare
SEQUENCE: 99
gaccagtagc atatagtttt tcttgtgttt gccatggtgg acgtgtcgaa ctttgtagaa    60
gccaatggca atgcagcagt atcgattcct gccatggaag ttgctgggag tcctcacgtc   120
ccgttcgttc ctcgggacgc gaacgcgaca gacagcaaga atgccaagga cgtcctcgac   180
ctctggcgc agcagaaaca aatcccggct cccttcatct ggccccacgc cgacgcgcgg   240
ccgtcgtcga tcttggagct ggacgtgccc gtggtcgaca tcggcgcggc cctgcacagc   300
gccgccggga tggcccgcgc cgcggcgcag gtggccgagg catgcgcgag ccacggcttc   360
ttccagacga ccgggcacgg cgtcgacccc gcgctggcc aagcagcgct cgacggcgca   420
gcggacttct tccgcctgcc gctcgccacc aagcagccg cccgccgatc cccgggacc    480
gtcaaagggt acgcctccgc ccacgccgac cgcttcgccg ccaagcttcc ctggaaggag   540
actctctcct tcatccacaa ccacgtccac gaggacgtcg gcgcccgcgc aagcagtcac   600
gtcgtcgact acttcacctc cgcccttggc gacgacttca tgcacctagg ggaggtgtac   660
caggagtact gtgaggcgat ggaggacgcg tcgctggcga taatggaggt gctggggtg   720
agcctggggc tggggagagg gtactacagg gacttcttcg ccgacggcag ctccatcatg   780
aggtgcaact actaccgcg tgcccggag ccggaccgga cgctgggac gggccgcac      840
tgcgacccgt cggcgctgac catcctgctg caggacggcg aggtggacgg gctccaggtg   900
ctcgtcgacg ggcgcatgcg ctccgtgcgg cccaagccgg gcgagctcgt cgtaaacatc   960
ggcgacacct tcatggcgct gtcgaacggc cggtacaaga gctgcctcca ccgcgcggtg  1020
gtgcaccggg agaaggagcg ccggtcgctg gcctacttcc tcgccccgcg ggaggaccgg  1080
gtggttcgcc cgccgccttc gccggcgccg gcgccgcggc tctacccgga cttcacctgg  1140
gcggagctca tgcgattcac gcagcgccac taccgccgcg acgcccgca gctcgagcgc  1200
ttcgcgtgct ggctcgacct gcccagctgc ccaccacgc cccaggccca agggactgtc  1260
tagtgtctgt gatgtatcat ctgtctcagc tgtttgtatac gaccacttgt gtctgctagc  1320
tctgcgcttg tgtttcttat gtgagctaac taactaaata gtgtgtatat ttcttgccgc  1380
gccttatgca agccctagtc tagaaacatgt aataattaac ttaagcatat acgttgatct  1440
ttggtgtatt tttcatattt ccttcataat gaataatcta ttatgc              1486

SEQ ID NO: 100          moltype = DNA   length = 1230
FEATURE                 Location/Qualifiers
source                  1..1230
                        mol_type = unassigned DNA
                        organism = Hordeum vulgare
SEQUENCE: 100
atggtggacg tgtcgaactt tgtagaagcc aatggcaatg cagcagtatc gattcctgcc    60
atggaagttg ctgggagtcc tcacgtcccg ttcgttcctc gggacgcgaa cgcgacagac   120
agcaagaatg ccaaggacgt cctcgacctc tggcggcagc agaaacaaat cccggctccc   180
```

```
ttcatctggc cccacgccga cgcgcggccg tcgtcgatct tggagctgga cgtgcccgtg    240
gtcgacatcg gcgcggccct gcacagcgcc gccgggatgg cccgcgccgc ggcgcaggtg    300
gccgaggcat gcgcgagcca cggcttcttc caggtgaccg ggcacggcgt cgaccccgcg    360
ctggcccaag cagcgctcga cggcgcagcg gacttcttcc gcctgccgct cgccaccaag    420
cagcgcgccc gccgatcccc ggggaccgtc aaagggtacg cctccgccca cgccgaccgc    480
ttcgccgcca agcttccctg gaaggagact ctctccttca tccacaacca cgtccacgag    540
gacgtcggcg cccgcgcaag cagtcacgtc gtcgactact tcacctccgc ccttggcgac    600
gacttcatgc acctagggga ggtgtaccag gagtactgtg aggcgatgga ggacgcgtcg    660
ctggcgataa tggaggtgct gggggtgagc ctggggctgg ggagagggta ctacagggac    720
ttcttcgccg acggcagctc catcatgagg tgcaactact acccgcggtg ccccgagccg    780
gaccgacgc tggggacggg gccgcactgc gacccgtcgg cgctgaccat cctgctgcag    840
gacggcgagg tggacgggct ccaggtgctc gtcgacggcg catggcgctc cgtgcggccc    900
aagcccggcg agctcgtcgt aaacatcggc gacaccttca tggcgctgtc gaacggccgg    960
tacaagagct gcctccaccg cgcggtggtg caccgggaga aggagcgccg gtcgctggcc   1020
tacttcctcg ccccgcggga ggaccgggtg gttcgcccgc cgccttcgcc ggcgccggcg   1080
ccgcggctct acccggactt cacctgggcg gagctcatgc gattcacgca gcgccactac   1140
cgcgccgacg cccgcacgct cgacgccttc gcgtgctggc tcgacctgcc cagctgcccc   1200
accacgcccc aggcccaagg gactgtctag                                    1230

SEQ ID NO: 101        moltype = AA   length = 409
FEATURE               Location/Qualifiers
source                1..409
                      mol_type = protein
                      organism = Hordeum vulgare
SEQUENCE: 101
MVDVSNFVEA NGNAAVSIPA MEVAGSPHVP FVPRDANATD SKNAKDVLDL WRQQKQIPAP     60
FIWPHADARP SSILELDVPV VDIGAALHSA AGMARAAAQV AEACASHGFF QVTGHGVDPA   120
LAQAALDGAA DFFRLPLATK QRARRSPGTV KGYASAHADR FAAKLPWKET LSFIHNHVHE   180
DVGARASSHV VDYFTSALGD DFMHLGEVYQ EYCEAMEDAS LAIMEVLGVS LGLGRGYYRD   240
FFADGSSIMR CNYYPRCPEP DRTLGTGPHC DPSALTILLQ DGEVDGLQVL VDGAWRSVRP   300
KPGELVVNIG DTFMALSNGR YKSCLHRAVV HREKERRSLA YFLAPREDRV VRPPPSPAPA   360
PRLYPDFTWA ELMRFTQRHY RADARTLDAF ACWLDLPSCP TTPQAQGTV                409

SEQ ID NO: 102        moltype = DNA   length = 1423
FEATURE               Location/Qualifiers
source                1..1423
                      mol_type = unassigned DNA
                      organism = Sorghum bicolor
SEQUENCE: 102
cctctcatca caggccccag cctcactctt ctcacagcaa gacatcgcag cctcacaacc     60
acacagcaac gtgatcgcca tgggcgggct caccatggag caggccttcg tgcaggcccc   120
cgagcaccgc cccaagccca ccgtcaccga ggccaccggc atcctggtca tcgacctctc   180
gcctctcacc gccagcgaca ccgacgcggc cgcggtggac gcgcggcgag ccgaggtgcg   240
cggcggcgag cgggactggg gcttcttcgt ggtggttggc cacggcgtgc ccgcggagac   300
cgtggcgcgc gcgacggcgg cgcagcgcgc gttcttcgcg ctgccggcgg agcggaaggc   360
cgccgtgcgc aggagcgagg cggagccgct cgggtactac gagtcggagc acaccaagaa   420
cgtcagggac tggaaggagg tgttcgacct cgtcccgcgc gatccgccgc cgccagcagc   480
cgtggccgac ggcgagctcg tcttcaagaa caagtggccc caggatcctg cgggcttcag   540
agaggcgctg gaggagtacg cggcagcgat ggaggagctg tcgttcaagc tgctggagct   600
gatcgcccgg agcttgaagc tgaggcccga ccggctgcac ggcttcttca aggaccagac   660
gacgttcatc cggctgaacc actaccctcc atgcccgagc ccggacctgg cgctgggagt   720
ggggcggcac aaggacgcgg gggcgctgac catcctgtac caggacgaag tgggcgggct   780
ggacgtccgg cggcgctcct ccgacggcgg cggcggcgag tgggtgcggg tgaggcccgt   840
gccggagtcg ttcgtcatca acgtcggcga cctcgtccag gtgtgcagca acgacaggta   900
cgagagcgcg gagcaccggg tgtcggtgaa ctcggcgagg gagaggttct ccatgcccta   960
cttcttcaac ccggcgagct acaccatggt ggagccggtg gaggagctgg tgagcgacga  1020
cgacccgccc aggtacgacg cctacagctg gggcgagttc ttcagcacca ggaagaacag  1080
caacttcaag aagctcagcg tggagaacat tcagatcgcg catttcaaga agaccctcgt  1140
cctcgcctag ataagcagca ggatactaca ggtctacagg actaggacaa gccgatcgag  1200
gtgaccggcc gtcgtcttca gattcagtat atgcgtgtcg ccgttcgtgt tagaacaaat  1260
taataatgtg cgcgctgtgt gctgtgtgtg tggagtaaaa aaaaactaaa catgcatgtg  1320
catgttcaaa aaaaaaaaca tggatgcgag tatgtttggg aataataaca ggcttgtgac  1380
ggtctggttt atttgcaaat tcaaaccgaa ttggttgatc ttc                     1423

SEQ ID NO: 103        moltype = DNA   length = 1071
FEATURE               Location/Qualifiers
source                1..1071
                      mol_type = unassigned DNA
                      organism = Sorghum bicolor
SEQUENCE: 103
atgggcgggc tcaccatgga gcaggccttc gtgcaggccc ccgagcaccg ccccaagccc     60
accgtcaccg aggccaccgg catcctggtc atcgacctct cgcctctcac cgccagcgac   120
accgacgcgg ccgcggtgga cgcgctggcc gccgaggtgc gcggcggcga gcgggactgg   180
ggcttcttcg tggtggttgg ccacggcgtg cccgcggaga ccgtggcgcg cgcgacggcg   240
gcgcagcgcg cgttcttcgc gctgccggcg gagcggaagg ccgccgtgcg caggagcgag   300
gcggagccgc tcgggtacta cgagtcggag cacaccaaga acgtcaggga ctggaaggag   360
gtgttcgacc tcgtcccgcg cgatccgccg ccgccagcag ccgtggccga cggcgagctc   420
gtcttcaaga caagtggcc ccaggatctg ccgggcttca gagaggcgct ggaggagtac   480
gcggcagcga tggaggagct gtcgttcaag ctgctggagc tgatcgcccg gagcttgaag   540
```

```
ctgaggcccg accggctgca cggcttcttc aaggaccaga cgacgttcat ccggctgaac    600
cactaccctc catgcccgag cccggacctg cgctgggag tggggcggca caaggacgcg    660
ggggcgctga ccatcctgta ccaggacgaa gtgggcgggc tggacgtccg gcggcgctcc    720
tccgacggcg gcggcggcga gtgggtgcgg gtgaggcccg tgccggagtc gttcgtcatc    780
aacgtcggcg acctcgtcca ggtgtggagc aacgacaggt acgagagcgc ggagcaccgg    840
gtgtcggtga actcggcgag ggagaggttc tccatgccct acttcttcaa cccggcgagc    900
tacaccatgg tggagccggt ggaggagctg gtgagcgacg acgacccgcc caggtacgac    960
gcctacagct ggggcgagtt cttcagcacc aggaagaaca gcaacttcaa gaagctcagc   1020
gtggagaaca ttcagatcgc gcatttcaag aagaccctcg tcctcgccta g            1071

SEQ ID NO: 104         moltype = AA   length = 356
FEATURE                Location/Qualifiers
source                 1..356
                       mol_type = protein
                       organism = Sorghum bicolor
SEQUENCE: 104
MGGLTMEQAF VQAPEHRPKP TVTEATGILV IDLSPLTASD TDAAAVDALA AEVGAASRDW    60
GFFVVVGHGV PAETVARATA AQRAFFALPA ERKAAVRRSE AEPLGYYESE HTKNVRDWKE   120
VFDLVPRDPP PPAAVADGEL VFKNKWPQDL PGFREALEEY AAAMEELSFK LLELIARSLK   180
LRPDRLHGFF KDQTTFIRLN HYPPCPSPDL ALGVGRHKDA GALTILYQDE VGGLDVRRRS   240
SDGGGGEWVR VRPVPESFVI NVGDLVQVWS NDRYESAEHR VSVNSAREF SMPYFFNPAS    300
YTMVEPVEEL VSDDDPPRYD AYSWGEFFST RKNSNFKKLS VENIQIAHFK KTLVLA       356

SEQ ID NO: 105         moltype = DNA   length = 1499
FEATURE                Location/Qualifiers
source                 1..1499
                       mol_type = unassigned DNA
                       organism = Sorghum bicolor
SEQUENCE: 105
cctctcatca caggcccag cctcactctt tcacagcaa gacatcgcag cctcacaacc      60
acacagcaac gtgatcgcca tgggcgggct caccatggag caggccttcg tgcaggcccc   120
cgagcaccgc cccaagccca ccgtcaccga ggccaccggc atcctggtca tcgacctctc   180
gcctctcacc gccagcgaca ccgacgcggg cgcggtggac gcgctggccg ccgaggtggg   240
cgcggcgagc cgggactggg gcttcttcgt ggtggttggc cacggcgtgc ccgcggagac   300
cgtggcgcgc gcggcgacgg cgcagcgcgc gttcttcgcg ctgccggcgg agcggaaggc   360
cgccgtgcgg aggagcgagg cggagccgct cgggtactac gagtcggagc acaccaagaa   420
cgtcagggac tggaaggagg tgttcgacct cgtcccgcgc gatccgccgc cgccagcagc   480
cgtggccgac ggcgagctcg tcttcaagaa caagtggccc caggatctgc cgggcttcag   540
gtgacgaaat caacttatct tttcgatcat attttaccat ttaatagttt aacaataatt   600
gaacttttt tttgcagagag cgctggagg agtacgccag agcgatggag gagctgtcgt   660
tcaagctgct ggagctgatc gcccggagct tgaagctgag gccgaccgg ctgcacggct    720
tcttcaagga ccagacgacg ttcatccggc tgaaccacta ccctccatgc ccgagcccgg   780
acctgcgct gggagtgggg cggacaaagg acgcggggc gctgaccatc ctgtaccagg    840
acgaagtggg cgggctggac gtccggcggc gctcctccga cggcggcggc ggcgagtggg   900
tgcgggtgag gcccgtgccg gagtcgttcg tcatcaacgt cggcgacctc gtccaggtgt   960
ggagcaacga caggtacgag agcgcggagc accgggtgtc ggtgaactcg gcgagggaga  1020
ggttctccat gccctacttc ttcaacccgg cgagctacac catggtggag ccggtggagg  1080
agctggtgag cgacgacgac ccgcccaggt acgacgccta cagctggggc gagttcttca  1140
gcaccaggaa gaacagcaac ttcaagaagc tcagcgtgga gaacattcag atcgcgcatt  1200
tcaagaagac cctcgtcctc gcctagtaa gcagcaggat actacaggtc tacaggacta  1260
ggacaaccg atcgaggtga ccggccgtcg tcttcagatt cagtatatgc gtgtcgccgt  1320
tcgtgttaga acaaattaat aatgtgcgcg ctgtgtgctg tgtgtgtgga gtaaaaaaaa  1380
actaaacatg gatgtgcatg ttcaaaaaaa aaaacatgga tgcgagtatg tttgggaata  1440
ataacaggct tgtgacggtc tggtttattt gcaaattcaa accgaattgg ttgatcttc    1499

SEQ ID NO: 106         moltype = DNA   length = 1490
FEATURE                Location/Qualifiers
source                 1..1490
                       mol_type = unassigned DNA
                       organism = Setaria italica
SEQUENCE: 106
accccacaca cacacccgca ctgcatgcgg cgtcctagct aatcagtcgc tgctggcagc    60
ctcacaagtc acacaaactcc gacgcaggaa agctcgatcc atcgccatgg gcggcttctc   120
catggatcag tccttcgtgc aggccccga gcaccgcccc aagcccaccg tcaccgagg    180
cacgggcatc ccgctcatcg acctctcgcc actcaccggc ggtggcggcg gcgacgcggc   240
cgccgtggac gcgctggccg ccgaggtggg cgcggcgagc cgggactggg gcttcttcgt   300
ggtggtgggc cacggtgtgc cggcggagac cgtggcgcgc gccacggagg cgcagcgcgc   360
gttcttcgcc ctgccggcgg agcggaaagc cgccgtgcgg aggagcgagg cggagccgct   420
cgggtactac gagtcggagc acaccaagaa cgtcagggac tggaaggagg tgtacgacct   480
cgtcccgggc gggcttcagc cgccgatagc cgtggccgac ggcgaggtcg tgttcgaaaa   540
caagtggccc gaagacctgc cgggattcag agaggcgttg gaggagtaca tgcaagcgat   600
ggaagagctg gcattcaaga tactggagct gatcgcccgg agcctgaacc tgaggcctga   660
cagactgcac ggcttcttca aggaccagac caccttcatc cggctcaacc actaccctcc   720
ctgcccgagc cccgaccctg cgctcggcgt cggccggcac aaggacgcag gcactgac    780
catcctctac caggacgacg tcggcgggct cgacgtccgg cgccgttccg acggcgattg   840
ggtccgcgtc aagcctgtcc ccgactcctc atcatcaac gtcggcgacc tcatccaggt    900
ttggagcaac gacaggtacg agagcgcgga gcacgggtt acgtgaact cggccaagga   960
gaggttctct aggcccctact tcttcaaccc ggcgggctac accatggtgg agccggtgga  1020
ggagctggtg agcgaggagg accgccccg gtacgacgcc tacaactggg gcaacttctt  1080
```

```
cagcaccagg aagaacagca acttcaagaa gctgagcgtg gagaacatcc agatcgcgca   1140
tttcaagagg agcgtcgccg cctaggatac gcacagaaag atcccatatg ctgacttgct   1200
gatgaggcga caggcggccg tgtcgtcttc agattcagag actgggagta aacatttgtg   1260
cggtgttctg taatcgtgat gtgacgagaa ctttagatat atgtttggaa ataacagcct   1320
tgtgttggtc tggcttatcc gcaaagtcaa gattttcttc tacattttgg gattattgtt   1380
ggtaagcatt aagcaacgtc cagttcttac ttcttagctc gatcagtgaa cgtaggaccg   1440
gcctctgatg acaagggtga tttatgagaa atgtcatgta tatatgttcc                 1490
```

SEQ ID NO: 107           moltype = DNA   length = 1059
FEATURE                  Location/Qualifiers
source                   1..1059
                         mol_type = unassigned DNA
                         organism = Setaria italica
SEQUENCE: 107
```
atgggcggct tctccatgga tcagtccttc gtgcaggccc ccgagcaccg ccccaagccc     60
accgtcaccg aggccacggg catcccgctc atcgacctct cgccactcac cggcggtggc    120
ggcgcgacgc cggccgccgt ggacgcgctg gccgccgagg tgggcgcggc gagccgggac    180
tggggcttct tcgtggtggt ggggcacggt gtgccggcgg agaccgtggc gtcgcgccacg   240
gaggcgcagc gcgcgttctt cgccctgccg gcggagcgga aagccgccgt gcggaggagc    300
gaggcggagc cgctcgggta ctacgagtcg gagcacacca agaacgtcag ggactggaag    360
gaggtgtacg acctcgtccc gggcgggctt cagccgccga tagccgtggc cgacggcgag    420
gtcgtgttcg aaaacaagtg gcccgaagac ctgccggacg tcagagaggc gttggaggag    480
tacatgcaag cgatggaaga gctggcattc aagatactgg agctgatcgc ccggagcctg    540
aacctgaggc ctgacagact gcacggcttc ttcaaggacc agaccacctt catccggctc    600
aaccactacc ctccctgccc gagccccgac ctcgccctcg cgtcggccg gcacaaggac     660
gccggagcac tgaccatcct ctaccaggac gacgtcggcg gctcgacgt                 720
tccgacggcg attgggtccg cgtcaagcct gtccccgact ccttcatcat caacgtcggc    780
gacctcatcc aggtttggag caacgacagg tacgagagcg cggagcaccg ggttacggtg    840
aactcggcca aggagaggtt ctccaggccc tacttcttca acccggcggg ctacaccatg    900
gtggagccgg tggaggagct ggtgagcgag gaggacccgc ccggtacga cgcctacaac     960
tggggcaact tcttcagcac caggaagaac agcaacttca agaagctgag cgtggagaac   1020
atccagatcg cgcatttcaa gaggagcgtc gccgcctag                           1059
```

SEQ ID NO: 108           moltype = AA   length = 352
FEATURE                  Location/Qualifiers
source                   1..352
                         mol_type = protein
                         organism = Setaria italica
SEQUENCE: 108
```
MGGFSMDQSF VQAPEHRPKP TVTEATGIPL IDLSPLTGGG GDAAAVDAL  AAEVGAASRD     60
WGFFVVVGHG VPAETVARAT EAQRAFFALP AERKAAVRRS EAEPLGYYES EHTKNVRDWK    120
EVYDLVPGGL QPPIAVADGE VVFENKWPED LPGFREALEE YMQAMEELAF KILELIARSL   180
NLRPDRLHGF FKDQTTFIRL NHYPPCPSPD LALGVGRHKD AGALTILYQD DVGGLDVRRR   240
SDGDWVRVKP VPDSFIINVG DLIQVWSNDR YESAEHRVTV NSAKERFSRP YFFNPAGYTM   300
VEPVEELVSE EDPPRYDAYN WGNFFSTRKN SNFKKLSVEN IQIAHFKRSV AA            352
```

SEQ ID NO: 109           moltype = DNA   length = 1886
FEATURE                  Location/Qualifiers
source                   1..1886
                         mol_type = unassigned DNA
                         organism = Setaria italica
SEQUENCE: 109
```
accccacaca cacacccgca ctgcatgcgg cgtcctagct aatcagtcgc tgctggcagc     60
ctcacaagtc acacaactcc gacgcaggaa agctcgatcc atcgccatgg gcggcttctc    120
catggatcag tccttcgtgc aggcccccga gcaccgcccc aaaccccaccg tcaccgaggc   180
cacgggcatc ccgctcatcg acctctcgcc actcaccggc ggtggcggcg acgcggc       240
cgccgtggac gcgctggccg ccgaggtggg cgcggcgagc gggactggg gcttcttcgt    300
ggtgtgggg cacggtgtgc cggcggagac cgtggcgcgc gccacggagg cgcagcgcgc    360
gttcttcgcc ctgccggcgg agcggaaagc cgccgtgcgg aggagcgagg cggagccgct   420
cgggtactac gagtcggagc acaccaagaa cgtcagggac tggaaggagg tgtacgacct   480
cgtcccgggc gggcttcagc cgccgatagc cgtggccgac ggcgaggtcg tgttcgaaaa   540
caagtggccc gaagacctgc cgggattcag gtgaatcaac ttgcgcatat tgttgtttct    600
ggcattgcat atgatcgtcg tgccagtatg ttttgacaat attttgttt tcatatttt     660
ggtgaagatg ggaaaatctt tgttgaaata atcagggaat tttcacatct tttttaatc    720
aaagatagaa taggttcggt tactgaattt tgatgatgaa cagaaaaagc tgtgttttca    780
cttttccatct cagcgatgtt ttttgtgga tgaattctcc taaatttttg tctttttcatg   840
ttaaaacttg aacgggaatt ctcgcagaga ggcgttggag gagtacatgc aagcgatgga    900
agagctggca ttcaagatac tggagctgat cgccgggagc ctgaacctga ggcctgcag     960
actgcacggc ttcttcaagg accagaccac cttcatccgg ctcaaccact cccctctg     1020
cccgagcccc gacctcgccc tcggcgtcgg ccgcacaag gacgccgag cactgaccat    1080
cctctaccag gacgacgtcg gcgggctcga cgtccgcgc cgttccgacg gcgattgggt    1140
ccgcgtcaag cctgtccccg actccttcat catcaacgtc ggcgacctca tccaggtaca   1200
acaaacaaaa cacacgtca ttctcaaatc tttttcgtgct gttaatgctc attcacgaat    1260
tgatatctta catgaacgac tgagacttt tcaggtttgg agcaacgaca gtacgagag     1320
cgcggagcac cgggttacgg tgaactcggc caaggagagg ttctccaggc cctacttctt    1380
caacccggcg ggctacacca tggtggagcc ggtggaggag ctggtgagcg aggaggaccc   1440
gccccggtac gacgcctaca actggggcaa cttcttcagc accaggaaga acagcaactt   1500
caagaagctg agcgtggaga acatccagat cgcgcatttc aagaggagcg tcgccgccta    1560
ggatacgcac agaaagatcc catatgctga cttgctgatg aggcgacagg cggccgtgtc    1620
```

```
gtcttcagat tcagagactg ggagtaaaca tttgtgcggt gttctgtaat cgtgatgtga   1680
cgagaacttt agatatatgt ttggaaataa cagccttgtg ttggtctggc ttatccgcaa   1740
agtcaagatt ttcttctaca tttttgggatt attgttggta agcattaagc aacgtccagt   1800
tcttacttct tagctcgatc agtggacgta ggaccggcct ctgatgacaa gggtgattta   1860
tgagaaatgt catgtatata tgttcc                                        1886

SEQ ID NO: 110          moltype = DNA   length = 1379
FEATURE                 Location/Qualifiers
source                  1..1379
                        mol_type = unassigned DNA
                        organism = Oryza sativa
SEQUENCE: 110
aagccacacg cacacacaca cacacgctga cacacgagac gaacacttgt gctacagctt   60
ctcgccacca gctactgatc gaccatgggc ggcctctcca tggaccaggc gttcgtgcag   120
gcccccgagc accgcccaa ggcgtccgtc gccgaggccg acggcatccc ggtcatcgac    180
ctctcccctc tcctcgccgc cggcgatggc gacgccgacg gggtgacgc gctcgcggcg    240
gaggtcggga gggcgagccg ggactgggc ttcttcgtgg tggtgcgcca cggtgtgccc    300
gcggaggcgg tggcgcgcgc ggcgagggcg cagaggacgt tcttcgcgct gccgccgagg   360
cggagggcgg ccgtggcgcg gagcgaggcg gcgccgatgg ggtactacgc gtccgagcac   420
accaagaacg tcagggactg gaaggaggtg ttcgacctcg tcccgcgcca gacgccgccg   480
ccgccgacga ccgccgtggc cgacggcgac ctggtgttcg acaacaagtg gcccgacgac   540
ctgccgggat tcagggaggc aatggcagta tacggccagg tgtgagga gctggcgttc     600
aagctgctgg agctgatcgc caggagcctc ggcctgagac ccgaccgcct ccatggcttc   660
ttcaaggacg accagaccac cttcatccgg ctcaaccact accctcctg cccgagcccc    720
gacctcgccc tcggcgtcgg ccgccacaag gacgccggcg cgctcaccgt gctctaccag   780
gacgatgtcg gcggcctcga cgtccgccgc cgatccgacg gcgagtgggt gcgcgtcagg   840
cccgtccctc actccttcat catcaacgtc ggcgacatca tccaggtgtg gagcaatgac   900
aggtacgaga gcgcggagca ccgggtggcg gtgaacgtgg agaaggagag gttctccatc   960
cctttcttct tcaaccgggc gggccacacc atggtggagc cactggagga ggtcgtgagc  1020
gacgagagcc cggccaggta caaccccctac aactgggacg aattcttcag caccaggaag 1080
aacagcaact tcaagaagct ggacgtggag aacgtccaga tcacgcattt caggaagaat  1140
taacgcgccg gctagatcat gttcagtaaa ttttcagatg atgatgctg gacaaccata   1200
tagcctttgc gtcataagtt aataatgtct gtgacagtat atcatgtaaa caatcgtatg  1260
atgtggcttc tctatctgcc ggtgatggta atgtgacatt gtagaagagg gtttgtgaga  1320
tacttccttc acttaacttt tacgaatgaa tatagacaac cacaacatcc ttgtcgtga   1379

SEQ ID NO: 111          moltype = DNA   length = 1059
FEATURE                 Location/Qualifiers
source                  1..1059
                        mol_type = unassigned DNA
                        organism = Oryza sativa
SEQUENCE: 111
atgggcggcc tctccatgga ccaggcgttc gtgcaggccc ccgagcaccg ccccaaggcg   60
tccgtcgccg aggccgacgg catcccggtc atcgacctct cccctctcct cgccgccggc   120
gatggcgacg ccgacggggt ggacgcgctc gcggcggagg tcgggagggc gagccgggac  180
tggggcttct tcgtggtggt gcgccacggt gtgcccgcgg aggcggtggc gcgcgcggcg   240
gaggcgcaga ggacgttctt cgcgctgccg ccggagcgga gggcgccggc ggccggagcc   300
gaggcggcgc cgatgggta ctacgcgtcc gagcacacca gaacgtcag ggactggaag    360
gaggtgttcg acctcgtccc gcgccagacg ccgccgccgc cgacgaccgc cgtggccgac   420
ggcgacctgt gttcgacaa caagtggccc gacgacctgc cgggattcag ggaggcaatg   480
gaggagtacg gcgaagcggt ggaggagctg cgttcaagc tgctggagct gatcgccagg    540
agcctcggcc tgagacccga ccgcctccat ggcttcttca aggacgacca gaccaccttc   600
atccggctca accactaccc tcccgcccg agccccgacc tcgccctcgg cgtcggccgc    660
cacaaggacg ccgcgcgct caccgtgctc taccaggacg atgtcggcgg cctcgacgtc    720
cgccgccgat ccgacggcga gtgggtgcgc gtcaggcccg tccctcactc cttcatcatc   780
aacgtcggcg acatcatcca ggtgtggagc aatgacaggt acgagagcgc ggagcaccgg   840
gtggcggtga acgtggagaa ggagaggttc tccatccctt tcttcttcaa cccggcgggc   900
cacaccatgt ggagccact ggaggaggtc gtgagcgacg agagcccggc caggtacaac    960
ccctacaact ggggcgaatt cttcagcacc aggaagaaca gcaacttcaa gaagctggac  1020
gtggagaacg tccagatcac gcatttcagg aagaattaa                         1059

SEQ ID NO: 112          moltype = AA    length = 352
FEATURE                 Location/Qualifiers
source                  1..352
                        mol_type = protein
                        organism = Oryza sativa
SEQUENCE: 112
MGGLSMDQAF VQAPEHRPKA SVAEADGIPV IDLSPLLAAG DGDADGVDAL AAEVGRASRD    60
WGFFVVVRHG VPAEAVARAA EAQRTFFALP PERRAAVARS EAAPMGYYAS EHTKNVRDWK   120
EVFDLVPRQT PPPPTTAVAD GDLVFDNKWP DDLPGFREAM EEYGEAVEEL AFKLLELIAR   180
SLGLRPDRLH GFFKDDQTTF IRLNHYPPCP SPDLALGVGR HKDAGALTVL YQDDVGGLDV   240
RRRSDGEWVR VRPVPHSFII NVGDIIQVWS NDRYESAEHR VAVNVEKERF SIPFFFNPAG   300
HTMVEPLEEV VSDESPARYN PYNWGEFFST RKNSNFKKLD VENVQITHFR KN          352

SEQ ID NO: 113          moltype = DNA   length = 2027
FEATURE                 Location/Qualifiers
source                  1..2027
                        mol_type = unassigned DNA
                        organism = Oryza sativa
```

```
SEQUENCE: 113
aagccacacg cacacacaca cacacgctga cacacgagac gaacacttgt gctacagctt   60
ctcgccacca gctactgatc gaccatgggc ggcctctcca tggaccaggc gttcgtgcag  120
gcccccgagc accgcccaa ggcgtccgtc gccgaggccg acggcatccc ggtcatcgac  180
ctctcccctc tcctcgccgc cggcgatggc gacgccgacg gggtggacgc gctcgcggcg  240
gaggtcggga gggcgagccg ggactggggc ttcttcgtgg tggtgcgcca cggtgtgccc  300
gcggaggcgg tggcgcgcgc ggcggaggcg cagaggacgt tcttcgcgct gccgccggag  360
cggagggcgg ccgtggcgcg gagcgaggcg gcgccgatgg ggtactacgc gtccgagcac  420
accaagaacg tcagggactg gaaggaggtg ttcgacctcg tcccgcgcca gacgccgccg  480
ccgccgacga ccgccgtggc cgacgccgac ctggtgttcg acaacaagtg gcccgacgac  540
ctgccgggat tcaggtcagg tcaccacatc gatcgatcgt cttcttcatc ctcgcatcaa  600
ttcagttcaa cctcatcgaa ttcttgagca gggaggcaat ggaggagtac ggcgaagcgg  660
tggaggagct ggcgttcaag ctgctggagc tgatcgccag gagcctcggc ctgagacccg  720
accgcctcca tggcttcttc aaggacgacc agaccacctt catccggctc aaccactcca  780
ctccctgccc gagccccgac ctcgccctcg gcgtcggccg ccacaaggac gccggcgcgc  840
tcaccgtgct ctaccaggac gatgtcgcg gcctcgacgt ccgccgccga tccgacggcc  900
agtgggtgcg cgtcaggccc gtccctcact ccttcatcat caacgtcggc gacatcatcc  960
aggtactttt ttttttgagc agctacatat ttatcaacaa attttcttct aacaatttat 1020
cggacataaa tatattacaa tgaaagaata attgtatcat aacttgtgtg tcctatatg  1080
taagttttag aaatcctata gtaacatggt attttcgcga aagcggagat tgtgagaccg 1140
tatcttttca cccatgcgcg tcatatgatt ttttttttctt gccaacttaa ataaatttca 1200
aagtaaatct aatagattaa aattatgtga aacttacata taagtttttct acggtaacac 1260
gctatttca cgaaacggag gtcgttccaa gttgaatgaa tcttgaagta aatctaacga 1320
tttaaaatta tgtgcataca cgttatatta cagttatata caagttataa tataattaca 1380
ctacaattat aacggtattc atagttgaca aactttaaa agagaattag ttaataaata 1440
tataacaaca ttgtagttta attgttacta tttgacatca tttttatttg cattttgaat 1500
ttgactgaaa aaattgagag tgcgcttgtc caggtgtgga gcaatgacag gtacgagagc 1560
gcggagcacc gggtggcggt gaacgtggag aaggagaggt tctccatccc tttcttcttc 1620
aacccggcgg gccacaccat ggtggagcca ctggaggagg tcgtgagcga cgagagcccg 1680
gccaggtaca accccctacaa ctggggcgaa ttcttcagca ccaggaagaa cagcaactc 1740
aagaagctgg acgtccagaa cgtccagatc acgcatttca ggaagaatta acgcgccggc 1800
tagatcatgt tcagtaaatt ttcagatgat gatgcgtgga caaccatata gcctttgcgt 1860
cataagttaa taatgtctgt gacagtatat catgtaaaca atcgtatgat gtggcttctc 1920
tatctgccgg tgatggtaat gtgacattgt agaagagggt ttgtgagata cttccttcac 1980
ttaacttta cgaatgaata tagacaacca caacatcctt gtcgtga              2027

SEQ ID NO: 114          moltype = DNA  length = 1747
FEATURE                 Location/Qualifiers
source                  1..1747
                        mol_type = unassigned DNA
                        organism = Triticum aestivum
SEQUENCE: 114
tcactcaagg ccacaacaca ctcgccagtc catcgccacc atacgtgaca acttgagtta   60
cttgatctgt tgctcatcga tctcgacatc gccatgggcg gcctctccat ggaccaggcc  120
ttcgtgcagg cccccgagca tcgcaccaag gcgaacctcg ccgacgcggc cggcatcccg  180
gtcatcgacc tctcccctct cgccgccggc gacaaggccg gcctggacgc cctcgcggcc  240
gaggtgggca gggcgagccg tgactggggg ttcttcgtgg tggtgcgcca cggcgtgccg  300
gcggagacgg tggcgcgggc gctgaggcg cagagggcct tcttcgcgct gcccgcggac  360
cggaaggcgg ccgtgcggag ggacgaggcg gcgccgctgg ggtactacga gtcggagcac  420
accaagaacg tcagggactg gaaggaggtg ttcgacctcg tccccgcga gccgccgccg  480
cctgccgcgg ttgccgacgg cgagctcatg ttcgagaaca agtggcccga ggacctgccg  540
gggttcagag aggctctcga agagtacgag aaagcgatgg aggagctggc gttcaagctg  600
ctggagctga tcgcccggag cctgggactg agaccggacc ggctgcacgg cttcttcaag  660
gaccagacca ccttcatccg gctgaaccac tacccgccct gccccagccc cgacctcgcc  720
ctcggcgtcg gtgccacaa ggacgccggc gcgtcacca tcctctacca ggacgacgtc  780
ggcgggctcg acgtccggcg ccgctccgac ggcgagtggg tgcgcgtcag gcctgtcccg  840
gactcctacg tcatcaacgt cggcgacatc atccaggtgt ggagcaacga caggtacgag  900
agcgcggagc acagggtgtc ggtgaactcg cacaaggaga ggtctccat gccctacttc  960
ttcgaccccg ggagcgacgc catgatcgag ccgttggagg agatggtgag cgacgaaagg 1020
ccggccaggt acgacgccta caactggggc aacttcttca gcaccaggaa gaacagcaac 1080
ttcaggaagc tcgccgtcga aaacgtccag atcgcacact tcagaaagga ccgaccttaa 1140
atgaaggatc cctcatgaat tcatgatcct tccgctctcc tcagtgatcc tagtgctaca 1200
actacaagca tctccccgtt tgtagtaatc atatataaat aagtattccc tccgtaaact 1260
aatataagag catttaaaac actactctag tgatctaatt gtcttatat tagtttacag 1320
agagagtatt gtgtattaat aatgactttc tctgtttcaa aataagtgat gacgtggttt 1380
tagttcaatt ttttttagag aggagcatc tgacgggcct taaactgagg accttagagt 1440
acaaacaagg ttcgacgaaa gtaagtttaa gggatacaag gccgtagcca acaaaacgcg 1500
acgcagcgcg caatctaaaa tcagcgtgct gtcaaggtag ctggagacgt ccatgccgtt 1560
aatctctctc aagaagctcg ccgaagctca gtgcaccttg cgtgcactct tgtgaagagc 1620
accttcacgt gtcctttgtc ctgagatttt gtcaacagtt tccatgactg caagaaaaac 1680
actagtttgt ataatagctc agcgggatgt cgaatgaatt gcccctcaat caaagcttta 1740
tttctag                                                            1747

SEQ ID NO: 115          moltype = DNA  length = 1047
FEATURE                 Location/Qualifiers
source                  1..1047
                        mol_type = unassigned DNA
                        organism = Triticum aestivum
SEQUENCE: 115
```

-continued

```
atgggcggcc tctccatgga ccaggccttc gtgcaggccc ccgagcatcg caccaaggcg    60
aacctcgccg acgcgccggg catcccggtc atcgacctct ccctctcgc cgccggcgac   120
aaggccggcg tggacgccct cgcggccgag gtgggcaggg cgagccgtga ctggggttc    180
ttcgtggtgg tgcgccacgg cgtgccggcg gagacggtgg cgcgggcgct ggaggcgcag   240
agggccttct tcgcgctgcc cgcggaccgg aaggcggcg tgccggaggg agaggcggcg   300
ccgctggggt actacgagtc ggagcacacc aagaacgtca gggactggaa ggaggtgttc   360
gacctcgtcc ccgcgagcc gccgccgcct gccgcgttg ccgacggcga gctcatgttc     420
gagaacaagt ggcccgagga cctgccgggg ttcagagagg ctctcgaaga gtacgagaaa   480
gcgatggagg agctggcgtt caagctgctg gagctgatcg cccggagcct gggactgaga   540
ccggaccggc tgcacggctt cttcaaggac cagaccacct tcatccggct gaaccactac   600
ccgcccctgcc ccagcccga cctcgccctc ggcgtcggtc gccacaagga cgccggcgcg   660
ctcaccatcc tctaccagga cgacgtcggc gggctcgacg tccggcgccg ctccgacggc   720
gagtgggtgc gcgtcaggcc tgtcccggac tcctacgtca tcaacgtcgg cgacatcatc   780
caggtgtgga gcaacgacag gtacgagagc gcggagcaca gggtgtcggt gaactcgaac   840
aaggagaggt tctccatgcc ctacttcttc gaccccggga gcgacgccat gatcgagccg   900
ttggaggaga tggtgagcga cgaaaggccg gccaggtacg acgcctacaa ctggggcaac   960
ttcttcagca ccaggaagaa cagcaacttc aggaagctcg ccgtcgaaaa cgtccagatc  1020
gcacacttca gaaaggaccg accttaa                                      1047
```

SEQ ID NO: 116          moltype = AA    length = 348
FEATURE                 Location/Qualifiers
source                  1..348
                        mol_type = protein
                        organism = Triticum aestivum
SEQUENCE: 116

```
MGGLSMDQAF VQAPEHRTKA NLADAAGIPV IDLSPLAAGD KAGLDALAAE VGRASRDWGF    60
FVVVRHGVPA ETVARALEAQ RAFFALPADR KAAVRRDEAA PLGYYESEHT KNVRDWKEVF   120
DLVPREPPPP AAVADGELMF ENKWPEDLPG FREALEEYEK AMEELAFKLL ELIARSLGLR   180
PDRLHGFFKD QTTFIRLNHY PPCPSPDLAL GVGRHKDAGA LTILYQDDVG GLDVRRRSDG   240
EWVRVRPVPD SYVINVGDII QVWSNDRYES AEHRVSVNSH KERFSMPYFF DPGSDAMIEP   300
LEEMVSDERP ARYDAYNWGN FFSTRKNSNF RKLAVENVQI AHFRKDRP               348
```

SEQ ID NO: 117          moltype = DNA    length = 1863
FEATURE                 Location/Qualifiers
source                  1..1863
                        mol_type = unassigned DNA
                        organism = Triticum aestivum
SEQUENCE: 117

```
tcactcaagg ccacaacaca ctcgccagtc catcgccacc atacgtgaca acttgagtta    60
cttgatctgt tgctcatcga tctcgacatc gccatgggcg gcctctccat ggaccaggcc   120
ttcgtgcagg cccccgagca tcgcaccaag gcgaacctcg ccgacgcggc cggcatcccg   180
gtcatcgacc tctcccctct cgccgccggc gacaaggccg gctggacgc cctcgcggcc    240
gaggtgggca gggcgagccg tgactggggg ttcttcgtgg tggtgcgcca cggcgtgccg   300
gcggagacgg tggcgcgggc gctggaggcg cagagggcct tcttcgcgct gcccgcggac   360
cggaaggcgg ccgtgcggag ggacgaggcg gcgccgctgg ggtactacga gtcggagcac   420
accaagaacg tcagggactg gaaggaggtg ttcgacctcg tccccgcga gccgccgccg    480
cctgccgcgg ttgccgacgg cgagctcatg ttcgagaaca agtggcccga ggacctgccg   540
gggttcaggt acgtcatca actcaatcaa ttctgcgacc ccgagagaaa tggttcacta    600
ttattcgtgg ttcatacgta tgattcagac gttaatctcg atgcaaattg atttgtgcat   660
gcagagaggc tctcgaagag tacgagaaag cgatggagga gctggcgttc aagctgctgg   720
agctgatcgc ccggagcctg ggactgagac cggaccggct gcacggcttc ttcaaggac    780
agaccacctt catccggctg aaccactacc cgccctgccc cagccccgac ctcgccctcg   840
gcgtcggtcg ccacaaggac gccggcgcgc tcaccatcct ctaccaggac gacgtcggcg   900
ggctcgacgt ccggcgccgc tccgacggcg agtgggtgcg cgtcaggcct gtcccggact  960
cctacgtcat caacgtcggc gacatcatcc aggtgtggag caacgacagg tacgagagcg  1020
cggagcacag ggtgtcggtg aactcgcaca aggagaggtt ctccatgccc tacttcttcg  1080
accccgggag cgacgccatg atcgagccgt tggaggagat ggtgagcgac gaaaggccgg  1140
ccaggtacga cgcctacaac tggggcaact tcttcagcac caggaagaac agcaacttca  1200
ggaagctcgc cgtcgaaaac gtccagatcg cacacttcag aaaggaccga ccttaaatga  1260
aggatccctc atgaattcat gatccttccg ctctcctcag tgatcctagt gctacaacta  1320
caagcatctc cccgtttgta gtaatcatat ataataagt attccctccg taaactaata   1380
taagagcatt taaacactca ctctagtgat ctaaatgctc ttatattagt ttacagagag  1440
agtattgtgt attaataatg actttctctg tttcaaaata agtgatgacg tggttttagt  1500
tcaattttttt ttagagagga ggcatctgac ctctgaggacct tagagtacaa           1560
acaaggttcg acgaaagtaa gttaaggga tacaaggccg tagccaacaa acgcgacgc     1620
agcgcgcaat ctaaaatcag cgtgctgtca aggtagctgg agacgtccat gccgttaatc  1680
tctctcaaga agctcgccga agctcagtgc accttgcgtg cactcttgtg aagagcacct  1740
tcacgtgtcc tttgtcctga gattttgtca acagttccca tgactgcaag aaaaacacta  1800
gtttgtataa tagctcagcg ggatgtcgaa tgaattgccc tcaatcaaaa gctttattc    1860
tag                                                                 1863
```

SEQ ID NO: 118          moltype = AA    length = 349
FEATURE                 Location/Qualifiers
source                  1..349
                        mol_type = protein
                        organism = Hordeum vulgare
SEQUENCE: 118

```
MGGLSMGQAF VQAPEHRTKP TLADADGIPV IDLSPLAAGD EAGVDALAAE VGRASRDWGF    60
FVVVRHGVPA ETVARALEAQ RAFFALPAER KAAVRRDEAA PLGYYESEHT KNVRDWKEVF   120
```

```
DFVPREPPPP AAVADGELVF ENKWPEDLPG FRVAFEEYAK AMEELAFKLL ELIARSLGLT    180
PDRLNGFFKD HQTTFIRLNH YPPCPSPDLA LGVGRHKDAG ALTVLYQDDV GGLDVRHRSD    240
GEWVRVRPVP DSYVINVGDI IQVWSNDRYE SAEHRVSVNS DKERFSMPYF FNPGSDAMVE    300
PLEEMVSDER PARYDAYNWG HFFSTRKNSN FKKLDVENVQ IAHFRKLHL                349

SEQ ID NO: 119           moltype = DNA  length = 1963
FEATURE                  Location/Qualifiers
source                   1..1963
                         mol_type = unassigned DNA
                         organism = Sorghum bicolor
SEQUENCE: 119
tataaatacc acgccatgta cttctctgct tctacacttc tccagcttct ctcatgccat     60
accactagtg caaggtccta gatttacact tggtgctaca gcttcttcct ccctccctcc    120
cctctctagg cagctagcac gcagcgcagc acacgaaaca tctattgacc ggccgcctcc    180
gccggggatc cataattact atactaccaa tcggccagcg tcatgccgac gccgtcgcac    240
ctcgcgaacc cgcgctactt cgacttccgt gcggcgcggc gggtgccgga gacgcacgcc    300
tggccggggc tgcacgacca ccccgtcgtg gacggcggcc gccggggcc agacgccgtc     360
cccgtggtgg acctcgcggg ggcggcggac gagccggacc ccgcggtggt ggcccaagtg    420
gcgcgcgccg ccgagcaatg gggcgcgttc ctgctcacgg gcacgggcgt ccccgcggag    480
ctgctgcgc gcgtcgagga ccggatcgcc accatgttcg cgctgccagc ggacgacaag     540
atgcgcgccg tgcgcgggcc tggcgacgcc tgcggctacg gctccccgcc catctcctcc    600
ttcttctcca agtgcatgtg gtcggaggga tacacctcct cgccggccaa cctccgcgcc    660
gacctccgca agctctggcc taaggccggc gacgactaca ccagcttctg tgatgtgatg    720
gaggagttcc acaagcacat gcgtgccctc cggacaagc tgctggagct gttcctcatg     780
gcgctggggc tcaccgacga gcaggtcggc ggcgtgagg cggagcggag gatcgccgag     840
acgatgaccg ccaccatgca cctcaactgg taccctcggg accgggaccc gccgcggacc    900
ctggggctga tcgcgcacac cgactcgggc ttcttcacct tcgtgctgca gagcctcgtc    960
ccggggctgc agctcttccg ccacgccccg gaccggtggg tggcggtgcc ggcggtaccg    1020
ggcgccttcg tcgtcaacgt gggcgacctc ttccacatcc tcaccaacgg ccggttccac    1080
agcgtgtacc accgcgccgt cgtgaaccgg gacctcgaca ggatatctct cggctacttc    1140
ctcggcccgc cgccgcacgc caaggtggcg ccgctaaggg aggccgtgcc gcccggccgc    1200
accccccgcgt accgcgccgt cacgtggccc gagtacatgg gcgtccgcaa gaaggccttc    1260
accaccggcg catccgcgct caagatggtc gccctcgccg ccgccgccgc cgccgccgac    1320
ctcgacgatg acgccggtgc tggcgccgcc gccgaacctg tcgtccatca gcagctactc    1380
gtctcgtcgt agccgatcga tcgccggatc ggtcgagact gatgatgatg atgcatatat    1440
actcgtcgat ggagtagaca gactaatcaa gcaaccctga aactatgaat gcatgcgtgc    1500
gcttcgtgct tgcttgcgca tgcagctagc aggcttcatt ccgttccgca gctgctctgc    1560
tccaacctgc tctgctggat tgatgtatat ggtagaagaa ttaagagatc gatggatgac    1620
ggaggaagaa gaaacgaag acgacgatga ggaaaaggac acgctgtacg tagctggttc     1680
ttctagtcta gtttacagca ggccgggcgg ccggctgctg cttccaatcg agtttgtcgt    1740
tactgacgat tgttagtgga tcgattaact aatctggaat tctggattat taatataatg    1800
catgtggttt ggcatctggc gtaaagcagg taatggtacc tagccagtag ccagtagcca    1860
ggctggtcaa tgataggtct atccctgat cctgtactgt tgtttctttc ggtctttctg      1920
agagagaaaa aaaacgaata tatggcgtac tcaattcatc aaa                      1963

SEQ ID NO: 120           moltype = DNA  length = 1170
FEATURE                  Location/Qualifiers
source                   1..1170
                         mol_type = unassigned DNA
                         organism = Sorghum bicolor
SEQUENCE: 120
atgccgacgc cgtcgcacct cgcgaacccg cgctacttcg acttccgtgc ggcgcggcgg     60
gtgccggaga cgcacgcctg gccggggctg cacgaccacc ccgtcgtgga cggcggcgcg    120
ccggggccag acgccgtccc cgtggtggac ctcgcggggg cggcggacga gccgagagcc    180
gcggtggtgg cccaagtggc gcgcgccgcc gagcaatggg gcgcgttcct gctcacgggg    240
cacggcgtcc ccgcggagct gctggcgcgc gtcgaggacc ggatcgccac catgttcgcg    300
ctgccagcgg acgacaagat gcgcgccgtg cgcgggcctg gcgacgcctg cggctacggc    360
tccccgccca tctcctcctt cttctccaag tgcatgtggt cggagggata caccttctcg    420
ccggccaacc tccgcgccga cctccgcaag tctggccta aggccggcga cgactacacc      480
agcttctgtg atgtgatgga ggagttccac aagcacatgc gtgccctcgc ggacaagctg    540
ctggagctgt tcctcatggc gctggggctc accgacgagc aggtcggcgg cgtgaggcg     600
gagcggagga tcgccgagac gatgaccgcc accatgcacc tcaactggta ccctcggtgc    660
ccggaccccg gccgcgcgct ggggctgatc gcgcacaccg actcgggctt cttcaccttc    720
gtgctgcaga gcctcgtccc ggggctgcag tcttccgca cgccccggac cggtggttc      780
gcggtgccgg cggtaccggg cgccttcgtc gtcaacgtgg cgacctctt ccacatcctc      840
accaacggcc ggttccacag cgtgtaccac cgcgccgtcg tgaaccggga cctcgacagg    900
atatctctcg gctacttcct cggccgccgc cgcacgcca aggtggcgcc gctaaggag       960
gccgtgccgc cggccgcac cccgcgtac cgcgccgtca cgtggcccga gtacatgggc      1020
gtccgcaaga aggccttcac caccggcgca tccgcgctca agatggtcgc cctcgccgcc    1080
gccgccgccg ccgccgacct cgacgatgac gccggtgctg gcgccgccgc cgaacctgtc    1140
gtccatcagc agctactcgt ctcgtcgtag                                     1170

SEQ ID NO: 121           moltype = AA  length = 389
FEATURE                  Location/Qualifiers
source                   1..389
                         mol_type = protein
                         organism = Sorghum bicolor
SEQUENCE: 121
MPTPSHLANP RYFDFRAARR VPETHAWPGL HDHPVVDGGA PGPDAVPVVD LAGAADEPRA     60
```

```
AVVAQVARAA EQWGAFLLTG HGVPAELLAR VEDRIATMFA LPADDKMRAV RGPGDACGYG   120
SPPISSFFSK CMWSEGYTFS PANLRADLRK LWPKAGDDYT SFCDVMEEFH KHMRALADKL   180
LELFLMALGL TDEQVGGVEA ERRIAETMTA TMHLNWYPRC PDPRRALGLI AHTDSGFFTF   240
VLQSLVPGLQ LFRHAPDRWV AVPAVPGAFV VNVGDLFHIL TNGRFHSVYH RAVVNRDLDR   300
ISLGYFLGPP PHAKVAPLRE AVPPGRTPAY RAVTWPEYMG VRKKAFTTGA SALKMVALAA   360
AAAAADLDDD AGAGAAAEPV VHQQLLVSS                                    389

SEQ ID NO: 122          moltype = DNA   length = 2321
FEATURE                 Location/Qualifiers
source                  1..2321
                        mol_type = unassigned DNA
                        organism = Sorghum bicolor
SEQUENCE: 122
tataaatacc acgccatgta cttctctgct tctacacttc tccagcttct ctcatgccat   60
accactagtg caaggtccta gatttacact tggtgctaca gcttcttcct ccctccctcc   120
cctctctagg cagctagcac gcagcgcagc acacgaaaca tctattgacc ggccgcctcc   180
gccggggatc cataattact atactaccaa tcggccagcg tcatgccgac gccgtcgcac   240
ctcgcgaacc cgcgctactt cgacttccgt gcggcgggtg ccggagacgc acgcc         300
tggccggggc tgcacgacca ccccgtcgtg gacggcggcg cgccggggcc agacgccgtc   360
cccgtggtgg acctcgcggg ggcggcggac gagccgagag ccgcggtggt ggcccaagtg   420
gcgcgcgccg ccgagcaatg gggcgcgttc ctgctcacgg gcacggcgt ccccgcggag    480
ctgctggcgc gcgtcgagga ccggatcgcc accatgttcg cgctgccagc ggacgacaag   540
atgcgcgccg tgcgcgggcc tggcgacgcc tgcggctacg gctccccgcc catctcctcc   600
ttcttctcca agtgcatgtg gtcggaggga tacaccttct cgccgccaa cctccgcgcc    660
gacctccgca agctctggcc taaggccggc gacgactaca ccagcttctg gtacgtgcac   720
ccgccgccg ccgccgccca cacaccgtac ccacacacgt gcgcgctgc gcctagctac    780
tagtagctgc tttgctttgc ttacctttga ttctcgcctt tgccatgcat atgcatgatg   840
cacgtacagg tactgcaggt acaacatgtc acacgcacgc acgcacgcac aacccatagt   900
ccgatacgat acatcatcga tcgacgtgtc gtcaccgtct aaggccatgc atgcatgcaa   960
gcacacgcct agaccttttt agcatgctgg ctgacgagga gtatactagc taataagcta   1020
cttgtcactg cgcgtcttgc ttaattacac tagtgcatat ttctacagtg atgtgatgga   1080
ggagttccac aagcacatgc gtgccctcgc ggacaagctg ctggagctgt tcctcatggc   1140
gctgggctc accgacgagc aggtcggcgg cgtggaggcg gagcggagga tcgccgagac   1200
gatgaccgcc accatgcacc tcaactggta ccctcggtgc ccgaccgcg gccgcgcgct    1260
ggggctgatc gcgcacaccg actcgggctt cttcaccttc gtgctgcaga gcctcgtccc    1320
ggggctgcag ctcttccgcc acgccccgga ccggtgggtg gcggtgccgg cggtaccggg    1380
cgccttcgtc gtcaacgtgg gcgacctctt ccacatcctc accaacggcc ggttccacag   1440
cgtgtaccac cgcgccgtcg tgaacccggga cctcgacagg atatctctcg gctacttcct   1500
cggcccgccg ccgcacgcca aggtcggcgcc gctaaggagg ccgtgccgc ccggccgcac   1560
ccccgcgtac cgcgccgtca cgtgcccga gtacatgggc gtccgcaaga aggccttcac   1620
caccggcgca tccgcgctca agatggtcgc cctcgccgcc gccgccgccg ccgccgacct   1680
cgacgatgac gccggtgctg gcgccgccgc cgaacctgtc gtccatcagc agctactcgt   1740
ctcgtcgtag ccgatcgatc gccggatcgg tcgagactga tgatgatgat gcatatatac   1800
tcgtcgatgg agtagacaga ctaatcaagc aaccctgaaa ctatgaatgc atgcgtgcgc   1860
ttcgtgcttg cttgcgcatg cagctagcag gcttcattcc gttccgcagc tgctctgctc   1920
caacctgctc tgctggattg atgtatatgg tagaagaatt aagagatcga tggatgacgg   1980
aggaagaaga acgaagac gacgatgagg aaaaggacac gctgtacgta gctggttctt    2040
ctagtctagt ttacagcagg ccgggcggcc ggctgctgct tccaatcgag tttgtcgtta   2100
ctgacgattg ttagtggatc gattaactaa tctggaattc tggattatta atataatgca   2160
tgtggtttgg catctggcgt aaagcaggta atggtaccta ccagtagcc agtagccagg    2220
ctggtcaatg ataggtctat accctgatcc tgtactgttg tttctttcgg tctttctgag   2280
agagaaaaaa aacgaatata tggcgtactc aattcatcaa a                      2321

SEQ ID NO: 123          moltype = DNA   length = 1796
FEATURE                 Location/Qualifiers
source                  1..1796
                        mol_type = unassigned DNA
                        organism = Setaria italica
SEQUENCE: 123
actagtgcaa ggtcctagat ttacacttgg tgcttgcttg tttcttccta gttgctactg    60
gtagcacgca gtggctggct ggccgtaatc tattgtctgg gctcgatcgg tgattaggaa    120
gtagccaaag caagctaagg ccgccgccgc cgccgccatg ccgacgccgt cgcacctcaa    180
gaacccgctc tacttcgact tccgcgccgc gcggcgggtg ccggagtccc acgcctggcc    240
ggggtcgac gaccaccccg tggtggacgg cggcggccg cggggtccc cggacgccgt      300
gccggtggtg gacctcgcgc agccgggcgc cgcggcggtg gccgcgtgg cgcgcgccgc   360
cgagcagtgg ggcgcgttcc tgctcaccgg ccacggcgtc cccgcggagc tcctggcgcg   420
cgtcgaggac cgcgtcgcgt gcatgttcgc gctgccggcc gccgacaaga tgcgcgccgt   480
gcgcgggccg ggggacgcct gcggctacgg ctcgccgccc atctcctcct tcttctccaa   540
gtgcatgtgg tccgagggct acaccttctc gccggccca cctccgccgcc accttcctcc... 600
gctctggccc aaggccggcg acgactacga cagcttctgt gacgtgatgg aggagttcca   660
caaggagatg cgcgccctcg ccgacaggct cctggagctg ttcctcaggg cgctcggct    720
caccggcgag caggtcggcg ccgtcgaggc ggagcggagg atcggcgaga cgatgaccgc    780
caccatgcac ctcaactggt atccgaggtg ccggacccg cggcgcgcgc tggggctgat    840
cgcgcacacg gactcgggct tcttcacctt cgtgctgcag agctcgtcgg agcctcgtcc     900
gctgttccgc cacgccccca accgtgtggg ggcggtgccg gccgtgccgg gcgccttcgt    960
cgtcaacgtc ggcgacctct tccacatcct cacgaacggc cgcttccaca gcgtgtacca   1020
ccgcgccgtc gtcaaccggg acctcgaccg gatatcgctc ggctacttcc tcggcccgcc   1080
gccccacgcc aaggtggcgc cgctccggga ggtcgtgccg cggccgggg ccccgcccta    1140
ccgcgccgtc acgtggcccg agtacatggg cgtccgcaag aaggccttca ccaccggcgc   1200
```

```
ctccgcgctc aagatggtcg ccgccgccgc cgccgccacc gaatccgacg acaccgacgc  1260
agccgccgcc gccgttcacc agccgccggt cgtcgtctca tcgtagccga tcgatcgccg  1320
gaaacacaga cgatgcatac cgtaccccga gcaatctaat caaaacaagg catccattct  1380
cgcgcgcatg cagcggccag ccgggcttcc gcagctgctc ggcctcctct gctggctgtg  1440
gaaatggaaa attttaatct gagatgaaga cgaagacgaa gacgaaacgg agaggaaaag  1500
gacatgctgt agctgtttct tctagttgcg caggccgctc ccagtcgagt ttgtcgttac  1560
tgacgattat tactctgatg aaaactaatc tgaattaatg catgtagttt ggcaatttgg  1620
tactaaaggt aggcacctag ccaggctggt caatgatagg tctataacct gatcctgttc  1680
tctgttgttt tcctttgtct gagaaaaaat ggaaataatt gatccggccg gacgggtgta  1740
ctgataggtg atgctgaatt gctgatgcaa gaggttgcga gctgcagtga gcagca       1796

SEQ ID NO: 124         moltype = DNA   length = 1149
FEATURE                Location/Qualifiers
source                 1..1149
                       mol_type = unassigned DNA
                       organism = Setaria italica
SEQUENCE: 124
atgccgacgc cgtcgcacct caagaacccg ctctacttcg acttccgcgc cgcgcggcgg    60
gtgccggagt cccacgcctg gccggggctc gacgaccacc ccgtggtgga cggcggcggc   120
gcgcggtggg ccccggacgc cgtgccggtg gtggacctgc gcgagccggg cgccgcggcg   180
gtggcccgcg tggcgcgcgc cgccgagcag tggggcgcgt tcctgctcac cggccacggc   240
gtcccgcgag agctcctggc gcgcgtcgag gaccgcgtcg cgtgcatgtt cgcgctgccg   300
gccgccgaca agatgcgcgc cgtgcgcggg ccggggacg cctgcggcta cggctcgccg    360
cccatctcct ccttcttctc caagtgcatg tggtccgagg gctacacctt ctcgccggcc   420
tccctccgcc gcgacctccg caagctctgg cccaaggccg cgacgacta cgacagcttc    480
tgtgacgtga tggaggagtt ccacaaggag atgcgcgccc tcgccgacag gctcctggag   540
ctgttcctca gggcgctcgg gctcaccggc gagcaggtcg gcgccgtcga ggcggagcgg   600
aggatcggcg agacgatgac cgccaccatg cacctcaact ggtatccgag gtgcccggac   660
ccgcggcgcg cgctggggct gatcgcgcac acggactcgg gcttcttcac cttcgtgctg   720
cagagccctg tgccggggct gcagctgttc cggcacggcc ccaaccggtg ggtggcggtg   780
ccggccgtgc cgggcgcctt cgtcgtcaac gtcggcgacc tcttccacat cctcacgaac   840
ggccgcttcc acagcgtgta ccaccgcgcc gtcgtcaacc gggacctcga ccggatatcg   900
ctcggctact cctcggccc gccgccccac gccaaggtgg cgccgctccg ggaggtcgtg    960
ccgcggggcc gggccccgc ctaccgcgcc gtcacgtggc ccgagtacat gggcgtccgc   1020
aagaaggcct tcaccaccgg cgcctccgcg ctcaagatgg tcgccgccgc cgccgccgcc  1080
accgaatccg acgacaccga cgcagccgcc gccgccgttc accagccgcc ggtcgtcgtc  1140
tcatcgtag                                                          1149

SEQ ID NO: 125         moltype = AA   length = 382
FEATURE                Location/Qualifiers
source                 1..382
                       mol_type = protein
                       organism = Setaria italica
SEQUENCE: 125
MPTPSHLKNP LYFDFRAARR VPESHAWPGL DDHPVVDGGG APGSPDAVPV VDLREPGAAA    60
VARVARAAEQ WGAFLLTGHG VPAELLARVE DRVACMFALP AADKMRAVRG PGDACGYGSP   120
PISSFFSKCM WSEGYTFSPA SLRRDLRKLW PKAGDDYDSF CDVMEEFHKE MRALADRLLE   180
LFLRALGLTG EQVGAVEAER RIGETMTATM HLNWYPRCPD PRRALGLIAH TDSGFFTFVL   240
QSLVPGLQLF RHGPNRWVAV PAVPGAFVVN VGDLFHILTN GRFHSVYHRA VVNRDLDRIS   300
LGYFLGPPPH AKVAPLREVV PPGRAPAYRA VTWPEYMGVR KKAFTTGASA LKMVAAAAAA   360
TESDDTDAAA AAVHQPPVVV SS                                            382

SEQ ID NO: 126         moltype = DNA   length = 2146
FEATURE                Location/Qualifiers
source                 1..2146
                       mol_type = unassigned DNA
                       organism = Setaria italica
SEQUENCE: 126
actagtgcaa ggtcctagat ttacacttgg tgcttgcttg tttcttccta gttgctactg    60
gtagcacgca gtggctggct ggccgtaatc tattgtctgg gctcgatcgg tgattaggaa   120
gtagccaaag caagctaagg ccgccgccgc cgccgccatg ccgacgccgt cgcacctcaa   180
gaacccgctc tacttcgact ccgcgccgc gcggcgggtg ccggagtccc acgcctggcc    240
ggggctcgac gaccacccg tggtggacgg cggcggcgcg ccggggtccc cggacgccgt    300
gccggtggtg gacctgcgcg agccggggcg ccgccgtgg gcccgcgtgg ccgcgccgcg    360
cgagcagtgg ggcgcgttcc tgctcaccgg ccacgcgtc cccgcggagc tcctggcgcg    420
cgtcgaggac cgcgtcgcgt gcatgttcgc gctgccggcc gccgacaaga tgcgcgccgt   480
gcgcgggccg gggacgcct gcggctacgg ctcgccgccc atctcctcct tcttctccaa    540
gtgcatgtgg tccgagggct acaccttctc gccggcctc cctccgccgc gacctccgca    600
gctctggcct caaggccgcg acgactacga cagcttctgg tacgtcgtcg tctatagcta   660
gtagctagcc gccggcacac gtgcgcctga cctgctccgc catgcatggt gcacgtatgc   720
agatcgatca cacgcaccga tcgatcgacg tgtcccggtc aaggccatgc atgcatgcaa   780
gcaaccaaca gcacgcctcc tgatactgct tgttgcttac accgttggta tgtgcctgtt   840
gcctacagtg acgtgatgga ggagttccac aaggagatgc gcgccctcgc cgacaggctc   900
ctggagctgt tcctcagggc gctcgggctc accggcgagc aggtcggcgc cgtcgaggcg   960
gagcggagga tcggcgagac gatgaccgcc accatgcacc tcaactggta tgtgccatgc  1020
catgaccacc tgcgtctatg aactaacgga agcttccatc gcgtgtccat gacgatttag  1080
aagctgtagt ccagagcttg agacaaacga acgaagcttt acatggtggc gtgacgtgtc  1140
gcgtgcaggt atccgaggtg cccggacccg cggcgcgcg tggggctgat cgcgcacacg   1200
gactcgggct tcttcacctt cgtgctgcag agcctgtgc cggggctgca gctgttccgg   1260
```

```
cacggcccca accggtgggt ggcggtgccg gccgtgccgg gcgccttcgt cgtcaacgtc    1320
ggcgacctct tccacatcct cacgaacggc cgcttccaca gcgtgtacca ccgcgccgtc    1380
gtcaaccggg acctcgaccg gatatcgctc ggctacttcc tcggcccgcc gccccacgcc    1440
aaggtggcgc cgctccggga ggtcgtgccg ccgggccggg ccccgccta ccgcgccgtc     1500
acgtggcccg agtacatggg cgtccgcaag aaggccttca ccaccggccg ctccgcgtc     1560
aagatggtcg ccgccgccgc cgccgccacc gaatccgacg acaccgacgc agccgccgcc    1620
gccgttcacc agccgccggt cgtcgtctca tcgtagccga tcgatcgccg gaaacacaga    1680
cgatgcatac cgtaccccga gcaatctaat caaaacaagg catccattct cgcgcgcatg    1740
cagcggccag ccgggcttcc gcagctgctc ggcctcctct gctggctgtg gaaatggaaa    1800
attttaatct gagatgaaga cgaagacgaa gacgaaacgg agaggaaaag gacatgctgt    1860
agctgtttct tctagttgcg caggccgctc ccagtcgagt ttgtcgttac tgacgattat    1920
tactctgatg aaaactaatc tgaattaatg catgtagttt ggcaatttgg tactaaaggt    1980
aggcacctag ccaggctggt caatgatagg tctataacct gatcctgttc tctgttgttt    2040
tcctttgtct gagaaaaaat ggaaataatt gatccggccg gacgggtgta ctgataggtg    2100
atgctgaatt gctcgatgcaa gaggttgcga gctgcagtga gcagca                  2146

SEQ ID NO: 127        moltype = DNA  length = 1933
FEATURE               Location/Qualifiers
source                1..1933
                      mol_type = unassigned DNA
                      organism = Oryza sativa
SEQUENCE: 127
actactcatt ccactattgt aaagtcatag aaaaaattta tatagagaga aaaaattagt     60
gttgttattg ttactggctt tctgccagac gagacgagcg agcgcgcgag tgtgttgctc    120
tctggtcatc gtcgtcgtcg tcgcgatgcc gacgccgtcg cacttgaaga acccgctctg    180
cttcgacttc cgggcggcga ggcggtgcc ggagacgcac gcgtggccgg ggctgacga     240
ccacccggtg gtggacggcg gcggcggcg cggcgaggac gcggtgccgg tggtggacgt    300
cggggcgggc gacggcggg cgcgggtggc gcggcggcg gagcagtggg gcgcgttcct     360
tctggtcggg cacggcgtgc cggcggcgct gctgtcgcgc gtcgaggagc gcgtcgcccg    420
cgtgttctcc ctgccggcgt cggagaagat gcgcgccgtc cgggccccg gcgagccctg    480
cggctacggc tcgccgccca tctcctcctt cttctccaag ctcatgtggt ccgagggcta    540
caccttctcc cctcctccc tccgctccga gctccgccgc ctctggccca agtccgggca    600
cgactacctc ctcttctgtg acgtgatgga ggagtttcac aaggagatgc ggcggctagc    660
cgacgagttg ctgaggttgt tcttgagggc gctggggctc accggcgagg aggtcgccgg    720
agtcgaggcg gagaggagga tcggcgagag gatgacgggcg aggtgcacc tcaactggta    780
cccgaggtgc ccggagccgc ggcgagcgct ggggctcatc gcgcacacgg actcgggctt    840
cttcaccttc gtgctccaga gcctcgtccc ggggctgcag ctgttccgtc gagggcccga    900
ccggtgggtg gcggtgccgg cggtggcggg ggccttcgtc gtcaacgtcg gcgacctctt    960
ccacatcctc accaacggcc gcttccacag cgtctaccac cggccgtcg tgaaccggca    1020
ccgcgaccgg gtctcgctcg gctacttcct cggcccgccg ccgacgccg aggtggcgcc    1080
gctgccggag gccgtgccgg ccggccggag ccccgcctac cgcgctgtca cgtgccgga    1140
gtacatggcc gtccgcaaga aggccttcgc caccggcggc tccgccctca agatggtctc    1200
caccgacgcc gccgccgccg ccgacgaaca cgacgacgtc gccgacgtca    1260
cgcataagct atagctacta gctacctcga tctcacgcaa aaaaaaaag aaacaattaa     1320
tagagcaaaa aaaaaaagaa gagaaatgg tggtacttgt gtttaaggtt tcctccatgc    1380
aaaatggttt gcatgcatgc atgcaaagct agcatctgca gctgcaagaa ttacaagagc    1440
agagaagcag acagctagat ggagataatt aattaattaa ttaatctaat taagcatgca    1500
ataattaaga ttattattct gatttcagaa ctgaaaaaaa aagtgtggtt aattaattat    1560
tggttaggct taatttatc tagatgtaga aaaagaatca agatcttcaa gcaagagaga    1620
agaggatcga agaagaagga aaagaaaacg aaaaggacat gctgtgttgt ctcttctagt    1680
tgtaccctgg ctgctgatta agtgctttgt tttgttgctg caagcttgtc gttactgatt    1740
attagttagt tatgcatcta attgattaaa ctaatctgtt tggcattttg gctcgagcta    1800
agctatagcc aggctggtca atgatagga cttgtacaat ttaagcaatt gaacctgatc    1860
ctgtactggc atgtatgtat atatgcaagt gatgagaacc actagctagt atagctagac    1920
atgtattgt ata                                                        1933

SEQ ID NO: 128        moltype = DNA  length = 1122
FEATURE               Location/Qualifiers
source                1..1122
                      mol_type = unassigned DNA
                      organism = Oryza sativa
SEQUENCE: 128
atgccgacgc cgtcgcactt gaagaacccg ctctgcttcg acttccgggc ggcgaggcgg     60
gtgccggaga cgcacgcgtg gccggggctg acgaccacc cggtggtgga cggcggcgg    120
ggcggcggcg aggacgcggt gccggtggtg gacgtcgggg cggcgacgcg ggcggcgcgg    180
gtggcgcggg cggcggagca gtgggcgcg ttccttctgg tcgggcacgg cgtgccggcg    240
gcgctgctgt cgcgcgtcga ggagcgcgtc gcccgcgtgt ctccctgcc ggcgtcggag    300
aagatgcgcg ccgtccgcgg ccccggcgag ccctgcggct acggctcgcc gccatctcc    360
tccttcttct ccaagctcat gtggtccgag ggctacagg tctcccccttc ctccctccgc    420
tccgagctcc gccgcctctg gcccaagtcc ggcgacgact acctcctctt ctgtgacgtg    480
atggaggagt ttcacaagga gatgcggcgg ctagccgacg agttgctgag gttgttcttg    540
agggcgctgg gctcaccgg cgaggaggtc gccggagtcg aggcggagag gaggatcggc    600
gagaggatga cggcgacggt gcacctcaac tggtacccga ggtgcccgga gccgcggcga    660
gcgctgggc tcatcgcgca cacggactcg ggcttcttca ccttcgtgct ccagagcctc    720
gtccccgggc tgcagctgtt ccgtcgaggg cccgaccggt gggtggcggt gccggcggtg    780
gcggggggcct tcgtcgtcaa cgtcggcgac ctcttccaca tcctcaccaa cggccgcttc    840
cacagcgtct accaccgcgc cgtcgtgaac cgcgaccgcg accgggtctc gctcggctac    900
ttcctcggcc gccgccgga cgccgaggtg gcgccgctgc cggaggccgt gccggccggc    960
cggagccccg cctaccgcgc tgtcacgtgg ccggagtaca tggccgtccg caagaaggcc    1020
```

```
ttcgccaccg gcggctccgc cctcaagatg gtctccaccg acgccgccgc cgccgccgac   1080
gaacacgacg acgtcgccgc cgccgccgac gtccacgcat aa                      1122

SEQ ID NO: 129          moltype = AA  length = 373
FEATURE                 Location/Qualifiers
source                  1..373
                        mol_type = protein
                        organism = Oryza sativa
SEQUENCE: 129
MPTPSHLKNP LCFDFRAARR VPETHAWPGL DDHPVVDGGG GGGEDAVPVV DVGAGDAAAR    60
VARAAEQWGA FLLVGHGVPA ALLSRVEERV ARVFSLPASE KMRAVRGPGE PCGYGSPPIS   120
SFFSKLMWSE GYTFSPSSLR SELRRLWPKS GDDYLLFCDV MEEFHKEMRR LADELLRLFL   180
RALGLTGEEV AGVEAERRIG ERMTATVHLN WYPRCPEPRR ALGLIAHTDS GFFTFVLQSL   240
VPGLQLFRRG PDRWVAVPAV AGAFVVNVGD LPHILTNGRF HSVYHRAVVN RDRDRVSLGY   300
FLGPPPDAEV APLPEAVPAG RSPAYRAVTW PEYMAVRKKA FATGGSALKM VSTDAAAAAD   360
EHDDVAAAAD VHA                                                     373

SEQ ID NO: 130          moltype = DNA  length = 2040
FEATURE                 Location/Qualifiers
source                  1..2040
                        mol_type = unassigned DNA
                        organism = Oryza sativa
SEQUENCE: 130
actactcatt ccactattgt aaagtcatag aaaaaattta tatagagaga aaaaattagt    60
gttgttattg ttactggctt tctgccagac gagacgagcg agcgcgcgag tgtgttgctc   120
tctggtcatc gtcgtcgtcg tcgcgatgcc gacgccgtcg cacttgaaga acccgctctg   180
cttcgacttc cgggcggcga ggcgggtgcc ggagacgcac gcgtggccgg ggctggacga   240
ccacccggtg gtggacggcg gcggcggcgg cggcgaggac gcggtgccgg tggtggacgt   300
cggggcgggc gacgcggcgg cgcgggtggc gcggcggcg gagcagtggg gcgcgttcct   360
tctggtcggg cacggcgtgc cggcgggcgct gctgtcgcgc gtcgaggagc gcgtcgcctc   420
cgtgttctcc ctgccggcgt cggagaagat gcgcgccgtc cgcggcccg gcgagccctg   480
cggctacggc tcgccgccca tctcctcctt cttctccaag ctcatgtggt ccgagggcta   540
caccttctcc cctcctccc tcgctccga gctccgccgc ctctggccca gtccggcga   600
cgactacctc ctcttctggt atatatacat atatactcac ccatgcattc catgcacata   660
cactctacgt atatatctac ctctacgtat atatctacgt attgatctac gtataatata   720
cgcagtgacg tgatggagga gtttcacaag gagatgcggc ggctagccga cgagttgctg   780
aggttgttct tgagggcgct ggggctcacc ggcgaggagg tcgccggagt cgaggcgag   840
aggaggatcg gcgagaggat gacggcgacg gtgcaccgca actggtaccc gaggtgcccg   900
gagccgcggc gagcgctggg gctcatcgcg cacacggact cggcttctt caccttcgtg   960
ctccagagcc tcgtcccggg gctgcagctg ttccgtcgag ggcccgaccg cgtgggtggcg  1020
gtgccggcgcg tggcgggggc cttcgtcgtc aacgtcggcg acctcttcca catcctcacc  1080
aacgccgct tccacagcgt ctaccaccgc gccgtcgtga accgcgaccg cgaccgggtc  1140
tcgctcggct acttcctcgg cccgccgccg gacgccgagg tggcgccgct gccggaggcc  1200
gtgccggccc gccggagccc cgcctaccgc gctgtcacgt ggccggagta catggccgtc  1260
cgcaagaagg ccttcgccac cggcggctcc gccctcaaga tggtctccac cgacgccgcc  1320
gccgccgccg acgaacacga cgacgtcgcc gccgccgccg acgtccacgc ataagctata  1380
gctactagct acctcgatct cacgcaaaaa aaaaaagaaa caattaatag agcaaaaaaa  1440
aaaagaagag aaaatggtgg tacttgtgtt taaggtttcc tccatgcaaa atggtttgca  1500
tgcatgcatc aaaagctagc atctgcagct gcaagaatta caagagcaga aagcagaca  1560
gctagatgga gataattaat taattaatta atctaattaa gcatgcaata attaagatta  1620
ttattctgat ttcagaactg aaaaaaaaag tgtggttaat taattattgg ttaggcttaa  1680
ttttatctag atgtagaaaa agaatcaaga tcttcaagca agagagaaga ggatcgaaga  1740
agaaggaaaa gaaaacgaaa aggacatgct gtgttgtctc ttctagttgt accctggctg  1800
ctgattaagt gctttgtttt gttgctgcaa gcttgtcgtt actgattatt agttagttat  1860
gcatctaatt gattaaacta atctgtttgg cattttggct cgagctaagc tatagccagg  1920
ctggtcaatg ataggaactt gtacaattta agcaattgaa cctgatcctg tactggcatg  1980
tatgtatata tgcaagtgat gagaaccact agctagtata gctagacatg tatttgtata  2040

SEQ ID NO: 131          moltype = DNA  length = 1332
FEATURE                 Location/Qualifiers
source                  1..1332
                        mol_type = unassigned DNA
                        organism = Hordeum vulgare
SEQUENCE: 131
acactcactc ctcaatccat ccgtctccac cattgctcgc tagctcgagc tctactagct    60
agcactgcaa agtcagccgg gccggagttg atttggtcct tgttagcttg accgatcgta   120
tacgtatcgc caggatgccg acgccgtcgc acctgagcaa ggacccgcac tacttcgact   180
tccgggcggc gcggcgggtg ccggagacac acgcgtggcc ggggctgcac gaccaccgg   240
tggtggacgg cggcggccgg gcggagggc cggacgcggt gccggtggtg gacatgccgg   300
acccgtgcgc gcgcggaggcg gtggcgctgg ccgcgcagga ctgggcgcc ttcctcttgc   360
agggccacgg cgtcccgttg gagctgctgg ccgcgtgga ggccgcgata gcgggcatgt   420
tcgcgctgcc ggcgtcggag aagatgcgcg ccgtgcggcg gccggcgac tcgtgcggct   480
acgggtcgcg gcccatctcc tccttcttct ccaagtgcat gtggtccgag gctacacct   540
tctcccccgc caacctctcg tccgacctcc gcaaggctcg gagccacgat   600
accgccactt ctgtgccgtg atggaggagt tccacaggga gatgcgcgtt ctggccgaca   660
gctgctgga gctgttcctg gtgggccctcg gctcaccgg cgagcaggtc gccgccgtcg   720
agtcggagca caagatcgcc gagaccatga ccgccacaat gcacctcaac tggtacccca   780
agtgcccgga cccgaagcga gcgctgggcc tgatcgcgca cacggactcg gcttcttca   840
ccttcgtgct ccagagcctg gtgccgggc tgcagctgtt ccggcacggc cccgaccgtt   900
```

-continued

```
gggtgacggt gcccgccgtg ccgggcgcca tggtcgtcaa cgtcggcgac ctcttccaca    960
tcctcaccaa tggccgcttc cacagcgtct accaccgcgc cgtcgtcaac cgcgacagcg   1020
accggatatc gctggggtac ttcctcggcc cgcccgccca cgttaaggtg gcgccgctca   1080
gggaggccct cgccggcacg cccgctgcct accgcgccgt cacgtgggcc gagtacatgg   1140
gcgtcgcaa  gaaggccttc accaccggcg cctccgcgct caagatggtc gccatctcca   1200
ccgacgacgc cgccgacgtc ctccccgacg tcctctcgtc gtagatcggc gccggccatc   1260
acccggccgg ccaagagacc gatctataca acaattagt  gaacaaaaaa aaaaaaaaaa   1320
aaaaaaaaaa aa                                                       1332

SEQ ID NO: 132          moltype = DNA length = 1110
FEATURE                 Location/Qualifiers
source                  1..1110
                        mol_type = unassigned DNA
                        organism = Hordeum vulgare
SEQUENCE: 132
atgccgacgc cgtcgcacct gagcaaggac ccgcactact tcgacttccg ggcggcgcgg    60
cgggtgccgg agacacacgc gtggccgggg ctgcacgacc acccgtggt  ggacggcggc   120
ggcgcggggcg gagggccgga cgcggtgccg gtggtggaca tgcgcgaccc gtgcgccgcg   180
gaggcggtgg cgctggccgc gcaggactgg ggcgccttcc tcttgcaggg ccacggcgtc   240
ccgttggagc tgctggcccg cgtggaggcc gcgatagcgg gcatgttcgc gctgccggcg   300
tcggagaaga tgcgcgccgt gcggcggccc ggcgactcgt gcggctacgg gtcgccgccc   360
atctcctcct tcttctccaa gtgcatgtgg tccgagggct acaccttctg cccggccaac   420
ctccgctccg acctccgcaa gctctggccc aaggccgacc acgactaccg ccacttctgt   480
gccgtgatgg aggagttcca cagggagatg cgcgttctgg ccgacaagct gctggagctg   540
ttcctggtgg ccctcgggct caccggcgag caggtcgccg ccgtcgagtc ggagcacaag   600
atcgccgaga ccatgaccgc cacaatgcac ctcaactggt accccaagtg cccggaccc    660
aagcgagcgc tgggcctgat cgcgcacacg gactcgggct tcttcacctt cgtgctccag   720
agcctggtgc ccgggctgca gctgttccgg cacggcccccg accgttgggt gacggtgccc   780
gccgtgccgg gcgccatggt cgtcaacgtc ggcgacctct ccacatcct  caccaatggc   840
cgcttccaca gcgtctacca ccgcgccgtc gtcaaccgca acagcgaccg gatatcgctg   900
gggtacttcc tcggcccgcc cgcccacgtt aaggtggcgc cgctcaggga ggcctcgcc   960
ggcacgcccg ctgcctaccg cgccgtcacg tggcccgagt acatgggcgt gcgcaagaag  1020
gccttcacca ccggcgcctc cgcgctcaag atggtcgcca tctccaccga cgacgccgcc  1080
gacgtcctcc ccgacgtcct ctcgtcgtag                                   1110

SEQ ID NO: 133          moltype = AA length = 369
FEATURE                 Location/Qualifiers
source                  1..369
                        mol_type = protein
                        organism = Hordeum vulgare
SEQUENCE: 133
MPTPSHLSKD PHYFDFRAAR RVPETHAWPG LHDHPVVDGG GAGGGPDAVP VVDMRDPCAA    60
EAVALAAQDW GAFLLQGHGV PLELLARVEA AIAGMFALPA SEKMRAVRRP GDSCGYGSPP   120
ISSFFSKCMW SEGYTFSPAN LRSDLRKLWP KAGHDYRHFC AVMEEFHREM RVLADKLLEL   180
FLVALGLTGE QVAAVESEHK IAETMTATMH LNWYPKCPDP KRALGLIAHT DSGFFTFVLQ   240
SLVPGLQLFR HGPDRWVTVP AVPGAMVVNV GDLFHILTNG RFHSVYHRAV VNRDSDRISL   300
GYFLGPPAHV KVAPLREALA GTPAAYRAVT WPEYMGVRKK AFTTGASALK MVAISTDDAA   360
DVLPDVLSS                                                          369

SEQ ID NO: 134          moltype = DNA length = 1653
FEATURE                 Location/Qualifiers
misc_feature            1594..1600
                        note = n is a, c, g, or t
misc_feature            1641
                        note = n is a, c, g, or t
source                  1..1653
                        mol_type = unassigned DNA
                        organism = Triticum aestivum
SEQUENCE: 134
cacgagatcc atccgtctcc accattgctc gctagctcga gctcctagct agtactgcaa    60
agtcagccgg ggagttgatt tggtccttct tggcttgacc gatcgtacgt gccgccagga   120
tgccgacgcc ggcgcacctg agcaaggacc cgcgctactt cgacttccgg gcggcgcggc   180
gggtgccgga gacacacgcg tggccgggct gcacgacca  cccgtggtg  gacggcagcg   240
gcgcggggcg agggccggac gcggtgccgg tggtggacat gcgcgacccg tcgccggcg   300
aggcggtggc gctggccgcg caggactggg gcgccttcct cctggagggc cacggcgtcc   360
cgttggagct gctggcgcgc gtggaggccg cgatcgcggg catgttcgcg ctgccggcgt   420
cggagaagat gcgcgccgtg cggcggcccg gcgactcgtg cggctacggg tcgccgccca   480
tctcctcctt cttctccaag tgcatgtggt ccgaggcta  caccttctcc ccggccaacc   540
tccgctccga cctccgcaag ctctggccca aggccgacca cgactaccgc cacttctgtg   600
ccgtgatgga ggagttccac agggagatgc gcgcgctggc cgacaagctg ctggagctgt   660
tcctggtggc cctcgggctc accggcgagc aggtcgccgc cgtcgagtcc gagcagaaga   720
tcgccgagac catgaccgcc acaatgcacc tcaactggta ccccaagtgc ccggaccga    780
agcgggcgct gggcctgatc gcgcacacgg actcgggctt cttcaccttc gtgctgcaga   840
gcctggtgcc cgggctgcag ctgttccgga cggccccg  accgttgggt gacggtgccc   900
ccgtgccggg ggccatggtc gtcaacgtcg gcgacctctt ccagatcctc accaacggcc   960
gcttccacag cgtctaccac cgcgccgtcg tcaaccgcga cagcgaccgg atatcgctcg  1020
gctacttcct cggcccgccc gcccacgtca aggtggcgcc gctcagggag gcctggccg   1080
gcacgcccgc gcctaccgc  gccgtcacgt ggcccgagta catgggcgtg cgcaagaagg  1140
ccttcaccac cggcgcctcc gcgctcaaga tggtcgccat ctccactgac aacgacgccg  1200
```

```
ccaaccacac ggacgacctg atctcgtcgt agatcggcgc cggccatcac cggccggcca    1260
agggatcgat ctacacacac aattagtgaa caaaaaaatg ccagagatgg tgcatggtgg    1320
gctggtagct tagctgaggt agctaggagg aagagcgcgc gtgcggctgt cgttcgtgcg    1380
gctgttcccg caaaaaaaaa aaaggtttcc tccatatatg tctccatgca gaactgcaga    1440
tgctggtggt ggatgcgtcc atgcagcagg gaacgaacta attgtaagaa aatcaagcaa    1500
acttagttct acatctgtaa ttaagtatgc atgccacttg gtttaattca attcaagtgc    1560
agaaaaaatt atgatgggaa aaaaaaagac atgnnnnnnn aaaaaaaaaa aaaaaaaaaa    1620
aaaaaaaaaa aaaaaaaaaa naaaaaaaaa aaa                                 1653

SEQ ID NO: 135          moltype = DNA  length = 1113
FEATURE                 Location/Qualifiers
source                  1..1113
                        mol_type = unassigned DNA
                        organism = Triticum aestivum
SEQUENCE: 135
atgccgacgc cggcgcacct gagcaaggac ccgcgctact tcgacttccg ggcggcgcgg    60
cgggtgccgg agacgcacgc gtggcccggg ctgcacgacc ccccgtggt ggacggcagc     120
ggcgcggggcg gagggccgga cgcggtgccg gtggtggaca tgcgcgaccc gtgccggcg    180
gaggcggtgg cgctggcggc gcaggactgg ggcgccttcc tcctggaggg ccacggcgtc    240
ccgttggagc tgctggcgcg cgtggaggcc gcgatcgcgg gcatgttcgc gctgccggcg    300
tcggagaaga tgcgcgccgt gcggcggccc ggcgactcgt gcggctacgg gtcgccgccc    360
atctcctcct tcttctccaa gtgcatgtgg tccgagggct acacttctg gaggccaaac    420
ctccgctccg acctccgcaa gctctggccc aaggccgcac acgactaccg ccacttctgt    480
gccgtgatgg aggagttcca cagggagatg cgcgcgctgg ccgacaagct gctggagctg    540
ttcctggtgg ccctcgggct caccggcgag caggtcgccg ccgtcgagtc cgagcagaag    600
atcgccgaga ccatgaccgc cacaatgcac ctcaactggt accccaagtg cccggaccccg    660
aagcgggcgc tgggcctgat cgcgcacacg gactcgggct tcttcaccttt cgtgctgcag    720
agccttgtgc ccgggctgca gctgttccgg cacggccccg accggtgggt gacggtgccc    780
gccgtgccgg gggccatggt cgtcaacgtc ggcgacctct ccagatcct caccaacggc    840
cgcttccaca gcgtctacca ccgcgccgtc gtcaaccgcg acagcgaccg gatatcgctc    900
ggctacttcc tcggccccgc cgcccacgtc aaggtggcgc cgctcaggga ggccctggcc    960
ggcacgcccg ccgcctaccg cgccgtcacg tgggccgagt acatgggcgt gcgcaagaag   1020
gccttcacca ccggcgcctc cgcgctcaag atggtcgcca tctccactga caacgacgcc   1080
gccaaccaca cggacgacct gatctcgtcg tag                                1113

SEQ ID NO: 136          moltype = AA   length = 370
FEATURE                 Location/Qualifiers
source                  1..370
                        mol_type = protein
                        organism = Triticum aestivum
SEQUENCE: 136
MPTPAHLSKD PRYFDFRAAR RVPETHAWPG LHDHPVVDGS GAGGGPDAVP VVDMRDPCAA    60
EAVALAAQDW GAFLLEGHGV PLELLARVEA AIAGMFALPA SEKMRAVRRP GDSCGYGSPP   120
ISSFFSKCMW SEGYTFSPAN LRSDLRKLWP KAGHDYRHFC AVMEEFHREM RALADKLLEL   180
FLVALGLTGE QVAAVESEQK IAETMTATMH LNWYPKCPDP KRALGLIAHT DSGFFTFVLQ   240
SLVPGLQLFR HGPDRWVTVP AVPGAMVVNV GDLFQILTNG RFHSVYHRAV VNRDSDRISL   300
GYFLGPPAHV KVAPLREALA GTPAAYRAVT WPEYMGVRKK AFTTGASALK MVAISTDNDA   360
ANHTDDLISS                                                          370

SEQ ID NO: 137          moltype = DNA  length = 1884
FEATURE                 Location/Qualifiers
source                  1..1884
                        mol_type = unassigned DNA
                        organism = Triticum aestivum
SEQUENCE: 137
tatatataca gctccttgta cttctctcgt tcttacactc actcctcaat ccatccgtct    60
ccaccattgc tcgctagctc gagctcctag ctagtactgc aaagtcagcc ggggagttga   120
tttggtcctt cttggcttga ccgatcgtac gtgccgccag gatgccgacg ccggcgcacc   180
tgagcaagga cccgcgctac ttcgacttcc gggcggcgcg gcgggtgccg gagacgcacg   240
cgtggcccgg gctgcacgac caccccgtgg tggacggcgg cggcgggc gagggccgga    300
acgcggtgcc ggtggtggac atgcgcgacc cgtgcgcggc ggaggcggtg gcgctggcgg   360
cgcaggactg gggcgccttc ctcctggagg gccacggcgt cccgttggag ctgctggcgc   420
gcgtggaggc cgcgatcgcg ggcatgttcg cgctgccggc gtcggagaag atgcgcgccg   480
tgcggcggcc cggcgactcg tgcggctacg ggtcgccacg catctcctcc ttcttcttca   540
agtgcatgtg gtccgagggc tacacctttt ccccggccaa cctccgctcc gacctccgca   600
agctctggcc caaggccggc cacgactacc gccacttctg tgtacgtacg cggccgccga   660
tgcgcatata cacgtcatag tacggcacct acctaactgg ctctgccaa ccgtccgtac     720
acacgtgaag gggcgacgtg tccgcatccg accatgcatg catgcacgcg cgcgaaactt    780
gttactcctg ttctgctatg gcagcagcta gccgcgtgtg tccgttcgta ggagtagtta    840
cttacacagt tacacttacg ccgtccgtcg tgttcctcga cgtcgcagcgc cgtcgatggag   900
gagttccaca gggagatgcg cgcgctggcc gacaagctgc tggagctgtt cctggtggcc    960
ctcgggctca ccggcgagca ggtcgccgcc gtcgagtccg agcagaagat cgccgagacc   1020
atgaccgcca caatgcacct caactggtac gttccactac tactccagta gtacaagtac   1080
aatatataga atacaaatgg cagcagccac gacgacacgt actccaccat gcagcaaagc   1140
atatattgtc ggtgcggcgg ttgacacgga gttgtcgt gtcgttgatt cacaggtacc     1200
ccaagtgccc ggaccccgaag cgggcgctgg gcctgatcgc gcacacggac tcgggcttct    1260
tcaccttcgt gctgcagagc cttgtgcccg ggctgcagct gttccggcac ggccccgacc   1320
ggtgggtgac ggtgcccgcc gtgccggggg ccatggtcgt caacgtcggc gacctcttcc   1380
agatcctcac caacggccgc ttccacagcg tctaccaccg cgccgtcgtc aaccgcgaca   1440
```

```
gcgaccggat atcgctcggc tacttcctcg gcccgcccgc ccacgtcaag gtggcgccgc  1500
tcagggaggc cctggccggc acgcccgccg cctaccgcgc cgtcacgtgg cccgagtaca  1560
tgggcgtgcg caagaaggcc ttcaccaccg gcgcctccgc gctcaagatg gtcgccatct  1620
ccactgacaa cgacgccgcc aaccacacgg acgacctgat ctcgtcgtag atcggcgccg  1680
gccatcaccg gccggccaag ggatcgatct acacacacaa ttagtgaaca aaaaaatgcc  1740
agagatgctg catggtgggc tggtagctta gctgaggtag ctaggaggaa gagcgcgcgt  1800
gcggctgtcg ttcgtgcggc tgttcccgca aaaaaaaaaa ggtttcctcc atatakgtcc  1860
ccakscaaaa tsgmaawgct gggg                                        1884
```

| | | |
|---|---|---|
| SEQ ID NO: 138 | moltype = RNA length = 20 | |
| FEATURE | Location/Qualifiers | |
| misc_feature | 1..20 | |
| | note = suppression oligo | |
| source | 1..20 | |
| | mol_type = other RNA | |
| | organism = synthetic construct | |
| SEQUENCE: 138 | | |
| acgggttctt ccaggtgtgc | | 20 |

```
SEQ ID NO: 139          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 139
cacgggttct tccaggtgtg                                                20

SEQ ID NO: 140          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 140
cattgacctc cccgctggca                                                20

SEQ ID NO: 141          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 141
ccagcgggga ggtcaatgct                                                20

SEQ ID NO: 142          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 142
cccagcattg acctccccgc                                                20

SEQ ID NO: 143          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 143
cgcgctcgtg tacccggaca                                                20

SEQ ID NO: 144          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 144
ctcccggcgc aggtcgaaca                                                20
```

```
SEQ ID NO: 145           moltype = RNA   length = 20
FEATURE                  Location/Qualifiers
misc_feature             1..20
                         note = suppression oligo
source                   1..20
                         mol_type = other RNA
                         organism = synthetic construct
SEQUENCE: 145
gtgtacccgg acacggtgcc                                                   20

SEQ ID NO: 146           moltype = RNA   length = 20
FEATURE                  Location/Qualifiers
misc_feature             1..20
                         note = suppression oligo
source                   1..20
                         mol_type = other RNA
                         organism = synthetic construct
SEQUENCE: 146
tgcagggaag ctgtccgggc                                                   20

SEQ ID NO: 147           moltype = RNA   length = 20
FEATURE                  Location/Qualifiers
misc_feature             1..20
                         note = suppression oligo
source                   1..20
                         mol_type = other RNA
                         organism = synthetic construct
SEQUENCE: 147
ttcttccagg tgtgcgggca                                                   20

SEQ ID NO: 148           moltype = RNA   length = 20
FEATURE                  Location/Qualifiers
misc_feature             1..20
                         note = suppression oligo
source                   1..20
                         mol_type = other RNA
                         organism = synthetic construct
SEQUENCE: 148
agatccccgc gccattcctg                                                   20

SEQ ID NO: 149           moltype = RNA   length = 20
FEATURE                  Location/Qualifiers
misc_feature             1..20
                         note = suppression oligo
source                   1..20
                         mol_type = other RNA
                         organism = synthetic construct
SEQUENCE: 149
atgcagggaa gctgtccggg                                                   20

SEQ ID NO: 150           moltype = RNA   length = 20
FEATURE                  Location/Qualifiers
misc_feature             1..20
                         note = suppression oligo
source                   1..20
                         mol_type = other RNA
                         organism = synthetic construct
SEQUENCE: 150
attcctgtgg ccgcaggaag                                                   20

SEQ ID NO: 151           moltype = RNA   length = 20
FEATURE                  Location/Qualifiers
misc_feature             1..20
                         note = suppression oligo
source                   1..20
                         mol_type = other RNA
                         organism = synthetic construct
SEQUENCE: 151
cagcggggag gtcaatgctg                                                   20

SEQ ID NO: 152           moltype = RNA   length = 20
FEATURE                  Location/Qualifiers
misc_feature             1..20
                         note = suppression oligo
source                   1..20
                         mol_type = other RNA
                         organism = synthetic construct
SEQUENCE: 152
caggaatggc gcgggatct                                                    20
```

```
SEQ ID NO: 153          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 153
gactacttcg tcggcaccct                                                       20

SEQ ID NO: 154          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 154
gccaggattt cgagccaatg                                                       20

SEQ ID NO: 155          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 155
ggaacatttg gagggaggcg                                                       20

SEQ ID NO: 156          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 156
gggaggtcaa tgctggggct                                                       20

SEQ ID NO: 157          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 157
ttggctcgaa atcctggccg                                                       20

SEQ ID NO: 158          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 158
acgggttctt ccaggtgtgc                                                       20

SEQ ID NO: 159          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 159
cacgggttct tccaggtgtg                                                       20

SEQ ID NO: 160          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 160
```

```
cattgacctc cccgctggca                                                         20

SEQ ID NO: 161          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 161
ccagcgggga ggtcaatgct                                                         20

SEQ ID NO: 162          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 162
cccagcattg acctccccgc                                                         20

SEQ ID NO: 163          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 163
cgcgctcgtg tacccggaca                                                         20

SEQ ID NO: 164          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 164
ctcccggcgc aggtcgaaca                                                         20

SEQ ID NO: 165          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 165
gtgtacccgg acacggtgcc                                                         20

SEQ ID NO: 166          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 166
tgcagggaag ctgtccgggc                                                         20

SEQ ID NO: 167          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 167
ttcttccagg tgtgcgggca                                                         20

SEQ ID NO: 168          moltype = AA    length = 228
FEATURE                 Location/Qualifiers
source                  1..228
                        mol_type = protein
                        organism = Zea mays
SEQUENCE: 168
MARERREIKR IESAAARQVT FSKRRRGLFK KAEELSVLCD ADVALIVFSS TGKLSQFASS              60
```

```
SMNEIIDKYS THSKNLGKAE QPSLDLNLEH SKYANLNEQL VEASLRLRQM RGEELEGLSV    120
EELQQLEKNL ESGLHRVLQT KDQQFLEQIS DLEKKSTQLA EENRQLRNQV SHIPPVGKQS    180
VADTENVIAE DGQSSESVMT ALHSGSSQDN DDGSDVSLKL GLPCVAWK                228

SEQ ID NO: 169          moltype = DNA   length = 687
FEATURE                 Location/Qualifiers
source                  1..687
                        mol_type = unassigned DNA
                        organism = Zea mays
SEQUENCE: 169
atggcgaggg agcgacggga gataaagagg atagagagcg cggcggcgcg gcaggtcacg    60
ttctccaagc gccgccgcgg cctcttcaag aaggctgagg agctctccgt gctgtgcgat   120
gccgacgtcg cgctcatcgt cttctcctcc acgggaaagc tctcccagtt cgccagcaga   180
agtatgaatg agatcattga caagtacagc acacattcta aaaacctggg gaaagcagaa   240
cagccttcac ttgacttgaa cttagaacat agcaaatatg caaatttgaa tgagcaactt   300
gtggaagcaa gccttcgact caggcagatg agaggtgaag aacttgaggg attgagtgtt   360
gaagaactcc agcaattgga gaagaatctg gaatctggtc tgcataggt gcttcaaaca    420
aaggatcaac aattcttgga acagatcagc gacctcgaaa aaaagagtac acaactggca   480
gaggagaaca ggcaactgag gaatcaagta tcccacatac ccccagttgg caagcaatca   540
gttgctgata ctgaaaatgt tatcgctgaa gatgggcaat cctctgaatc agtcatgact   600
gcgttgcatt ctgggagttc acaggataat gatgatggtt cggatgtctc tctaaaatta   660
gggctgcctt gtgttgcatg gaagtga                                      687

SEQ ID NO: 170          moltype = DNA   length = 1528
FEATURE                 Location/Qualifiers
source                  1..1528
                        mol_type = unassigned DNA
                        organism = Oryza sativa
SEQUENCE: 170
ggaagctaac tagtcacggc gaatacatga cgacatcggc ctacaacgca caacttcttg    60
gcataaaagc ttcaatttca atgcccctat ctggaagccc taggcgccgc gcaaatgtaa   120
aacattcgct tcgcttggct tgttatccaa aatagagtat ggacctccga cagattggca   180
acccgtgggt aatcgaaaat ggctccatct gccccttttgt cgaaggaatc aggaaacggc   240
cctcacctcc tggcggagtg tagatatgtg aaagaattca ggcgacactt gcagactgga   300
caacatgtga acaaataaga ccaacgttat ggcaacaagc ctcgacgcta ctcaagtcgt   360
gggaggccac cgcatgttcc aacgaagcgc aaagaaagc cttgcagact ctaatgctat    420
tagtcgccta ggatatttgg aatgaaagga accgcagagt ttttcagcac caagagcttc   480
cggtggctag tctgatagcc aaaattaagg aggatgccaa aacatgggtc ttggcgggcg   540
cgaaacacct tgataggtgg cttacctttt aacatgttcg ggccaaaggc cttgagacgg   600
taaagttttc tatttgcgct tgcgcatgta caatttatt cctctattca atgaaattgg    660
tggctcactg gttcattaaa aaaaaagaa tctagcctgt cgggaagaa gaggattta     720
ttcgtgagag agagagagag agagagagag agggagag agaaggagga ggaggatttt    780
caggcttcgc attgcccaac ctctgcttct gttggccaaa gaagaatccc aggcgcccat   840
gggctggcag tttaccacgg acctacctag cctaccttag ctatctaagc gggccgacct   900
agtagctacg tgcctagtgt agattaaagt tggcgggcca gcaggaagcc acgctgcaat   960
ggcatcttcc cctgtccttc gcgtacgtga aaacaaaccc aggtaagctt agaatcttct   1020
tgcccgttgg actgggacac ccaccaatcc caccatgccc cgatattcct ccggtctcgg   1080
ttcatgtgat gtcctctctt gtgtgatcac ggagcaagca ttcttaaacg gcaaaagaaa   1140
atcaccaact tgctcacgca gtcacgctgc accgcgcgaa gcgacgcccg ataggccaag   1200
atcgcgagat aaaataacaa ccaatgatca taaggaaaca agcccgcgat gtgtcgtgtg   1260
cagcaatctt ggtcatttgc gggatcgagt gcttcacggt taccaaata ttcggccgat    1320
gatttaacac attatcagcg tagatgtacg tacgatttgt taattaatct acgagccttg   1380
ctagggcagg tgttctgcca gccaatccag atcgccctcg tatgcacgct cacatgatgg   1440
cagggcaggg ttcacatgag ctctaacggt cgattaatta atcccggggc tcgactataa   1500
ataccctccct aatcccatga tcaaaacc                                     1528

SEQ ID NO: 171          moltype = DNA   length = 99
FEATURE                 Location/Qualifiers
source                  1..99
                        mol_type = unassigned DNA
                        organism = Oryza sativa
SEQUENCE: 171
atctcaagca gcctaatcat ctccagctga tcaagagctc ttaattagct agctagtgat    60
tagctgcgct tgtgatcgat cgatctcggg tacgtagca                           99

SEQ ID NO: 172          moltype = DNA   length = 804
FEATURE                 Location/Qualifiers
source                  1..804
                        mol_type = unassigned DNA
                        organism = Zea mays
SEQUENCE: 172
accgtcttcg gtacgcgctc actccgcccct ctgcctttgt tactgccacg tttctctgaa    60
tgctctcttg tgtggtgatt gctgagagtg gtttagctgg atctagaatt acactctgaa   120
atcgtgttct gcctgtctg attacttgcc gtccttgta gcagcaaaat ataggacat      180
ggtagtacga aacgaagata gaacctacac agcaatacga gaaatgtgta atttggtgct   240
tagcggtatt tatttaagca catgttggt ttatagggca cttggattca gaagtttgct    300
gttaatttag gcacaggctt catactcat gggtcaatag tatagggatt catattatag    360
gcgatactat aataatttgt tcgtctgcag agcttattat ttgccaaaat tagatattcc   420
tattctgttt ttgtttgtgt gctgttaaat tgttaacgcg tgaaggaata aatataaatg   480
```

```
acgaaatttt gatgtttatc tctgctcctt tattgtgacc ataagtcaag atcagatgca    540
cttgttttaa atattgttgt ctgaagaaat aagtactgac agtattttga tgcattgatc    600
tgcttgtttg ttgtaacaaa atttaaaaat aaagagtttc cttttgttg ctctccttac     660
ctcctgatgt tatctagtat ctaccaactg acactatatt gcttctcttt acatacgtat    720
cttgctcgat gccttctccc tagtgttgac cagtgttact cacatagtct ttgctcattt    780
cattgtaatg cagataccaa gcgg                                            804

SEQ ID NO: 173           moltype = DNA   length = 250
FEATURE                  Location/Qualifiers
source                   1..250
                         mol_type = unassigned DNA
                         organism = Oryza sativa
SEQUENCE: 173
ggattgggaa gcaagcttgg gaattggttt gagatttgag gaggaaaagc ataatggcag     60
cttatttggg taattaattg gtgtgggttt aattttcctt tttccgtatg gattgtaaat    120
tagtcgtcgg aggccatggc caccgaacga tcgaatttag tgttttcatc ggggtttaat    180
caatcgcgaa caattgtaat caaatacact tgtttaaatc tcatcaatgt tttcatgaaa    240
atcatctcga                                                            250

SEQ ID NO: 174           moltype = DNA   length = 997
FEATURE                  Location/Qualifiers
misc_feature             1..997
                         note = Promoter sequence, with original source from Zea mays
source                   1..997
                         mol_type = other DNA
                         organism = synthetic construct
SEQUENCE: 174
gctgcttccg gtagcctgaa gcagaaaaaa actgaaagaa acatgacaga taattccctc     60
ggagaaactt ggcatgtttc ccgttggtca tgtaggacga cgataatgat aaattggtaa    120
gcaaagaaaa aggctactaa gctcgagcag tagaagctac ctagctcgtc gtaacgaaga    180
aacttctcgt ccttcaggta gaccttgct tgtttgcagt actttagtta gggttcggtc      240
tttaattctt ttgctgggca gcagtaaacg gagatgagaa gcgcgagctg atcattgttg    300
ccattctgtg caacgaagct aggggaccaa tgctgactcg cacgagggca tagttgctga    360
tggtcataga cgacgcgttc acttaaaaata ataaagaatt ataaattgtt gtcataagtc    420
gtgcagccta ataggagag gtgcggcatt gctgtagcta attaagagag tattccgtac      480
atgcttgagc ttggagaatt tttgagggtc cgttcgcttg gagagtcgga gattttttgag   540
ggcccgttcg cttgcacaat aataaacaaa gatttgttct agctcatcca aatctatata    600
aattaaagaa gtaattcggt taggaatcaa tccagagctc taattcttaa aaaccgaaca    660
gggcctgagt tgtttgtcta gacgacatta ttattttcat cttcaattc                720
aaatgtgatc tagcggcata aaacttgttg tctgacagat atttgacttc cacacgggcc    780
acagctcaat tacaaacata cttcaaacat caggcagagg cagagcacta gcagcattcg    840
ctacgtggcg gtgggcagca gtggccagca cattcgacaa ctgccacgga tcccgtacta    900
cttcaaacac gtatcgcttc cagaatccag agtcacacgt gtgcagctgc atgaacccag    960
ctcactccct taagaacagc tcgacgctca cctgtct                             997

SEQ ID NO: 175           moltype = AA    length = 228
FEATURE                  Location/Qualifiers
source                   1..228
                         mol_type = protein
                         organism = Zea mays
SEQUENCE: 175
MARERREIKR IESAAARQVT FSKRRRGLFK KAEELSVLCD ADVALIVFSS TGKLSQFASS      60
SMNEIIDKYS THSKNLGKAE QPSLDLNLEH SKYANLNEQL VEASLRLRQM RGEELEGLSV    120
EELQQLEKNL ESGLHRVLQT KDQQFLEQIS DLEQKSTQLA EENRQLRNQV SHIPPVGKQS    180
VADTENVIAE DGQSSESVMT ALHSGSSQDN DDGSDVSLKL GLPCVAWK                 228

SEQ ID NO: 176           moltype = AA    length = 228
FEATURE                  Location/Qualifiers
source                   1..228
                         mol_type = protein
                         organism = Zea mays
SEQUENCE: 176
MARERREIKR IESAAARQVT FSKRRRGLFK KAEELSVLCD ADVALIVFSS TGKLSQFASS      60
SMNEIIDKYS THSKNLGKAE QPSLDLNLEH SKYANLNEQL VEASLRLRQM RGEELEGLSV    120
EELQQLEKNL ESGLHRVLQT KDQQFLEQIS DLEQKSTQLA EENRQLRNQV SHIPPVGKQS    180
VADAENVIAE DGQSSESVMT ALHSGSSQDN DDGSDVSLKL GLPCVAWK                 228

SEQ ID NO: 177           moltype = AA    length = 228
FEATURE                  Location/Qualifiers
source                   1..228
                         mol_type = protein
                         organism = Zea mays
SEQUENCE: 177
MARERREIKR IESAAARQVT FSKRRRGLFK KAQELSVLCD ADVALIVFSS TGKLSQFASS      60
SMNEIIDKYN THSKNLGKTE QPSLDLNLEH SKYANLNEQL AEASLRLRQM RGEELEGLNV    120
EELQQLEKNL ESGLHRVLQT KDQQFLEQIN DLERKSTQLA EENMQLRNQV SQIPPAGKQA    180
VADTENVIAE EGQSSESVMT ALHSGSSQDN DDGSDVSLKL GLPCVAWK                 228

SEQ ID NO: 178           moltype = AA    length = 228
```

```
FEATURE                 Location/Qualifiers
source                  1..228
                        mol_type = protein
                        organism = Zea mays
SEQUENCE: 178
MARERREIKR IESAAARQVT FSKRRRGLFK KAQELSVLCD ADVALIVFSS TGKLSQFASS    60
SMNEIIDKYN THSKNLGKTE QPSLDLNLEH SKYANLNEQL AEASLRLRQM RGEELEGLNV   120
EELQQLEKNL ESGLHRVLQT KDSQFLEQIN DLERKSTQLA EENMQLRNQV SQIPPAGKQA   180
VADTENVIAE EGQSSESVMT ALHSGSSQDN DGGSDVSLKL GLPCVAWK                228

SEQ ID NO: 179          moltype = AA  length = 228
FEATURE                 Location/Qualifiers
source                  1..228
                        mol_type = protein
                        organism = Lolium perenne
SEQUENCE: 179
MARERREIKR IESAAARQVT FSKRRRGLFK KAEELSVLCD ADVALIVFSS TGKLSQFASS    60
SMNEIIDKYS THSKNLGKAD QPSLDLNLEH SKYANLNDQL AEASLRLRQM RGEGLEGLTV   120
DELQQLEKNL ETGLHRVLQT KDQQFLEQIN ELQRKSSQLA EENMQLRNQV SQIPIAGKPV   180
VADTENVIAE DGQSSESVMT ALHSGSSQDN DDGSDVSLKL GLPCSAWK                228

SEQ ID NO: 180          moltype = AA  length = 228
FEATURE                 Location/Qualifiers
source                  1..228
                        mol_type = protein
                        organism = Triticum aestivum
SEQUENCE: 180
MARERREIKR IESAAARQVT FSKRRRGLFK KAEELSVLCD ADVALIVFSS TGKLSQFASS    60
STNEIIDKYS THSKNLGKTD QPALDLNLEH SKYANLNDQL AEASLRLRQM RGEELEGLSV   120
DELQQLEKNL ETGLHRVLQT KDQQFLEQIN ELHRKSSQLA EENMKLRNQV GQIPTAGKLV   180
VADTENVVAE DGQSSESVMT ALHSGSSQDN DDGSDVSLKL GLPCLPWK                228

SEQ ID NO: 181          moltype = AA  length = 228
FEATURE                 Location/Qualifiers
source                  1..228
                        mol_type = protein
                        organism = Triticum aestivum
SEQUENCE: 181
MARERREIKR IESAAARQVT FSKRRRGLFK KAEELSVLCD ADVALIVFSS TGKLSQFASS    60
SMNEIIDKYS THSKNLGKTD QPALDLNLEH SKYANLNDQL AEASLRLRQM RGEELEGLSV   120
DELQLLEKNL ETGLHRVLQT KDQQFLEQIN ELHRKSSQLA EENMKLRNQV GQIPTAGKLV   180
VADTENVVAE DGQSSESVMT ALHSGSSQDN DDGSDVSLKL GLPCLPWK                228

SEQ ID NO: 182          moltype = AA  length = 228
FEATURE                 Location/Qualifiers
source                  1..228
                        mol_type = protein
                        organism = Triticum aestivum
SEQUENCE: 182
MARERREIKR IESAAARQVT FPKRRRGLFK KAEELSVLCD ADVALIVFSS TGKLSQFASS    60
SMNEIIDKYS THSKNLGKTD RPALDLNLEH SKYANLNDQL AEASLRLRQM RGEELEGLSV   120
DELQQLEKNL ETGLHRVLQT KDQQFLEQIN ELHRKSSQLA EENMKLRNQV GQIPTAGKLV   180
VADTENVVAE DGQSSESVMT ALHSGSSQDN DDGSDVSLKL GLPCLPWK                228

SEQ ID NO: 183          moltype = AA  length = 225
FEATURE                 Location/Qualifiers
source                  1..225
                        mol_type = protein
                        organism = Hordeum vulgare
SEQUENCE: 183
MARERREIKR IESAAARQVT FSKRRRGLFK KAEELSVLCD ADVALIVFSS TGKLSQFASS    60
SMNEIIDKYS THSKNLGKTD QPTLDLNLEH SKYANLNDQL AEASLRLRQM RGEELEGLSV   120
DELQQLEKNL ETGLHKVLQT KDQQFLEQIN ELHRKSSQLA EENKKLRNQV AQVPTAGKLV   180
VVDTENVIAE DGQSSESVMT ALHSGSSQDN DDGSDVSLKL ALPWK                   225

SEQ ID NO: 184          moltype = AA  length = 229
FEATURE                 Location/Qualifiers
source                  1..229
                        mol_type = protein
                        organism = Oryza sativa
SEQUENCE: 184
MARERREIKR IESAAARQVT FSKRRRGLFK KAEELSVLCD ADVALIVFSS TGKLSHFASS    60
SMNEIIDKYN THSNNLGKAE QPSLDLNLEH SKYAHLNEQL AEASLRLRQM RGEELEGLSI   120
DELQQLEKNL EAGLHRVMLT KDQQFMEQIS ELQRKSSQLA EENMQLRNQV SQISPAEKQV   180
VDTENFVTEE GQSESVMTA LHSGSSQSQD NDDGSDVSLK LGLPCGAWK                229

SEQ ID NO: 185          moltype = AA  length = 228
FEATURE                 Location/Qualifiers
source                  1..228
```

```
                        mol_type = protein
                        organism = Oryza sativa
SEQUENCE: 185
MARERREIKR IESAAARQVT FSKRRRGLFK KAEELSVLCD ADVALIVFSS TGKLSHFASS    60
SMNEIIDKYN THSNNLGKAE QPSLDLNLEH SKYAHLNEQL AEASLRLRQM RGEELEGLSI   120
DELQQLEKNL EAGLHRVMLT KDQQFMEQIS ELQRKSSQLA EENMQLRNQV SQISPAEKQV   180
VDTENFVTEG QSSESVMTAL HSGSSQSQDN DDGSDVSLKL GLPCGAWK                228

SEQ ID NO: 186          moltype = AA   length = 223
FEATURE                 Location/Qualifiers
source                  1..223
                        mol_type = protein
                        organism = Oryza sativa
SEQUENCE: 186
MARERREIRR IESAAARQVT FSKRRRGLFK KAEELAVLCD ADVALVVFSS TGKLSQFASS    60
NMNEIIDKYT THSKNLGKTD KQPSIDLNLE HSKCSSLNEQ LAEASLQLRQ MRGEELEGLS   120
VEELQQMEKN LEAGLQRVLC TKDQQFMQEI SELQRKGIQL AEENMRLRDQ MPQVPTAGLA   180
VPDTENVLTE DGQSSESVMT ALNSGSSQDN DDGSDISLKL GLP                     223

SEQ ID NO: 187          moltype = AA   length = 226
FEATURE                 Location/Qualifiers
source                  1..226
                        mol_type = protein
                        organism = Festuca arundinacea
SEQUENCE: 187
MARERREIRR IESAAARQVT FSKRRRGLFK KAEELGVLCD ADVALVVFSS TGKLSQFGSS    60
SMDEIIDKYS THSKNLGKSQ EKPALDLNVE HSKYNSLNEQ LAEASLHLRH MRGEELAGLS   120
VGELQQMEKD LETGLQRVLC TKDQQFMQQI SDLQQKGTQL AEENMRLRNQ MPQVPTAGMM   180
AVADTENVVT EDVLSSESVM TAVHSGSSQD NDDGSDISLK LALPWK                  226

SEQ ID NO: 188          moltype = AA   length = 226
FEATURE                 Location/Qualifiers
source                  1..226
                        mol_type = protein
                        organism = Triticum aestivum
SEQUENCE: 188
MARERRAIRR IESAAARQVT FSKRRRGLFK KAEELAVLCD ADVALVVFSS TGKLSQFASS    60
SMNEIIDKYS THSKNLGKSD QQPAIDLNLE HCKYDSLNEQ LAEASLRLRH MRGEELDGLS   120
VGELQQMEKN LETGLQKVLC TKDRQFMQQI SDLQQKGTQL AEENMRLKNQ MHEVPTVSTV   180
AVAEAENVVP EDAHSSDSVM TAVHSGSSQD NDDGSDISLK LALPWK                  226

SEQ ID NO: 189          moltype = AA   length = 226
FEATURE                 Location/Qualifiers
source                  1..226
                        mol_type = protein
                        organism = Triticum aestivum
SEQUENCE: 189
MARERRAIRR IESAAARQVT FSKRRRGLFK KAEELAVLCD ADVALVVFSS TGKLSQFASS    60
SMNEIIDKYS THSKNLGKSD QQPAIDLNLE HCKYDSLNEQ LAEASLRLRH MRGEELDGLS   120
VGELQQMEKN LETGLQRVLC TKDRQFMQQI SDLQQKGTQL AEENMRLKNQ MHEVPTASTV   180
AVAEAENVVP EDAHSSDSVM TAVHSGSSQD NDDGSDISLK LALPWK                  226

SEQ ID NO: 190          moltype = AA   length = 226
FEATURE                 Location/Qualifiers
source                  1..226
                        mol_type = protein
                        organism = Triticum aestivum
SEQUENCE: 190
MARERRAIRR IESAAARQVT FSKRRRGLFK KAEELAVLCD ADVALVVFSS TGKLSQFASS    60
SMNEIIDKYS THSKNLGKSD QQPAIDLNLE HCKYDSLNEQ LAEASLRLRH MRGEELDGLS   120
VGELQQMEKN LETGLQRVLC TKDRQFMQQI SDLQHKGTQL AEENMRLKNQ MHEVPTASTV   180
AVAEAENVVP EDAHSSDSVM TAVHSGSSQD NDDGSDISLK LALPWK                  226

SEQ ID NO: 191          moltype = AA   length = 221
FEATURE                 Location/Qualifiers
source                  1..221
                        mol_type = protein
                        organism = Oryza sativa
SEQUENCE: 191
MARERREIRR IESAAARQVT FSKRRRGLFK KAEELAVLCD ADVALVVFSS TGKLSQFASS    60
NMNEIIDKYT THSKNLGKTD KQPSIDLNLE HSKCSSLNEQ LAEASLQLRQ MRGEELEGLS   120
VEELQQMEKN LEAGLQRVLC TKDQQFMQEI SELQRKGIQL AEENMRLRDQ MPQVPTAGLA   180
VPDTENVLTE DGQSSESVMT ALNSGSSQDN DDGSDISLKL G                       221

SEQ ID NO: 192          moltype = AA   length = 228
FEATURE                 Location/Qualifiers
source                  1..228
                        mol_type = protein
                        organism = Triticum aestivum
```

```
SEQUENCE: 192
MARERRAIRR IESAAARQVT FSKRRRGLFK KAEELAVLCD ADVALVVFSS TGKLSQFASS      60
SMNEIIDKYS THSKNLGKSD QQPAIDLNLE HCKYDSLNEQ LAEASLRLRR MRGEELDGLS     120
VGELQQMEKN LETGLQRVLC TKDRQFMQQI NDLQQKGTQL AEENMRLKNQ MHEVPTASMV     180
AVADADAENV VPDDVHSSDS VMTAVHSASS QDNDDGSDIS LKLALPWK                  228

SEQ ID NO: 193           moltype = AA   length = 245
FEATURE                  Location/Qualifiers
source                   1..245
                         mol_type = protein
                         organism = Oryza sativa
SEQUENCE: 193
MARERRAIRR IESAAARQVT FSKRRRGLFK KAEELAVLCD ADVALVVFSS TGKLSQFASS      60
NMNEIIDKYT THSKNLGKTD KQPSIDLNFF LIILLRTYTN SYAYIHLLLQ LEHSKCSSLN     120
EQLAEASLQL RQMRGEELEG LSVEELQQME KNLEAGLQRV LCTKDQQFMQ EISELQRKGI     180
QLAEENMRLR DQMPQVPTAG LAVPDTENVL TEDGQSSESV MTALNSGSSQ DNDDGSDISL     240
KLGLP                                                                  245

SEQ ID NO: 194           moltype = AA   length = 223
FEATURE                  Location/Qualifiers
source                   1..223
                         mol_type = protein
                         organism = Hordeum vulgare
SEQUENCE: 194
MARERRAIRR IESAAARQVT FSKRRRGLFK KAEELAVLCD ADVALVVFSS TGKLSQFASS      60
SMNEIIDKYS THSKNLGKSD QQPAIDLNLE HCKYDSLNEQ LAEASLRLRH MRGEELDGLS     120
VGELQQMEKN LETGLQRVLC TKDRQFMQQI SDLQQKGTQL AEENMRLKNQ MHEVPTASMV     180
AVADVVPEDV HSSDSVMTAV HSASSQDNDD GSDISLKLAL PWK                        223

SEQ ID NO: 195           moltype = AA   length = 219
FEATURE                  Location/Qualifiers
source                   1..219
                         mol_type = protein
                         organism = Lolium perenne
SEQUENCE: 195
MARERREIRR IESAAARQVT FSKRRRGLFK KAEELGVLCD ADVALVVFSA TGKLSQFASS      60
SMDEIIDKYS AHSKNLGKSQ EKPALDLNVE HSKYNSLNEK LAEASLHLRH MRGEELGGLS     120
VGELQQMEKD LETGLQRVLC TKDQQFMQQI SDLQQKGTQL AEENMRLRNQ MPQVPTAGMM     180
AITEDVLSSE SVMTAVHSGS SQDNDDGSDI SLKLALPWK                             219

SEQ ID NO: 196           moltype = AA   length = 225
FEATURE                  Location/Qualifiers
source                   1..225
                         mol_type = protein
                         organism = Sorghum bicolor
SEQUENCE: 196
MARERREIRR IENAAARQVT YSKRRRGLFK KAEELAVLCD ADVALVVFSA TGKLSQFAST      60
SMNHIIDKYS THSKNLGKSH QQSPIDLNIE QSKYTGLNEQ LAEATHGLRQ MRGENLEGLS     120
VEELHQMERK LEAGLHRVLS TKDQLFTQQI SELQQKGTQL EDENRRLKEQ MPQVLTAGTM     180
VVGAGAENIL TEDGQSSESV MTALHSGSSL DNDDGSDICL KLSLP                      225

SEQ ID NO: 197           moltype = AA   length = 225
FEATURE                  Location/Qualifiers
source                   1..225
                         mol_type = protein
                         organism = Zea mays
SEQUENCE: 197
MARERREIRR IESAAARQVT FSKRRRGLFK KAEELAVLCD ADVALVVFSA TGRLSQFASS      60
SVNDIVDKYS THSKNLGKSH QQPSIDLNVE QSKYSGLNEQ LAEETNGLRQ MRGEDLEGLS     120
VEELHRMERK LEAGLHRVIS TKDQLFMQQI GELLQKGTQL EDENRRLKEQ MPQVLTAGTM     180
VVAAAAENIL TEDGQSSESV MTALHSGSSL DCDDGSDISL KLSLP                      225

SEQ ID NO: 198           moltype = AA   length = 225
FEATURE                  Location/Qualifiers
source                   1..225
                         mol_type = protein
                         organism = Zea mays
SEQUENCE: 198
MARERREIRR IESAAARQVT FSKRRRGLFK KAEELAVLCD ADVALVVFSA TGRLSQFASS      60
SVNDIVDKYS THSKNLGKSH QQPSIDLNVE QSKYSGLNEQ LAEETNGLRQ MRGEDLEGLS     120
VEELHRMERK LEAGLHRVIS TKDQLFMQQI GELLQKGTQL EDENRRLKEQ MPQVLTGGTM     180
VVAAAAENIL TEDGQSSESV MTALHSGSSL DCDDGSDISL KLSLP                      225

SEQ ID NO: 199           moltype = AA   length = 183
FEATURE                  Location/Qualifiers
source                   1..183
                         mol_type = protein
                         organism = Zea mays
SEQUENCE: 199
```

```
MARERRREIRR IESAAARQVT FSKRRRGLFK KAEELAVLCD ADVALVVFSA TGRLSQFASS    60
SVNDIVDKYS THSKNLGKSH QQPSIDLNVE QSKYSGLNEQ LAEETNGLRQ MRGEDLEGLS   120
VEELHRMERK LEAGLHRVIS TKDQLFMQQI GELLQKGTQL EDENRRLKEQ KISSLKTGSR   180
LNL                                                                183

SEQ ID NO: 200           moltype = DNA   length = 363
FEATURE                  Location/Qualifiers
source                   1..363
                         mol_type = unassigned DNA
                         organism = Zea mays
SEQUENCE: 200
catacaaatt atatatatat attttaaata tcaaatcttt ataagaatga tgatccactg    60
tccactgctg cccacttccc acgcccaaaa caagttcacc tccgtggcgc gtgttccgaa   120
aagtcctctt gttgtgggcg ggagaatgga ggcgtaatat ttcggcgtcc ccgaaatttg   180
cttgcacctt attggccgag ccaccccctcc cacggatcgt gccctgctgg caacattgca   240
gccatcggtg cccctctaga tccaaccatc cactgtcctc gcacgcggat ccacgggccc   300
accagcctcg gcagccgagt tgtttaaact ttataaaatac ccgtcgccgc ctgctacttt   360
ccc                                                                 363

SEQ ID NO: 201           moltype = DNA   length = 3912
FEATURE                  Location/Qualifiers
source                   1..3912
                         mol_type = unassigned DNA
                         organism = Arabidopsis thaliana
SEQUENCE: 201
acaccaataa aaatacacag caataaaatc gctacgtata tatatatata atatgtatta    60
tctattacaa gatagtaata gagtatagca agttgtatca tctaacaaac tatgcgaata   120
aaatttgaac attgtgacat gtagatgtag tgtaatttag ctaagtgctt atcatcagta   180
acatagaccg acttaacttt ttacgaaaaa aaaaagtaa catagaccga aaaaatgcat    240
atcgtaaatt taatgaaaaa cacaatttac gataagtaaa aaacaaaaag aaattacgat   300
aagtcgagaa aaatgcaaca aattgagata aagtattgat aaaaccatga agtgtcggc   360
gtatgtaaat gcggtgatta atgtgatcat tagagcgtgt gtgttaaacg cggcggtttt   420
agtggagatt gatcagctga taacactctt accgggacga atctaattcc atattcatgg   480
cttgttaaaa cctaagacat acgcaatctc taatttgcta gtataguttag ttctatatta   540
tttttcgact aataatgtaa acatatgatt attaagtcgc aaaaagagtg cttaacaacc   600
aaaaagtgga ttaattaact tggtgggaaa agttacaaaa cctttaatga ttactctttg   660
taccaagaat agtggcgaag cactataaga gcagagaaaa gaagctcaat aatgtactaa   720
aagttgtaga ttttacagc ttaaatacac caaattaat agaaaagttg gtaatttttt    780
aattcatggc tactgattta gatttttagaa aacaatagta gtatcattgt cacatcttaa   840
acacacaata ggtatgtttt aaatcaaagg ccgtagttaa tttgtcaaaa atgtatgcat   900
ttggtatttg gatgtctccg aaaggatgga tatatgggact tgttagataa tttcatacct   960
cagtatcaat agtcatggag cccaaattgc tcaaaaacat atttttaatt ccaagacttt  1020
gatgaaacg taataatgag tccaatgggc catcagatac aatgttcgga atttaacggg  1080
tttgttagtt ataagtattg ggcttgacct atctggttca atgatatgta ggaacaaccc  1140
aatttgcaaa gctttattaa aagactcttt agttgtcgtc aaggtttaac ttgtagtagt  1200
tggtaagaaa ttctacgtga aataggcaac attacaaaaa caaaaatcaa ttcgaaatca  1260
tacaaaacga aaccaagtag taaccaacta cactattatg acattaagta ttagacattc  1320
ccaaatcata caagttcctg tcatgaagga aacaatggtc cgtatttgca aacgattaca  1380
aaaattcaaa ccaaaaatga aaaaacgagt taaattattt ggtttataaa aatagtaatg  1440
tcaacagaag actagattgg gaaacctgaa gcgaacagag cttttaaaaa cgagtttgaa  1500
cggctgggat catttggtac aatacccacc gtaagtttgt ttaccctagg gatgcaagcc  1560
aaaggcccaa atcagttact acttactgct acaaccatcg tctcagcttt ttgtctcagc  1620
tttttactaa tgaagcatac aatttcttgg gcatgtcaca tctcgacacg tgtccactat  1680
tctcttctct tattggctac tcgttcgtag gcttctgtta atagatgatc tctctataac  1740
tctaacagtc ttttctttct cttttatttcg ttttggtatt ttaagtttca aattgaaaat  1800
aataggagga aaagtctagt tttaaatatt gtttttttac aagtgaacgt gaaccaattt  1860
acctcttttt ttttatatat cctatcggct aatctggtta gtatcggtag aaatgcaccg  1920
aggtgctaca gagattaatg ctagggatag tcagaccgct tgtatttctg actatcaagt  1980
aaatctacgc ccaactcaca tatttcccaa acaaatgtga ttttttttt ttttttttt    2040
tttttttttt ttttgtaaca aatgtgattt tgttttcaag gaaaatagaa cttacgtttg  2100
ggaatttcac ccttcactaa agcttccttc tgccattaga ccacaaaggc ttgggcaatt  2160
taccattttt gtaaaagtag aaaacaaaat gcctaaaatg ttcatacttc attacatcaa  2220
caaggttatg cccacgatat agaggcatgt aacatttata tatatagtgg aagaagccta  2280
cgagcttttat taataagtat aaactctgat tattaggtaa ataaattact aaaaacgatt  2340
actcaactga caaaaccgta gttgaataat aaggttacta tgaataccga ttgaatattg  2400
caaagccgga attgaaaaat atataacaga tcaaatgttc aagtgtggtc ataattctca  2460
cataggtcat atagctgaac ccatgcatct atttactagt ctatagaaag tactagagac  2520
gcatacagct gaacctactc tattcttttta ttaattttag ttctcgtgga tacaaaattc  2580
ctccaacatt tattagaacg aataaaaacca atatgatgat gattagttat tggtaaacat  2640
ataaacgttg agtaaacttc aaaatagatt gaagtactat taagacttgc atttttttcc  2700
cttgggttat attcttgaat cgtttcgaag tattttaact ttcaagaata gaaggttcct  2760
caactataaa caattacatt aatcaaaacc atttctatgt aaacaacata atttttgtat  2820
attttagtct tccccaaaag tttgaccgat agggcggttt agaccgtata gtacgactgt  2880
acaacaaaaa ggactctgga gacctaaaga tccaaaacta tgcaaaataa agatacggtc  2940
ggaccaattt aatctaacaa aaccaaatcc ttatactaaa ctatttaccg atacatttgc  3000
atataacaca gtacacacaa ttaaatcaaa cattattgga agaacaagat agaatattgg  3060
cttaatctcg aacgattaga gttatcctag agcctcggag cttttgtcac atataatata  3120
aactatggta tatataaaca tgactctcat tgtatttat cgcaaggtac aattccacca   3180
attttttcg tcccactcat acagctttaa ttgtgaaatc aatccataaa aaaccaacat   3240
```

```
gtgacatggt ctctataact ataactataa gatagtaaaa aattcacatc aacataaaag   3300
aaaaccaatc atattggcta aaaaaaacta acggtcgaaa aacgtataac cacaaaacca   3360
aaccggtcca accggtgtcc ccaatcacta tcaaagcatt aactaacttt cacaaggaaa   3420
agcatagttc agtttctcta catcgcttcc catcctctta accctgttta ctcgaatcat   3480
ccaccgttgg atcaaacacg cgctacaaat ctagcgcgtg accgaggttt ttacacagtg   3540
gaatattacc atgcattgga aagcggcgtc tacaacaaac ggcgggtcat gtcaccgtca   3600
aaatcaacct ttcttaattc ctaacgccgt tacttatctc cgtttactaa aaatgttaat   3660
gcgtgtgaga gtgaagatca tatactaatt agaagtggct aatgttttaa cgtgacatta   3720
ttatcatagt taatggttcg atcagagttt taagtagtaa atgataatgtgtgtgtata   3780
taattgcata catatatact ctcacactct gacagatttg tcgtggtctt agtattctct   3840
ttcatggcta gttatatagg gctctagtac attatctctc tctccccatt tctctgtctc   3900
tctcttcttt aa                                                       3912

SEQ ID NO: 202        moltype = DNA  length = 1600
FEATURE               Location/Qualifiers
source                1..1600
                      mol_type = unassigned DNA
                      organism = Zea mays
SEQUENCE: 202
agctcgtaga gtgaggccga ggcagtgagc caccgtgtgt acgtacgcac gcactggtgg     60
tactgaaaaa caaaaggtgc gcgcgcggcc gcgaatatta tgcaggctgc ctgccgcgcg    120
tacctagcta gctacgactt tcaccctgtc catgaaacga tcatgcgtc ccgaagaaac    180
cgtacaaagg ctactactag tactccgcct gtgtgaaaaa catggcgtac atttcgcatc    240
ctgaattcgt aacacatgtt caatttctta aataaaatga atcaacagga aataaaaaag    300
aatttggggtg tttcttcttt ctgtctgaac tagtgtattt tagatgcaag ttaatggaaa    360
cagggagttg ctcgatttaa aaaatattcc ctccgttttt tttagttgt cgctggatag    420
ttcaattta cactatccag cgacaactaa aacaaaacaa agggagtact aaagcaaaaa    480
aaaaactgac atatggggta agacatctcc tgacattata ttaagaatag cttctcacat    540
aagtcgagaa aactcttgaa tcccttcctc acacatacat agcggtaccg tagctcatat    600
gagaaacgac cgagacagac cggaccatag atctacgctt tgacgtggga caaacgagga    660
gattttttaa ccacgtccta aaattcgctc ctacggagga cttaggacct aagaaatgat    720
acatagatca actaaccatc tcggttagag gaattctcga aaaaaaatac tagagcgagc    780
aatgatgcac tacctagtga tactatgact cggtgctata tggcatggtt gcatgggtag    840
cctttttgcag tttgcatcaa gcagggagac agacagggc ttggcttggc catgctagac    900
gttgcggttg cagttgccac aagggagcc tgccattcca cacacctcct actctgcatg    960
cgctctctct ctctctctct ctctctcaaa ttctcaacaa gtgttgaagc ggccgaagct   1020
agagccttcg ggggtgtttg gtttgaggaa tcatttaatc caaatgtag tgatgcatca   1080
tgggtccatt cctcaaagttt ggtgggatga cctcattcct catattagta ctaactaaat   1140
aactaataagg aacgaggtga tgatggatca actcaatcca ttccacaaac caaataaaaa   1200
agtgatgagt gagaagacga tggattagat cattcctcaa accaaacagc ttattcgtgt   1260
gtcaacttca cttgtctctc tccaaaagat atcgtcgtat cccatgatcc ttcctcccgg   1320
cgccaaccta tatctcacca tgcacctagc acgcagctac gcgctctctc tctctctctc   1380
tctctctctc tctgcatgct agctagcttt cctctagcct ctatagctcc tatgatatgc   1440
accccggcct cctttataac cctcctcaat gcctctccct tttccaaggc aaggccaagg   1500
cggcaaaccc ttccctcctc ctccttggcg cagaccggag agatcacagg agctcaggaa   1560
ggccggtgtg accagctgct gaggcatggc ggccaacgtg                         1600

SEQ ID NO: 203        moltype = DNA  length = 2000
FEATURE               Location/Qualifiers
source                1..2000
                      mol_type = unassigned DNA
                      organism = Zea mays
SEQUENCE: 203
gttctatgag gtggaccaat gaaatggcac acaccatctg tgtcagcttc aattatatat     60
taacaatcaa ttttgctatt tgatatgata tttcttttat attttatac ttaaatctca    120
accacgaagt ttttaattgt atttaactaa aatcagtcag taatctttcg atgatcaaag    180
gtaaccaact aagaaggtta cttgcaagga accatgacac ttgtaatggt ggttgtaaat    240
acagatacta catcatcatc tgcccataag gtattctaga atacttagcg cagtttacat    300
gcaacatgtg agtacatatg gtggttatgt aggagacaca ctggttgct acatggccag    360
ttcaacaatt tgttcagtta ttcatgcatc aaaaactatt gtcattccat caccgcaatt    420
tggttggcct agtagttat tcagagcttc tagtattctc actttaaaat catcaatgaa    480
cacatacata tagcttgttg tactcataaa actatagcgt aaagcaatat atctactgct    540
cattcaagaa tatatgtggt tttataaga tggaccaatt aaaggtgcac tcaatctatg    600
tcatctatgg tgaaaaggtg aaacttctat atatattaat aaccaatttt gctacatgat    660
acgatatctg taataataat tttatactta attatgcacc gctatatttt taaattatat    720
cttttatctaa aaccgaaagc ttttccgtga ttaatggtaa ccgtatagaa aggttgctta    780
aaaggaacca caacacttgg catggcagta gtaaatatag gcactatacc attgtctggc    840
cacaaaggta cttttagcaca ctccgcatat cttttcgtaca atgtgttgat acatatggtg    900
gatatctaga ggacattgct tgttgttaca tcacaactca aacaattata gtcattcatg    960
catcagaaat cactggcatt ccttcaccac aatttgtttg gcccaagtaa cttattaata   1020
gcttttggta tccccctct ctaaaatcac taatgataac atacacatag cttgatttac   1080
tcatgaaact atagcataaa gtaatctatc tagtgcccat tgaagaatat acgtggttct   1140
atggagatga accgatgaaa cgcgcactca agctatgtta tcttcggtgc gaaggcacaa   1200
cttctatatt acatcatcat tttgctatct gatatgtat ctctaataat attttatac   1260
gtaaatatcc gccgttaaat ctgcaccgct atgttttat aattatattt atttgaaacc   1320
gaaagcttttt ccgtgattaa tggtaaccgg ctaaaaagat tacttataag aaagcttaag   1380
atctttaaca tgaatgaatg ccatacatca aggatactat gccatcctat atatgtccac   1440
aaatatactc tagcatgacg gtaatataat gggatatata taccctcata aatcatggat   1500
actatttgta aggactttgg tatttgtaca gtcattcatg catcagaaac tactaaaaag   1560
```

```
caaaatgaaa agttaatcta tgtagatttt gcattgcatt cccctcaacc aagcaagcat  1620
ccagaggaac gaaggacaaa tgttattcaa ttttgtattg cttcccctc aaccaagcaa  1680
gcagcccaaa gaacaacaaa tggcattccc atgagagaaa aaaaaaatac ttgtaggtgg  1740
ggccaccctc ccctacctat atataccct gttcacgccg ttcccaagac cacaccacca  1800
gtccatccat cctgcgctgc gctgcgctcg tgacaagcat cgcaagcagc tcctcctcct  1860
cccctgtag ccaacacctt cctgttccgg gcgcagagc ggctgtcggc cctcgatctg  1920
acgagccatg acgaagcacg ccgcctactc cagcgaggac gtggtcgcgg ccgtggcggc  1980
gccggcgccg gccggccggc                                              2000
```

| SEQ ID NO: 204 | moltype = DNA length = 1860 |
|---|---|
| FEATURE | Location/Qualifiers |
| source | 1..1860 |
| | mol_type = unassigned DNA |
| | organism = Zea mays |

SEQUENCE: 204
```
tactccgcat ggcacaccgg acaatccggt gctacatcgg acagtccggt gaatcatagc  60
ggagaggctc cccgaaaacc cgaagctagt tagttggagt tgatccaccc tggtgcaccg  120
gacactgtcc agtggcacac tgaacagtcc ggtgcgccag accagggcag acttcggttt  180
tcattgctat tttcatttga accctttctt ataactttgt attggtttat tgtgaaccttt 240
tggcacctgt ggaacatata ttctattaca aactagttag tccaataatt tgtgttggtc  300
aattcatcca ccaacattta ggaaaatgtt tgacctatt tcccttcag tagtcattta   360
aacacgacaa tattttcacc acataaatgc atttaaaata tatacgccta gtatttcgaa 420
attcaaactc tctccatcgt agttctcatg gtattttttc aaaccgacgt taaattcatt  480
atctaaaagt cgtcacaaga aatttgttta gtgggtgtt ggtttatata gagaagagat   540
tgatttttttg tccctcaatc ttcttcaatt ttttatcgct aaattagcaa atacggaaac  600
taaaatacat atgttgttt taattataa tatgtacata ttatataatt caacaaaatt    660
tgaactaaca gctagttaaa aatttattag attataatat aatctagata tattataatc   720
tcaaacccctt aagaactaaa aaaattagt agggtgggc cattttttac cataaaccga   780
accgaaccga accgaaattt tggttttttt ggtagttcgg ttcggtttcg ttttttgtat   840
ctaagaagtt cggtttttcgg tatcgtaatc ggttttcacc gtataccgaa ccgaaaaaac  900
cgaataccaa actttatcaa ttctcaaatt tgactattcg attatgtgaa ctaattgtgt   960
gatacaatta aattgttatt cacttatttg tatgtgatgt atgatgtata tctaaatatt  1020
tgtacctata taattttttac tttttaaaat tatatgtaat ctatcatgta aacttgttgt  1080
atgtattgtc ttgattataa gtttggtatt cggttttac cgaaaaatcg aagtaaaaaa  1140
ccgaaaccga acttctcggt tttcattttt ctagaaaacc gaacggtttc taatgtttga  1200
aaaccgaag ttttttaaaa ccgaaaaacc gaaccgaagt ttagaaaaaa accgaatgcc  1260
cagcccctaaa aattagtacc ccataagaac taaaaaaaga taaaatgact aaaaattaat  1320
cagttgaaac caaacctatt ttcccccaca cctcacggta ttgtttcgca ttccaagttt  1380
gaaacagac tggaaacaaa acccaaaacg actggaggga ccgagcttgt gctgagcagc  1440
agagatggcg ggaaatgctg cgtctccccgc ctcagttttcg gatgcccccgc cctttcccaa  1500
accggccacc gccgccgccc gtgtctccccc accgacaggt gggtccaatc cttaaccacg  1560
gaccaggggc cccacctgtc aggtggacct tccgaagcaa ggatcggcca ggcgggaaaa  1620
cattcgccgg caggtggcgg ttgcgccaaa tttctcccctc ccttttccgt tcgggcgtccc  1680
caaacgcctc cctattaatc tccccgcgtt cccccttccct cgcgccgccg ctcccccctc  1740
ccaaagctcg cccgctccc agctagggtt tcctcttccc atccacagcc gccggggcgc  1800
cgccgacgag gacagcgccg ccacgatgtt ggagttgcgt ctggtgcagg ggagcctcct  1860
```

| SEQ ID NO: 205 | moltype = DNA length = 1000 |
|---|---|
| FEATURE | Location/Qualifiers |
| source | 1..1000 |
| | mol_type = unassigned DNA |
| | organism = Zea mays |

SEQUENCE: 205
```
aggcggggga acgaacgcgg gtgtgggcgg gcgaacggtg tggattcaca gaagcgaacg  60
gatggtacag attcaccgaa ggcagaacac aaaaaggcag gctactattg cttacttaat  120
aagtagtaga gatttgcgcc catcttcaat gttaaggaaa agcataacgt ttgtgctgcc  180
gcgataattg ctgtctgcgt ttgggtccca ccgccagggg gccggtcgac gtctccgtcc  240
acgggtcagg tctcctcccg ctgcccgacg caaggagcca ttgaccaccc aagggccccct  300
gcctaggacg gcccccacctg tctgtcgtgc cgctgatcgc ccgtcgctga tggggcccgg  360
ccagcccacc caccccttccg cacgtcacgg cgtaacgcgc ggcgcgaccc atccgtcccc  420
tccgtgttct gtccgcatgc gcgcgccgcc cgtaatttct ttccgccgcg agtcgcggcg  480
cccgctcgtg gccggtgcgc gcgtccacaa ccgccgccac cgccttccca cttccaaata  540
cgcctgctgc cactttccccc attcctgtct gaccatcccc acgccccct gctgtggcct  600
ctgctctctc ctgccagttc acctgctgcc tccggtgccc tctgctgtgc ctcgctcgcc  660
caccaccacc aatcgccacc ccgtgcggca gccgcgctgc catcccgcgg aggactggag  720
gagcacgcat atccgagcct tccctgccgc gtcgcatgga ctcatgctgt cgcgggcgcc  780
ctcccgcatc gcctccaacc gggtgcctgc ctaactggcc gattttcttc ctcgcgtagc  840
cccattccgc agcacaaata gcgcgtcact ttcccaattt ctatcgcgtg cccccccttcc  900
gatcctgcca tttcgtgcat cctgtagcgt ctggcagtgc ggggtcatc ggggatggag   960
tgggtggaca ggaccaaggc ctccgccgcc gccgccgcag                        1000
```

| SEQ ID NO: 206 | moltype = DNA length = 1528 |
|---|---|
| FEATURE | Location/Qualifiers |
| source | 1..1528 |
| | mol_type = unassigned DNA |
| | organism = Oryza sativa |

SEQUENCE: 206
```
ggaagctaac tagtcacggc gaatacatga cgacatcggc ctacaacgca caacttcttg  60
gcataaaagc ttcaatttca atgcccctat ctggaagccc taggcgccgc gcaaatgtaa  120
```

```
aacattcgct tcgcttggct tgttatccaa aatagagtat ggacctccga cagattggca    180
acccgtgggt aatcgaaaat ggctccatct gccccttttgt cgaaggaatc aggaaacggc    240
cctcacctcc tggcggagtg tagatatgtg aaagaatcta ggcgacactt gcagactgga    300
caacatgtga acaaataaga ccaacgttat ggcaacaagc ctcgacgcta ctcaagtggt    360
gggaggccac cgcatgttcc aacgaagcgc caaagaagca cttgcagact ctaatgctat    420
tagtcgccta ggatatttgg aatgaaagga accgcagagt ttttcagcac caagagcttc    480
cggtggctag tctgatagcc aaaattaagg aggatgccaa acatgggtc ttggcgggcg    540
cgaaacacct tgataggtgg cttaccttt aacatgttcg ggccaaaggc cttgagacgg    600
taaagttttc tatttgcgct tgcgcatgta caatttatt cctctattca atgaaattgg    660
tggctcactg gttcattaaa aaaaaagaa tctagcctgt tcgggaagaa gaggatttta    720
ttcgtgagag agagagagag agagagagag agggagag agaaggagga ggaggatttt    780
caggcttcgc attgcccaac ctctgcttct gttggcccaa gaagaatccc aggcgcccat    840
gggctggcag tttaccacgg acctacctag cctaccttag ctatctaagc gggccgacct    900
agtagctacg tgcctagtgt agattaaagt tggcgggcca gcaggaagcc acgctgcaat    960
ggcatcttcc cctgtccttc gcgtacgtga aaacaaaccc aggtaagctt agaatccttc   1020
tgcccgttgg actgggacac ccaccaatcc caccatgccc cgatattcct ccggtctcgg   1080
ttcatgtgat gtcctctctt gtgtgatcac ggagcaagca ttcttaaacg gcaaaagaaa   1140
atcaccaact tgctcacgca gtcacgctgc accgcgcgaa gcgacgcccg ataggccaag   1200
atcgcgagat aaaataacaa ccaatgatca taaggaaaca agcccgcgat gtgtcgtgtg   1260
cagcaatctt ggtcatttgc gggatcgagt gcttcacggc taaccaaata ttcggccgat   1320
gatttaacac attatcagcg tagatgtacg tacgatttgt taattaatct acgagccttg   1380
ctagggcagg tgttctgcca gccaatccag atcgccctcg tatgcacgct cacatgatgg   1440
cagggcaggg ttcacatgag ctctaacggt cgattaatta atcccggggc tcgactataa   1500
ataccttccct aatcccatga tcaaaacc                                      1528

SEQ ID NO: 207           moltype = DNA  length = 1280
FEATURE                  Location/Qualifiers
source                   1..1280
                         mol_type = unassigned DNA
                         organism = Setaria italica
SEQUENCE: 207
tccaccgatc atcacacaca gccagtagtg ggggtgggcc aagcaatcag gcacccggca     60
atgcgagctg atgcgtgatg atggtgctac caacaaactg actataaaat ttctgatttg    120
aaagggattg gcctcgatat tttattagct ccccggcttt tgtcacgaca cgttagcatg    180
cgtgccttct agaagctagt ccgggtatta ccgctagaaa gttcccgaaa tgaagcattt    240
accacccgta aagctcattt ttctttatga tgagtagaca cggtaccaac attgaggacc    300
gattggttgg ctcccaaaat ctgccctgcc aaactagggc aagttcataa attttgacat    360
tcgcttggtt ggcaatcaat taaatcctat tctaaaattc ttgcctaggt tttgatataa    420
catgccctat attttggtct actcaaattt tggtatgqta aattttgaac accaacaaat    480
caggctatta tttatcttat ctcttttctca atttcattac acagcaaggc agtaattaaa    540
aggaccgtat atacaatgga tgtaagaata aaatgtataa gtagaaatat attggcatgc    600
ctcgtgctgg tgcatgtcga tatgctctca attgaagtt ggagacaggt tatgcttagg     660
atagtcccaa cctatgatat ctgtgtgtct atactgccac ataagtaaga catcacttta    720
gaaattacat tctacaacct ataatttctt agtgtggatc cttaattaat tcatcatctc    780
tcctctcaat tcctcatcaa ttatgaagac accatcttct tccaatgcaa atttaacact    840
gtctaggatc taggttcagg tgttgatact gggtcttgca tgagatccag tttcttgttc    900
ttccaattct ctctcattta atatataatc acataagcaa agatcctat gtagctgcac     960
aattaatgct atggaaacta tcctaatcgg aggqttggga ctgctcctgc ctatggcggc   1020
ttattcccca tttgcctaac ctgaaaatcg aaagggagtg catgcacggg caaacactag   1080
tgttgcctgc atcaataatc gtccatgatt atatagaggt agcatgactt ttttaggcgt   1140
cgtgtcctaa tcaatcagaa aagaaagcca acctaatcgc tatgggccgc aaccaccgat   1200
gcgactatgc gagtatatgg aaacccgttgc tactccccca ctatatatcg tggagtctga   1260
tggcaatcca acggcagacg                                                1280

SEQ ID NO: 208           moltype = DNA  length = 1435
FEATURE                  Location/Qualifiers
source                   1..1435
                         mol_type = unassigned DNA
                         organism = Arabidopsis thaliana
SEQUENCE: 208
taggaaaaaa gttatatattc ctacccaaac tttcggcacc agagacaaat taggtttgtt     60
cagaaaatca gtcgctcatc gacagactta acaccacaaa atcatcagaa tttctttggg    120
acaaaatgga aaatgttctt cacggctcca cctaccaaaa tttcgatatc aagctcaaaa    180
gcatacacaa actataacta attccatagt tacgtaatct taacttcgaa ttcaacaaca    240
catgcatgca tcgactgaat cttcaacaaa tgcaatcaaa cacacaaaat tgctaccaaa    300
aaaatatgat tttttttta tgatttcaat tttcatccgg cacttagtcc aaaactttt     360
ttgtgtgtca acatttttta aaaaaatctt taaacggata tctgatcaa gagcatgttc    420
ataggtgata cttacaaaat attttttaaga aattttttag tattatttat aatgtttgtt    480
taataaatat atataagatt ttttgctttt atcaaatgtg accaatcaga agaaaccacg    540
tcagatgata ctgatatgac aaaatatgata ctgatcaaac atattctaat tgctttacta    600
atataaaaat aattttgga cttgtgatac tctaaaaata tcacccatat acatggtcta    660
atatatggat cgtaaaaaac tcatatataa tattaataag tagtagaaga gcgtagacca    720
tgtcctgggt cgtcgtccaa atgaccacaa gaagatttca aaacagagga aaatatttct    780
cattaaataa gtttctctga cgcataagat aacattatta caagattcag aaaaagaaag    840
gtgaaaggat aatgtttctc ctactatata agatgtgtac atctgaaaaa atatgaatat    900
atttgtaacg tttgactgtt attacatgat taatacgata taaatattaa catttttttt    960
caaaataaaa gtaatatagt aaggaaatga aaagaggcat gaagcatgcc tctttttttg   1020
gtcggctgcc gtttacaatt gccaattgcg atagttactc ttcttgcgtg tacgacttt   1080
gttttttttt acatattcgc caataatttg acgttttcta ttagtttgtt tgatactctg   1140
```

| | | | | |
|---|---|---|---|---|
| ttgtcttgct | aaaactcaat | aaaacattaa | attactttct | tgaatgaagc tggaacaaat | 1200 |
| ctaacataaa | tagaaaatga | tgggcaagtt | gatgttattc | gtaaatttat ttagattata | 1260 |
| ttatataaaa | agcaatccaa | ttatatatct | catatataca | atttcttatc ttactttgtc | 1320 |
| aatgtcatat | acgtaactaa | aacttgcgga | aatagaaaat | gccacgtgta tggtggacat | 1380 |
| aatccgaatc | tctctctttc | ttctataaat | agtggccatt | cccattggtt gaaat | 1435 |

```
SEQ ID NO: 209         moltype = DNA   length = 1940
FEATURE                Location/Qualifiers
source                 1..1940
                       mol_type = unassigned DNA
                       organism = Zea mays
SEQUENCE: 209
```

| | | | | | |
|---|---|---|---|---|---|
| caaatatcca | ctcacagcca | tacccgtggt | tgcaacaaat | atctatccac aaccatacct | 60 |
| gcgggtaaat | tcatatccat | gtacgtgctc | attaggtttt | ggacaggttt tgtatatatg | 120 |
| tcggatatga | cagagacaat | catttttcaac | aactcaatag | cataatcaat caaaattctt | 180 |
| cccaatttta | cctgaacaca | caattaaaaa | cttaataaaa | aaattatata aatacacatg | 240 |
| tcttttaaca | atcaatattc | tcaacacgac | aacatggaag | acgcgtcgga ctagaagggg | 300 |
| tggagcgctg | gggaccactg | gggaagcgac | agtgaggctc | accggcagtg tggactaaag | 360 |
| atccgagagc | agttgggcgg | gcgactggtg | tcggattgag | ggacacgaag gggcgacgat | 420 |
| agtgtggact | gaataaccaa | gagcagttgg | cgcgagcggt | tggcgtagtc ttgaggtgta | 480 |
| ggcaagaagg | gacaaccacg | agcgtatgag | gtgcgggttg | tggctagggg cactagagat | 540 |
| tagaaggggt | agacgtctgc | caggtgcgaa | cggtacaggt | gttgcggccc cgtaggactt | 600 |
| ggaaggggac | acatgacgta | gttcaagaaa | ccagcaaggc | tagaaggggt gaccataagt | 660 |
| gggaaattag | gagttcacgg | agttagggtt | tgctctttgt | tgtgtaatat gagcaaaaca | 720 |
| aaaataaata | aactatatgc | tgatttcgga | tatgcaacag | gtaatccgtg ggtggaaggt | 780 |
| aatattctaa | tccgtgtccg | ctcgactttg | gatctggtac | gaatctgacc catgcttcag | 840 |
| aacatgtatc | catgctcgtt | tccattggat | cctatggata | tttgaatcca tgatcaaatt | 900 |
| tccattccta | gatagctaga | ttagagtaat | gttccgttta | gatgtcgata ttggagggtg | 960 |
| tggaattgaa | ttgggttcaa | ttacaaatca | gccatgctat | tgaaatgagt tgtaattcca | 1020 |
| atactaatgt | ttggatgtca | ctgaattgga | gtttggaatt | gtgtggtcta attccattca | 1080 |
| atacagagga | gtaatgctct | gtattaggag | aggggggtctc | tagttgtagt ccaattccag | 1140 |
| gggattgggt | atttgattcc | aaatctcaat | tatgtgcata | accaaacaat agaattctag | 1200 |
| aaaagctgat | ttcaattcct | aattcggtgc | tccaatatct | acatccaaac agggtataat | 1260 |
| gcaattcttc | gcttcctatg | gatggtcttt | tagattttgt | attggctaat gatattagac | 1320 |
| gtttcttatt | tttgtctttc | gttgaatgtt | tttcgattga | tgtcggggta tgaatccatg | 1380 |
| acttttttcca | tcactagaaa | atatactgtc | agaaaaaata | gtgctgaatt agtgaatttg | 1440 |
| atccatcata | atggagttgt | cattctactt | tgcacttgca | ctaccggcag cccgcagcag | 1500 |
| gacggctgac | aagctcgcac | taagtcatcg | atttgtggtc | actaatgcgg agctcgcact | 1560 |
| tgcgtgactc | atcgagttgt | gggcttgtgg | ccttgtgggt | ggaacggtgg aatccacctc | 1620 |
| aggatgccac | agaaaaaggt | ttaaaaaaac | tgttgcaccg | agccaccgag agagcacaag | 1680 |
| accccccacga | ccgcaggtca | agccgtactg | gactggaccg | gaccggacac acgcccagaa | 1740 |
| agccctgcag | cagaactgca | gaagacacgg | ccgcggcaga | agagcccaaa tcacggccgc | 1800 |
| aaaagccacg | cacgcggcgc | ttgtcctgcg | cggcgcacgg | aaacccaccct ccacggccgc | 1860 |
| accccgtgcg | tcggctgctt | gctgccccag | tgccgccccg | cgttcccttc gctccgccg | 1920 |
| acaccgacgc | cgccactgcc | | | | 1940 |

```
SEQ ID NO: 210         moltype = DNA   length = 51
FEATURE                Location/Qualifiers
source                 1..51
                       mol_type = unassigned DNA
                       organism = Arabidopsis thaliana
SEQUENCE: 210
```

| | | | | |
|---|---|---|---|---|
| tatatcatcg | ttctctctat | aaactttata | gaactttgtt | ctgatttct c | 51 |

```
SEQ ID NO: 211         moltype = DNA   length = 1386
FEATURE                Location/Qualifiers
source                 1..1386
                       mol_type = unassigned DNA
                       organism = Zea mays
SEQUENCE: 211
```

| | | | | | |
|---|---|---|---|---|---|
| gaggtgcata | aggctggcaa | gacgacagtt | aggaacgcat | gcgagcgagg ttgacggacg | 60 |
| cgataaggtt | agcgcatgcg | tcgaacgcgg | gctggcgagg | gtggaaggca tgataaggct | 120 |
| attgggtagc | gcaaaatgtg | tagacagcgg | gcgagtgagg | atggcagtgg tggcatgcat | 180 |
| ggacgcggtt | ggagcatacg | cgacaagaat | ggagcacgac | gtagatttcg ggagcgccgg | 240 |
| gttgagcgc | ccgcgggcga | gatgcggcc | atggttagag | cgcccgtggt tacgggtggg | 300 |
| ttcatgcgcga | gcggaggggt | tgcaagattt | ccagggcgct | cgggtcggtt gcaagctcca | 360 |
| cggtggaggc | gtgacggaga | cgacgtgggg | agggaggtcg | tggggaaatt cggacgagca | 420 |
| gaggcgtggc | aggtgtggca | tggggaggga | ggtcgcgggg | agggcgcagg gaggtggcat | 480 |
| ggggagggag | gctggggacg | aagatgatgt | gggcccaagg | gagcgcggga caaagaattg | 540 |
| cgtatgataa | cgggttgatt | cgtagaattt | taggcggtat | tttataaaat gacgcaggac | 600 |
| agccattggt | actgatactt | taatatagta | gagaagagat | ataaattagg acgggtacaa | 660 |
| caagaccaca | cgtactaaca | ttttttttg | tcacaggctg | ctctaataca tatctctatg | 720 |
| ataagcgagc | tagggatgct | agcgtgtcca | tttgattcct | atataaatct ccaattatag | 780 |
| ctgtagcaat | taatttaata | aacacccaac | aatagtcaa | atctcatagc aaatcataat | 840 |
| catgaatgct | ccaaaatcag | ctagctggct | ctccccttatc | ttcgttttttc cttcttctcc | 900 |
| tgcaacgaaa | agaaaaaaaa | agaaaagaaa | agaaaacggc | cgcttgtggt actaactccc | 960 |
| aactacgcac | ctaccgcgcg | cataactctt | ggccgcctgc | cctcatcacc tccgcgtcgc | 1020 |
| cgtcgactca | tccttatcct | ccccatcacg | ctcacccgc | gcccgcaccg cgccatccgt | 1080 |
| actttcccgg | ccgccccacc | gctggccgcc | ccgacgtgtc | gcgccgccac cggaaggtcc | 1140 |

```
cgggccgtcg ggcgggcaga gcgcctgcag cggtggaccc acgccacgct gacgcgggcg    1200
cgcgtccgtc caagaaacct gacgtaagca gtgacagaat tggcgccgcc tctcggcgtc    1260
cacgtgtcgt ggtcaacctg tcagagtggg gctccgtgtg tgcgctaccg caggggcccg    1320
gcgcacgggc cacacgtgtc gcggtcgacc cggctataa atgcccggct ccgcactcgg    1380
aacaag                                                                1386

SEQ ID NO: 212          moltype = DNA  length = 997
FEATURE                 Location/Qualifiers
source                  1..997
                        mol_type = unassigned DNA
                        organism = Zea mays
SEQUENCE: 212
gctgcttccg gtagcctgaa gcagaaaaaa actgaaagaa acatgacaga taattccctc     60
ggagaaactt ggcatgtttc ccgttggtca tgtaggacga cgataatgat aaattggtaa    120
gcaaagaaaa aggctactaa gctcgagcag tagaagctac ctagctcgtc gtaacgaaga    180
aacttctcgt ccttcaggta gacccttgct tgtttgcagt actttagtta gggttcggtc    240
tttaattctt ttgctgggca gcagtaaacg gagatgagaa gcgcgagctg atcattgttg    300
ccattctgtg caacgaagct aggggaccaa tgctgactcg cacgagggca tagttgctga    360
tggtcataga cgacgcgttc acttaaaata ataaagaatt ataaattgtt gtcataagtc    420
gtgcagccta atataggaga gtgcggcatt gctgtagcta attaagagag tattccggtc    480
atgcttgagc ttgagaatt tttgagggtc cgttcgcttg gagagtcgga gattttgag    540
ggcccgttcg cttgcacaat aataaacaaa gatttgttct agctcatcca aatctatata    600
aattaaagaa gtaattcggt taggaatcaa tccagagctc taattcttaa aaaccgaaca    660
gggcctgagt tgtttgtcta gacgacatta tctgattaag ttattttcat cttcaatttc    720
aaatgtgatc tagcggcata aaacttgttg tctgacagat atttgacttc cacacgggcc    780
acagctcaat tacaaacata cttcaaacat caggcagagg cagagcacta gcagcattcg    840
ctacgtggcg gtgggcagca gtggccagca cattcgacaa ctgccacgga tcccgtacta    900
cttcaaacac gtatcgcttc cagaatccag agtcacacgt gtgcagctgc atgaacccag    960
ctcactccct taagaacagc tcgacgctca cctgtct                              997

SEQ ID NO: 213          moltype = DNA  length = 1318
FEATURE                 Location/Qualifiers
source                  1..1318
                        mol_type = unassigned DNA
                        organism = Arabidopsis thaliana
SEQUENCE: 213
atcaacaaat tactcctcaa tcacactcct atagaaaacg gtttaagcta tcattacatg     60
tctagttggt tttactcagc cctagaagtg ttgtttattg catcacttc cacgaagcac    120
aattttctt ttttacaatc accagacctc acaggctgca acatatgctt tagagcacat    180
tctaaacttt gaactataaa agctgttaac actaatacac tatgcgttct ttttgctcc    240
aaacactttt gatccattat taggagacac tccacttaga aagattttct aatcctttgg    300
tcaactagga agttcaaggt ttttctaaac agaaattcat ttcacaagta atttaattta    360
taaggaaatg aatagagaaa tcaaatcatt gaagaactac aaaatataga ttcaaggtca    420
ggtctaagaa atattcctg aagctcaaaa aagagttttc ctctcacatt atagaattgg    480
cctttacttc aacatttcc cacctattcc acatttggtc agaacatttt taattacttg    540
tggatcaatt tccggttgaa atgggtttgg tgaatatccg gttcagttat atggtggccg    600
ttggaattgg cttattagtt gtggccgttg ttgaagccgt tggtattggt aagggagaag    660
cagacttgtg gctatgagtc tatgaccatg actcgtgatt atggagctgt cttatgaccc    720
tgaccatcac cttgatctgg tggattccaa tgtttctttc ttcttctaat aaaatattat    780
ggtcaataca ggtgctaatt aagatggtaa taatttctta tgtttctgtg gtaaagtttg    840
attcaattcc gtagttttag ataatcttat ttccatacat aaattttata gtttatcta    900
ctttgttctt atgttttatc tctagccaag agttattatt attatcagaa gaagaaaaaa    960
aaaagaagca tatatacaaa aggtttaata aaatgtatta tacaaggcaa ttatccaaat   1020
tttttttgtt ttggtttaca ttgatgctct caggatttca taaggataga gagatctatt   1080
cgtatacgtg tcacgtcatg agtgggtgtt tcgccaatcc atgaaacgca cctagatatc   1140
taaaacacat atcaattgcg aatctgcgaa gtgcgagcca ttaaccacgt aagcaaacaa   1200
acaatctaaa ccccaaaaaa aatctatgac tagccaatag caacctcaga gattgatatt   1260
tcaagataag acagtattta gatttctgta ttatatatag cgaaatcgc atcaatac      1318

SEQ ID NO: 214          moltype = DNA  length = 1500
FEATURE                 Location/Qualifiers
source                  1..1500
                        mol_type = unassigned DNA
                        organism = Zea mays
SEQUENCE: 214
acactttttat tatcgcgtca aatcagtacc tcaatcgata ttgtagccta gtgttcttat     60
taaatgggaa gaattcgagg acacactaat tccttgctaa cacacactta tgctccattt    120
ggatgtcgat attggagggc atgaaactga attggtttca attacaaatc agccatgata    180
ttgtaatgag agtaatttc aattctattc tttgatgtc actgaattgg agttttggaat    240
tgtgtggtcc aattccacct tatatagaag agggatgctc tgtattggga gagtgagttt    300
ctagttatag tctagcttcg ggaaattgag tctctcgttc caaatctcaa ttccatgtgc    360
aaccaaacaa tagaattctg gaaagctgat tccaattcct aattccgtgc tccaatatct    420
acatccaaac gggtgttaca taaatataga atgacatat caaccatgca aaaccacatt    480
ggcgatgttg aacaaaggcg aacacccaca tactatgtca aacacacggc atctcttcct    540
caaaggtcga accacgtgtg ttccatgcat gcgtggaaca tgcaaggttg tcacgtatag    600
ggaatgatga cacacgagag cgcctacaag gcaacaaaca ccttacgtac cacgtagagt    660
gcattttgct accacctgcc accggatgac atgtatgcat gcatgcgttg tgtacgcata    720
cactgctgtc tgctggtgcc caagaccat ctagaacagc atcttttaat tctccatttc    780
cctcacgcca ttgctagtgc cttgcacatg ctcgcactcc ctaacacatc ttcctccctt    840
```

```
tatttttcgt tgccaattgc tagttgttca aatgccacgt tttccttaca cagctgtagg    900
gcaccgtacc acgtagaatg cattcctcgc caccaacaga caaacacgcc gggcatatgt    960
acgtcttacg ccggaccatc accagtatat atgatgctag ggatcagtgg gcgcccttt    1020
tgcctcgtcc tcccggggcg gcattcctat gtcctaactg aagcaaccca cgcgccgcca   1080
tttctgttgc gaatgagtcc atggacatat gtgccaacga aaccctcgg aaggcaccat    1140
ctatctatct atctctcaag caatattata tttggcacct acgctcaagt acatagacag   1200
tgtgcacggc attgtgcagc tggaaagccc gcccgacacg agggctgcca aatcgacagc   1260
tccgcgccct tggaaatcct agtcacttgt tcacaattga ccaatctacc cttgaagcac   1320
acggtggatg gtactgccac atttggctta taggggcata gaggacaatg aatgcaactg   1380
gagcgggaag gagagcttta atttgtaagt actcggtgaa caccgcacct gatgatgatg   1440
atgatggaca gcgaggaatt gttataaaag gcgcccgtcc ctcccatggc tcaagaacaa   1500

SEQ ID NO: 215          moltype = DNA  length = 2000
FEATURE                 Location/Qualifiers
source                  1..2000
                        mol_type = unassigned DNA
                        organism = Zea mays
SEQUENCE: 215
aatgctagaa actacagggt ccaatatatg aaaatcaggg catggatgta attaatttac     60
aatagcagtg gacggcgggt taattcagta attccctagg ggcacttaag caaatatcca    120
tcgcaaaggg gtattgttgg atcccgaccg ttggatcaga tccgaaggcc gagaatagat    180
cgcgcccaca caactgcgtc gtgcactgac caccctccgg ttaagattcg acggaccaaa    240
tttaatgaaa tccaaaccac ccacagcccc acgatcagca atctacggtc cctcttaacc    300
cagatgaatc ggtatccgac ttctaatcta agcagttcct caatcgatca acgctccagg    360
gccttcttct atctcccaac gcagatcgag ctacggtcgc ttgcacccga ggaacgccga    420
cacagcgagc ggcggaccag cggttctggg taatgatttg gcacaaaac aatattggcg     480
cgacatagga atgatggcaa ctattaggtt gtgaccttac tagtgtcagc ggtgtgggca    540
gggtcgccca cgggaaacca gtgcgacggt gctcccggct tgttaatgac ggtgtgctgg    600
tcccgacacg gtgatgcccc aaacgccccc gccgtacgag aacaccgcag acgcccctgc    660
tcgactccgc cctcggcttc ccgcgcccac ctcgcacttc gacggccgca ccgaccctct    720
gacctctcct tttctctcct ttctcactcc tatcggtagc tacaacgaaa gcgactccca    780
acgtggcgca aaccctcgaa gcatacggct ggggaaggtg gcagccaggt ttatatccta    840
ggcgcccgag gaaatcgtgt ggacggctgt tacgtttcgc ccgcggggcg cgattcgcgc    900
gaagaagact gtatgcgagg tagggcccac tagcagtgag ccatcacccg gggaagcgcg    960
catgcatcga ttgacacgcg accccaacag tcaggcgacc cgagtgtgca gacggtcgcg   1020
atggtgaaag tggctagctc gcgcggacgc gtaggggcat tgggccgaaa tgcgtttcag   1080
cggtccaact tctttttttc ttgtcttttt tctttcctt tccttttcta tttttagatt   1140
tcaaatttaa gttcaaattt tttgtggtga atttttctaaa aatccacata tcagtatgaa   1200
aagaatttat atataaatct attttattat atatttttat atattttcaa tttatttcaa   1260
tttctaaaat gtaaattagg ttaaatcgcc atttggacac taatatatct ttattagtat   1320
tactattatt atatgcacaa ccaaataaac tccaacatga tgcatcgatt atttgtatgt   1380
cattggttaa ttattcactt taaatatgtt ccttaacgat tctcatgaaa cagaaggcca   1440
tgcacataaa gatgtatccc ttttttctat attcccaagt ttgggtatta caacattcat   1500
ctatgcattc taggatttca attactctca atcttttagt atttgttcct tcattgtcaa   1560
atcacttctc atctaactac tatgcttgtt taaccagcag aacaatacta caacaatatc   1620
catttataaa ggctttaata gcaaacttta catattcata tcatgttaag gttgtcacat   1680
gtgtaaaggt gaagagatca tgcatgtcat tccacataaa tgaaaagaat tcctatataa   1740
aaatgacatg ttttgttgta ggtagtggaa attatctttc cagcaaagac catataatcc   1800
gataaagctg ataactaaat gtcaaaatcg agtaagtgcc atatcatcta tatcttatct   1860
gttgtttgga aaaagacaaa atccaaaaaa aaatatatga gatctcacat gtataaatag   1920
ctcccaaatc agtagttaat acatctccca taatattttc agcattcaaa aacacaccaa   1980
gcgaagcgca ctagcaacga                                               2000

SEQ ID NO: 216          moltype = DNA  length = 1456
FEATURE                 Location/Qualifiers
source                  1..1456
                        mol_type = unassigned DNA
                        organism = Zea mays
SEQUENCE: 216
tgtttggact ccagaaaatt tacgggagtt ggtggagcag gtcattaagt actataaaaa     60
atcatgtagc tgaagctgca agtatttaga agacatttag ataagttatt ttatttatca    120
tttagattaa gaaaatttaa aactatttaa attgatatta taaactacag ctccacactg    180
gagctagatc ctggagtcat tacaaacacc cccttaatgg gaaaagagaa gataatgtat    240
atctaattat tgtttctgtg tcacctatag ctattagttc aaaaccttcat aatcactggt    300
acaaataagc tctagagagg cggttcggaa cccattttta ttgttgtttt tcaaaaccac    360
tagtgttagg gaccgccagt ggaaactgaa acgccattgg aaattgatttt tcactgatgg    420
tgagctaaga aaaccgccat tggtaatcct ttgcagaaaa cataaactag gttttaaaaa    480
tagtaaacaa atatttttat taggagaggc cccacatagt cgcaccattt ttcgcgcatt    540
attcacgcgc tacgcaacca atggtaattg aacctcagag acttcactct tgtgtagcct    600
cctttgccac tccactaaac acttacttgt gtcttgattg catttttgttg cccacatatt    660
agaacaaaca gagtgtaaat tgattgtttg aggctgtaaa caaattcaaa tgaaaaagta    720
gtcaactact aaattgaata attgtttatg ttctaccact tttattttgg tactttttccc    780
atcggaggcg gtttgtaaaa tttgcatttt aagtttttaca aatttcaatg aaattttgag   840
agcccaaatg attttcaaata aaaaagttgt caactacaat gttttataac tttaatttg    900
gtggtttttt aaacaagctc atttgaaaaa ctaaatgat cgattctaca tgattttag     960
gtcgatttt taaggaatcg cctgtacaaa tatttctact gacagttttt aagaaaccac   1020
ctgtggaaat catagatttg tactagcggt ttttctcaag taactgctag tagaaaatg    1080
gtggttttct taagaaaact gtttgtagga atgcacgatt tatataaatg gatttgttaa   1140
gaaaccgct agtggaatgt tcttttcaact aacggttatt gagtcgtgac agccaattta  1200
```

-continued

```
atttccttga taactaaaag cggctgtaaa aattagacca tgatgtaggc acggagctgt   1260
tttgtactga atgcgcccac tgttttgttg gaaaagtgca tgtacttatt attcattctg   1320
tttatttcta gctggcattc agttcttaca gccacagatt atgcaaaacg cctatttctg   1380
ccagcaaatt tacaggaaaa gtcatggact tttccgggtt attttcctat aagtacagcc   1440
attcctttca cttaca                                                   1456

SEQ ID NO: 217          moltype = DNA  length = 710
FEATURE                 Location/Qualifiers
source                  1..710
                        mol_type = unassigned DNA
                        organism = Zea mays
SEQUENCE: 217
ttcagcgtta tttgaacacc gtaaagcctc tccagcagat tgtgaataca cagttgtgga     60
gaacgctatt tataacgcag acactattta taatgcagat gtgtaaaagt gaaatttaaa    120
atagtagatg agataggaga gatagaatga gtaaactgct ggagagcaaa tcgtgcatat    180
gatcgtgcaa aacaccgttt ttcgtagagt gaagtttaaa atagcaggtg agagagtaga    240
taggatgagt aagctgatgg agagcaaata ttgtatatac gtggtcggtg caatagagtg    300
aaatttgaaa taactgacac agttttggtg cgtggaaata gacgaggata attctagtgc    360
aatccgcact gccagtggac cccgcccgac gataattcta cgcacgggcg gcgcactgca    420
ctactagttc atcgatcgga tgcgttagcg tgcccctcct catattgttt ccttgtacgt    480
actagtgcaa tccgtcagcc gcacggctcc agtccactcc agtccagcaa cagcgtcacc    540
tccagctccg aaaggcttat ccttgcaaca aacatcgtac gaaaaaggcg caggaaaaag    600
aaaagtgtcg aaatacgaca taaaaaaagc atcaaaatac gctgcgagtg agcgagacat    660
tggcctcccc atcccatata tatatagcta tagctatccc tcggttcttc               710
```